(12) United States Patent
Pedersen et al.

(10) Patent No.: US 12,116,576 B2
(45) Date of Patent: Oct. 15, 2024

(54) OLIGONUCLEOTIDES FOR MODULATING SCN9A EXPRESSION

(71) Applicant: Hoffmann-La Roche Inc., Little Falls, NJ (US)

(72) Inventors: Lykke Pedersen, Copenhagen (DK); Søren Rasmussen, Espergærde (DK); Gianluigi Lichinchi, Hørsholm (DK); Christoffer Sondergaard, Hørsholm (DK)

(73) Assignee: Hoffmann-La Roche Inc., Little Falls, NJ (US)

(*) Notice: Subject to any disclaimer, the term of this patent is extended or adjusted under 35 U.S.C. 154(b) by 244 days.

(21) Appl. No.: 17/130,451

(22) Filed: Dec. 22, 2020

(65) Prior Publication Data

US 2021/0238608 A1   Aug. 5, 2021

Related U.S. Application Data

(63) Continuation of application No. PCT/EP2019/066223, filed on Jun. 19, 2019.

(30) Foreign Application Priority Data

Jun. 22, 2018  (EP) .................................... 18179339
Sep. 18, 2018  (EP) .................................... 18194982

(51) Int. Cl.
  *C12N 15/113*    (2010.01)
  *A61K 47/54*     (2017.01)

(52) U.S. Cl.
  CPC ........ *C12N 15/1138* (2013.01); *A61K 47/549* (2017.08); *C12N 2310/11* (2013.01); *C12N 2310/14* (2013.01); *C12N 2310/315* (2013.01); *C12N 2310/321* (2013.01); *C12N 2310/322* (2013.01); *C12N 2310/3231* (2013.01); *C12N 2310/341* (2013.01); *C12N 2310/351* (2013.01)

(58) Field of Classification Search
  None
  See application file for complete search history.

(56) References Cited

U.S. PATENT DOCUMENTS

| | | | |
|---|---|---|---|
| 7,691,997 B2 | 4/2010 | Khvorova et al. | |
| 2005/0080031 A1* | 4/2005 | McSwiggen ........... | C12N 15/87 536/23.1 |
| 2007/0026394 A1* | 2/2007 | Blatt .................... | C12N 15/113 435/372 |
| 2007/0212685 A1 | 9/2007 | MacDonald et al. | |
| 2010/0273857 A1 | 10/2010 | Thakker et al. | |
| 2011/0306654 A1 | 12/2011 | MacDonald et al. | |
| 2016/0024208 A1 | 1/2016 | MacDonald et al. | |
| 2017/0283496 A1 | 10/2017 | Pedersen et al. | |
| 2019/0153477 A1* | 5/2019 | Lundberg ............... | C12N 15/11 |

FOREIGN PATENT DOCUMENTS

| | | |
|---|---|---|
| JP | 2019-531287 A | 10/2019 |
| KR | 2011-0087436 A | 8/2011 |
| WO | WO-01/05831 A1 | 1/2001 |
| WO | WO-02/18637 A2 | 3/2002 |
| WO | WO-02/083945 A2 | 10/2002 |
| WO | WO-02/18637 A3 | 11/2002 |
| WO | WO-02/083945 A3 | 10/2003 |
| WO | WO-2007/056326 A2 | 5/2007 |
| WO | WO-2012/162732 A1 | 12/2012 |
| WO | WO-2014/159595 A2 | 10/2014 |
| WO | WO-2014/159595 A3 | 12/2014 |
| WO | WO-2018/007980 A1 | 1/2018 |
| WO | WO-2018/051175 A1 | 3/2018 |
| WO | WO-2019/138057 A1 | 7/2019 |
| WO | WO-2019/141723 A1 | 7/2019 |
| WO | WO-2019/233921 A1 | 12/2019 |
| WO | WO-2020/002487 A1 | 1/2020 |
| WO | WO-2021/008637 A3 | 8/2021 |

OTHER PUBLICATIONS

Cai et al., "shRNA mediated knockdown of Nav1.7 in rat dorsal root ganglion attenuates pain following burn injury," BMC Anesthesiol. 16(59) 1-7 (2016).
Campbell et al., "Functional expression of the voltage-gated Na+-channel Nav1.7 is necessary for EGF-mediated invasion in human non-small cell lung cancer cells," J Cell Sci. 126(21): 4939-49 (2013).
Cox et al., "An SCN9A channelopathy causes congenital inability to experience pain," Nature. 444(7121): 894-898 (2006).
Cummins et al., "Electrophysiological Properties of Mutant Nav1.7 Sodium Channels in a Painful Inherited Neuropathy," J Neurosci. 24(38): 8232-8236 (2004).
Fertleman et al., "What's in a name-familial rectal pain syndrome becomes paroxysmal extreme pain disorder," J Neurol Neurosurg Psychiatry. 77(11) 1294-1295 (2006).
Khasar et al., "A tetrodotoxin-resistant sodium current mediates inflammatory pain in the rat," Neurosci Lett. 256(1): 17-20 (1998).
Kis-Toth et al., "Voltage-Gated Sodium Channel Nav1.7 Maintains the Membrane Potential and Regulates the Activation and Chemokine-Induced Migration of a Monocyte-Derived Dendritic Cell Subset," J Immunol. 187(3): 1273-1280 (2011) (9 pages).
Li et al., "Chitosan oligosaccharide reduces Propofol requirements and Propofol-related side effects," Mar Drugs.14(12): 234 (2016) (16 pages).
Meguro et al., "Function and role of voltage-gated sodium channel NaV1. 7 expressed in aortic smooth muscle cells," Am J Physiol Heart Circ Physiol. 296(1): H211-H219 (2009).
Mohan et al., "Antisense oligonucleotides selectively suppress target RNA in nociceptive neurons of the pain system and can ameliorate mechanical pain," J of the Int Assoc for the Study of Pain. 159(1): 139-149 (2018).

(Continued)

*Primary Examiner* — Sean McGarry
(74) *Attorney, Agent, or Firm* — Clark & Elbing LLP; Thomas J. Takara

(57) ABSTRACT

The present invention relates to oligonucleotides (oligomers) that are complementary to voltage-gated sodium ion channel encoding nucleic acids, such as SCN9A, which encodes the voltage-gated sodium channel $Na_v1.7$. The oligonucleotides of the invention are capable of inhibiting the expression of voltage-gated sodium ion channels, such as $Na_v1.7$, and are useful in the prevention or the treatment of pain.

16 Claims, No Drawings

Specification includes a Sequence Listing.

(56) References Cited

OTHER PUBLICATIONS

Muroi et al., "Selective silencing of NaV1.7 decreases excitability and conduction in vagal sensory neurons," J Physiol. 589(23): 5663-5676 (2011).

Nakajima et al., "Eicosapentaenoic acid inhibits voltage-gated sodium channels and invasiveness in prostate cancer cells," Br J Pharmacol. 156(3): 420-431 (2009).

Nassar et al., "Nociceptor-specific gene deletion reveals a major role for Nav1.7 (PN1) in acute and inflammatory pain," Proc Natl Acas Sci U S A. 101(34): 12706-11 (2004).

Pan et al., "Effect of down-regulation of voltage-gated sodium channel Nav1.7 on activation of astrocytes and microglia in DRG in rats with cancer pain," Asian Pac J Trop Med. 8(5): 405-411 (2015).

Parada et al., "Activation of presynaptic NMDA receptors coupled to NaV1.8-resistant sodium channel C-fibers causes retrograde mechanical nociceptor sensitization," Proc Natl Acad U S A. 100(5): 2923-8 (2003).

Porreca et al., "A comparison of the potential role of the tetrodotoxin-insensitive sodium channels, PN3ySNS and NaNySNS2, in rat models of chronic pain," *Proc Natl Acad Sci U S A*. 96(14): 7640-4 (1999) (6 pages).

Ruangsri et al., "Relationship of Axonal Voltage-gated Sodium Channel 1.8 (NaV1.8) mRNA accumulation to sciatic nerve injury-induced painful neuropathy in rats," J Biol Chem. 286(46): 39836-39847 (2011).

Sun et al., "Increased Nav1.7 expression in the dorsal root ganglion contributes to pain hypersensitivity after plantar incision in rats," Mol Pain. 14:1-8 (2018), including Supplementary Figures "Figure", A X ' Jun. 19, 2018 (Jun. 19, 2018), XP55624115, Retrieved from the Internet: URL:https://journals.sagepub.com/doi/suppl /10.1177/1744806918782323/suppl_file/Supplementary Figures.pdf [retrieved on Sep. 19, 2819].

Yamane et al., "A functional coupling between CRMPI and Nav1.7 for retrograde propagation of Semaphorin3A signaling," J Cell Sci. 130(8): 1393-1403 (2017).

Yang et al., "Mutations in SCN9A, encoding a sodium channel alpha subunit, in patients with primary erythermalgia," J Med Genet. 41(3):171-174 (2004).

Yoshimura et al., "The involvement of the tetrodotoxin-resistant sodium channel NaV1.8 (PN3/SNS) in a rat model of visceral pain," J Neurosci. 21(21): 8690-6 (2001).

International Search Report and Written Opinion for International Patent Application No. PCT/EP2019/066223, dated Oct. 2, 2019 (21 pages).

Nassar et al., "Neuropathic pain develops normally in mice lacking both $Na_v$ 1.7 and $Na_v$ 1.8," Mol Pain. 1:24 (2004) (9 pages).

Wan et al., "The Medicinal Chemistry of Therapeutic Oligonucleotides," J Med Chem. 59(21):9645-9667 (2016) (23 pages).

Yu et al., "Antisense-Mediated Knockdown of $Na_v$1.8, but Not $Na_v$1.9, Generates Inhibitory Effects on Complete Freund's Adjuvant-Induced Inflammatory Pain in Rat," PLoS One, 6(5):e19865 (2011) (9 pages).

Koch et al., Chapter 19: Locked Nucleic Acid. *Antisense Drug Technology: Principles, Strategies, and Applications, Second Edition*. Stanley T. Crooke, 519-64 (2008).

Smith et al., "Therapeutic Oligonucleotides: State of the Art," Annu Rev Pharmacol Toxicol. 59:605-30 (Oct. 9, 2018).

Sun et al., "Increased Nav1.7 expression in the dorsal root ganglion contributes to pain hypersensitivity after plantar incision in rats," Molecular Pain. 14:1-8 (May 7, 2018) (10 pages).

Vickers et al., "Efficient Reduction of Target RNAs by Small Interfering RNA and RNase H-dependent Antisense Agents", 2003, J. of Biol. Chem., vol. 278(9), 7108-7118 (Year: 2003).

* cited by examiner

OLIGONUCLEOTIDES FOR MODULATING SCN9A EXPRESSION

SEQUENCE LISTING

The instant application contains a Sequence Listing which has been submitted electronically in ASCII format and is hereby incorporated by reference in its entirety. Said ASCII copy, created on Jan. 19, 2021 is named "51551-003001_Sequence_Listing_1.19.21_ST25" and is 2,511,302 bytes in size.

FIELD OF INVENTION

The present invention relates to oligonucleotides (oligomers) that are complementary to voltage-gated sodium ion channel encoding nucleic acids, such as SCN9A, which encodes the voltage-gated sodium channel $Na_v1.7$. The oligonucleotides of the invention are capable of inhibiting the expression of voltage-gated sodium ion channels, such as $Na_v1.7$, and are useful in the prevention or the treatment of pain.

BACKGROUND

Voltage-gated sodium channels ($Na_vs$) play essential roles in excitable tissues, with their activation and opening resulting in the initial phase of the action potential. The cycling of $Na_vs$ through open, closed and inactivated states, and their closely choreographed relationships with the activities of other ion channels lead to exquisite control of intracellular ion concentrations $Na_v1.7$ is a voltage activated ion channel involved expressed almost exclusively in the small cell peripheral sensory nerves. Mice with a conditional knock-out of $Na_v1.7$ in sensory neurons displayed an antinociceptive phenotype (Nassar et al., 2004, Proc Natl Acad Sci USA. 2004 Aug. 24; 101(34):12706-11). The role of $Na_v1.7$ in pain sensation in humans was demonstrated by association between the spontaneous pain syndrome inherited erythromelalgia (IEM) (Yang et al., J Med Genet. 2004; 41(3):171-4) and paroxysmal extreme pain disorder (PEPD) (Fertleman et al., J Neurol Neurosurg Psychiatry. 2006 November; 77(11):1294-5) and gain of function mutation in Nav1.7 of these patients (Cummins et al., J Neurosci. 2004; 24(38):8232-8236). Further support for Nav1.7 was generated by identification of loss of function mutations that resulted in congenital insensitivity to pain (Cox et al., Nature AAA. 2006; 7121:894-8). These findings have kicked of a number of small molecule drug discovery programs for identification of $Na_v1.7$ modulators, however it appears that finding good compounds with high selectivity and good PK/PD properties have been challenging.

US2016024208 discloses human antibodies to $Na_v1.7$.

WO02083945 refers to synthetic oligonucleotides with antisense sequence to specific regions of SCN5A and optionally also SCN9A for use in the treatment of breast cancer.

US2007/212685 refers to methods of identifying analgesic agents and mentions that specific compounds which will modulate the gene expression or gene transcript levels in a cell of SCN9A include antisense nucleic acids.

US2010273857A refers to methods, sequences and nucleic acid molecules used to treat pain via locally administering siRNA molecules that suppress the expression of amino acid sequences that encode for Nav1.7 channels or that otherwise inhibit the function of Nav1.7 channels, and reports that local suppression of Nav1.7 channel levels and/or function will occur in the peripheral sensory neurons of the dorsal root ganglia.

WO12162732 relates to novel screening assays for modulating sodium channels, particularly voltage-gated sodium channels.

KR20110087436 discloses an SCN9A antisense oligonucleotide.

Mohan et al., Pain (2018) Volume 159 Number 1, p139-149 discloses antisense oligonucleotides targeting $Na_v1.7$, and characterize the pharmacodynamic activity of ASOs in spinal cord and dorsal root ganglia (DRG) in rodents.

WO18051175 discloses SCN9A antisense peptide nucleic acid oligonucleotides targeting a part of the human SCN9A pre-mRNA. The peptide nucleic acid derivatives potently induce splice variants of the SCN9A mRNA in cells, and are useful to safely treat pains or conditions involving Nav1.7 activity.

There is therefore a need for antisense oligonucleotides therapeutics which are effective in inhibiting expression of voltage-gated sodium ion channel encoding nucleic acids, such as SCN9A in humans, such as for the prevention or treatment of pain.

OBJECTIVE OF THE INVENTION

The present invention provides oligonucleotides, including LNA antisense oligonucleotides targeting SCN9A which are capable of inhibiting the expression of $Na_v1.7$ in a cell which is expressing $Na_v1.7$. The present invention further provides oligonucleotides targeting SCN10A which inhibit the expression of $Na_v1.8$ in a cell which is expressing $Na_v1.8$. In some aspects, the invention provides oligonucleotides which target both SCN9A and SCN10A nucleic acid targets. The oligonucleotide of the invention may be used in the prevention or treatment of pain. The invention further provides advantageous target site sequences on the human Nav1.7 pre-mRNA which may be targeted by oligonucleotide inhibitors of human Nav1.7 such as antisense oligonucleotides or RNAi agents, such as siRNAs or shRNAs.

SUMMARY OF INVENTION

The present invention relates to oligonucleotides targeting a nucleic acid encoding a voltage-gated sodium ion channel encoding nucleic acids, such as SCN9A or SCN10A, or in some embodiments both SCN9A (a $Na_v1.7$ nucleic acid target) and SCN10A (a $Na_v1.8$ nucleic acid target).

The oligonucleotide of the invention may be an antisense oligonucleotide.

The oligonucleotides of the invention are capable of inhibiting the expression of the target nucleic acid, such as SCN9A or SCN10A, or in some embodiments are capable of inhibiting the expression of both SCN9A and SCN10A, in a cell which is expressing said target nucleic acid(s). Suitably the target nucleic acid expressed in the cell may be a mammalian cell, such as cynomolgus monkey cell or a pig cell, or preferably a human SCN9A or a human SCN10A mRNA or pre-mRNA sequence.

Alternatively stated, the oligonucleotides of the invention are capable of inhibiting the expression of Nav1.7 or Nav1.8 in a cell, such as a mammalian or human cell, or in some embodiments are capable of inhibiting the expression of both Nav1.7 or Nav1.8 in a cell such as in a mammalian, such as a cynomolgus monkey cell or a pig cell, or preferably in a human cell. The cell is expressing the target voltage-gated sodium ion channel protein.

The invention further provides target sequences of the human SCN9A pre-mRNA which are useful in targeting complementary oligonucleotides for inhibition of SCN9A expression.

Advantageously the oligonucleotide of the invention is an antisense oligonucleotide such as an LNA antisense oligonucleotide.

The invention provides an antisense oligonucleotide (e.g. an LNA antisense oligonucleotide) of 10 to 30 nucleotides in length, which comprises a contiguous nucleotide sequence of 10 to 30 nucleotides in length with at least 90% complementarity, such as 100% complementarity, to SEQ ID NO: 1.

The invention provides for an oligonucleotide of 10 to 30 nucleotides in length, which comprises a contiguous nucleotide sequence of 10 to 30 nucleotides in length with at least 90% complementarity, such as 100% complementarity, to SEQ ID NO: 1, which is capable of inhibiting the expression of capable of inhibiting the expression of both Nav1.7 and Nav1.8 in a cell, wherein the contiguous nucleotide sequence is complementary to human Nav1.7 and human Nav1.8 target nucleic acids, for example the target nucleic acids shown as SEQ ID NO 1 and SEQ ID NO 651 respectively.

The invention provides for an oligonucleotide of 10 to 30 nucleotides in length, which comprises a contiguous nucleotide sequence of 10 to 30 nucleotides in length with at least 90% complementarity, such as 100% complementarity, to a human Nav1.7 target nucleic acid and a human Nav1.8 target nucleic acid, and is which is capable of inhibiting the expression of capable of inhibiting the expression of both Nav1.7 or Nav1.8 in a cell. In some embodiments, the contiguous nucleotide sequence of the oligonucleotide of the invention is 100% complementary to SEQ ID NO 1, and is at least 90% complementary such as advantageously 100% complementary to SEQ ID NO 651.

The invention provides for an oligonucleotide of 10 to 30 nucleotides in length, which comprises a contiguous nucleotide sequence of 10 to 30 nucleotides in length with at least 90% complementarity, such as 100% complementarity, to SEQ ID NO: 1, which is capable of inhibiting the expression of capable of inhibiting the expression of both Nav1.7 or Nav1.8 in a cell, wherein the contiguous nucleotide sequence is 100% complementary to SEQ ID NO 1 and is at least 90% complementary such as 100% complementary to SEQ ID NO 651.

In some embodiments, the oligonucleotide of the invention comprises at least 10, or at least 12 contiguous nucleosides present in a sequence selected from the group consisting of SEQ ID NOs 512, 513, 514, 515, 516, 517, 518, 519, 520, 521, 522, 523, 524, 525, 557, 558, 559, 560, 577, 579, 583, 638, and 587.

The invention provides an antisense oligonucleotide selected from the group consisting of CMP ID 50_1; 51_1; 52_1; 53_1; 54_1; 55_1; 56_1; 57_1; 58_1; 59_1; 60_1; 61_1; 62_1; 63_1; 64_1; 65_1; 66_1; 67_1; 68_1; 69_1; 70_1; 71_1; 72_1; 73_1; 74_1; 75_1; 76_1; 77_1; 78_1; 79_1; 80_1; 81_1; 82_1; 83_1; 84_1; 85_1; 86_1; 87_1; 88_1; 89_1; 90_1; 91_1; 92_1; 93_1; 94_1; 95_1; 96_1; 97_1; 98_1; 99_1; 100_1; 101_1; 102_1; 103_1; 104_1; 105_1; 106_1; 107_1; 108_1; 109_1; 110_1; 111_1; 112_1; 113_1; 114_1; 115_1; 116_1; 117_1; 118_1; 119_1; 120_1; 121_1; 122_1; 123_1; 124_1; 125_1; 126_1; 127_1; 128_1; 129_1; 130_1; 131_1; 132_1; 133_1; 134_1; 135_1; 136_1; 137_1; 138_1; 139_1; 140_1; 141_1; 142_1; 143_1; 144_1; 145_1; 146_1; 147_1; 148_1; 149_1; 150_1; 151_1; 152_1; 153_1; 154_1; 155_1; 156_1; 157_1; 158_1; 159_1; 160_1; 161_1; 162_1; 163_1; 164_1; 165_1; 166_1; 167_1; 168_1; 169_1; 170_1; 171_1; 172_1; 173_1; 174_1; 175_1; 176_1; 177_1; 178_1; 179_1; 180_1; 181_1; 182_1; 183_1; 184_1; 185_1; 186_1; 187_1; 188_1; 189_1; 190_1; 191_1; 192_1; 193_1; 194_1; 195_1; 196_1; 197_1; 198_1; 199_1; 200_1; 201_1; 202_1; 203_1; 204_1; 205_1; 206_1; 207_1; 208_1; 209_1; 210_1; 211_1; 212_1; 213_1; 214_1; 215_1; 216_1; 217_1; 218_1; 219_1; 220_1; 221_1; 222_1; 223_1; 224_1; 225_1; 226_1; 227_1; 228_1; 229_1; 230_1; 231_1; 232_1; 233_1; 234_1; 235_1; 236_1; 237_1; 238_1; 239_1; 240_1; 241_1; 242_1; 243_1; 244_1; 245_1; 246_1; 247_1; 248_1; 249_1; 250_1; 251_1; 252_1; 253_1; 254_1; 255_1; 256_1; 257_1; 258_1; 259_1; 260_1; 261_1; 262_1; 263_1; 264_1; 265_1; 266_1; 267_1; 268_1; 269_1; 270_1; 271_1; 272_1; 273_1; 274_1; 275_1; 276_1; 277_1; 278_1; 279_1; 280_1; 281_1; 282_1; 283_1; 284_1; 285_1; 286_1; 287_1; 288_1; 289_1; 290_1; 291_1; 292_1; 293_1; 294_1; 295_1; 296_1; 297_1; 298_1; 299_1; 300_1; 301_1; 302_1; 303_1; 304_1; 305_1; 306_1; 307_1; 308_1; 309_1; 310_1; 311_1; 312_1; 313_1; 314_1; 315_1; 316_1; 317_1; 318_1; 319_1; 320_1; 321_1; 322_1; 323_1; 324_1; 325_1; 326_1; 327_1; 328_1; 329_1; 330_1; 331_1; 332_1; 333_1; 334_1; 335_1; 336_1; 337_1; 338_1; 339_1; 340_1; 341_1; 342_1; 343_1; 344_1; 345_1; 346_1; 347_1; 348_1; 349_1; 350_1; 351_1; 352_1; 353_1; 354_1; 355_1; 356_1; 357_1; 358_1; 359_1; 360_1; 361_1; 362_1; 363_1; 364_1; 365_1; 366_1; 367_1; 368_1; 369_1; 370_1; 371_1; 372_1; 373_1; 374_1; 375_1; 376_1; 377_1; 378_1; 379_1; 380_1; 381_1; 382_1; 383_1; 384_1; 385_1; 386_1; 387_1; 388_1; 389_1; 390_1; 391_1; 392_1; 393_1; 394_1; 395_1; 396_1; 397_1; 398_1; 399_1; 400_1; 401_1; 402_1; 403_1; 404_1; 405_1; 406_1; 407_1; 408_1; 409_1; 410_1; 411_1; 412_1; 413_1; 414_1; 415_1; 416_1; 417_1; 418_1; 419_1; 420_1; 421_1; 422_1; 423_1; 424_1; 425_1; 426_1; 427_1; 428_1; 429_1; 430_1; 431_1; 432_1; 433_1; 434_1; 435_1; 436_1; 437_1; 438_1; 439_1; 440_1; 441_1; 442_1; 443_1; 444_1; 445_1; 446_1; 447_1; 448_1; 449_1; 450_1; 451_1; 452_1; 453_1; 454_1; 455_1; 456_1; 457_1; 458_1; 459_1; 460_1; 461_1; 462_1; 463_1; 464_1; 465_1; 466_1; 4671; 468_1; 469_1; 470_1; 471_1; 472_1; 473_1; 474_1; 475_1; 476_1; 477_1; 478_1; 479_1; 480_1; 481_1; 482_1; 483_1; 484_1; 485_1; 486_1; 487_1; 488_1; 489_1; 490_1; 491_1; 492_1; 493_1; 494_1; 495_1; 496_1; 497_1; 498_1; 499_1; 500_1; 501_1; 502_1; 503_1; 504_1; 505_1; 506_1; 507_1; 508_1; 509_1; 510_1; 511_1; 512_1; 512_2; 512_3; 513_1; 513_2; 513_3; 513_4; 514_1; 514_2; 514_3; 514_4; 515_1; 515_2; 515_3; 515_4; 515_5; 515_6; 516_1; 516_2; 516_3; 516_4; 516_5; 516_6; 516_7; 517_1; 517_2; 517_3; 517_4; 517_5; 517_6; 517_7; 517_8; 518_1; 518_2; 518_3; 518_4; 518_5; 518_6; 519_1; 519_2; 519_3; 519_4; 519_5; 519_6; 520_1; 520_2; 520_3; 520_4; 520_5; 521_1; 521_2; 521_3; 521_4; 521_5; 522_1; 522_2; 522_3; 522_4; 523_1; 523_2; 523_3; 523_4; 523_5; 524_1; 525_1; 526_1; 527_1; 528_1; 529_1; 530_1; 531_1; 532_1; 533_1; 534_1; 535_1; 536_1; 537_1; 538_1; 539_1; 540_1; 541_1; 542_1; 543_1; 544_1; 545_1; 546_1; 547_1; 548_1; 549_1; 550_1; 551_1; 552_1; 553_1; 554_1; 555_1; 556_1; 557_1; 558_1; 559_1; 560_1; 561_1; 562_1; 563_1; 564_1; 565_1; 566_1; 567_1; 568_1; 569_1; 570_1; 571_1; 572_1; 573_1; 574_1; 575_1; 576_1; 577_1; 578_1; 579_1; 580_1; 581_1; 582_1; 583_1; 584_1; 585_1; 586_1; 5871; 588_1; 589_1; 590_1; 591_1; 592_1; 593_1; 594_1; 595_1; 596_1; 597_1; 598_1; 599_1; 600_1; 601_1; 602_1; 603_1; 604_1; 605_1; 606_1; 607_1; 608_1; 609_1; 610_1; 611_1; 612_1; 613_1; 614_1; 615_1; 616_1; 617_1; 618_1; 619_1; 620_1; 621_1; 622_1; 623_1; 624_1; 625_1; 626_1; 627_1; 628_1; 629_1; 630_1; 631_1; 632_1; 633_1; 634_1; 635_1; 636_1; 637_1;

638_1; 639_1; 640_1; and 641_1; or selected from the group selected of 642_1, 643_1, 644_1, 645_1, 646_1, 647_1, 648_1, 649_1 and 650_1.

The invention provides an oligonucleotide capable of inhibiting the expression of human SNC9A in a cell, wherein the oligonucleotide comprises a contiguous nucleotide sequence comprising at least 10 or at least 12 contiguous nucleotides of a sequence selected from the group consisting of 51, 59, 127, 161, 67, 106, 72, 124, 163, 99, 125, 110, 65, 94, 64, 57, 136, 158, 159, 356, 197, 132, 83, 76, 130, 135, 77, 186, 105, 445, 325, 265, 200, 288, 346, 86, 281, 339, 256, 289, 414, 286, 241, 82, 475, 91, 50, 97, 322, 148, 443, 251, 451, 179, 466, 357, 109,472, 471, 376, 413, 270, 379, 416, 311, 411, 368, 333, 347, 152, 89, 380, 390, 429, 63, 90, 415, 199, 503, 476, 92, 268, 371, 302, 485, 205, 274, 122, 419, 470, 498, 156,478, 393, 312, 287, 96, 226, 71, 137, 365, 58, 370, 280, 385, 442, 134, 463, 140, 440, 230, 310, 479, 363, 340, 495, 467, 444, 418, 338, 335, 496, 196, 317, 341, 406, 330, 173, 377, 474, 482, 282, 266, 73, 257, 342, 190, 492, 87, 188, 456, 372, 417, 404, 239, 206, 433, 486, 175, 461, 56, 408, 334, 504, 453, 222, 410, 104, 460, 439, 255, 489, 203, 398, 171, 407, 172, 412, 321, 305, 328, 120, 434, 449, 350, 487, 146, 420, 426, 352, 150, 316, 353, 469, 306, 384, 155, 450, 279, 267, 337, 184, 459, 360, 75, 468, 180, 245, 387, 345, 98, 435, 295, 369, 218, 182, 448, 300, 481, 427, 207, 367, 240, 231, 364, 355, 431, 497, 397, 465, 271, 502, 151, 178, 499, 421, 131, 309, 491, 261, 121, 128, 84, 304, 264, 493, 185, 237, 139, 441, 169, 160, 102, 296, 164, 362, 500, and 100.

The invention provides an oligonucleotide capable of inhibiting the expression of human SNC9A in a cell, wherein the oligonucleotide comprises a contiguous nucleotide sequence comprising at least 10 or at least 12 contiguous nucleotides of a sequence selected from the group consisting of SEQ ID NO 642, 643, 644, 645, 646, 647, 648, 649 and 650.

The invention provides an oligonucleotide capable of inhibiting the expression of human SNC9A in a cell, wherein the oligonucleotide comprises a contiguous nucleotide sequence comprising at least 10 or at least 12 contiguous nucleotides of a sequence selected from the group consisting of SEQ ID NOs 512-641.

The invention provides an oligonucleotide capable of inhibiting the expression of human SNC9A in a cell, wherein the oligonucleotide comprises a contiguous nucleotide sequence comprising at least 10 or at least 12 contiguous nucleotides of a sequence selected from the group consisting of SEQ ID NOs 642-650.

The invention provides an antisense oligonucleotide capable of inhibiting the expression of human SNC9A in a cell, wherein the oligonucleotide comprises a contiguous nucleotide sequence comprising at least 10 or at least 12 contiguous nucleotides of a sequence selected from the group consisting of SEQ ID NOs 512-641.

The invention provides an antisense oligonucleotide capable of inhibiting the expression of human SNC9A in a cell, wherein the oligonucleotide comprises a contiguous nucleotide sequence comprising at least 10 or at least 12 contiguous nucleotides of a sequence selected from the group consisting of SEQ ID NOs 642-650.

The invention provides an antisense gapmer oligonucleotide capable of inhibiting the expression of human SNC9A in a cell, wherein the oligonucleotide comprises a contiguous nucleotide sequence comprising at least 12 contiguous nucleotides of a sequence selected from the group consisting of SEQ ID NOs 512-641.

The invention provides an antisense oligonucleotide capable of inhibiting the expression of human SNC9A in a cell, wherein the oligonucleotide comprises a contiguous nucleotide sequence comprising at least 10 or at least 12 contiguous nucleotides of a sequence selected from the group consisting of SEQ ID NOs 642-650.

The invention provides an antisense gapmer oligonucleotide capable of inhibiting the expression of human SNC9A in a cell, wherein the oligonucleotide comprises a contiguous nucleotide sequence comprising at least 14 contiguous nucleotides of a sequence selected from the group consisting of SEQ ID NOs 512-641.

The invention provides an antisense oligonucleotide capable of inhibiting the expression of human SNC9A in a cell, wherein the oligonucleotide comprises a contiguous nucleotide sequence comprising at least 10 or at least 12 contiguous nucleotides of a sequence selected from the group consisting of SEQ ID NOs 642-650.

The invention provides a conjugate comprising the antisense oligonucleotide according to the invention and at least one conjugate moiety covalently attached to said oligonucleotide.

The invention provides for an oligonucleotide of 10 to 30 nucleotides in length, which comprises a contiguous nucleotide sequence of 10 to 30 nucleotides in length with at least 90% complementarity, such as 100% complementarity, to SEQ ID NO: 1, which is capable of inhibiting the expression of capable of inhibiting the expression of both Nav1.7 or Nav1.8 in a cell.

The invention provides for an antisense oligonucleotide of 10 to 30 nucleotides in length, which comprises a contiguous nucleotide sequence of 10 to 30 nucleotides in length with at least 90% complementarity, such as 100% complementarity, to SEQ ID NO: 1, which is capable of inhibiting the expression of capable of inhibiting the expression of both Nav1.7 or Nav1.8 in a cell.

In some embodiments of the invention the oligonucleotide comprises a contiguous nucleotide sequence which comprises at least 10, or at least 12 contiguous nucleosides present in a sequence selected from the group consisting of SEQ ID NOs 512, 513, 514, 515, 516, 517, 518, 519, 520, 521, 522, 523, 524, 525, 557, 558, 559, 560, 577, 579, 583, 638, and 587.

In some embodiments of the invention the oligonucleotide comprises a contiguous nucleotide sequence which comprises at least 14 contiguous nucleosides present in a sequence selected from the group consisting of SEQ ID NOs 512, 513, 514, 515, 516, 517, 518, 519, 520, 521, 522, 523, 524, 525, 557, 558, 559, 560, 577, 579, 583, 638, and 587.

The invention provides a pharmaceutically acceptable salt of the antisense oligonucleotide according to the invention, or the conjugate according to the invention.

The invention provides a pharmaceutical composition comprising the antisense oligonucleotide of the invention or the conjugate of the invention and a pharmaceutically acceptable diluent, solvent, carrier, salt and/or adjuvant.

The invention provides an in vivo or in vitro method for inhibiting SCN9A expression in a target cell which is expressing SCN9A, said method comprising administering an oligonucleotide of the invention or the conjugate of the invention or the pharmaceutical salt or composition of the invention in an effective amount to said cell.

The invention provides an in vivo or in vitro method for inhibiting SCN9A and SCN10A expression in a target cell which is expressing SCN9A and SCN10A, said method comprising administering an oligonucleotide of the invention or the conjugate of the invention or the pharmaceutical salt or composition of the invention in an effective amount to said cell.

The invention provides a method for treating or preventing pain in a subject such as a human, who is suffering from or is likely to suffer pain, comprising administering a therapeutically or prophylactically effective amount of an antisense oligonucleotide of the invention or the conjugate of the invention or the pharmaceutical salt or composition of the invention, such as to prevent or alleviate the pain.

The invention provides for the antisense oligonucleotide of the invention or the conjugate of the invention or the pharmaceutical salt or composition of the invention for use in medicine.

The invention provides for the antisense oligonucleotide of the invention or the conjugate of the invention or the pharmaceutical salt or composition of the invention for use in the treatment or prevention or alleviation of pain The invention provides for the use of the antisense oligonucleotide of the invention or the conjugate of the invention or the pharmaceutical salt or composition of the invention, for the preparation of a medicament for the treatment, prevention or alleviation of pain.

In some embodiments the pain is chronic pain, neuropathic pain, inflammatory pain, spontaneous pain, or nociceptive pain.

In some embodiments the pain is caused by or associated with a disorder selected from the group consisting of diabetic neuropathies, cancer, cranial neuralgia, postherpetic neuralgia and post-surgical neuralgia; or In some embodiments the pain is caused by or associated with inherited erythromelalgia (EIM) or paroxysmal extreme pain disorder (PEPD) or trigeminal neuralgia; or In some embodiments the pain is neurophathic pain, chronic pain, but also general treatment of nociceptive pain (e.g. decompression of a nerve), or neuropathic pain (e.g. diabetic neuropathy), visceral pain, or mixed pain.

Definitions

Oligonucleotide

The term "oligonucleotide" as used herein is defined as it is generally understood by the skilled person as a molecule comprising two or more covalently linked nucleosides. Such covalently bound nucleosides may also be referred to as nucleic acid molecules or oligomers.

Oligonucleotides are commonly made in the laboratory by solid-phase chemical synthesis followed by purification and isolation. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides, such as 2' sugar modified nucleosides.

The oligonucleotide of the invention may be an antisense oligonucleotide, or may form part of a siRNA, such as the antisense strand of a siRNA targeting the target nucleic acid.

Advantageously, the oligonucleotide is an antisense oligonucleotide. Advantageous designs of antisense oligonucleotides for use in the antisense oligonucleotide of the invention, or contiguous nucleotide sequence thereof, include gapmers.

RNAi Agents

The terms 'iRNA," "RNAi agent," 'iRNA agent," and "RNA interference agent" as used interchangeably herein, refer to an agent that contains RNA nucleosides herein and which mediates the targeted cleavage of an RNA transcript via an RNA-induced silencing complex (RISC) pathway. iRNA directs the sequence-specific degradation of mRNA through a process as RNA interference (RNAi). The iRNA modulates. e g., inhibits, the expression of the target nucleic acid in a cell. e.g. a cell within a subject. such as a mammalian subject. RNAi agents includes single stranded RNAi agents and double stranded siRNAs, as well as short hairpin RNAs (shRNAs). The oligonucleotide of the invention or contiguous nucleotide sequence thereof may be in the form of a RNAi agent, or form part of a RNAi agent, such as an siRNA or shRNA. In some embodiments of the invention, the oligonucleotide of the invention or contiguous nucleotide sequence thereof is a RNAi agent, such as a siRNA.

siRNAs

The term siRNA refers to a small interfering ribonucleic acid RNAi agents, is a class of double-stranded RNA molecules, also known in the art as short interfering RNA or silencing RNA. siRNAs typically comprise a sense strand (also referred to as a passenger strand) and an antisense strand (also referred to as the guide strand), wherein each strand are of 17-30 nucleotides in length, typically 19-25 nucleosides in length, wherein the antisense strand is complementary, such as fully complementary, to the target nucleic acid (suitably a mature mRNA sequence), and the sense strand is complementary to the antisense strand so that the sense strand and antisense strand form a duplex or duplex region. siRNA strands may form a blunt ended duplex, or advantageously the sense and antisense strand 3' ends may form a 3' overhang of e.g. 1, 2 or 3 nucleosides. In some embodiments, both the sense strand and antisense strand have a 2nt 3' overhang. The duplex region may therefore be, for example 17-25 nucleotides in length, such as 21-23 nucleotide in length.

Once inside a cell the antisense strand is incorporated into the RISC complex which mediate target degradation or target inhibition of the target nucleic acid. siRNAs typically comprise modified nucleosides in addition to RNA nucleosides, or in some embodiments all of the nucleotides of an siRNA strand may be modified (the sense. 2' sugar modified nucleosides such as LNA (see WO2004083430, WO2007085485 for example), 2'fluoro, 2'-O-methyl or 2'-O-methoxyethyl may be incorporated into siRNAs. In some embodiments the passenger stand of the siRNA may be discontinuous (see WO2007107162 for example). The incorporation of thermally destabilizing nucleotides occurring at a seed region of the antisense strand of siRNAs have been reported as useful in reducing off-target activity of siRNAs (see WO18098328 for example).

In some embodiments, the dsRNA agent, such as the siRNA of the invention, comprises at least one modified nucleotide. In some embodiments, substantially all of the nucleotides of the sense strand comprise a modification; substantially all of the nucleotides of the antisense strand comprise a modification or substantially all of the nucleotides of the sense strand and substantially all of the nucleotides of the antisense strand comprise a modification. In yet other embodiments, all of the nucleotides of the sense strand comprise a modification; all of the nucleotides of the antisense strand comprise a modification; or all of the nucleotides of the sense strand and all of the nucleotides of the antisense strand comprise a modification.

In some embodiments, the modified nucleotides may be independently selected from the group consisting of a deoxy-nucleotide, a 3-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxly-modified nucleotide, a 2'-methoxyethyl modified nucleotide, a 2'-O-alkyl-modified nucleotide, a morpholino nucleotide, a phosphoramidate, a non-natural base comprising nucleotide, an unlinked nucleitide, a tetrahydropyran modified nucleotide, a 1,5-anhydrohexitol modif'ied nucleotide, a cyclohexenyl modified nucleotide, a nucleotide comprising a phosphorothioate group, a nucleotide comprising a methylphosphonate group, a nucleotide comprising a 5*-phosphate, a nucleotide comprising a 5'-phosphate mimic, a glycol modified nucleotide, and a 2-O—(N-methylacetamide) modified nucleotide, and combinations thereof. Suitable the siRNA comprises a 5' phosphate group or a 5'-phosphate mimic at the 5' end of the antisense strand. In some embodiments the 5' end of the antisense strand is a RNA nucleoside.

In one embodiment, the dsRNA agent further comprises at least one phosphorothioate or methylphosphonate internucleotide linkage.

The phosphorothioaie or methylphosphonate internucleoiide linkage may be at the 3'-terminus one or both strand (e.g., the antisense strand; or the sense strand); or the phosphorothioaie or methylphosphonaie internucleoside linkage may be at the 5'-terminus of one or both strands (e.g., the antisense strand; or the sense strand); or the phosphorothioate or methylphosphonate internucleoside linkage may be at the both the 5'- and 3-terminus of one or both strands (e.g., the antisense strand; or the sense strand). In some embodiments the remaining internucleoside linkages are phosphodiester linkages.

The dsRNA agent may further comprise a ligand. In some embodiments, the ligand is conjugated to the 3' end of the sense strand.

For biological distribution, siRNAs may be conjugated to a targeting ligand, and/or be formulated into lipid nanoparticles, for example.

Other aspects of the invention relate to pharmaceutical compositions comprising these dsRNA, such as siRNA molecules suitable for therapeutic use, and methods of inhibiting the expression of the target gene by administering the dsRNA molecules such as siRNAs of the invention, e.g., for the treatment of various disease conditions as disclosed herein.

Antisense Oligonucleotides

The term "Antisense oligonucleotide" as used herein is defined as oligonucleotides capable of modulating expression of a target gene by hybridizing to a target nucleic acid, in particular to a contiguous sequence on a target nucleic acid. The antisense oligonucleotides are not essentially double stranded and are therefore not siRNAs or shRNAs. Preferably, the antisense oligonucleotides of the present invention are single stranded. It is understood that single stranded oligonucleotides of the present invention can form hairpins or intermolecular duplex structures (duplex between two molecules of the same oligonucleotide), as long as the degree of intra or inter self-complementarity is less than 50% across of the full length of the oligonucleotide.

Advantageously, the single stranded antisense oligonucleotide of the invention does not contain RNA nucleosides (2'-OH unmodified ribose).

Advantageously, the antisense oligonucleotide of the invention comprises one or more modified nucleosides or nucleotides, such as 2' sugar modified nucleosides. Furthermore, it is advantageous that the nucleosides which are not modified are DNA nucleosides. LNA antisense oligonucleotides are highly advantageous in the context of the antisense oligonucleotide of the invention.

Contiguous Nucleotide Sequence

The term "contiguous nucleotide sequence" refers to the region of the oligonucleotide which is complementary to the target nucleic acid. The term is used interchangeably herein with the term "contiguous nucleobase sequence" and the term "oligonucleotide motif sequence". In some embodiments all the nucleotides of the oligonucleotide constitute the contiguous nucleotide sequence. In some embodiments the oligonucleotide comprises the contiguous nucleotide sequence, such as a gapmer region (as illustrated herein by the formula F-G-F'), and may optionally comprise further nucleotide(s), for example a nucleotide linker region which may be used to attach a functional group to the contiguous nucleotide sequence. The nucleotide linker region may or may not be complementary to the target nucleic acid.

Nucleotides

Nucleotides are the building blocks of oligonucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

Modified Nucleoside

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. In a preferred embodiment the modified nucleoside comprise a modified sugar moiety. The term modified nucleoside may also be used herein interchangeably with the term "nucleoside analogue" or modified "units" or modified "monomers". Nucleosides with an unmodified DNA or RNA sugar moiety are termed DNA or RNA nucleosides herein. Nucleosides with modifications in the base region of the DNA or RNA nucleoside are still generally termed DNA or RNA if they allow Watson Crick base pairing.

Modified Internucleoside Linkage

The term "modified internucleoside linkage" is defined as generally understood by the skilled person as linkages other than phosphodiester (PO) linkages, that covalently couples two nucleosides together. The oligonucleotides of the invention may therefore comprise modified internucleoside linkages. In some embodiments, the modified internucleoside linkage increases the nuclease resistance of the oligonucleotide compared to a phosphodiester linkage. For naturally occurring oligonucleotides, the internucleoside linkage includes phosphate groups creating a phosphodiester bond between adjacent nucleosides. Modified internucleoside linkages are particularly useful in stabilizing oligonucleotides for in vivo use, and may serve to protect against nuclease cleavage at regions of DNA or RNA nucleosides in the oligonucleotide of the invention, for example within the gap region G of a gapmer oligonucleotide, as well as in regions of modified nucleosides, such as region F and F'.

In an embodiment, the oligonucleotide comprises one or more internucleoside linkages modified from the natural phosphodiester In some embodiments at least 50% of the internucleoside linkages in the oligonucleotide, or contiguous nucleotide sequence thereof, are modified, such as at least 60%, such as at least 70%, such as at least 75%, such as at least 80% or such as at least 90% of the internucleoside linkages in the oligonucleotide, or contiguous nucleotide sequence thereof, are modified. In some embodiments all of the internucleoside linkages of the oligonucleotide, or contiguous nucleotide sequence thereof, are modified. It will be recognized that, in some embodiments the nucleosides which link the oligonucleotide of the invention to a non-nucleotide functional group, such as a conjugate, may be phosphodiester. In some embodiments all of the internucleoside linkages of the oligonucleotide, or contiguous nucleotide sequence thereof, are nuclease resistant internucleoside linkages.

With the oligonucleotides of the invention it is advantageous to use phosphorothioate internucleoside linkages.

Phosphorothioate internucleoside linkages are particularly useful due to nuclease resistance, beneficial pharmacokinetics and ease of manufacture. In some embodiments at least 50% of the internucleoside linkages in the oligonucleotide, or contiguous nucleotide sequence thereof, are phosphorothioate, such as at least 60%, such as at least 70%, such as at least 75%, such as at least 80% or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate.

Advantageously, all the internucleoside linkages of the contiguous nucleotide sequence of the oligonucleotide are phosphorothioate, or all the internucleoside linkages of the oligonucleotide are phosphorothioate linkages.

It is recognized that, as disclosed in EP 2 742 135, antisense oligonucleotides may comprise other internucleoside linkages (other than phosphodiester and phosphorothioate), for example alkyl phosphonate/methyl phosphonate internucleoside, which according to EP 2 742 135 may for example be tolerated in an otherwise DNA phosphorothioate the gap region.

Nucleobase

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

In a some embodiments the nucleobase moiety is modified by changing the purine or pyrimidine into a modified purine or pyrimidine, such as substituted purine or substituted pyrimidine, such as a nucleobased selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

Modified Oligonucleotide

The term modified oligonucleotide describes an oligonucleotide comprising one or more sugar-modified nucleosides and/or modified internucleoside linkages. The term chimeric" oligonucleotide is a term that has been used in the literature to describe oligonucleotides with modified nucleosides.

Complementarity

The term "complementarity" describes the capacity for Watson-Crick base-pairing of nucleosides/nucleotides. Watson-Crick base pairs are guanine (G)-cytosine (C) and adenine (A)-thymine (T)/uracil (U). It will be understood that oligonucleotides may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research vol 45 page 2055 and Bergstrom (2009) Current Protocols in Nucleic Acid Chemistry Suppl. 37 1.4.1).

The term "% complementary" as used herein, refers to the proportion of nucleotides (in percent) of a contiguous nucleotide sequence in a nucleic acid molecule (e.g. oligonucleotide) which across the contiguous nucleotide sequence, are complementary to a reference sequence (e.g. a target sequence or sequence motif). The percentage of complementarity is thus calculated by counting the number of aligned nucleobases that are complementary (from Watson Crick base pair) between the two sequences (when aligned with the target sequence 5'-3' and the oligonucleotide sequence from 3'-5'), dividing that number by the total number of nucleotides in the oligonucleotide and multiplying by 100. In such a comparison a nucleobase/nucleotide which does not align (form a base pair) is termed a mismatch. Insertions and deletions are not allowed in the calculation of % complementarity of a contiguous nucleotide sequence. It will be understood that in determining complementarity, chemical modifications of the nucleobases are disregarded as long as the functional capacity of the nucleobase to form Watson Crick base pairing is retained (e.g. 5'-methyl cytosine is considered identical to a cytosine for the purpose of calculating % identity).

The term "fully complementary", refers to 100% complementarity.

Identity

The term "Identity" as used herein, refers to the proportion of nucleotides (expressed in percent) of a contiguous nucleotide sequence in a nucleic acid molecule (e.g. oligonucleotide) which across the contiguous nucleotide sequence, are identical to a reference sequence (e.g. a sequence motif). The percentage of identity is thus calculated by counting the number of aligned nucleobases that are identical (a Match) between two sequences (in the contiguous nucleotide sequence of the compound of the invention and in the reference sequence), dividing that number by the total number of nucleotides in the oligonucleotide and multiplying by 100. Therefore, Percentage of Identity= (Matches×100)/Length of aligned region (e.g. the contiguous nucleotide sequence). Insertions and deletions are not allowed in the calculation the percentage of identity of a contiguous nucleotide sequence. It will be understood that in determining identity, chemical modifications of the nucleobases are disregarded as long as the functional capacity of the nucleobase to form Watson Crick base pairing is retained (e.g. 5-methyl cytosine is considered identical to a cytosine for the purpose of calculating % identity).

Hybridization

The term "hybridizing" or "hybridizes" as used herein is to be understood as two nucleic acid strands (e.g. an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature ($T_m$) defined as the temperature at which half of the oligonucleotides are duplexed with the target nucleic acid. At physiological conditions $T_m$ is not strictly proportional to the affinity (Mergny and Lacroix, 2003, *Oligonucleotides* 13:515-537). The standard state Gibbs free energy $\Delta G°$ is a more accurate representation of binding affinity and is related to the dissociation constant ($K_d$) of the reaction by $\Delta G°=-RTln(K_d)$, where R is the gas constant and T is the absolute temperature. Therefore, a very low $\Delta G°$ of the reaction between an oligonucleotide and the target nucleic acid reflects a strong hybridization between the oligonucleotide and target nucleic acid. $\Delta G°$ is the energy associated with a reaction where aqueous concentrations are 1M, the pH is 7, and the temperature is 37° C. The hybridization of oligonucleotides to a target nucleic acid is a spontaneous reaction and for spontaneous reactions $\Delta G°$ is less than zero. $\Delta G°$ can be measured experimentally, for example, by use of the isothermal titration calorimetry (ITC) method as described in Hansen et al., 1965, *Chem. Comm.* 36-38 and Holdgate et al., 2005, Drug Discov Today. The skilled person will know that commercial equipment is available for $\Delta G°$ measurements. $\Delta G°$ can also be estimated numerically by using the nearest neighbor model as described by SantaLucia, 1998, *Proc Natl Acad Sci USA.* 95: 1460-1465 using appropriately derived thermodynamic parameters described by Sugimoto et al., 1995, *Biochemistry* 34:11211-11216 and McTigue et al., 2004, *Biochemistry* 43:5388-5405. In order to have the possibility of modulating its intended nucleic acid target by hybridization, oligonucleotides of the present invention hybridize to a target nucleic acid with estimated $\Delta G°$ values below -10 kcal for oligonucleotides that are 10-30 nucleotides in length. In some embodiments the degree or strength of hybridization is measured by the standard state Gibbs free energy $\Delta G°$. The oligonucleotides may hybridize to a target nucleic acid with estimated $\Delta G°$ values below the range of -10 kcal, such as below -15 kcal, such as below -20 kcal and such as below -25 kcal for oligonucleotides that are 8-30 nucleotides in length. In some embodiments the oligonucleotides hybridize to a target nucleic acid with an estimated $\Delta G°$ value of -10 to -60 kcal, such as -12 to -40, such as from -15 to -30 kcal or -16 to -27 kcal such as -18 to -25 kcal.

Target Nucleic Acid

According to the present invention, the target nucleic acid is a nucleic acid which encodes mammalian or human voltage-gated sodium ion channel and may for example be a gene, a RNA, a mRNA, and pre-mRNA, a mature mRNA or a cDNA sequence.

The target may therefore be referred to as a target nucleic acid. The oligonucleotide of the invention may for example target exon regions of a mammalian such as a human SCN9A target nucleic acid, or may for example target intron region of a mammalian such as a human SCN9A pre-mRNA (see Table 1).

TABLE 1

Human SCN9A Exons and Introns — Based upon SCN9A transcript SCN9A-201:

| Exon Number | Position on SEQ ID NO 1 | | Intron Number | Position on SEQ ID NO 1 | |
|---|---|---|---|---|---|
| | Exon start | Exon end | | Intron Start | Intron End |
| E1 | 101 | 298 | I1 | 298 | 64196 |
| E2 | 64196 | 64503 | I2 | 64503 | 68928 |
| E3 | 68928 | 69046 | I3 | 69046 | 69403 |
| E4 | 69403 | 69492 | I4 | 69492 | 70082 |
| E5 | 70082 | 70210 | I5 | 70210 | 71673 |
| E6 | 71673 | 71764 | I6 | 71764 | 72700 |
| E7 | 72700 | 72912 | I7 | 72912 | 81340 |
| E8 | 81340 | 81403 | I8 | 81403 | 82630 |
| E9 | 82630 | 82771 | I9 | 82771 | 87359 |
| E10 | 87359 | 87565 | I10 | 87565 | 89379 |
| E11 | 89379 | 89666 | I11 | 89666 | 91178 |
| E12 | 91178 | 91549 | I12 | 91549 | 94194 |
| E13 | 94194 | 94323 | I13 | 94323 | 95407 |
| E14 | 95407 | 95645 | I14 | 95645 | 97689 |
| E15 | 97689 | 97862 | I15 | 97862 | 98663 |
| E16 | 98663 | 99019 | I16 | 99019 | 103127 |
| E17 | 103127 | 103603 | I17 | 103603 | 124117 |
| E18 | 124117 | 124237 | I18 | 124237 | 133346 |
| E19 | 133346 | 133500 | I19 | 133500 | 137735 |
| E20 | 137735 | 137908 | I20 | 137908 | 142540 |
| E21 | 142540 | 142662 | I21 | 142662 | 147030 |
| E22 | 147030 | 147311 | I22 | 147311 | 148279 |
| E23 | 148279 | 148332 | I23 | 148332 | 149298 |
| E24 | 149298 | 149435 | I24 | 149435 | 171538 |
| E25 | 171538 | 171642 | I25 | 171642 | 171777 |
| E26 | 171777 | 172047 | I26 | 172047 | 176138 |
| E27 | 176138 | 180813 | | | |

According to ENSEMBL, there are at least 13 human SCN9A transcript variants—the target nucleic acid may therefore be a SCN9A transcript (mRNA) selected from the group consisting of SEQ ID NOs 4-16:

| Tname | Strand | Tstart (chr2) | Tend (chr2) | rel_start (SEQ ID NO1) | rel_end (SEQ ID NO1) | SEQ ID NO |
|---|---|---|---|---|---|---|
| SCN9A-203 | -1 | 166195185 | 166375993 | 9 | 180817 | 4 |
| SCN9A-201 | -1 | 166195189 | 166375901 | 101 | 180813 | 5 |
| SCN9A-212 | -1 | 166197462 | 166375901 | 101 | 178540 | 6 |
| SCN9A-213 | -1 | 166198299 | 166205239 | 170763 | 177703 | 7 |
| SCN9A-209 | -1 | 166198411 | 166311756 | 64246 | 177591 | 8 |
| SCN9A-207 | -1 | 166198611 | 166375914 | 88 | 177391 | 9 |
| SCN9A-202 | -1 | 166198672 | 166311756 | 64246 | 177330 | 10 |
| SCN9A-208 | -1 | 166242624 | 166272749 | 103253 | 133378 | 11 |
| SCN9A-210 | -1 | 166276417 | 166278313 | 97689 | 99585 | 12 |
| SCN9A-205 | -1 | 166277716 | 166375969 | 33 | 98286 | 13 |
| SCN9A-204 | -1 | 166288615 | 166375944 | 58 | 87387 | 14 |
| SCN9A-211 | -1 | 166301174 | 166304089 | 71913 | 74828 | 15 |
| SCN9A-206 | -1 | 166302063 | 166376001 | 1 | 73939 | 16 |

Suitably, the target nucleic acid may encode an $Na_v1.7$ protein, in particular mammalian $Na_v1.7$, such as human $Na_v1.7$ (See for example tables 2 and 3) which provides the mRNA and pre-mRNA sequences for human, monkey, and pig $Na_v1.7$ encoding transcripts.

In some embodiments, the target nucleic acid is selected from the group consisting of SEQ ID NO: 1, 2, and 3 or naturally occurring variants thereof (e.g. sequences encoding a mammalian $Na_v1.7$ protein). In some embodiments the target nucleic acid is a transcript variant of SCN9A, such as a transcript variant selected from the group consisting of SEQ ID NOs 4-16.

If employing the oligonucleotide of the invention in research or diagnostics the target nucleic acid may be a cDNA or a synthetic nucleic acid derived from DNA or RNA.

For in vivo or in vitro application, the oligonucleotide of the invention is typically capable of inhibiting the expression of the target nucleic acid, for example the SCN9A target nucleic acid, in a cell which is expressing the SCN9A target nucleic acid target nucleic acid. The contiguous sequence of nucleobases of the oligonucleotide of the invention is complementary, such as fully complementary to the SCN9A target nucleic acid, as measured across the length of the oligonucleotide optionally excluding nucleotide based linker regions which may link the oligonucleotide to an optional functional group such as a conjugate, or other non-complementary terminal nucleotides (e.g. region D' or D"). The target nucleic acid may, in some embodiments, be a RNA or DNA, such as a messenger RNA, such as a mature mRNA or a pre-mRNA.

In some embodiments the target nucleic acid is a RNA or DNA which encodes mammalian Nav1.7 protein, such as human SCN9A target, e.g. the human SCN9A pre-mRNA sequence, such as that disclosed as SEQ ID NO 1, or human SCN9A mature mRNA, such as that disclosed as SEQ ID NO 2. Further information on exemplary target nucleic acids is provided in tables 2 and 3.

target nucleic acid with a nucleobase sequence that is complementary to the contiguous nucleotide sequence of the oligonucleotide of the invention. This region of the target nucleic acid may interchangeably be referred to as the target nucleotide sequence, target sequence or target region. In some embodiments the target sequence is longer than the complementary sequence of a single oligonucleotide, and may, for example represent a preferred region of the target nucleic acid which may be targeted by several oligonucleotides of the invention.

The oligonucleotide of the invention comprises a contiguous nucleotide sequence which is complementary to or hybridizes to the target nucleic acid, such as a target sequence described herein. Advantageously, the contiguous nucleotide sequence of the oligonucleotide of the invention is 100% complementary to the target nucleic acid across at least 10 contiguous bases, more advantageously across at least 12 contiguous bases, more advantageously, the contiguous nucleotide sequence of the oligonucleotide of the invention is 100% complementary to the target nucleic acid across the length of the contiguous nucleotide sequence.

According to the invention, the contiguous nucleotide sequence is between 10 to 30 nucleotides, such as 12 to 30, such as 14 to 20, such as 15 to 18 contiguous nucleotides.

The invention also provides target sequences (sub-sequences) present in SEQ ID NO 1 which may be targeted by

TABLE 2

Genome and assembly information for SCN9A across species.

| Species | Chr. | Strand | Genomic coordinates | | | NCBI reference sequence* accession number for mRNA |
| --- | --- | --- | --- | --- | --- | --- |
| | | | Start | End | Assembly | |
| Human | 2 | Rev | 166195185 | 166376001 | GRCh38.p12 | ENSG00000169432 |
| Cynomolgus monkey | 12 | Rev | 55071072 | 55190227 | Macaca_fascicularis_5.0 | ENSMFAG00000034634 |
| Pig | 15 | Rev | 72745114 | 72912407 | Sscrofa11.1 | ENSSSCG00000015913 |
| Rat | 3 | Rev | 52583951 | 52664209 | Rnor_6.0 | ENSRNOG00000006639 |
| Mouse | 2 | Rev | 66480080 | 66634962 | GRCm38.p6 | ENSMUSG00000075316 |

Fwd = forward strand. The genome coordinates provide the pre-mRNA sequence (genomic sequence). The NCBI reference provides the mRNA sequence (cDNA sequence).
*The National Center for Biotechnology Information reference sequence database is a comprehensive, integrated, non-redundant, well-annotated set of reference sequences including genomic, transcript, and protein. It is hosted at www.ncbi.nlm.nih.gov/refseq.

TABLE 3

Exemplary SCN9A target nucleic acid sequences.

| Species | RNA type | SEQ ID NO |
| --- | --- | --- |
| Human | premRNA | 1 |
| Cynomologous monkey | premRNA | 2 |
| Pig | premRNA | 3 |

In some embodiments the target nucleic acid is the human SCN10A premRNA transcript, for example a SCN10A target nucleic acid selected from the group consisting of NCBI Genbank references: NM_006514.3 GI: 693073569, NM_001293307.2 GI: 693072645 &NM_001293306.2 GI: 693064349—hereby incorporated by reference.

Target Sequence

The term "target sequence" as used herein refers to a sequence of nucleotides present in the target nucleic acid which comprises the nucleobase sequence which is complementary to the oligonucleotide of the invention. In some embodiments, the target sequence consists of a region on the the oligonucleotides of the invention. The oligonucleotide of the oligonucleotide of the invention may therefore comprise of a contiguous nucleotide sequence which is at least 90% complementary, advantageously fully complementary to a target sequence (as measured across the length of the contiguous nucleotide sequence).

In some advantageous embodiments of the invention the oligonucleotide of the invention targets both Nav1.7 and Nav1.8 target sequences. A reference human Nav1.8 pre-mRNA sequence is provided herein as SEQ ID NO 651 (see also above SCN10A premRNA transcript information). Compounds which target both Nav1.7 and Nav1.8 are suitably capable of inhibiting the expression of both SCN9A and SCN10A in a cell which is expressing both SCN9A and SCN10A.

Target Sequence List 1

In some embodiments the target sequence is a region of SEQ ID NO 1 selected from the group consisting of 617-630; 852-868; 963-976; 1039-1053; 1070-1085; 1375-1388; 1512-1526; 1689-1702; 2673-2691; 3189-3202; 3275-3290; 3900-3921; 4132-4145; 4795-4808; 4941-4955; 5165-5182; 5359-5372; 5430-5444; 5453-5529; 5544-5588; 5608-5675;

5695-5717; 5719-5732; 5765-5809; 5896-5909; 6019-6032; 6066-6085; 6151-6164; 6167-6180; 6357-6370; 6629-6657; 6859-6872; 6959-6972; 6998-7019; 7032-7056; 7060-7079; 7085-7098; 7102-7129; 7131-7152; 7156-7185; 7233-7247; 7254-7271; 7273-7295; 7297-7317; 7381-7412; 7456-7499; 7502-7522; 7527-7561; 7575-7592; 8087-8100; 8438-8454; 8475-8490; 8502-8515; 8531-8572; 8592-8610; 8612-8635; 8653-8677; 8700-8715; 8726-8741; 9093-9106; 9333-9346; 9386-9399; 9446-9463; 9468-9481; 9535-9550; 9592-9606; 10627-10643; 10767-10780; 11442-11458; 11489-11502; 11712-11725; 11797-11810; 11822-11843; 11879-11901; 12017-12030; 12302-12315; 13542-13555; 13740-13754; 14186-14199; 14451-14464; 15059-15072; 15354-15367; 15747-15789; 15800-15824; 15851-15864; 15869-15911; 15931-15959; 15987-16005; 16019-16037; 16039-16053; 16066-16079; 16136-16158; 16245-16258; 16304-16317; 16486-16499; 16680-16693; 16753-16766; 16962-16975; 16983-16998; 17032-17045; 17146-17167; 17536-17550; 17574-17587; 17634-17647; 17660-17676; 17696-17711; 17713-17739; 17741-17755; 17758-17783; 17805-17827; 17830-17846; 17851-17875; 17878-17893; 17905-17967; 18802-18816; 18829-18843; 18857-18870; 18991-19005; 19024-19037; 19475-19488; 19943-19967; 19969-19984; 19992-20043; 20045-20072; 20090-20150; 20153-20183; 20196-20213; 20298-20312; 20422-20436; 20481-20494; 20739-20752; 20774-20790; 20808-20826; 20830-20843; 20848-20866; 20883-20905; 20928-20950; 21042-21055; 21084-21097; 21680-21693; 21781-21805; 21952-21965; 22150-22163; 22764-22782; 22797-22810; 22823-22836; 22880-22909; 22914-22927; 22978-22992; 23917-23930; 25991-26006; 26018-26031; 26047-26071; 26091-26113; 26123-26160; 26171-26208; 26270-26309; 26404-26418; 26446-26460; 26621-26634; 26688-26701; 26842-26876; 26961-26978; 27014-27027; 27034-27049; 27126-27154; 27744-27759; 27792-27805; 28740-28754; 29019-29033; 29068-29081; 30376-30389; 30808-30821; 30935-30948; 31683-31696; 32174-32204; 32260-32273; 32313-32326; 32334-32360; 32596-32609; 32722-32735; 33245-33258; 33261-33274; 33376-33389; 33925-33938; 34197-34212; 35003-35016; 35106-35126; 35150-35169; 35388-35402; 35517-35530; 35626-35639; 35894-35908; 36515-36530; 36742-36755; 36832-36845; 37259-37272; 37648-37673; 37819-37832; 38077-38093; 38215-38228; 39849-39862; 40022-40035; 41312-41326; 41753-41766; 42181-42198; 42208-42231; 42583-42596; 42939-42957; 43053-43092; 43465-43478; 44750-44763; 46413-46426; 46577-46590; 46944-46957; 46972-46985; 47548-47566; 47670-47685; 47688-47709; 47728-47745; 48575-48597; 48600-48614; 48616-48630; 48713-48730; 48922-48946; 49929-49942; 50292-50308; 50709-50722; 50875-50888; 51576-51589; 51695-51720; 51734-51753; 51755-51776; 51796-51830; 51842-51856; 52867-52883; 53956-53969; 53975-53988; 54188-54213; 54393-54406; 54463-54487; 54707-54723; 55116-55129; 55840-55855; 55961-55975; 56298-56311; 56785-56798; 57416-57429; 58378-58391; 58394-58410; 58626-58639; 58670-58684; 58837-58851; 59251-59264; 59294-59320; 59328-59351; 59353-59417; 59419-59434; 59471-59490; 59505-59531; 59566-59585; 59722-59744; 59949-59962; 60076-60092; 60094-60110; 60120-60184; 60210-60266; 60281-60303; 60306-60368; 60370-60413; 60415-60444; 60458-60474; 60476-60565; 60572-60614; 60620-60633; 60635-60655; 60678-60692; 60731-60750; 60762-60784; 60786-60802; 60805-60822; 60824-60839; 60847-60863; 60865-60882; 60884-60932; 60934-60980; 61025-61065; 61067-61081; 61122-61144; 61154-61169; 61171-61191; 61193-61209; 61221-61258; 61260-61288; 61298-61315; 61325-61384; 61416-61443; 61445-61460; 61469-61500; 61505-61544; 61562-61612; 61622-61651; 61661-61675; 61677-61691; 61693-61710; 61712-61738; 61741-61773; 61775-61789; 61791-61837; 61839-61873; 61875-61888; 61897-61935; 61937-61950; 61958-61999; 62003-62019; 62021-62041; 62043-62064; 62085-62104; 62135-62160; 62162-62184; 62186-62204; 62220-62233; 62235-62260; 62267-62281; 62289-62305; 62307-62361; 62364-62412; 62416-62431; 62438-62464; 62480-62496; 62540-62562; 62569-62631; 62649-62698; 62730-62752; 62762-62788; 62798-62837; 62855-62868; 62875-62888; 62890-62903; 62910-62923; 62925-62940; 62957-62972; 62980-63008; 63013-63046; 63050-63111; 63135-63151; 63166-63238; 63266-63279; 63290-63344; 63346-63390; 63392-63409; 63411-63425; 63427-63451; 63465-63537; 63575-63592; 63594-63618; 63624-63643; 63676-63700; 63719-63758; 63775-63804; 63820-63861; 63863-63888; 63890-63906; 63908-63934; 63942-63956; 63975-64000; 64002-64015; 64035-64052; 64054-64072; 64078-64095; 64101-64132; 64144-64174; 64176-64286; 64288-64367; 64378-64397; 64399-64476; 64478-64502; 64504-64529; 64542-64597; 64610-64684; 64686-64703; 64718-64751; 64756-64769; 64920-64944; 65067-65112; 65129-65144; 65146-65169; 65193-65223; 65240-65268; 65349-65395; 65439-65479; 65517-65531; 65533-65580; 65593-65611; 65622-65640; 65682-65705; 65714-65758; 65805-65823; 65842-65875; 65880-65902; 65907-65943; 65945-65983; 65985-66004; 66006-66019; 66074-66091; 66152-66169; 66171-66195; 66246-66264; 66266-66282; 66315-66356; 66366-66379; 66381-66397; 66424-66438; 66440-66466; 66468-66495; 66510-66569; 66571-66589; 66591-66643; 66645-66673; 66681-66715; 66723-66745; 66750-66770; 66784-66806; 66818-66836; 66838-66888; 66898-66929; 66944-66966; 66991-67037; 67055-67083; 67091-67113; 67126-67169; 67186-67203; 67208-67256; 67258-67294; 67310-67333; 67336-67366; 67368-67436; 67444-67457; 67490-67518; 67535-67548; 67558-67575; 67582-67604; 67606-67629; 67631-67644; 67671-67721; 67729-67775; 67777-67799; 67801-67840; 67842-67879; 67941-67954; 67971-67992; 68012-68030; 68039-68058; 68083-68097; 68125-68172; 68199-68292; 68297-68310; 68312-68332; 68334-68354; 68356-68427; 68436-68459; 68461-68478; 68480-68493; 68495-68541; 68544-68566; 68568-68582; 68584-68622; 68625-68642; 68648-68662; 68665-68683; 68692-68723; 68761-68776; 68781-68807; 68809-68834; 68836-68909; 68922-69056; 69058-69076; 69100-69123; 69125-69169; 69171-69200; 69202-69219; 69221-69247; 69249-69311; 69314-69365; 69384-69461; 69463-69498; 69500-69526; 69528-69558; 69580-69596; 69598-69626; 69660-69680; 69695-69730; 69743-69780; 69800-69829; 69843-69879; 69881-69902; 69916-69935; 69937-69956; 69994-70011; 70022-70234; 70243-70257; 70259-70277; 70341-70401; 70403-70422; 70437-70474; 70478-70528; 70530-70576; 70593-70607; 70609-70626; 70628-70690; 70708-70740; 70742-70768; 70770-70785; 70802-70817; 70830-70864; 70877-70902; 70955-70996; 70998-71036; 71053-71074; 71093-71149; 71192-71212; 71214-71244; 71246-71262; 71264-71318; 71334-71377; 71389-71406; 71442-71500; 71502-71530; 71546-71577; 71584-71634; 71655-71847; 71849-72043; 72047-72099; 72101-72131; 72140-72190; 72194-72207; 72218-72232; 72234-72259; 72261-72349; 72351-72370; 72372-72386; 72388-72415; 72430-72460; 72462-72476; 72518-72542; 72550-72584; 72586-72619; 72621-72639; 72652-72674; 72682-72715; 72717-72751; 72753-72836; 72854-72925; 72938-72954; 72956-72975; 72981-73018; 73068-73121; 73143-73166; 73169-73229; 73233-73260; 73262-73280; 73316-73334; 73345-73358; 73379-73403; 73413-73462; 73468-73492;

73500-73543; 73567-73600; 73602-73630; 73632-73646; 73648-73718; 73725-73743; 73749-73797; 73820-73846; 73860-73885; 73897-73948; 73951-74003; 74025-74038; 74046-74069; 74077-74098; 74105-74157; 74176-74201; 74228-74268; 74280-74298; 74303-74332; 74367-74384; 74395-74415; 74429-74465; 74480-74498; 74524-74538; 74540-74568; 74604-74659; 74668-74711; 74723-74737; 74750-74777; 74793-74819; 74828-74865; 74900-74940; 74970-75002; 75006-75020; 75022-75040; 75042-75058; 75115-75130; 75166-75204; 75206-75234; 75243-75256; 75259-75287; 75319-75345; 75358-75378; 75396-75426; 75428-75448; 75460-75482; 75484-75646; 75681-75708; 75710-75726; 75744-75760; 75762-75785; 75801-75822; 75831-75853; 75856-75878; 75880-75923; 75938-75975; 75982-76000; 76003-76017; 76023-76069; 76071-76124; 76126-76142; 76144-76240; 76258-76302; 76321-76337; 76367-76387; 76392-76460; 76462-76512; 76514-76540; 76545-76564; 76566-76588; 76590-76643; 76665-76691; 76693-76740; 76746-76786; 76811-76828; 76830-76851; 76853-76906; 76927-76941; 76949-77035; 77037-77066; 77077-77100; 77120-77147; 77157-77178; 77194-77244; 77246-77259; 77282-77314; 77319-77358; 77360-77381; 77425-77487; 77504-77518; 77531-77576; 77578-77602; 77604-77618; 77627-77661; 77663-77702; 77704-77722; 77724-77766; 77787-77800; 77810-77824; 77826-77839; 77855-77885; 77897-77932; 77962-77996; 78030-78058; 78074-78103; 78105-78129; 78153-78190; 78197-78214; 78216-78238; 78240-78255; 78292-78310; 78312-78325; 78327-78346; 78366-78393; 78401-78415; 78435-78459; 78507-78530; 78532-78565; 78567-78604; 78606-78653; 78672-78708; 78710-78751; 78772-78826; 78852-78865; 78867-78888; 78890-78909; 78911-78953; 78955-78986; 78989-79039; 79041-79056; 79058-79075; 79088-79128; 79130-79149; 79187-79265; 79286-79312; 79314-79334; 79337-79379; 79382-79401; 79414-79430; 79432-79450; 79463-79497; 79499-79530; 79532-79596; 79603-79653; 79668-79684; 79695-79710; 79712-79734; 79736-79818; 79820-79954; 79956-79972; 79986-79999; 80009-80043; 80062-80086; 80099-80165; 80171-80184; 80198-80246; 80248-80277; 80285-80299; 80311-80335; 80359-80374; 80394-80408; 80410-80442; 80444-80461; 80463-80482; 80484-80525; 80527-80553; 80555-80599; 80615-80642; 80644-80659; 80674-80709; 80711-80725; 80737-80791; 80819-80841; 80855-80874; 80889-80905; 80921-80953; 80977-81008; 81010-81049; 81051-81096; 81098-81120; 81140-81154; 81168-81206; 81231-81244; 81254-81267; 81287-81300; 81308-81323; 81325-81343; 81345-81358; 81360-81448; 81450-81463; 81465-81517; 81527-81542; 81544-81601; 81612-81625; 81636-81675; 81678-81697; 81706-81721; 81740-81806; 81819-81832; 81834-81853; 81861-81895; 81909-81945; 81965-81983; 81999-82013; 82015-82029; 82031-82063; 82072-82134; 82139-82155; 82157-82182; 82192-82210; 82212-82227; 82238-82253; 82286-82306; 82308-82325; 82337-82353; 82355-82401; 82403-82452; 82454-82514; 82526-82551; 82553-82566; 82571-82618; 82634-82654; 82656-82761; 82763-82777; 82779-82818; 82820-82833; 82852-82895; 82897-82917; 82951-82969; 82971-82996; 83001-83015; 83017-83042; 83055-83083; 83085-83098; 83100-83176; 83202-83224; 83226-83241; 83250-83263; 83270-83287; 83321-83341; 83343-83358; 83388-83402; 83404-83421; 83468-83499; 83512-83531; 83533-83564; 83596-83631; 83633-83688; 83702-83743; 83745-83775; 83781-83800; 83811-83939; 83941-83968; 83971-84013; 84019-84040; 84042-84145; 84150-84166; 84168-84256; 84258-84286; 84304-84323; 84325-84349; 84351-84390; 84392-84461; 84477-84518; 84532-84580; 84608-84628; 84630-84677; 84693-84721; 84740-84771; 84773-84807; 84809-84822; 84824-84873; 84887-84920; 84922-84944; 84955-85003; 85005-85018; 85020-85043; 85045-85075; 85095-85113; 85147-85239; 85242-85277; 85279-85297; 85304-85334; 85336-85350; 85352-85400; 85442-85495; 85497-85510; 85523-85580; 85586-85622; 85624-85645; 85647-85664; 85672-85692; 85694-85743; 85745-85769; 85771-85815; 85817-85869; 85871-85900; 85922-85950; 85952-85970; 85972-85997; 86022-86038; 86047-86060; 86087-86107; 86109-86175; 86195-86210; 86212-86246; 86248-86269; 86283-86324; 86340-86356; 86358-86394; 86396-86421; 86430-86570; 86572-86588; 86629-86654; 86669-86693; 86695-86708; 86711-86726; 86750-86789; 86797-86825; 86827-86853; 86858-86879; 86885-86902; 86905-86937; 86950-86972; 86984-87015; 87027-87068; 87070-87143; 87145-87185; 87187-87229; 87232-87266; 87292-87318; 87327-87381; 87383-87442; 87444-87462; 87464-87537; 87539-87593; 87595-87611; 87613-87631; 87644-87674; 87676-87691; 87693-87712; 87748-87775; 87777-87799; 87801-87843; 87845-87858; 87877-87908; 87917-87932; 87945-87971; 88019-88059; 88067-88083; 88085-88107; 88124-88137; 88144-88158; 88164-88212; 88214-88232; 88268-88290; 88297-88334; 88336-88356; 88370-88391; 88393-88415; 88417-88437; 88448-88485; 88492-88513; 88515-88560; 88574-88606; 88620-88658; 88682-88696; 88698-88744; 88746-88775; 88777-88834; 88852-88878; 88880-88894; 88906-88935; 88942-89030; 89032-89051; 89075-89096; 89098-89148; 89168-89200; 89205-89231; 89233-89281; 89283-89296; 89298-89383; 89397-89539; 89541-89561; 89588-89617; 89619-89638; 89640-89661; 89663-89678; 89711-89742; 89748-89765; 89767-89794; 89813-89834; 89848-89862; 89864-89885; 89893-89914; 89923-89953; 89955-89982; 90070-90095; 90097-90147; 90153-90166; 90171-90207; 90209-90225; 90236-90255; 90262-90275; 90289-90323; 90330-90349; 90390-90406; 90408-90426; 90437-90509; 90511-90536; 90542-90598; 90607-90653; 90673-90689; 90691-90706; 90732-90748; 90750-90775; 90780-90794; 90811-90834; 90847-90868; 90877-90909; 90911-90926; 90928-90948; 90950-90984; 91026-91042; 91055-91123; 91135-91151; 91164-91252; 91254-91407; 91409-91604; 91626-91673; 91675-91694; 91698-91803; 91805-91823; 91831-91849; 91865-91996; 92026-92043; 92061-92093; 92150-92167; 92187-92215; 92225-92243; 92265-92287; 92289-92308; 92318-92353; 92355-92379; 92382-92406; 92417-92522; 92528-92546; 92548-92600; 92622-92700; 92703-92731; 92747-92780; 92790-92803; 92805-92818; 92832-92851; 92861-92901; 92910-92947; 92960-92986; 92997-93048; 93056-93077; 93093-93117; 93124-93143; 93154-93220; 93226-93246; 93262-93276; 93285-93313; 93315-93329; 93332-93378; 93402-93448; 93455-93480; 93496-93525; 93549-93579; 93593-93632; 93634-93650; 93663-93685; 93687-93704; 93718-93732; 93743-93770; 93772-93793; 93797-93814; 93816-93834; 93845-93863; 93879-93899; 93903-93927; 93938-93979; 93981-94028; 94038-94059; 94061-94087; 94089-94109; 94111-94172; 94185-94198; 94200-94267; 94269-94343; 94351-94395; 94437-94469; 94483-94507; 94529-94562; 94578-94616; 94631-94666; 94686-94713; 94716-94768; 94770-94796; 94798-94852; 94892-94921; 94923-94983; 94986-95015; 95029-95086; 95088-95185; 95187-95206; 95208-95228; 95230-95250; 95279-95306; 95314-95329; 95336-95363; 95367-95392; 95394-95596; 95598-95666; 95670-95685; 95687-95700; 95702-95731; 95767-95781; 95794-95810; 95843-95902; 95904-95949; 95953-95977; 95993-96014; 96016-96041; 96043-96073; 96080-96115; 96117-96138; 96155-96170; 96172-96186; 96189-96205; 96213-96230; 96267-96313; 96320-96335; 96338-96403;

96442-96462; 96469-96500; 96502-96517; 96531-96558; 96560-96580; 96591-96606; 96608-96623; 96625-96646; 96648-96688; 96690-96715; 96718-96774; 96784-96855; 96863-96888; 96895-96972; 96974-97006; 97011-97046; 97048-97177; 97179-97193; 97195-97219; 97221-97288; 97298-97320; 97322-97382; 97384-97444; 97452-97501; 97553-97643; 97648-97675; 97677-97835; 97837-97905; 97913-97929; 97944-97981; 97983-98025; 98035-98056; 98058-98086; 98094-98137; 98152-98203; 98205-98225; 98229-98268; 98270-98288; 98290-98314; 98352-98401; 98416-98442; 98444-98457; 98511-98533; 98543-98575; 98594-98619; 98639-98730; 98732-98751; 98753-98856; 98858-98958; 98960-99003; 99005-99037; 99041-99108; 99136-99155; 99157-99179; 99213-99261; 99292-99320; 99330-99415; 99417-99464; 99477-99490; 99492-99518; 99520-99580; 99582-99601; 99625-99643; 99649-99664; 99675-99691; 99711-99753; 99755-99776; 99797-99818; 99838-99860; 99868-99903; 99905-99946; 99961-100010; 100012-100063; 100065-100092; 100109-100128; 100143-100196; 100204-100227; 100233-100246; 100248-100271; 100302-100335; 100337-100361; 100370-100430; 100433-100462; 100484-100501; 100511-100550; 100552-100588; 100598-100621; 100623-100649; 100653-100669; 100671-100685; 100720-100734; 100748-100785; 100787-100858; 100866-100881; 100887-100918; 100920-100962; 100964-100983; 100993-101015; 101041-101055; 101057-101075; 101117-101158; 101184-101218; 101222-101250; 101262-101275; 101277-101305; 101308-101326; 101336-101349; 101351-101374; 101389-101446; 101448-101508; 101531-101550; 101555-101579; 101597-101617; 101635-101688; 101690-101713; 101715-101767; 101769-101841; 101880-101906; 101908-101942; 101945-102000; 102007-102026; 102028-102045; 102047-102063; 102065-102083; 102104-102118; 102122-102153; 102155-102185; 102195-102253; 102255-102270; 102272-102346; 102360-102396; 102412-102456; 102463-102523; 102525-102563; 102579-102597; 102599-102621; 102639-102706; 102745-102787; 102789-102802; 102804-102834; 102849-102879; 102881-102900; 102922-102948; 102963-102993; 102995-103030; 103032-103045; 103063-103158; 103160-103260; 103262-103296; 103304-103330; 103332-103372; 103374-103444; 103458-103485; 103487-103515; 103529-103558; 103560-103581; 103583-103634; 103636-103668; 103681-103697; 103706-103722; 103735-103757; 103759-103772; 103775-103824; 103829-103850; 103885-103947; 103957-103987; 103989-104040; 104052-104068; 104080-104097; 104110-104128; 104153-104171; 104173-104227; 104240-104255; 104271-104299; 104301-104360; 104364-104377; 104384-104407; 104428-104441; 104453-104499; 104501-104518; 104529-104557; 104570-104637; 104639-104662; 104676-104693; 104695-104709; 104712-104728; 104731-104744; 104748-104768; 104782-104798; 104806-104820; 104822-104875; 104884-104907; 104926-104946; 104948-104969; 104999-105029; 105061-105088; 105104-105119; 105121-105182; 105195-105214; 105220-105239; 105242-105282; 105287-105303; 105305-105319; 105321-105375; 105378-105391; 105397-105434; 105468-105517; 105519-105533; 105581-105607; 105628-105642; 105648-105710; 105748-105764; 105774-105804; 105806-105820; 105822-105856; 105867-105888; 105895-105929; 105932-105959; 105965-105993; 106000-106037; 106039-106057; 106059-106097; 106099-106122; 106124-106149; 106152-106165; 106181-106207; 106209-106242; 106252-106318; 106320-106384; 106386-106431; 106433-106446; 106463-106476; 106478-106496; 106513-106539; 106563-106583; 106592-106634; 106649-106678; 106680-106694; 106696-106711; 106729-106743; 106761-106782; 106789-106803; 106805-106819; 106830-106846; 106848-106868; 106871-106892; 106903-106925; 106974-106997; 107011-107026; 107032-107052; 107076-107093; 107105-107187; 107208-107222; 107237-107270; 107285-107304; 107306-107322; 107325-107355; 107357-107377; 107379-107409; 107437-107454; 107458-107521; 107523-107541; 107571-107607; 107609-107630; 107643-107661; 107663-107713; 107726-107770; 107778-107794; 107796-107809; 107811-107836; 107843-107860; 107880-107924; 107951-107976; 107986-108110; 108112-108132; 108134-108152; 108160-108202; 108204-108221; 108223-108236; 108249-108286; 108294-108318; 108339-108356; 108381-108412; 108424-108439; 108441-108460; 108483-108535; 108537-108595; 108597-108650; 108656-108675; 108692-108728; 108742-108766; 108773-108860; 108891-108920; 108930-108999; 109017-109033; 109065-109090; 109092-109120; 109122-109144; 109146-109161; 109166-109226; 109228-109327; 109347-109364; 109374-109395; 109397-109440; 109442-109479; 109481-109499; 109511-109528; 109530-109579; 109583-109606; 109608-109634; 109636-109651; 109685-109706; 109708-109754; 109765-109787; 109865-109879; 109892-109905; 109913-109940; 109942-109968; 109970-109988; 109990-110010; 110012-110056; 110058-110081; 110087-110147; 110149-110165; 110167-110194; 110196-110219; 110221-110237; 110247-110274; 110285-110322; 110324-110373; 110375-110422; 110424-110449; 110467-110483; 110491-110506; 110522-110579; 110599-110642; 110662-110685; 110687-110727; 110729-110764; 110774-110793; 110840-110861; 110868-110895; 110897-110924; 110933-110948; 110952-110977; 111004-111028; 111030-111085; 111092-111110; 111112-111128; 111131-111154; 111156-111171; 111173-111196; 111218-111239; 111241-111272; 111274-111292; 111298-111312; 111321-111343; 111368-111415; 111417-111438; 111457-111487; 111489-111526; 111533-111552; 111554-111628; 111632-111647; 111656-111682; 111684-111712; 111725-111743; 111801-111814; 111835-111849; 111852-111866; 111887-111913; 111922-111937; 111939-111971; 111979-111993; 112001-112019; 112034-112060; 112062-112096; 112112-112176; 112197-112218; 112220-112248; 112250-112268; 112290-112311; 112324-112381; 112383-112408; 112437-112505; 112507-112552; 112554-112599; 112643-112658; 112660-112681; 112695-112711; 112716-112736; 112738-112776; 112778-112814; 112846-112882; 112934-112961; 112990-113006; 113008-113028; 113044-113060; 113119-113142; 113144-113220; 113224-113248; 113255-113276; 113278-113302; 113367-113385; 113399-113427; 113429-113444; 113452-113545; 113547-113580; 113582-113613; 113619-113680; 113682-113704; 113733-113762; 113779-113819; 113846-113859; 113884-113901; 113903-113994; 113996-114082; 114084-114099; 114101-114158; 114190-114231; 114246-114268; 114270-114285; 114298-114316; 114318-114360; 114389-114405; 114407-114469; 114478-114495; 114509-114549; 114556-114570; 114573-114593; 114595-114609; 114612-114631; 114633-114679; 114681-114698; 114700-114725; 114740-114759; 114785-114798; 114800-114817; 114819-114869; 114871-114896; 114899-114912; 114937-114975; 115013-115033; 115035-115063; 115081-115094; 115122-115141; 115143-115180; 115185-115209; 115219-115260; 115276-115326; 115328-115415; 115453-115491; 115493-115540; 115547-115578; 115581-115601; 115603-115651; 115663-115689; 115695-115742; 115749-115786; 115794-115824; 115830-115871; 115875-115894; 115901-115917; 115927-115954; 115956-115989; 115991-116019; 116034-116047; 116067-116103; 116105-116154; 116167-116218; 116220-116290; 116317-116356; 116363-116378; 116380-116454; 116482-116513; 116525-116546; 116557-116571; 116573-116588;

116590-116619; 116621-116690; 116693-116720; 116722-116735; 116737-116860; 116862-116877; 116887-116906; 116922-116943; 116957-117089; 117098-117131; 117133-117149; 117161-117222; 117224-117260; 117305-117318; 117320-117358; 117378-117423; 117425-117473; 117475-117488; 117490-117518; 117520-117551; 117553-117600; 117602-117619; 117639-117668; 117679-117702; 117704-117761; 117768-117803; 117818-117831; 117877-117943; 117945-117985; 118009-118036; 118038-118052; 118064-118080; 118089-118130; 118132-118204; 118207-118240; 118242-118267; 118269-118327; 118329-118349; 118351-118365; 118397-118450; 118482-118534; 118552-118601; 118603-118623; 118626-118657; 118702-118720; 118731-118754; 118796-118815; 118825-118844; 118846-118871; 118877-118899; 118903-118941; 118950-118965; 118970-119016; 119064-119088; 119107-119145; 119179-119239; 119241-119273; 119291-119309; 119311-119358; 119373-119395; 119408-119479; 119481-119598; 119600-119625; 119627-119667; 119680-119714; 119716-119738; 119740-119789; 119791-119805; 119807-119820; 119822-119838; 119841-119855; 119906-119925; 119936-119971; 119987-120003; 120009-120057; 120074-120093; 120095-120133; 120163-120213; 120215-120323; 120327-120344; 120363-120397; 120399-120429; 120435-120481; 120492-120512; 120531-120556; 120562-120628; 120630-120721; 120736-120803; 120805-120897; 120918-120945; 120955-120970; 120972-121108; 121112-121139; 121165-121179; 121195-121262; 121267-121328; 121330-121370; 121385-121426; 121428-121441; 121451-121471; 121473-121490; 121507-121560; 121562-121582; 121619-121638; 121652-121672; 121674-121716; 121727-121753; 121770-121786; 121790-121809; 121854-121880; 121906-121919; 121949-121967; 121969-122013; 122031-122055; 122058-122118; 122122-122147; 122149-122165; 122167-122199; 122208-122245; 122256-122284; 122304-122317; 122348-122434; 122436-122451; 122467-122493; 122509-122590; 122604-122620; 122631-122644; 122662-122694; 122735-122757; 122761-122797; 122799-122877; 122879-122901; 122950-122974; 122976-123047; 123049-123064; 123083-123113; 123115-123184; 123186-123213; 123218-123269; 123271-123284; 123297-123327; 123329-123362; 123365-123435; 123453-123475; 123481-123561; 123585-123621; 123627-123650; 123654-123690; 123692-123709; 123721-123791; 123810-123868; 123890-124126; 124129-124220; 124222-124273; 124304-124318; 124325-124396; 124410-124439; 124441-124474; 124483-124505; 124532-124554; 124577-124627; 124629-124652; 124654-124704; 124706-124738; 124741-124786; 124788-124817; 124820-124881; 124897-124927; 124929-124958; 124960-125024; 125030-125071; 125078-125101; 125103-125165; 125178-125195; 125213-125237; 125239-125271; 125294-125317; 125321-125348; 125361-125411; 125439-125471; 125489-125507; 125512-125631; 125633-125657; 125659-125688; 125696-125723; 125725-125743; 125745-125784; 125786-125803; 125828-125868; 125894-125918; 125933-125949; 125958-125981; 125991-126008; 126021-126041; 126054-126075; 126077-126095; 126097-126139; 126141-126175; 126189-126209; 126212-126228; 126230-126247; 126253-126272; 126307-126340; 126355-126369; 126382-126411; 126413-126451; 126458-126489; 126491-126533; 126535-126550; 126552-126565; 126567-126587; 126595-126654; 126657-126675; 126690-126716; 126720-126804; 126862-126880; 126884-126897; 126901-126926; 126939-126953; 126955-126974; 126983-127000; 127015-127037; 127039-127130; 127142-127173; 127186-127211; 127214-127231; 127238-127295; 127297-127332; 127340-127353; 127371-127402; 127404-127464; 127466-127487; 127489-127573; 127581-127609; 127612-127632; 127650-127682; 127684-127752; 127771-127803; 127859-127880; 127894-127908; 127910-127943; 127955-127979; 127981-128003; 128017-128030; 128078-128104; 128106-128124; 128126-128140; 128146-128227; 128233-128292; 128300-128325; 128327-128422; 128428-128447; 128451-128476; 128499-128520; 128533-128561; 128584-128671; 128692-128706; 128708-128761; 128763-128786; 128799-128815; 128818-128850; 128852-128968; 128976-128991; 128993-129019; 129027-129042; 129044-129074; 129076-129089; 129091-129138; 129140-129242; 129244-129258; 129269-129290; 129292-129332; 129371-129395; 129402-129434; 129469-129530; 129535-129560; 129568-129582; 129594-129629; 129631-129693; 129695-129724; 129727-129741; 129743-129770; 129772-129798; 129800-129832; 129870-129883; 129885-129916; 129918-129937; 129939-130035; 130037-130082; 130087-130100; 130102-130123; 130125-130156; 130158-130179; 130189-130207; 130237-130255; 130257-130279; 130281-130297; 130299-130320; 130322-130340; 130342-130359; 130392-130441; 130456-130481; 130486-130507; 130560-130622; 130624-130655; 130673-130686; 130689-130783; 130791-130805; 130808-130869; 130887-130906; 130915-130938; 130952-130982; 130984-131010; 131018-131035; 131037-131076; 131101-131131; 131133-131159; 131164-131184; 131187-131207; 131209-131244; 131265-131278; 131280-131319; 131342-131358; 131360-131409; 131421-131440; 131481-131495; 131497-131510; 131522-131578; 131590-131613; 131630-131646; 131648-131665; 131706-131728; 131730-131755; 131757-131785; 131820-131835; 131837-131865; 131877-131896; 131910-131934; 131959-131977; 131981-132008; 132045-132060; 132127-132149; 132152-132173; 132181-132199; 132211-132247; 132262-132297; 132323-132346; 132348-132362; 132365-132408; 132413-132445; 132447-132514; 132524-132550; 132553-132573; 132588-132601; 132603-132622; 132637-132661; 132682-132704; 132712-132756; 132769-132783; 132800-132822; 132831-132858; 132889-132938; 132967-132988; 132990-133003; 133025-133073; 133075-133097; 133099-133116; 133127-133148; 133169-133196; 133222-133264; 133285-133308; 133310-133353; 133366-133484; 133486-133525; 133542-133557; 133559-133625; 133641-133660; 133662-133732; 133747-133787; 133789-133810; 133826-133847; 133867-133883; 133885-133955; 133914-133927; 133952-133969; 133971-134022; 134052-134073; 134075-134090; 134092-134129; 134141-134181; 134197-134210; 134215-134249; 134263-134284; 134293-134362; 134372-134420; 134434-134447; 134449-134464; 134476-134497; 134499-134530; 134534-134557; 134559-134617; 134619-134644; 134646-134661; 134663-134677; 134691-134714; 134727-134743; 134761-134827; 134832-134846; 134855-134873; 134895-134954; 134967-134991; 134993-135017; 135033-135077; 135079-135106; 135114-135134; 135145-135191; 135193-135212; 135240-135288; 135296-135343; 135361-135374; 135376-135391; 135418-135478; 135483-135524; 135571-135609; 135624-135700; 135702-135744; 135764-135779; 135794-135820; 135832-135855; 135857-135897; 135902-135927; 135937-135988; 135999-136088; 136090-136109; 136112-136164; 136185-136198; 136202-136242; 136244-136309; 136311-136340; 136342-136356; 136359-136377; 136379-136464; 136467-136555; 136566-136597; 136614-136629; 136632-136679; 136704-136786; 136788-136859; 136867-136920; 136936-136949; 136951-136967; 136978-137020; 137025-137044; 137055-137097; 137134-137158; 137171-137187; 137189-137228; 137251-137271; 137273-137302; 137313-137353; 137355-137373; 137383-137403; 137405-137497; 137499-137537; 137539-137574; 137599-137638; 137642-137669; 137690-137708; 137710-137748;

137750-137838; 137840-137865; 137867-137907; 137909-137937; 137939-137953; 137955-137977; 137993-138020; 138030-138056; 138058-138085; 138087-138103; 138116-138134; 138137-138214; 138216-138248; 138254-138292; 138305-138334; 138342-138374; 138425-138475; 138477-138506; 138508-138542; 138551-138576; 138610-138647; 138664-138685; 138712-138729; 138731-138745; 138763-138781; 138792-138845; 138858-138907; 138909-138943; 138945-138995; 138999-139015; 139024-139040; 139060-139105; 139107-139133; 139145-139178; 139180-139198; 139207-139236; 139238-139253; 139255-139292; 139294-139320; 139329-139488; 139512-139542; 139544-139567; 139582-139596; 139631-139662; 139671-139684; 139686-139699; 139729-139748; 139773-139790; 139799-139820; 139822-139844; 139846-139890; 139896-139920; 139930-139991; 139999-140018; 140023-140112; 140153-140213; 140215-140232; 140234-140268; 140291-140326; 140338-140360; 140367-140415; 140447-140475; 140497-140524; 140529-140624; 140639-140654; 140658-140674; 140676-140716; 140745-140787; 140790-140815; 140817-140841; 140843-140868; 140882-140903; 140905-140929; 140949-140967; 140996-141013; 141026-141055; 141080-141103; 141105-141126; 141138-141192; 141194-141207; 141209-141349; 141383-141396; 141402-141419; 141472-141509; 141511-141533; 141535-141569; 141571-141587; 141596-141639; 141641-141725; 141729-141749; 141756-141831; 141833-141899; 141901-141932; 141948-141991; 141993-142013; 142022-142082; 142084-142104; 142120-142176; 142178-142206; 142208-142221; 142254-142295; 142297-142375; 142398-142413; 142433-142471; 142473-142527; 142529-142601; 142603-142687; 142695-142730; 142732-142751; 142773-142928; 142930-142993; 142996-143020; 143022-143042; 143056-143071; 143073-143092; 143102-143127; 143129-143145; 143158-143187; 143206-143283; 143286-143347; 143349-143378; 143384-143416; 143418-143436; 143447-143478; 143480-143512; 143514-143547; 143560-143599; 143601-143646; 143664-143756; 143758-143771; 143773-143793; 143817-143848; 143850-143863; 143865-143881; 143883-143900; 143902-143919; 143921-143936; 143949-143994; 144018-144086; 144088-144102; 144104-144121; 144148-144164; 144166-144193; 144208-144275; 144277-144293; 144297-144315; 144326-144410; 144421-144505; 144538-144580; 144582-144622; 144624-144637; 144675-144802; 144817-144833; 144835-144849; 144882-144944; 144948-144995; 145005-145044; 145046-145065; 145074-145125; 145136-145158; 145178-145192; 145194-145217; 145219-145254; 145256-145271; 145276-145330; 145332-145345; 145347-145444; 145446-145462; 145493-145507; 145539-145568; 145593-145617; 145619-145647; 145694-145716; 145718-145735; 145737-145809; 145836-145850; 145883-145942; 145944-146005; 146007-146051; 146053-146096; 146150-146174; 146194-146210; 146217-146251; 146253-146294; 146318-146373; 146377-146390; 146392-146417; 146419-146432; 146435-146448; 146451-146471; 146486-146528; 146543-146657; 146659-146766; 146777-146793; 146795-146825; 146837-146887; 146910-146928; 146930-146943; 146945-147005; 147007-147026; 147033-147085; 147087-147163; 147165-147208; 147210-147322; 147361-147387; 147391-147419; 147421-147449; 147454-147472; 147474-147587; 147602-147616; 147618-147642; 147645-147757; 147759-147799; 147801-147866; 147868-147896; 147905-147951; 147975-148005; 148010-148041; 148043-148056; 148099-148130; 148139-148179; 148186-148215; 148217-148242; 148261-148283; 148285-148325; 148327-148369; 148381-148434; 148445-148499; 148527-148542; 148553-148618; 148625-148638; 148640-148678; 148680-148696; 148698-148739; 148752-148768; 148798-148869; 148871-148885; 148913-148930; 148934-149001; 149011-149030; 149040-149099; 149110-149127; 149130-149176; 149193-149225; 149232-149250; 149268-149351; 149353-149461; 149463-149533; 149535-149591; 149602-149651; 149653-149738; 149742-149784; 149786-149799; 149814-149830; 149848-149871; 149917-149932; 149934-149995; 149998-150021; 150025-150041; 150043-150120; 150151-150201; 150206-150229; 150236-150258; 150262-150279; 150283-150318; 150320-150364; 150366-150388; 150402-150442; 150450-150466; 150473-150561; 150563-150597; 150599-150623; 150628-150641; 150656-150679; 150694-150718; 150744-150775; 150796-150822; 150824-150846; 150852-150899; 150908-150928; 150930-150945; 150947-150988; 150990-151022; 151024-151057; 151060-151087; 151101-151127; 151129-151158; 151160-151203; 151216-151233; 151241-151256; 151258-151298; 151310-151330; 151332-151351; 151353-151423; 151439-151464; 151466-151487; 151489-151516; 151534-151554; 151556-151573; 151577-151592; 151612-151645; 151658-151683; 151694-151713; 151740-151774; 151776-151831; 151837-151856; 151861-151874; 151877-151947; 151949-151969; 151984-152046; 152048-152061; 152063-152095; 152097-152112; 152114-152156; 152167-152199; 152213-152270; 152272-152299; 152301-152336; 152361-152374; 152376-152398; 152401-152420; 152426-152479; 152481-152495; 152498-152511; 152513-152526; 152569-152589; 152591-152606; 152613-152631; 152642-152661; 152663-152690; 152705-152720; 152759-152814; 152816-152846; 152848-152895; 152903-152994; 153028-153081; 153083-153115; 153125-153179; 153181-153199; 153202-153253; 153255-153294; 153301-153342; 153358-153418; 153427-153448; 153461-153476; 153478-153535; 153560-153649; 153668-153696; 153732-153747; 153759-153844; 153846-153859; 153861-153888; 153891-153905; 153930-153949; 153951-153986; 153989-154039; 154041-154059; 154063-154112; 154114-154127; 154129-154166; 154168-154224; 154226-154270; 154278-154299; 154301-154315; 154317-154334; 154357-154374; 154378-154398; 154443-154463; 154465-154484; 154520-154574; 154586-154622; 154624-154675; 154706-154723; 154725-154740; 154742-154774; 154776-154808; 154828-154852; 154854-154867; 154883-154899; 154901-154927; 154938-154959; 154981-155001; 155003-155041; 155043-155080; 155082-155100; 155112-155129; 155131-155146; 155148-155182; 155188-155232; 155234-155291; 155293-155314; 155316-155334; 155340-155379; 155383-155401; 155411-155437; 155466-155495; 155497-155511; 155522-155555; 155563-155583; 155585-155641; 155643-155656; 155682-155701; 155703-155718; 155720-155764; 155769-155783; 155785-155820; 155822-155874; 155877-155901; 155913-155927; 155929-155948; 155950-156015; 156083-156110; 156112-156127; 156135-156159; 156161-156201; 156203-156250; 156252-156308; 156314-156327; 156337-156362; 156364-156404; 156414-156428; 156459-156481; 156483-156534; 156549-156601; 156613-156642; 156654-156671; 156673-156687; 156696-156758; 156780-156813; 156832-156848; 156864-156897; 156900-156936; 156954-157019; 157030-157054; 157056-157138; 157141-157216; 157218-157233; 157235-157374; 157377-157394; 157396-157432; 157434-157461; 157573-157591; 157597-157614; 157628-157645; 157687-157704; 157750-157764; 157775-157809; 157822-157858; 157860-157876; 157878-157935; 157940-157963; 157980-158026; 158028-158049; 158052-158072; 158074-158097; 158115-158135; 158143-158189; 158191-158221; 158226-158297; 158324-158378; 158390-158410; 158435-158463; 158465-158498; 158522-158540; 158542-158598; 158606-158621; 158623-158654; 158659-158678; 158680-158709;

158722-158747; 158753-158794; 158824-158886; 158888-158920; 158922-158968; 158975-158998; 159019-159033; 159051-159087; 159089-159112; 159126-159162; 159203-159287; 159289-159303; 159319-159405; 159407-159430; 159433-159507; 159519-159573; 159575-159590; 159592-159606; 159608-159629; 159631-159655; 159667-159715; 159736-159788; 159806-159820; 159822-159868; 159870-159916; 159918-159955; 159982-160009; 160020-160074; 160086-160100; 160143-160224; 160242-160280; 160282-160339; 160341-160355; 160357-160380; 160382-160404; 160406-160472; 160474-160496; 160505-160551; 160553-160595; 160597-160615; 160617-160650; 160652-160674; 160687-160700; 160702-160758; 160760-160773; 160792-160805; 160825-160889; 160904-160940; 160950-161003; 161005-161030; 161032-161050; 161055-161075; 161102-161116; 161118-161132; 161144-161167; 161173-161188; 161190-161331; 161339-161386; 161388-161423; 161425-161461; 161465-161527; 161529-161548; 161560-161657; 161663-161676; 161684-161724; 161729-161743; 161769-161800; 161804-161827; 161843-161874; 161883-161896; 161898-161912; 161933-161967; 161969-162006; 162008-162025; 162051-162111; 162127-162147; 162150-162168; 162183-162197; 162199-162221; 162234-162248; 162273-162291; 162293-162311; 162313-162331; 162341-162367; 162379-162443; 162464-162499; 162507-162550; 162585-162599; 162776-162789; 162967-162980; 163097-163117; 163275-163289; 163362-163406; 163416-163444; 163447-163472; 163481-163495; 163497-163516; 163518-163599; 163601-163632; 163641-163662; 163669-163695; 163708-163767; 163769-163791; 163798-163842; 163846-163866; 163875-163907; 163918-163964; 163998-164023; 164025-164039; 164041-164088; 164090-164111; 164113-164157; 164159-164179; 164192-164234; 164256-164275; 164278-164304; 164337-164408; 164410-164424; 164449-164479; 164831-164844; 164922-164940; 164957-164980; 164985-165004; 165034-165060; 165072-165088; 165090-165103; 165123-165143; 165148-165168; 165185-165204; 165206-165224; 165298-165313; 165319-165332; 165465-165484; 165508-165522; 165543-165556; 165641-165654; 165720-165754; 165821-165836; 165838-165855; 165868-165902; 165919-165934; 165948-165980; 166016-166048; 166144-166190; 166235-166252; 166254-166274; 166312-166326; 166328-166359; 166379-166392; 166484-166498; 166504-166519; 166664-166677; 167174-167188; 167827-167844; 167847-167868; 167872-167889; 167904-167918; 167920-167935; 167952-167992; 167994-168034; 168104-168124; 168140-168180; 168182-168243; 168247-168260; 168272-168314; 168316-168402; 168404-168457; 168459-168606; 168617-168637; 168646-168670; 168697-168744; 168769-168794; 168796-168851; 168874-168908; 168914-168932; 168935-168960; 168970-169018; 169027-169051; 169059-169083; 169085-169110; 169112-169125; 169127-169206; 169208-169231; 169233-169253; 169256-169271; 169273-169335; 169341-169361; 169376-169392; 169401-169424; 169435-169460; 169521-169579; 169581-169612; 169614-169629; 169641-169659; 169661-169782; 169791-169819; 169833-169864; 169898-169916; 169927-169953; 169959-169980; 170012-170026; 170033-170059; 170071-170085; 170100-170119; 170121-170135; 170138-170245; 170247-170309; 170311-170348; 170350-170364; 170385-170412; 170434-170504; 170506-170585; 170597-170610; 170624-170645; 170714-170731; 170736-170763; 170765-170817; 170835-170852; 170859-170872; 170888-170901; 170903-170923; 170926-170940; 170942-171001; 171014-171056; 171058-171135; 171153-171168; 171198-171214; 171221-171244; 171250-171292; 171294-171308; 171310-171330; 171347-171363; 171365-171378; 171388-171411; 171422-171464; 171487-171584; 171586-171635; 171637-171721; 171739-171752; 171766-171820; 171831-171894; 171909-171983; 171985-171998; 172000-172091; 172093-172107; 172145-172161; 172163-172195; 172204-172235; 172237-172267; 172269-172321; 172323-172360; 172365-172379; 172381-172455; 172457-172489; 172492-172519; 172522-172550; 172552-172575; 172578-172617; 172636-172653; 172669-172733; 172739-172755; 172764-172781; 172843-172861; 172875-172909; 172932-172951; 172957-172972; 172977-172994; 173002-173022; 173027-173056; 173058-173082; 173094-173128; 173146-173179; 173181-173222; 173224-173291; 173293-173347; 173349-173365; 173367-173388; 173390-173408; 173429-173459; 173491-173516; 173518-173535; 173537-173568; 173583-173598; 173619-173662; 173671-173686; 173705-173767; 173772-173842; 173844-173887; 173915-173995; 174005-174052; 174068-174134; 174137-174151; 174154-174171; 174209-174272; 174275-174296; 174332-174349; 174358-174371; 174387-174400; 174416-174429; 174445-174458; 174474-174487; 174503-174516; 174532-174545; 174561-174580; 174652-174665; 174701-174760; 174764-174777; 174781-174807; 174816-174829; 174878-174902; 174904-174947; 174949-174962; 174983-175001; 175010-175041; 175053-175073; 175087-175125; 175132-175166; 175176-175191; 175195-175264; 175342-175365; 175368-175416; 175418-175490; 175492-175506; 175526-175550; 175564-175582; 175586-175624; 175659-175706; 175710-175802; 175804-175848; 175856-176047; 176049-176083; 176104-176132; 176136-176165; 176167-176223; 176225-176291; 176293-176310; 176317-176348; 176350-176375; 176377-176477; 176479-176501; 176512-176600; 176602-176714; 176716-176735; 176753-176828; 176830-176855; 176857-176987; 176989-177014; 177016-177053; 177055-177170; 177172-177314; 177316-177331; 177333-177402; 177404-177438; 177440-177459; 177461-177520; 177522-177551; 177572-177592; 177594-177610; 177613-177661; 177668-177692; 177697-177727; 177729-177764; 177766-177784; 177795-177864; 177866-177896; 177898-177957; 177972-177993; 177995-178008; 178010-178042; 178044-178059; 178061-178126; 178130-178148; 178159-178177; 178199-178261; 178268-178287; 178289-178339; 178353-178368; 178372-178406; 178408-178426; 178433-178448; 178455-178499; 178508-178555; 178562-178613; 178618-178697; 178699-178732; 178734-178749; 178752-178765; 178767-178807; 178809-178826; 178858-178887; 178903-178920; 178922-178968; 178976-178989; 179038-179108; 179110-179125; 179148-179164; 179166-179196; 179198-179232; 179234-179255; 179285-179325; 179357-179406; 179410-179426; 179430-179450; 179467-179483; 179485-179556; 179564-179582; 179596-179673; 179687-179719; 179721-179739; 179754-179771; 179787-179805; 179810-179856; 179858-179886; 179888-179905; 179912-179947; 179970-179994; 179996-180070; 180083-180135; 180142-180174; 180185-180205; 180208-180233; 180235-180258; 180260-180274; 180288-180365; 180376-180393; 180395-180410; 180412-180426; 180438-180485; 180493-180536; 180538-180551; 180562-180603; 180605-180658; 180660-180693; 180695-180728; 180730-180770; and 180772-180806. In some embodiments, the contiguous nucleotide sequence of the oligonucleotide of the invention comprises at least 14 contiguous nucleotides which are present in one of the above listed target sequences.

Target Sequence List 2

In some embodiments the target sequence is a region of SEQ ID NO 1 selected from the group consisting of 852-868; 1070-1085; 1512-1526; 2673-2691; 3900-3921; 5165-5182; 5430 -5444; 5610-5624; 5765-5809; 5896-5909;

6859-6872; 6998-7017; 7165-7178; 7297-7317; 8726-8739; 9386-9399; 11712-11725; 11823-11843; 11882-11901; 14186-14199; 15749-15785; 15931-15944; 16137-16150; 17146-17166; 17916-17967; 20196-20213; 20422-20435; 20481-20494; 20883-20900; 21042-21055; 22764-22781; 22978-22992; 25991-26004; 26180-26193; 26621-26634; 26688-26701; 26842-26876; 27744-27759; 30376-30389; 32174-32204; 35003-35016; 35388-35402; 36516-36529; 41753-41766; 42185-42198; 43053-43066; 46413-46426; 48933-48946; 50295-50308; 51695-51709; 54188-54212; 54463-54482; 55841-55854; 55961-55975; 57416-57429; 58396-58410; 58671-58684; 59251-59264; 59294-59308; 60959-60973; 61339-61354; 61631-61644; 63172-63189; 64225-64251; 64254-64280; 64300-64332; 64340-64367; 64399-64421; 64423-64442; 64462-64476; 64478-64502; 64625-64671; 64720-64733; 65457-65479; 65963-65978; 66330-66343; 66660-66673; 66754-66770; 67055-67079; 67231-67245; 67778-67791; 68135-68148; 68548-68566; 68629-68642; 68665-68678; 68821-68834; 68925-68938; 68943-68974; 68991-69043; 69140-69153; 69223-69236; 69263-69276; 69393-69417; 69419-69438; 69440-69461; 69500-69514; 69598-69612; 70079-70126; 70128-70145; 70147-70162; 70164-70186; 70188-70217; 70344-70359; 70377-70390; 70716-70732; 70742-70762; 71359-71373; 71390-71406; 71481-71494; 71548-71566; 71599-71614; 71655-71729; 71731-71788; 71790-71824; 71834-71847; 71856-71903; 71929-71945; 71947-71991; 71995-72010; 72047-72065; 72101-72130; 72154-72172; 72273-72288; 72518-72532; 72622-72639; 72652-72666; 72753-72776; 72981-72994; 73174-73188; 73239-73253; 73659-73672; 73760-73779; 73820-73833; 74025-74038; 74127-74154; 74849-74865; 75190-75204; 75601-75614; 75831-75844; 75987-76000; 76430-76443; 76547-76564; 77078-77092; 77442-77456; 77740-77753; 78041-78054; 78625-78644; 78682-78696; 78772-78808; 78955-78970; 79466-79479; 79545-79558; 80688-80704; 81031-81048; 81360-81417; 81429-81443; 81527-81542; 81555-81580; 81707-81720; 81924-81939; 82166-82179; 82376-82389; 82670-82695; 82709-82729; 82745-82761; 82763-82777; 83468-83484; 83512-83529; 83671-83685; 83848-83861; 84565-84580; 85147-85163; 85464-85477; 85607-85620; 86283-86298; 86341-86354; 86371-86387; 86776-86789; 87084-87097; 87209-87223; 87237-87265; 87341-87354; 87383-87399; 87404-87442; 87464-87489; 87503-87534; 87579-87593; 87677-87690; 87826-87843; 87877-87908; 88033-88048; 88393-88409; 88574-88588; 89078-89091; 89442-89469; 89475-89521; 89523-89536; 89595-89617; 89780-89793; 89896-89909; 89927-89945; 90609-90622; 90887-90900; 90964-90977; 91076-91091; 91173-91191; 91193-91218; 91220-91247; 91310-91324; 91326-91347; 91360-91383; 91409-91425; 91484-91556; 91565-91579; 91639-91665; 91790-91803; 91955-91968; 92064-92077; 92289-92302; 92387-92401; 92434-92457; 92580-92593; 92753-92771; 93022-93035; 93402-93423; 93634-93650; 93845-93862; 94044-94059; 94090-94103; 94296-94318; 94798-94811; 95141-95155; 95400-95413; 95418-95431; 95436-95460; 95463-95506; 95510-95548; 95550-95596; 95613-95626; 95632-95645; 95768-95781; 95843-95863; 95888-95902; 96058-96071; 96469-96487; 96591-96606; 96664-96681; 96785-96799; 96871-96886; 97126-97145; 97149-97164; 97221-97258; 97298-97313; 97325-97344; 97358-97372; 97686-97699; 97701-97720; 97731-97756; 97776-97795; 97848-97867; 97913-97929; 98097-98110; 98352-98365; 98598-98616; 98646-98670; 98672-98688; 98725-98751; 98759-98772; 98783-98811; 98813-98847; 98879-98910; 98912-98949; 98972-99003; 99005-99037; 99221-99234; 99804-99818; 99870-99884; 100038-100052; 100346-100359; 100404-100421; 100567-100581; 101224-101238; 101663-101676; 101783-101798; 102325-102342; 102490-102504; 102643-102657; 102815-102828; 103063-103076; 103078-103100; 103110-103123; 103160-103185; 103244-103260; 103265-103296; 103376-103395; 103487-103515; 103560-103581; 103583-103601; 103655-103668; 103810-103823; 104053-104068; 104110-104127; 104595-104608; 104676-104690; 104845-104868; 104886-104904; 105220-105239; 105412-105431; 105786-105800; 106108-106121; 106851-106864; 107384-107403; 107506-107521; 107670-107683; 107778-107794; 108395-108408; 109411-109427; 110200-110215; 110617-110630; 111065-111079; 111133-111149; 111376-111389; 112034-112047; 113468-113481; 113560-113574; 115512-115528; 115628-115651; 116119-116132; 116171-116186; 116321-116334; 116602-116619; 116668-116682; 116705-116720; 116749-116778; 116793-116819; 116839-116860; 116922-116939; 116966-116982; 117046-117059; 117183-117201; 117779-117792; 117922-117939; 117948-117968; 117970-117983; 118089-118107; 118218-118233; 118825-118838; 119198-119218; 119245-119263; 119374-119388; 119654-119667; 120076-120089; 120540-120556; 120859-120882; 121515-121528; 121538-121551; 122088-122107; 122407-122422; 122516-122530; 122827-122841; 122843-122860; 122982-122995; 123083-123099; 123170-123184; 123186-123203; 123218-123247; 123300-123326; 123369-123393; 123521-123534; 123628-123645; 123896-123909; 123918-123936; 124093-124107; 124154-124169; 124171-124190; 124602-124615; 124689-124702; 124981-124997; 125140-125158; 125593-125606; 125752-125765; 126258-126272; 126383-126396; 127155-127168; 127319-127332; 127589-127605; 127657-127676; 127862-127875; 128818-128847; 128856-128871; 128976-128991; 129107-129121; 129671-129685; 130005-130025; 130049-130063; 130689-130706; 130732-130745; 131020-131034; 131103-131118; 131846-131861; 132413-132426; 132719-132733; 132841-132856; 133295-133308; 133324-133337; 133395-133412; 133414-133432; 133444-133469; 133471-133484; 133565-133579; 133667-133684; 134235-134248; 134730-134743; 134833-134846; 135091-135106; 135161-135175; 135451-135464; 135497-135517; 135588-135603; 135640-135656; 135728-135741; 136146-136159; 136413-136429; 136758-136782; 137502-137520; 137557-137574; 137690-137708; 137730-137748; 137774-137793; 137813-137838; 137844-137862; 137873-137896; 138185-138198; 138671-138684; 138800-138813; 139896-139910; 139950-139963; 140058-140081; 140195-140211; 140291-140304; 140312-140326; 140453-140466; 140756-140769; 141209-141222; 141238-141255; 141297-141312; 141622-141639; 142152-142174; 142262-142281; 142358-142371; 142537-142559; 142561-142583; 142615-142637; 142639-142681; 142717-142730; 143077-143090; 143169-143182; 143236-143266; 143268-143283; 143354-143368; 143616-143646; 144061-144074; 144430-144458; 144589-144603; 144783-144796; 144982-144995; 145194-145208; 145718-145731; 145737-145754; 145770-145793; 145907-145924; 146150-146166; 146220-146235; 146238-146251; 146600-146629; 146695-146736; 146846-146864; 146987-147002; 147054-147079; 147087-147103; 147111-147128; 147144-147163; 147171-147185; 147222-147272; 147282-147295; 147297-147318; 147727-147755; 148194-148209; 148302-148316; 148752-148767; 149049-149067; 149195-149210; 149237-149250; 149295-149313; 149325-149338; 149353-149419; 149421-149457; 149473-149486; 149682-149700; 149786-149799; 149849-149868; 150328-150341; 150452-150465; 150701-150714; 150865-150880; 151556-151571; 151577-151590; 151700-151713; 151837-151855; 151906-151921; 152173-152186; 152613-152631; 152770-152785;

152957-152970; 153028-153074; 153221-153235; 153359-153376; 153806-153819; 153972-153986; 153993-154006; 154283-154296; 154586-154602; 154608-154621; 154627-154641; 154780-154796; 154914-154927; 155159-155172; 155749-155762; 155884-155900; 156707-156721; 156960-156976; 156993-157018; 157200-157216; 157289-157306; 157573-157591; 158033-158046; 158733-158747; 158826-158842; 159019-159032; 159090-159107; 159149-159162; 159203-159225; 159339-159361; 159882-159896; 160203-160224; 160434-160447; 160513-160526; 161476-161502; 162507-162542; 163573-163590; 164410-164423; 164923-164938; 165090-165103; 165465-165484; 165967-165980; 166254-166274; 166504-166519; 167830-167844; 168140-168153; 168545-168576; 169037-169050; 169288-169301; 169542-169555; 169725-169739; 169760-169774; 170045-170058; 170257-170273; 170552-170566; 170979-170995; 171222-171235; 171388-171401; 171425-171449; 171489-171511; 171518-171551; 171565-171581; 171586-171605; 171637-171651; 171778-171808; 171834-171850; 171852-171880; 171924-171937; 171939-171964; 171966-171983; 171985-171998; 172011-172034; 172036-172053; 172070-172083; 172182-172195; 172702-172717; 173158-173171; 173187-173200; 173429-173442; 173497-173510; 173754-173767; 173788-173801; 173820-173835; 173864-173881; 173940-173953; 174154-174167; 174275-174288; 174701-174740; 174782-174795; 174816-174829; 175351-175364; 175398-175412; 175434-175447; 175493-175506; 175985-176026; 176167-176219; 176245-176285; 176317-176348; 176382-176402; 176404-176423; 176449-176469; 176515-176555; 176662-176678; 176683-176708; 176716-176735; 176767-176801; 176803-176816; 176830-176846; 176869-176915; 176927-176948; 176950-176981; 176989-177008; 177022-177047; 177064-177078; 177103-177140; 177181-177206; 177235-177248; 177253-177269; 177282-177308; 177349-177366; 177419-177438; 177476-177498; 177594-177610; 177631-177658; 177795-177813; 177866-177886; 177928-177941; 177943-177957; 178012-178030; 178218-178231; 178268-178282; 178781-178795; 178809-178826; 179174-179187; 179213-179227; 179287-179306; 179358-179382; 179500-179519; 179696-179709; 180302-180316; 180340-180357; 180378-180393; 180395-180410; 180438-180454; 180462-180480; 180582-180596; 180634-180658; 180679-180693; 180699-180726; and 180753-180771. In some embodiments, the contiguous nucleotide sequence of the oligonucleotide of the invention comprises at least 14 contiguous nucleotides which are present in one of the above listed target sequences.

Target Sequence List 3

In some embodiments the target sequence is a region of SEQ ID NO 1 selected from the group consisting of 852-865; 2091-2104; 2620-2633; 2675-2692; 3441-3454; 3882 3921; 3970-3983; 4532-4553; 4814-4827; 5068-5082; 5167-5182; 5184-5198; 5430-5444; 5466-5502; 5511-5529; 5544-5585; 5610-5633; 5644-5662; 5695-5717; 6067-6085; 6087-6100; 6117-6130; 6859-6873; 6998-7019; 7033-7053; 7089-7121; 7131-7152; 7155-7184; 7206-7221; 7254-7271; 7273-7295; 7297-7315; 7381-7414; 7456-7475; 7478-7499; 7509-7522; 7618-7632; 8388-8401; 8508-8529; 8538-8562; 8596-8610; 8612-8638; 8655-8677; 8693-8715; 8944-8957; 9534-9547; 9914-9928; 10068-10081; 10252-10265; 10363-10376; 10402-10415; 10626-10640; 11437-11450; 11879-11901; 11981-11994; 12145-12158; 12980-12993; 13998-14011; 15098-15111; 15628-15642; 15749-15792; 15801-15821; 15847-15863; 15869-15911; 15931-15959; 15972-15985; 16019-16037; 16039-16052; 16740-16753; 17660-17676; 17696-17731; 17761-17774; 17800-17827; 17851-17871; 17878-17896; 17906-17967; 18825-18843; 19063-19080; 19821-19834; 19932-19983; 20024-20039; 20045-20062; 20090-20125; 20153-20183; 20196-20212; 20288-20301; 20416-20435; 20481-20494; 20715-20728; 20739-20756; 20808-20826; 20830-20843; 20847-20874; 20892-20905; 20932-20959; 21684-21697; 22764-22780; 22819-22836; 22856-22869; 22880-22907; 22979-22992; 23370-23383; 23917-23930; 25007-25020; 26048-26068; 26104-26160; 26170-26200; 26224-26238; 26270-26301; 26618-26635; 26843-26878; 26915-26932; 26945-26958; 26961-26978; 27013-27027; 27068-27085; 27218-27231; 27927-27941; 28777-28795; 29103-29116; 29389-29403; 29985-29998; 30360-30374; 30376-30390; 30768-30782; 32173-32206; 32237-32251; 32260-32274; 32334-32360; 32569-32583; 32597-32611; 32749-32763; 33254-33268; 33299-33314; 33492-33506; 34233-34247; 34360-34375; 34562-34576; 34689-34703; 35106-35135; 35142-35169; 35259-35275; 35280-35308; 35333-35346; 35382-35470; 35477-35490; 35494-35534; 35883-35896; 36784-36797; 37504-37518; 39690-39704; 40005-40018; 41020-41037; 41749-41762; 43000-43013; 43043-43061; 44274-44287; 44297-44312; 44707-44720; 45664-45677; 46383-46397; 46412-46439; 46690-46703; 47443-47456; 47692-47707; 48415-48429; 48575-48597; 48608-48628; 48637-48650; 48657-48672; 48712-48728; 48798-48811; 48826-48840; 51683-51720; 51734-51752; 51759-51776; 51795-51825; 51897-51910; 52031-52044; 53317-53332; 53975-53988; 54189-54210; 54303-54316; 54334-54347; 54425-54438; 54463-54492; 54557-54573; 54618-54639; 55625-55639; 55821-55834; 56023-56036; 56641-56655; 56689-56703; 57413-57427; 59206-59219; 59282-59313; 59328-59353; 59360-59382; 59384-59413; 59444-59461; 59505-59540; 59566-59580; 60084-60097; 60292-60305; 61606-61619; 62447-62460; 62763-62776; 63174-63187; 63859-63874; 64171-64184; 64462-64475; 64623-64671; 64800-64817; 64858-64873; 64875-64902; 64928-64949; 64959-64983; 64985-65003; 65044-65065; 65078-65113; 65115-65169; 65171-65186; 65188-65238; 65240-65294; 65323-65365; 65368-65438; 65448-65512; 65517-65611; 65619-65640; 65692-65712; 65714-65765; 65767-65840; 65842-65894; 65920-65973; 65985-66014; 66025-66042; 66074-66091; 66101-66120; 66156-66182; 66216-66232; 66266-66282; 66284-66301; 66324-66346; 66366-66382; 66406-66423; 66440-66469; 66480-66495; 67055-67089; 67091-67113; 67128-67170; 67186-67202; 67231-67256; 67258-67294; 67310-67333; 67336-67351; 67597-67616; 67754-67768; 67862-67875; 68793-68806; 69042-69055; 69686-69699; 70176-70193; 70622-70635; 70756-70769; 71228-71241; 71564-71577; 71926-71941; 73372-73386; 74239-74252; 74809-74822; 74848-74880; 74890-74941; 74963-74993; 75005-75027; 75037-75066; 75075-75092; 76262-76276; 76615-76628; 76940-76953; 77233-77246; 78634-78647; 78772-78825; 78867-78888; 78890-78909; 78914-78940; 78955-78986; 78989-79024; 79026-79039; 79041-79056; 79058-79075; 80011-80024; 80858-80871; 81031-81044; 81088-81101; 81166-81179; 82854-82868; 83250-83263; 83621-83636; 83781-83796; 83848-83861; 83867-83885; 83887-83921; 83927-83950; 83986-84001; 84015-84040; 84060-84073; 84075-84097; 84168-84183; 84302-84319; 84335-84348; 84368-84390; 84419-84453; 84480-84501; 84503-84518; 84534-84547; 84549-84567; 84569-84583; 84653-84667; 84693-84708; 84740-84771; 84776-84795; 84824-84839; 84855-84873; 84878-84894; 84896-84911; 85017-85038; 85059-85076; 85079-85102; 85113-85126; 85147-85194; 85252-85267; 85281-85294; 85359-85378; 85470-85486; 85668-85682; 85713-85734; 85771-85793; 85825-85838; 85842-85873; 85876-85902; 86132-86151; 86303-86316; 86438-86468; 86489-86522; 86524-86548;

86554-86570; 86575-86588; 86603-86618; 86636-86651; 86676-86689; 86717-86741; 86776-86803; 86965-86978; 87641-87654; 87707-87720; 87826-87839; 87845-87858; 87879-87910; 88019-88059; 88602-88616; 89155-89168; 89484-89497; 89866-89879; 90038-90051; 92157-92170; 92940-92953; 93333-93348; 93404-93418; 93488-93511; 94835-94851; 96790-96805; 98015-98029; 98877-98892; 98918-98931; 100403-100426; 100436-100456; 100462-100475; 100492-100534; 100562-100588; 100607-100627; 100653-100667; 100671-100685; 102125-102138; 102391-102404; 102992-103005; 104110-104128; 104153-104171; 104224-104243; 104336-104349; 105025-105038; 105219-105240; 105260-105273; 105287-105300; 105321-105336; 105353-105367; 105417-105431; 105462-105478; 105777-105793; 106242-106256; 107381-107403; 107554-107567; 107801-107814; 108248-108261; 108503-108517; 108882-108899; 108928-108944; 109070-109086; 109294-109307; 109411-109427; 109935-109950; 110122-110145; 110196-110210; 110366-110379; 110512-110525; 110563-110576; 110690-110705; 111068-111083; 111506-111520; 111626-111639; 111974-111987; 112693-112706; 112899-112912; 113806-113819; 114115-114128; 115700-115713; 116267-116280; 116833-116846; 117447-117461; 117562-117575; 117932-117945; 118556-118569; 118652-118665; 119346-119359; 120785-120798; 120858-120890; 120974-120988; 122466-122479; 123217-123231; 123785-123798; 124982-124997; 125621-125634; 126633-126646; 127044-127057; 127066-127090; 127108-127130; 127196-127211; 127244-127265; 127269-127296; 127322-127335; 128260-128275; 128300-128318; 128339-128360; 128363-128381; 128394-128422; 128425-128444; 128822-128848; 130000-130013; 131029-131042; 131184-131197; 131926-131939; 133001-133014; 133472-133493; 134969-134982; 135682-135697; 136759-136791; 136794-136829; 136858-136871; 137867-137883; 138425-138438; 138521-138534; 138969-138983; 139291-139320; 139337-139422; 139436-139471; 139515-139544; 139550-139581; 140314-140327; 140582-140596; 141239-141252; 142647-142660; 142816-142829; 143236-143274; 144208-144246; 144250-144275; 144308-144322; 144326-144340; 144348-144387; 144393-144415; 144431-144454; 145603-145618; 146615-146628; 147007-147020; 147063-147076; 147108-147121; 147267-147280; 147455-147468; 147480-147531; 147545-147597; 147601-147615; 147618-147641; 147644-147668; 147679-147706; 147708-147755; 147972-147998; 148303-148316; 149483-149496; 150121-150136; 151760-151773; 152089-152102; 152533-152546; 152616-152630; 152825-152838; 152956-152972; 153029-153059; 153061-153076; 153093-153114; 153125-153177; 153181-153198; 153211-153253; 153255-153289; 153301-153341; 153359-153376; 153381-153395; 153398-153417; 153421-153442; 153461-153476; 153483-153504; 153507-153532; 153577-153596; 153603-153627; 153629-153643; 153805-153819; 154379-154401; 154483-154501; 154535-154552; 154586-154602; 154823-154840; 154918-154931; 156311-156324; 156466-156484; 156521-156535; 156576-156590; 156614-156629; 156654-156678; 156707-156721; 156723-156753; 156777-156798; 156833-156849; 156871-156885; 156984-157019; 157078-157111; 157154-157170; 157192-157217; 157236-157289; 157293-157307; 157338-157375; 157412-157426; 157430-157443; 157561-157588; 157593-157619; 157628-157655; 157673-157739; 158005-158018; 158258-158278; 158422-158435; 158522-158545; 158694-158708; 159274-159292; 159346-159360; 159590-159603; 159859-159872; 159968-159981; 160208-160223; 160251-160267; 161102-161115; 161187-161332; 161337-161386; 161388-161502; 161618-161631; 162043-162056; 162561-162575; 163052-163065; 163084-163097; 164109-164123; 164923-164938; 164958-164980; 165017-165032; 165034-165047; 165049-165063; 165065-165079; 165134-165149; 165185-165224; 165467-165483; 165516-165529; 165587-165604; 165608-165621; 165644-165665; 165697-165718; 165720-165748; 165750-165774; 165777-165836; 165838-165852; 165862-165946; 165948-165980; 166005-166050; 166060-166102; 166122-166160; 166163-166218; 166220-166239; 166254-166307; 166312-166359; 166366-166391; 166508-166522; 167252-167265; 167319-167332; 168224-168237; 168272-168313; 168334-168348; 168356-168394; 168416-168447; 168477-168491; 168503-168519; 168541-168579; 169037-169052; 169342-169366; 169376-169400; 169411-169424; 169435-169460; 169496-169517; 169519-169540; 169555-169573; 169600-169629; 169631-169653; 169655-169695; 169697-169722; 169729-169782; 169791-169807; 169831-169847; 169850-169883; 169898-169925; 169937-169954; 169959-169980; 169982-170005; 170007-170021; 170036-170058; 170069-170097; 170105-170136; 170138-170232; 170247-170309; 170311-170347; 170350-170385; 170395-170418; 170434-170466; 170469-170483; 170485-170503; 170509-170532; 170534-170562; 170568-170585; 170624-170641; 170654-170675; 170685-170709; 170712-170731; 170745-170758; 170778-170791; 170859-170892; 170948-170969; 171019-171059; 171070-171086; 171090-171123; 171465-171478; 171526-171539; 171571-171584; 171645-171660; 172651-172670; 172985-172999; 173795-173808; 174279-174304; 174323-174355; 175105-175123; 175143-175166; 175221-175241; 175350-175364; 175493-175506; 175707-175793; 175804-175849; 175854-175941; 175944-176027; 176245-176258; 176323-176337; 176620-176636; 176719-176732; 179965-179994; 180044-180060; 180072-180104; 180136-180149; 180208-180225; 180266-180280; and 180634-180647. Oligonucleotides, such as antisense oligonucleotides which target these regions (Target Sequence List 3) of SEQ ID NO 1 may further target the human SCN10A nucleic acid target. In some embodiments, the contiguous nucleotide sequence of the oligonucleotide of the invention comprises at least 14 contiguous nucleotides which are present in one of the above listed target sequences.

Target Sequence List 4

In some advantageous embodiments the target sequence is a region of SEQ ID NO 1 selected from the group consisting of 99525-99542; 70094-70110; 133396-133411; 20666-20682; 103244-103261; 20666-20683; 103244-103262; 147238-147253; 171787-171803; 171787-171803; 147238-147253; 171788-171803; 103244-103260; 103244-103262; 130009-130025; 103244-103261; 98600-98616; 103244-103262; 171788-171803; 103244-103261; 70094-70110; 70094-70110; 70094-70110; 70094-70110; 70094-70110; 70094-70110; 70094-70110; 20666-20683; 97712-97728; 75261-75277; 75260-75276; 97713-97730; 75261-75277; 97712-97729; 20666-20683; 97712-97729; 20666-20683; 4426-4443; 75260-75276; 97715-97731; 20666-20683; 97712-97728; 4427-4443; 20666-20683; 97712-97729; 89475-89493; 99308-99324; 13076-13094; 87509-87527; 103272-103290; 82676-82692; 99526-99543; 82675-82691; 87510-87528; 97704-97720; 82675-82691; 89477-89495; and 13076-13094. In some embodiments, the contiguous nucleotide sequence of the oligonucleotide of the invention comprises at least 14 contiguous nucleotides which are present in one of the above listed target sequences.

Target Sequence List 5

In some advantageous embodiments the target sequence is an exon region of SEQ ID NO 1 selected from the group consisting of E1; E2; E3; E4; E5; E6; E7; E8; E9; E10; E11;

E12; E13; E14; E15; E16; E17; E18; E19; E20; E21; E22; E23; E24; E25; E26; and E27.

Target Sequence List 6

In some advantageous embodiments the target sequence is an intron region of SEQ ID NO 1 selected from the group consisting of I1; I2; I3; I4; I5; I6; I7; I8; I9; I10; I11; I12; I13; I14; I15; I16; I17; I18; I19; I20; I21; I22; I23; I24; I25; and I26.

In some embodiments, the contiguous nucleotide sequence of the oligonucleotide of the invention comprises at least 12 contiguous nucleotides which are present in the target sequence, such as a target sequence selected from those presented in Target Sequence list 1, 2, 3, 4, 5 & 6.

In some embodiments, the contiguous nucleotide sequence of the oligonucleotide of the invention comprises at least 14 contiguous nucleotides which are present in the target sequence, such as a target sequence selected from those presented in Target Sequence list 1, 2, 3, 4, 5 & 6.

In some embodiments, the contiguous nucleotide sequence of the oligonucleotide of the invention comprises at least 15 contiguous nucleotides which are present in the target sequence, such as a target sequence selected from those presented in Target sequence list 1, 2, 3, 4, 5 & 6.

Advantageous Target Regions

In some embodiments, the invention provides an oligonucleotide according to the invention which comprises a contiguous nucleotide sequence of at least 12 nucleotides in length which is 100% complementary to a sequence selected from the group consisting of SEQ ID NO 17-49.

In some embodiments, the invention provides an oligonucleotide according to the invention which comprises a contiguous nucleotide sequence of at least 14 nucleotides in length which is 100% complementary to a sequence selected from the group consisting of SEQ ID NO 17-49.

| SEQID | Target_seq | Region of SEQ ID No 1 start | end | length |
|---|---|---|---|---|
| 17 | GAAAATACGATATCCA | 16910 | 16925 | 16 |
| 18 | GAAGAGGAATTAAAATATA | 64215 | 64233 | 19 |
| 19 | GATTAGTGAAATTTAGTGAA | 64574 | 64593 | 20 |
| 20 | TATTTGTAAAAGAGCTGT | 70638 | 70655 | 18 |
| 21 | TGGATTTTTTTATGAATGGA | 71294 | 71313 | 20 |
| 22 | AAGAGGTGTTTAAATCA | 75259 | 75275 | 17 |
| 23 | TGAATGAGTAGTTATATAT | 76831 | 76849 | 19 |
| 24 | TGGTTGATAGATCATGA | 77336 | 77352 | 17 |
| 25 | TATTATGGAGAAATATACTGT | 77664 | 77684 | 21 |
| 26 | TGGTGAATGAAAAGTAAGA | 80259 | 80277 | 19 |
| 27 | GAGAATATATGAGAAAATAGTA | 81183 | 81204 | 22 |
| 28 | GAATTAGAATTTCAACAGA | 87509 | 87527 | 19 |
| 29 | TGTGTAAAGAAAACGAT | 89233 | 89249 | 17 |
| 30 | AAGAGATATAGGATCTG | 91258 | 91274 | 17 |
| 31 | TGTAAAAAGGTACTTGT | 91752 | 91768 | 17 |
| 32 | TTGGGAGTTGATAATGATT | 95878 | 95896 | 19 |
| 33 | AATGGTATTAAAACTGAT | 97715 | 97732 | 18 |
| 34 | TGTTTACATGATGGTCAT | 98983 | 99000 | 18 |
| 35 | TATTTGTGATGATGTGATCTATT | 99064 | 99087 | 24 |
| 36 | ATGAAGTTAATAATGGAC | 99356 | 99373 | 18 |
| 37 | TAAGTGGTTAAAATAATCA | 99525 | 99543 | 19 |
| 38 | TGGTGTGAGAGTTATGTTT | 101191 | 101209 | 19 |
| 39 | TAGAATTAAAATTTAAGGAAA | 101406 | 101426 | 21 |
| 40 | ATTGAAATGGTTAAGGA | 101534 | 101550 | 17 |
| 41 | TGAGAAAAAAAATAATTAA | 102373 | 102392 | 20 |
| 42 | TAAGAATTGAGAAATAATGAAGGTTCAAGATCTAGAGGAAATTTGTTTGATAAGATATTAAGCTGT | 107237 | 107302 | 66 |
| 43 | TGAAATAGTGATGGTTGT | 107586 | 107603 | 18 |

-continued

| SEQID | Target_seq | Region of SEQ ID No 1 | | |
|---|---|---|---|---|
| | | start | end | length |
| 44 | TATGTGTAAAATAGATTGTAA | 107812 | 107832 | 21 |
| 45 | TTGGTAATAATGTGTGATTT | 113551 | 113570 | 20 |
| 46 | TGAATTGATTATAAAAGTAA | 117040 | 117059 | 20 |
| 47 | TGATAAATTTGTAAGTGAA | 120589 | 120607 | 19 |
| 48 | GATGATTGAGTTTAAAGAA | 121347 | 121365 | 19 |
| 49 | ATGATTGGAAAATAAAGA | 125835 | 125852 | 18 |

Target Cell

The term a "target cell" as used herein refers to a cell which is expressing the target nucleic acid. In some embodiments the target cell may be in vivo or in vitro. In some embodiments the target cell is a mammalian cell such as a pig cell or a rodent cell, such as a mouse cell or a rat cell, or a primate cell such as a monkey cell or a human cell.

In some embodiments the target cell may be a dorsal root ganglion cell, such as a C fiber cell, or a somatosensory cell.

For in vitro assessment, the target cell may be an established cell line, such as SK-N-AS neuroblastoma cells, which is available from ATCC (CRL-2137).which as illustrated in the examples may be used for in vitro screening. Other exemplary target cells include SH-SY5Y cells (also available from ATCC, CRL-2266), or neuronal cells derived from human or pig IPSCs, or primary neurons such as pig primary neurons or human primary neurons (such as primary neurons isolated from dorsal root ganglions)—these may also be used for in vitro screening.

Advantageously the target cell expresses the SCN9A target.

Inhibition of the Target

The oligonucleotide of the invention is capable of down-regulating (inhibiting) the expression of human SCN9A in a cell which is expressing human SCN9A (such as the human $Na_v1.7$ encoded by SEQ ID NO 1). The inhibition of SCN9A results in the inhibition of $Na_v1.7$ protein in the cell, which may be determined by the protein level of $Na_v1.7$ or by a $Na_v1.7$ activity assay.

Therefore, advantageously the oligonucleotide of the invention is capable of down-regulating (inhibiting) the expression of human $Na_v1.7$ in a cell which is expressing human $Na_v1.7$ (such as the human $Na_v1.7$ encoded by SEQ ID NO 1).

In some embodiments the antisense oligonucleotide of the invention is capable of modulating the expression of the target by inhibiting or down-regulating it. Preferably, such modulation produces an inhibition of expression of at least 20% compared to the normal expression level of the target, more preferably at least 30%, at least 40%, at least 50%, at least 60%, at least 70%, at least 80%, or at least 90% inhibition compared to the normal expression level of the target. In some embodiments oligonucleotides of the invention may be capable of inhibiting expression levels of SCN9A mRNA by at least 50% or 60% in vitro following gymnotic application of 5 μM oligonucleotide in SK-N-AS neuroblastoma cells, which are available from ATCC (CRL-2137)—see the examples for suitable methodology using gymnotic delivery. In some embodiments compounds of the invention may be capable of inhibiting expression levels of SCN9A protein by at least 70% in vitro using 5 μM oligonucleotide to SK-N-AS neuroblastoma cells as described above.

Suitably, the examples provide assays which may be used to measure SCN9A inhibition.

Naturally Occurring Variant

The term "naturally occurring variant" refers to variants of SCN9A or SCN10A gene or transcripts which originate from the same genetic loci as the target nucleic acid, but may differ for example, by virtue of degeneracy of the genetic code causing a multiplicity of codons encoding the same amino acid, or due to alternative splicing of pre-mRNA, or the presence of polymorphisms, such as single nucleotide polymorphisms (SNPs), and allelic variants. Based on the presence of the sufficient complementary sequence to the oligonucleotide, the oligonucleotide of the invention may therefore target the target nucleic acid and naturally occurring variants thereof.

In some embodiments, the naturally occurring variants have at least 95% such as at least 98% or at least 99% homology to a mammalian SCN9A or SCN10A target nucleic acid, such as a target nucleic acid selected form the group consisting of SEQ ID NO: 1, 2, and 3. In some embodiments the naturally occurring variants have at least 99% homology to the human SCN9A target nucleic acid, such as that presented as SEQ ID NO: 1.

Modulation of Expression

The term "inhibition of expression" as used herein is to be understood as an overall term for an oligonucleotide's ability to decrease the level of target nucleic acid or target protein when compared to the amount of target nucleic acid or target protein before administration of the oligonucleotide. It will be understood that depending upon the mechanism of action, and antisense oligonucleotide may decrease the level of the target nucleic acid (e.g. via RNaseH cleavage), or may decrease the functionality (or alter the functionality) of the target nucleic acid, e.g. via modulation of splice switching or the pre-RNA.

Modulation, such as inhibition of expression may be determined by reference to a control experiment. It is generally understood that the control is an individual or target cell treated with a saline composition or an individual or target cell treated with a non-targeting oligonucleotide (mock).

One type of modulation is the ability of an oligonucleotide to inhibit, down-regulate, reduce, suppress, remove, stop, block, prevent, lessen, lower, avoid or terminate expression of the target or target nucleic acid, e.g. by degradation of mRNA or blockage of transcription.

High Affinity Modified Nucleosides

A high affinity modified nucleoside is a modified nucleotide which, when incorporated into the oligonucleotide enhances the affinity of the oligonucleotide for its complementary target, for example as measured by the melting temperature ($T_m$). A high affinity modified nucleoside of the present invention preferably result in an increase in melting temperature between +0.5 to +12° C., more preferably between +1.5 to +10° C. and most preferably between +3 to +8° C. per modified nucleoside. Numerous high affinity modified nucleosides are known in the art and include for example, many 2' substituted nucleosides as well as locked nucleic acids (LNA) (see e.g. Freier & Altmann; Nucl. Acid Res., 1997, 25, 4429-4443 and Uhlmann; Curr. Opinion in Drug Development, 2000, 3(2), 293-213).

Sugar Modifications

The oligomer of the invention may comprise one or more nucleosides which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of oligonucleotides, such as affinity and/or nuclease resistance.

Such modifications include those where the ribose ring structure is modified, e.g. by replacement with a hexose ring (HNA), or a bicyclic ring, which typically have a biradicle bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'-OH group naturally found in DNA and RNA nucleosides. Substituents may, for example be introduced at the 2', 3', 4' or 5' positions.

2' Sugar Modified Nucleosides

A 2' sugar modified nucleoside is a nucleoside which has a substituent other than H or —OH at the 2' position (2' substituted nucleoside) or comprises a 2' linked biradicle capable of forming a bridge between the 2' carbon and a second carbon in the ribose ring, such as LNA (2'-4' biradicle bridged) nucleosides.

Indeed, much focus has been spent on developing 2' sugar substituted nucleosides, and numerous 2' substituted nucleosides have been found to have beneficial properties when incorporated into oligonucleotides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside. For further examples, please see e.g. Freier & Altmann; Nucl. Acid Res., 1997, 25, 4429-4443 and Uhlmann; Curr. Opinion in Drug Development, 2000, 3(2), 293-213, and Deleavey and Damha, Chemistry and Biology 2012, 19, 937. Below are illustrations of some 2' substituted modified nucleosides.

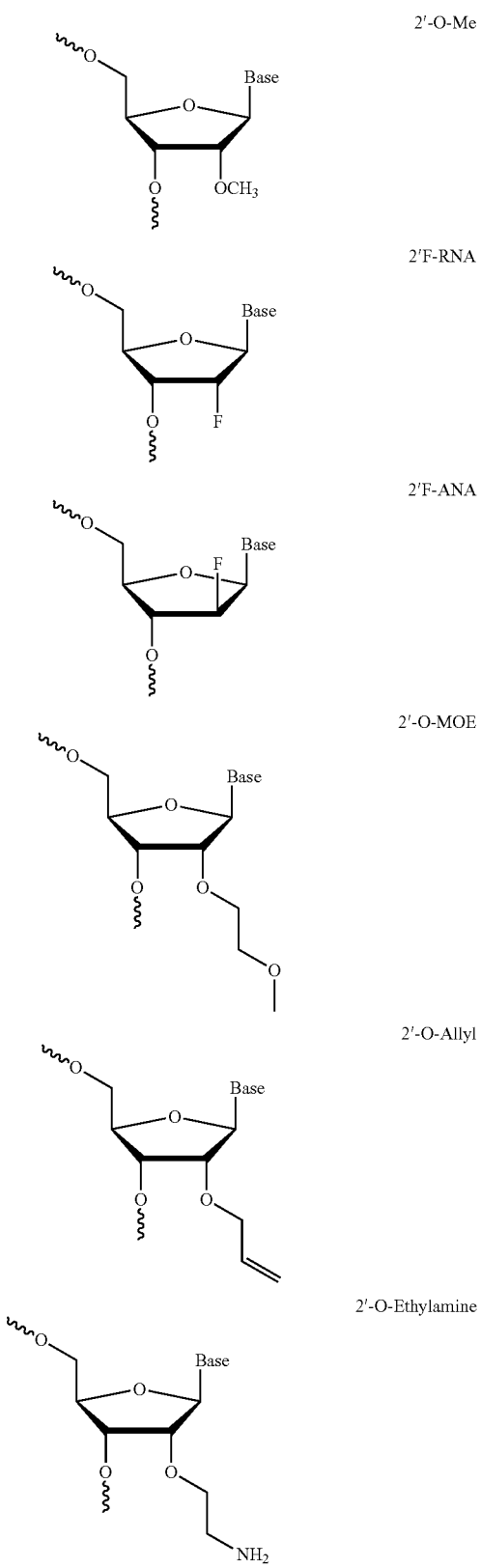

In relation to the present invention 2' substituted sugar modified nucleosides does not include 2' bridged nucleosides like LNA.

Locked Nucleic Acid Nucleosides (LNA Nucleoside)

A "LNA nucleoside" is a 2'-modified nucleoside which comprises a biradical linking the C2' and C4' of the ribose sugar ring of said nucleoside (also referred to as a "2'-4' bridge"), which restricts or locks the conformation of the ribose ring. These nucleosides are also termed bridged nucleic acid or bicyclic nucleic acid (BNA) in the literature. The locking of the conformation of the ribose is associated with an enhanced affinity of hybridization (duplex stabilization) when the LNA is incorporated into an oligonucleotide for a complementary RNA or DNA molecule. This can be routinely determined by measuring the melting temperature of the oligonucleotide/complement duplex.

Non limiting, exemplary LNA nucleosides are disclosed in WO 99/014226, WO 00/66604, WO 98/039352, WO 2004/046160, WO 00/047599, WO 2007/134181, WO 2010/077578, WO 2010/036698, WO 2007/090071, WO 2009/006478, WO 2011/156202, WO 2008/154401, WO 2009/067647, WO 2008/150729, Morita et al., Bioorganic & Med. Chem. Lett. 12, 73-76, Seth et al. J. Org. Chem. 2010, Vol 75(5) pp. 1569-81, and Mitsuoka et al., Nucleic Acids Research 2009, 37(4), 1225-1238, and Wan and Seth, J. Medical Chemistry 2016, 59, 9645-9667.

Further non limiting, exemplary LNA nucleosides are disclosed in Scheme 1.

Scheme 1

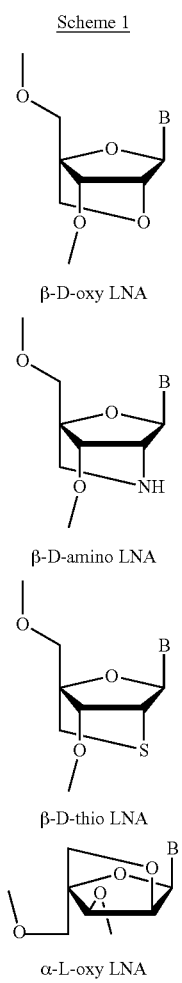

β-D-oxy LNA

β-D-amino LNA

β-D-thio LNA

α-L-oxy LNA

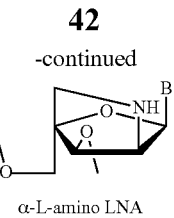

α-L-amino LNA

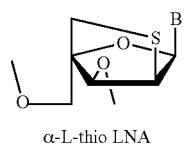

α-L-thio LNA

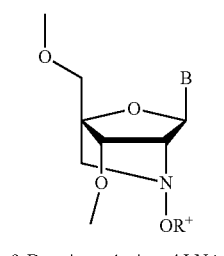

β-D-amino substituted LNA

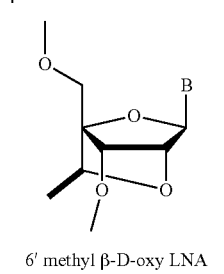

6' methyl β-D-oxy LNA

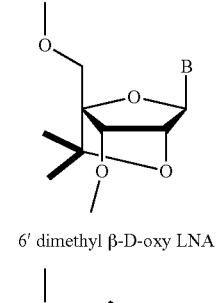

6' dimethyl β-D-oxy LNA

5' methyl β-D-oxy LNA

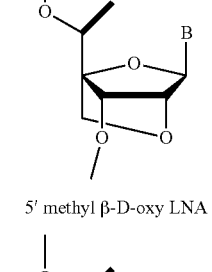

5' methyl, 6' dimethyl β-D-oxy LNA

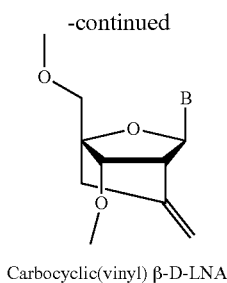

Carbocyclic(vinyl) β-D-LNA

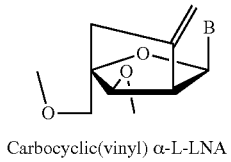

Carbocyclic(vinyl) α-L-LNA

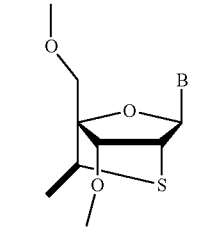

6' methyl thio β-D LNA

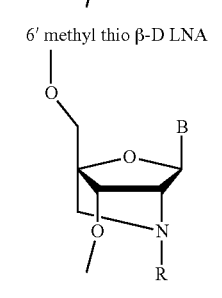

Substituted β-D amino LNA

Particular LNA nucleosides are beta-D-oxy-LNA, 6'-methyl-beta-D-oxy LNA, such as (S)-6'-methyl-beta-D-oxy-LNA (ScET) and ENA.

A particularly advantageous LNA is beta-D-oxy-LNA.

The compounds described herein can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

Pharmaceutically Acceptable Salts

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

Protecting Group

The term "protecting group", alone or in combination, signifies a group which selectively blocks a reactive site in a multifunctional compound such that a chemical reaction can be carried out selectively at another unprotected reactive site. Protecting groups can be removed. Exemplary protecting groups are amino-protecting groups, carboxy-protecting groups or hydroxy-protecting groups.

Nuclease Mediated Degradation

Nuclease mediated degradation refers to an oligonucleotide capable of mediating degradation of a complementary nucleotide sequence when forming a duplex with such a sequence.

In some embodiments, the oligonucleotide may function via nuclease mediated degradation of the target nucleic acid, where the oligonucleotides of the invention are capable of recruiting a nuclease, particularly and endonuclease, preferably endoribonuclease (RNase), such as RNase H. Examples of oligonucleotide designs which operate via nuclease mediated mechanisms are oligonucleotides which typically comprise a region of at least 5 or 6 consecutive DNA nucleosides and are flanked on one side or both sides by affinity enhancing nucleosides, for example gapmers, headmers and tailmers.

RNase H Activity and Recruitment

The RNase H activity of an antisense oligonucleotide refers to its ability to recruit RNase H when in a duplex with a complementary RNA molecule. WO01/23613 provides in vitro methods for determining RNaseH activity, which may be used to determine the ability to recruit RNaseH. Typically an oligonucleotide is deemed capable of recruiting RNase H if it, when provided with a complementary target nucleic acid sequence, has an initial rate, as measured in pmol/l/min, of at least 5%, such as at least 10% or more than 20% of the of the initial rate determined when using a oligonucleotide having the same base sequence as the modified oligonucleotide being tested, but containing only DNA monomers with phosphorothioate linkages between all monomers in the oligonucleotide, and using the methodology provided by Example 91-95 of WO01/23613 (hereby incorporated by reference). For use in determining RHase H activity, recombinant human RNase H1 is available from Lubio Science GmbH, Lucerne, Switzerland.

Gapmer

The antisense oligonucleotide of the invention, or contiguous nucleotide sequence thereof, may be a gapmer, also termed gapmer oligonucleotide or gapmer designs. The antisense gapmers are commonly used to inhibit a target nucleic acid via RNase H mediated degradation. A gapmer oligonucleotide comprises at least three distinct structural regions a 5'-flank, a gap and a 3'-flank, F-G-F' in the '5→3' orientation. The "gap" region (G) comprises a stretch of contiguous DNA nucleotides which enable the oligonucleotide to recruit RNase H. The gap region is flanked by a 5' flanking region (F) comprising one or more sugar modified nucleosides, advantageously high affinity sugar modified nucleosides, and by a 3' flanking region (F') comprising one or more sugar modified nucleosides, advantageously high affinity sugar modified nucleosides. The one or more sugar modified nucleosides in region F and F' enhance the affinity of the oligonucleotide for the target nucleic acid (i.e. are affinity enhancing sugar modified nucleosides). In some embodiments, the one or more sugar modified nucleosides in region F and F' are 2' sugar modified nucleosides, such as high affinity 2' sugar modifications, such as independently selected from LNA and 2'-MOE.

In a gapmer design, the 5' and 3' most nucleosides of the gap region are DNA nucleosides, and are positioned adjacent to a sugar modified nucleoside of the 5' (F) or 3' (F') region respectively. The flanks may further defined by having at least one sugar modified nucleoside at the end most distant from the gap region, i.e. at the 5' end of the 5' flank and at the 3' end of the 3' flank.

Regions F-G-F' form a contiguous nucleotide sequence. Antisense oligonucleotides of the invention, or the contiguous nucleotide sequence thereof, may comprise a gapmer region of formula F-G-F'.

The overall length of the gapmer design F-G-F' may be, for example 12 to 32 nucleosides, such as 13 to 24, such as 14 to 22 nucleosides, Such as from 14 to 17, such as 16 to 18 nucleosides.

By way of example, the gapmer oligonucleotide of the present invention can be represented by the following formulae:

$F_{1-8}$-$G_{6-16}$-$F'_{1-8}$, such as $F_{1-8}$-$G_{8-16}$-$F'_{2-8}$ with the proviso that the overall length of the gapmer regions F-G-F' is at least 12, such as at least 14 nucleotides in length.

In an aspect of the invention the antisense oligonucleotide or contiguous nucleotide sequence thereof consists of or comprises a gapmer of formula 5'-F-G-F'-3', where region F and F' independently comprise or consist of 1-8, such as 2-6, such as 3-4 2' sugar modified nucleosides, wherein there is at least one 2' sugar modified nucleoside positioned at the 3' end of region F (adjacent to a DNA nucleoside of region G), and at least one 2'sugar modified nucleoside positioned at the 5' end of region F' (positioned adjacent to a DNA nucleoside of region G), and G is a region between 6 and 16 nucleosides which are capable of recruiting RNaseH, such as a region of 6-16 DNA nucleosides, such as such as 10-15 contiguous DNA nucleosides, such as 10-14 contiguous DNA nucleotides, such as 11-15 contiguous DNA nucleotides, such as 13-15 contiguous DNA nucleotides.

LNA Gapmer

An LNA gapmer is a gapmer wherein either one or both of region F and F' comprises or consists of LNA nucleosides. A beta-D-oxy gapmer is a gapmer wherein either one or both of region F and F' comprises or consists of beta-D-oxy LNA nucleosides.

In some embodiments the LNA gapmer is of formula: [LNA]$_{1-5}$-[region G]-[LNA]$_{1-5}$, wherein region G is as defined in the Gapmer region G definition.

MOE Gapmers

A MOE gapmers is a gapmer wherein regions F and F' consist of MOE nucleosides. In some embodiments the MOE gapmer is of design [MOE]$_{1-8}$-[Region G]-[MOE]$_{1-8}$, such as [MOE]$_{2-7}$-[Region G]$_{5-16}$-[MOE]$_{2-7}$, such as [MOE]$_{3-6}$-[Region G]-[MOE]$_3$-6, wherein region G is as defined in the Gapmer definition. MOE gapmers with a 5-10-5 design (MOE-DNA-MOE) have been widely used in the art.

Mixed Wing Gapmer

A mixed wing gapmer is an LNA gapmer wherein one or both of region F and F' comprise a 2' substituted nucleoside, such as a 2' substituted nucleoside independently selected from the group consisting of 2'-O-alkyl-RNA units, 2'-O-methyl-RNA, 2'-amino-DNA units, 2'-fluoro-DNA units, 2'-alkoxy-RNA, MOE units, arabino nucleic acid (ANA) units and 2'-fluoro-ANA units, such as a MOE nucleosides. In some embodiments wherein at least one of region F and F', or both region F and F' comprise at least one LNA nucleoside, the remaining nucleosides of region F and F' are independently selected from the group consisting of MOE and LNA. In some embodiments wherein at least one of region F and F', or both region F and F' comprise at least two LNA nucleosides, the remaining nucleosides of region F and F' are independently selected from the group consisting of MOE and LNA. In some mixed wing embodiments, one or both of region F and F' may further comprise one or more DNA nucleosides.

Mixed wing gapmer designs are disclosed in WO2008/049085 and WO2012/109395.

Alternating Flank Gapmers

Flanking regions may comprise both LNA and DNA nucleoside and are referred to as "alternating flanks" as they comprise an alternating motif of LNA-DNA-LNA nucleosides. Gapmers comprising such alternating flanks are referred to as "alternating flank gapmers". "Alternative flank gapmers" are thus LNA gapmer oligonucleotides where at least one of the flanks (F or F') comprises DNA in addition to the LNA nucleoside(s). In some embodiments at least one of region F or F', or both region F and F', comprise both LNA nucleosides and DNA nucleosides. In such embodiments, the flanking region F or F', or both F and F' comprise at least three nucleosides, wherein the 5' and 3' most nucleosides of the F and/or F' region are LNA nucleosides.

An alternating flank region may comprise up to 3 contiguous DNA nucleosides, such as 1 to 2 or 1 or 2 or 3 contiguous DNA nucleosides.

Region D' or D" in an Oligonucleotide

The oligonucleotide of the invention may in some embodiments comprise or consist of the contiguous nucleotide sequence of the oligonucleotide which is complementary to the target nucleic acid, such as the gapmer F-G-F', and further 5' and/or 3' nucleosides. The further 5' and/or 3' nucleosides may or may not be fully complementary to the target nucleic acid. Such further 5' and/or 3' nucleosides may be referred to as region D' and D" herein.

The addition of region D' or D" may be used for the purpose of joining the contiguous nucleotide sequence, such as the gapmer, to a conjugate moiety or another functional group. When used for joining the contiguous nucleotide sequence with a conjugate moiety is can serve as a biocleavable linker. Alternatively it may be used to provide exonuclease protection or for ease of synthesis or manufacture.

Region D' and D" can be attached to the 5' end of region F or the 3' end of region F', respectively to generate designs of the following formulas D'-F-G-F', F-G-F'-D" or D'-F-G-F'-D". In this instance the F-G-F' is the gapmer portion of the oligonucleotide and region D' or D" constitute a separate part of the oligonucleotide.

Region D' or D" may independently comprise or consist of 1, 2, 3, 4 or 5 additional nucleotides, which may be complementary or non-complementary to the target nucleic acid. The nucleotide adjacent to the F or F' region is not a sugar-modified nucleotide, such as a DNA or RNA or base modified versions of these. The D' or D' region may serve as a nuclease susceptible biocleavable linker (see definition of linkers). In some embodiments the additional 5' and/or 3' end nucleotides are linked with phosphodiester linkages, and are DNA or RNA. Nucleotide based biocleavable linkers suitable for use as region D' or D" are disclosed in WO2014/076195, which include by way of example a phosphodiester linked DNA dinucleotide. The use of biocleavable linkers in poly-oligonucleotide constructs is disclosed in WO2015/113922, where they are used to link multiple antisense constructs (e.g. gapmer regions) within a single oligonucleotide.

In one embodiment the oligonucleotide of the invention comprises a region D' and/or D" in addition to the contiguous nucleotide sequence which constitutes the gapmer.

In some embodiments, the oligonucleotide of the present invention can be represented by the following formulae:

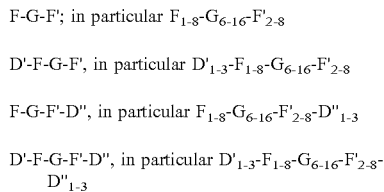

F-G-F'; in particular $F_{1-8}$-$G_{6-16}$-$F'_{2-8}$

D'-F-G-F', in particular $D'_{1-3}$-$F_{1-8}$-$G_{6-16}$-$F'_{2-8}$

F-G-F'-D", in particular $F_{1-8}$-$G_{6-16}$-$F'_{2-8}$-$D''_{1-3}$

D'-F-G-F'-D", in particular $D'_{1-3}$-$F_{1-8}$-$G_{6-16}$-$F'_{2-8}$-$D''_{1-3}$ In some embodiments the internucleoside linkage positioned between region D' and region F is a phosphodiester linkage. In some embodiments the internucleoside linkage positioned between region F' and region D" is a phosphodiester linkage.

Conjugate

The term conjugate as used herein refers to an oligonucleotide which is covalently linked to a non-nucleotide moiety (conjugate moiety or region C or third region).

Conjugation of the oligonucleotide of the invention to one or more non-nucleotide moieties may improve the pharmacology of the oligonucleotide, e.g. by affecting the activity, cellular distribution, cellular uptake or stability of the oligonucleotide. In some embodiments the conjugate moiety modify or enhance the pharmacokinetic properties of the oligonucleotide by improving cellular distribution, bioavailability, metabolism, excretion, permeability, and/or cellular uptake of the oligonucleotide. In particular the conjugate may target the oligonucleotide to a specific organ, tissue or cell type and thereby enhance the effectiveness of the oligonucleotide in that organ, tissue or cell type. A the same time the conjugate may serve to reduce activity of the oligonucleotide in non-target cell types, tissues or organs, e.g. off target activity or activity in non-target cell types, tissues or organs.

In an embodiment, the non-nucleotide moiety (conjugate moiety) is selected from the group consisting of carbohydrates, cell surface receptor ligands, drug substances, hormones, lipophilic substances, polymers, proteins, peptides, toxins (e.g. bacterial toxins), vitamins, viral proteins (e.g. capsids) or combinations thereof.

Linkers

A linkage or linker is a connection between two atoms that links one chemical group or segment of interest to another chemical group or segment of interest via one or more covalent bonds. Conjugate moieties can be attached to the oligonucleotide directly or through a linking moiety (e.g. linker or tether). Linkers serve to covalently connect a third region, e.g. a conjugate moiety (Region C), to a first region, e.g. an oligonucleotide or contiguous nucleotide sequence complementary to the target nucleic acid (region A).

In some embodiments of the invention the conjugate or oligonucleotide conjugate of the invention may optionally, comprise a linker region (second region or region B and/or region Y) which is positioned between the oligonucleotide or contiguous nucleotide sequence complementary to the target nucleic acid (region A or first region) and the conjugate moiety (region C or third region).

Region B refers to biocleavable linkers comprising or consisting of a physiologically labile bond that is cleavable under conditions normally encountered or analogous to those encountered within a mammalian body. Conditions under which physiologically labile linkers undergo chemical transformation (e.g., cleavage) include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic enzymes or hydrolytic enzymes or nucleases. In one embodiment the biocleavable linker is susceptible to S1 nuclease cleavage. In a preferred embodiment the nuclease susceptible linker comprises between 1 and 10 nucleosides, such as 1, 2, 3, 4, 5, 6, 7, 8, 9 or 10 nucleosides, more preferably between 2 and 6 nucleosides and most preferably between 2 and 4 linked nucleosides comprising at least two consecutive phosphodiester linkages, such as at least 3 or 4 or 5 consecutive phosphodiester linkages. Preferably the nucleosides are DNA or RNA. Phosphodiester containing biocleavable linkers are described in more detail in WO 2014/076195 (hereby incorporated by reference)—see also region D' or D" herein. Region Y refers to linkers that are not necessarily biocleavable but primarily serve to covalently connect a conjugate moiety (region C or third region), to an oligonucleotide (region A or first region). The region Y linkers may comprise a chain structure or an oligomer of repeating units such as ethylene glycol, amino acid units or amino alkyl groups The oligonucleotide conjugates of the present invention can be constructed of the following regional elements A-C, A-B-C, A-B-Y-C, A-Y-B-C or A-Y-C. In some embodiments the linker (region Y) is an amino alkyl, such as a C2-C36 amino alkyl group, including, for example C6 to C12 amino alkyl groups. In a preferred embodiment the linker (region Y) is a C6 amino alkyl group.

Treatment

The term 'treatment' as used herein refers to both treatment of an existing disease (e.g. a disease or disorder as herein referred to), or prevention of a disease, i.e. prophylaxis. It will therefore be recognized that treatment as referred to herein may, in some embodiments, be prophylactic.

In some embodiments treatment is performed on a subject who is suffering chronic pain, or is expected to suffer chromic pain (prophylactic treatment).

DETAILED DESCRIPTION OF THE INVENTION

The Oligonucleotides of the Invention

The invention relates to oligonucleotides capable of inhibiting the of voltage-gated sodium ion channel encoding nucleic acids, such as SCN9A or SCN10A, or both SCN9A and SCN10A.

The invention relates to oligonucleotides capable of inhibiting the expression of voltage-gated sodium ion channels, such as Nav1.7 or Nav1.8 or both Nav1.7 or Nav1.8. Oligonucleotides targeting both Nav1.7 and Nav1.8 (or optionally Nav1.9) may be designed by selecting the regions of identity or high sequence similarity between the SCN9A and SCN10A transcripts (or optionally SCN11A). In some embodiments the oligonucleotide of the invention may target both SCN9A and SCN10A transcripts, wherein the contiguous nucleotide sequence of the oligonucleotide is either fully complementary to one of SCN9A and SCN10A transcripts, and has no more than a single mismatch to the other of SCN9A and SCN10A transcript. In some embodiments, the contiguous nucleotide sequence comprises a single mismatch to both SCN9A and SCN10A transcript at the same position in the contiguous nucleotide sequence. In some embodiments it is useful to include a universal base at the site of a mismatch against one of, or both of SCN9A and SCN10A transcripts.

In some embodiments the oligonucleotide of the invention may target both SCN9A and SCN10A transcripts, wherein the contiguous nucleotide sequence of the oligonucleotide is either fully complementary to one of SCN9A and SCN11A transcripts, and has no more than a single mismatch to the other of SCN9A and SCN11A transcript. In some embodiments, the contiguous nucleotide sequence comprises a single mismatch to both SCN9A and SCN11A transcript at the same position in the contiguous nucleotide sequence. In some embodiments it is useful to include a universal base at the site of a mismatch against one of, or both of SCN9A and SCN11A transcripts.

In some embodiments the oligonucleotide of the invention may target SCN9A and SCN10A and SCN11A transcripts, wherein the contiguous nucleotide sequence of the oligonucleotide is either fully complementary to one of SCN9A, SCN10A and SCN11A transcripts, and has no more than a single mismatch to the others of SCN9A, SCN10A and SCN11A transcripts. The human SCN11A pre-mRNA transcript is disclosed as ENSG00000168356 (Ensembl version ENSG00000168356.11).

The modulation may be achieved by hybridizing to a target nucleic acid encoding the voltage-gated sodium ion channels. The target nucleic acid may be a mammalian SCN9A or SCN10A sequence, such as a sequence selected from the group consisting of SEQ ID NO: 1, 2, and 3.

The oligonucleotide of the invention is an antisense oligonucleotide which targets SCN9A or SCN10A. The antisense oligonucleotide is complementary to a target sequence present in the target nucleic acid. Suitable target regions are disclosed herein (see for example Target Sequence Lists 1, 2, 3, & 4).

Certain illustrated target sequences are SEQ ID NOs 17-49.

In some embodiments the contiguous nucleotide sequence of the antisense oligonucleotide is at least 90% complementary to, such as fully complementary to an intron region of the SCN9A target nucleic acid sequence such as a target sequence selected 11-126 of SEQ ID NO 1.

In some embodiments the contiguous nucleotide sequence of the antisense oligonucleotide is at least 90% complementary to, such as fully complementary to an exon region of the SCN9A target nucleic acid sequence such as a target sequence selected E1-E27 of SEQ ID NO 1.

Contiguous Nucleotide Sequences

In some embodiments, the antisense oligonucleotides of the invention comprises a contiguous nucleotide sequence selected from the group consisting of SEQ ID NO 50-641.

In some embodiments, the antisense oligonucleotides of the invention comprises a contiguous nucleotide sequence of at least 12 nucleotides in length which are identical to a sequence selected from the group consisting of SEQ ID NO 50-641.

In some embodiments, the antisense oligonucleotides of the invention comprises a contiguous nucleotide sequence of at least 14 nucleotides in length which are identical to a sequence selected from the group consisting of SEQ ID NO 50-641.

In determining identity, unless otherwise specified fully identity is meant, and identity of the antisense oligonucleotides of the invention which comprises a contiguous nucleotide sequence which is identical to a sequence selected from the group consisting of SEQ ID NO 50-641, is measured across the length of the contiguous nucleotide sequence. In some embodiments the contiguous nucleotide sequence of the antisense oligonucleotide of the invention comprises a sequence selected from the group consisting of SEQ ID NO 50-641.

It will be understood that the antisense oligonucleotide may comprise a modified base where a unmodified base is indicated in the reference sequence—for example a U base may be used in place of a T, and 5-methyl cytosine may be used in place of a C.

| SEQID | Contiguous Nucleotide Sequence |
|---|---|
| 50 | ATGTTTACTATAATCACA |
| 51 | GGCATATCATATATCC |
| 52 | CCAATTTTTTCTTAAAATAT |
| 53 | TCTCATAAATCCTCATAT |
| 54 | TATTCTACCCACATTCT |
| 55 | AGTATTCTACCCACATT |
| 56 | AAGTATTCTACCCACAT |
| 57 | TATCTCATATTCCACAAA |
| 58 | TTATCTCATATTCCACA |
| 59 | GTTATCTCATATTCCAC |
| 60 | TTCAATGAAGAAATTTCA |
| 61 | GCTCAATTTTCCAATTATT |
| 62 | TCTAATCTTATTTATCTTTC |
| 63 | TCCCATAATATTTACCTA |
| 64 | ATCACTTCAACTTTATAATA |
| 65 | TTCATCACTTCAACTTTA |
| 66 | TCCTACCTGAATTACC |
| 67 | GCTTTTAACACTTTATA |
| 68 | CTCCTAATATATAATATACT |
| 69 | TCTCCTAATATATAATATA |
| 70 | ATATATCTCCTAATATATA |
| 71 | ACATATATATCTCCTAATA |
| 72 | CTCATATCTACTTATCAT |
| 73 | TACTCATATCTACTTATCA |
| 74 | TCTACTCATATCTACTTA |
| 75 | ACATCTACTCATATCTACT |

-continued

| SEQID | Contiguous Nucleotide Sequence |
|---|---|
| 76 | AATTACACCATTCCTCT |
| 77 | CCCTTTTAATTACACCAT |
| 78 | ACACTATTATACATTCCCA |
| 79 | AGCTACACTATTATACAT |
| 80 | ACTTCCATATTATTTTCCAT |
| 81 | TCTCCTTAAATACATCAAAT |
| 82 | ATATTACTGTACTCCC |
| 83 | ATATTTATACAACAACTCA |
| 84 | TAGTCACCATTTTTCAT |
| 85 | AGAAAATAATTCCTATCCT |
| 86 | ATACATGTATCCACTTC |
| 87 | TTCCAATATTATTATACA |
| 88 | ACCCTTATTTAAATAATTA |
| 89 | TCACGTTAAATCCCATCT |
| 90 | ACGTTAAATCCCATC |
| 91 | TTCACGTTAAATCCCA |
| 92 | GGATATCGTATTTTCT |
| 93 | TCTGGATATCGTATT |
| 94 | GATATATTATCCATCTCA |
| 95 | TGATATATTATCCATCT |
| 96 | AGCATCTACATTTTAATT |
| 97 | TCTTAATTCTTATCATTTTA |
| 98 | AACTTCTTAATTCTTATCA |
| 99 | TACAATAATTATCTTCTCA |
| 100 | TGCAAATAATACCCTAT |
| 101 | CTCTATTCTAAATAAACCTT |
| 102 | ACTCTATTCTAAATAAACC |
| 103 | ATGACTCTATTCTAAATA |
| 104 | TAAGCATATATTTTCCCA |
| 105 | TCATTTCCATTAAATCCAA |
| 106 | TTTCATTTCCATTAAATCC |
| 107 | TTTTATCCTACTTCTAC |
| 108 | TCCCTCAAATATAAATTC |
| 109 | ACTGTTTTCTCTAAACC |
| 110 | AGATTCACTACATCCA |
| 111 | GCACTCTGATTACATTTCCT |
| 112 | TATTTAATCACTTTATCTAA |
| 113 | ATATTTAATCACTTTATCT |

-continued

| SEQID | Contiguous Nucleotide Sequence |
|---|---|
| 114 | ATCAACCACACAATTACTTT |
| 115 | TATCAACCACACAATTACTT |
| 116 | TTATCAACCACACAATTAC |
| 117 | TCAATAAAATTCCTTATACT |
| 118 | TCATTTTATTTATTTCAATT |
| 119 | TATACACTCTTTCTCTATTC |
| 120 | TGACCATCTTATTCATC |
| 121 | CCTGATACTCATTCCCA |
| 122 | TTTCTCTTTATCTTTTATC |
| 123 | AAATCAACCCTAAACCC |
| 124 | AAAGTACCATTTACTCCC |
| 125 | TTCATATACTCTTATTTTA |
| 126 | CTAATTTTTCATATACTCTT |
| 127 | TCTAATTTTTCATATACTC |
| 128 | CTCTAATTTTTCATATACT |
| 129 | ACATTTTTCCTACAAACTA |
| 130 | CTACTATTCCATCATTTTT |
| 131 | CAATTACACCTACAACTTC |
| 132 | TCCAATTACACCTACAAC |
| 133 | GCCTTAATCAATTTCTCAA |
| 134 | CACTTTCCAATATTACT |
| 135 | TTACACTTTCCAATATTAC |
| 136 | CATTACACTTTCCAATATTA |
| 137 | ACATTACACTTTCCAATA |
| 138 | ATATACCCCAATTACTCCA |
| 139 | ATACTAGCAATTCATCA |
| 140 | ATACCATTAACTATCACC |
| 141 | AGATACCATTAACTATCA |
| 142 | CCCATCTTCATTATATTA |
| 143 | TTCTGATCTCTCTTATA |
| 144 | ATTTCATTCAGGAAATAC |
| 145 | TCATTTCATCAATAACATTA |
| 146 | TTGCTTTTTACTAACA |
| 147 | GTTTCATTTCTTTATTAT |
| 148 | GCTATTATATTACTTTT |
| 149 | GTCCTCTAATCATATCACA |
| 150 | TAGTCCTCTAATCATATC |
| 151 | TTAGTCCTCTAATCATA |

-continued

| SEQID | Contiguous Nucleotide Sequence |
|---|---|
| 152 | ACTTAGTCCTCTAATCA |
| 153 | TAAATAAAACAATCCCCA |
| 154 | TAATTAAATAAACAATCCC |
| 155 | ATACATACCTCTATTATT |
| 156 | TCAATACATACCTCTATTA |
| 157 | CTCAATACATACCTCTATT |
| 158 | GAACTCAATACATACCTC |
| 159 | AGAACTCAATACATACC |
| 160 | TGAATTTTATTCCCTTC |
| 161 | ACACAATACCATATTTCA |
| 162 | TGCTATAATATTTTATCT |
| 163 | ACAAACTTTCAATACTCTA |
| 164 | TCTTCTACACTATTATTC |
| 165 | ATATCTTCTACACTATTATT |
| 166 | TATATCTTCTACACTATTA |
| 167 | TTATATCTTCTACACTA |
| 168 | AGCTCATTTCCTATAC |
| 169 | TACTTTTTTTCTATCCAA |
| 170 | TCTACTTTTTTTCTATC |
| 171 | TTTATTAATTTACTCCTT |
| 172 | ATTTTATTAATTTACTCC |
| 173 | ACCAATACCATAAATTCCA |
| 174 | ATTAATATTTTTTCTCCAT |
| 175 | TTTATTAATATTTTTTCTCC |
| 176 | TCCTTTTATTAATATTTTTT |
| 177 | CCTCCTTTTATTAATATT |
| 178 | GCCTCCTTTTATTAATAT |
| 179 | TAACATATCTACCATCTC |
| 180 | AATCCCTTACCATTATT |
| 181 | ACAGCTTCATTTAACTA |
| 182 | TTAACCAAATCTATACACT |
| 183 | TTAGACTAACCATCCTA |
| 184 | TATTAGACTAACCATCC |
| 185 | ACCTCATAATACTTTTC |
| 186 | TACCTGATAACATCTTT |
| 187 | TTACTAATCTAAATACCT |
| 188 | TCTCATTTTACTAATCTA |
| 189 | TTCTCATTTTACTAATCT |
| 190 | AACCAAGTCTATATCCA |
| 191 | TCACCTTCATAACTTATC |
| 192 | ATTTTAAATTACTCTCCTAT |
| 193 | ATATTTAAATTACTCTCCT |
| 194 | AGTACAATTTAACTCCCT |
| 195 | ATTATCTATAATATACCTA |
| 196 | TCCATAAATCTATTCCAA |
| 197 | TTCCATAAATCTATTCCA |
| 198 | TTTCCATAAATCTATTCC |
| 199 | AGCAAATAAATTCCAACAC |
| 200 | TCATGCTTCCATAATTA |
| 201 | CCTTTCCCATTACAATTT |
| 202 | ACATGATACTTAATACC |
| 203 | CAACAATATCAATCTTCC |
| 204 | TTATTAATATTTCTTCTTCA |
| 205 | TCAGTTAATCATCTCAC |
| 206 | TTGCCATTAAAATTTCC |
| 207 | GATGAACAGACCAAACT |
| 208 | ATCCATACATCCTAAAAT |
| 209 | CTCATCCATACATCCTA |
| 210 | GTCCAAATATCATATCAT |
| 211 | TGTCCAAATATCATATC |
| 212 | ACCATTAATCTCATATT |
| 213 | TCACCATTAATCTCATAT |
| 214 | CACCATTAATCTCATA |
| 215 | ATCAATCAATATTTATTCTT |
| 216 | ATACTTTACTTTTCAAATTT |
| 217 | TATACTTTACTTTTCAAATT |
| 218 | CTTTATACTTTACTTTTCAA |
| 219 | TCTTTATACTTTACTTTTCA |
| 220 | CCAATATTCCTATTCTC |
| 221 | TGTAACCACTCTTATCAAT |
| 222 | AATGTAACCACTCTTATC |
| 223 | TTCCAATTTCCTATTAAT |
| 224 | CATTCCAATTTCCTATTA |
| 225 | AAATTTTCCTAAATTCCCC |
| 226 | TTCACTAATCTCAATTTA |
| 227 | ACTAAATTTCACTAATCTCA |

| SEQID | Contiguous Nucleotide Sequence |
|---|---|
| 228 | TTATTCACTAAATTTCACT |
| 229 | TGCTAAACAATTATACTA |
| 230 | AATTATTCATCCATTCTTTC |
| 231 | ATCAATTTTTCACATCAATA |
| 232 | TTATACCCACTTACTC |
| 233 | GTACTTATACCCACTTAC |
| 234 | ATGTACTTATACCCACTT |
| 235 | TGTACTTATACCCACT |
| 236 | AAATGTACTTATACCCAC |
| 237 | CATCTAATTTTTCTAATCT |
| 238 | TTATAAAACATACACCCA |
| 239 | ATTATAAAACATACACCC |
| 240 | CTTCTATCAAAAATTCACC |
| 241 | CAAAAGTATATATTCCA |
| 242 | TACGCAAAAACAATGAC |
| 243 | TTACGCAAAAACAATG |
| 244 | TACTTACGCAAAAACA |
| 245 | CAGCTCTTTTACAAATAT |
| 246 | TCTATGACATTACCT |
| 247 | ACACCAATTACTTCTTACC |
| 248 | CACACCAATTACTTCTTAC |
| 249 | TTCACACCAATTACTTCTTA |
| 250 | GCTTCACACCAATTACTTC |
| 251 | CCTAATGCTTCACACC |
| 252 | ACAACTCCCAAATAGTT |
| 253 | AAATTTAATTAAAATTGC |
| 254 | ATGCATTATATCAAATCA |
| 255 | AAAACACAAGCTTTCCTA |
| 256 | TCATCCAATATTCATCA |
| 257 | ATATTACTTTTTATTATCTA |
| 258 | GCTAAATTCCTCATCAAAT |
| 259 | TGCTAAATTCCTCATCAAA |
| 260 | ATATGCTAAATTCCTCATCA |
| 261 | ATGCTAAATTCCTCATC |
| 262 | TATGCTAAATTCCTCAT |
| 263 | GAAAATATGCTAAATTCCT |
| 264 | TGCAATCTAACTTCATA |
| 265 | CTTGATTTAAACACCTCT |
| 266 | ACTTGATTTAAACACCT |
| 267 | GCTTCTTACTATCTTTTA |
| 268 | GTCTTCTTTAATCCATCA |
| 269 | CTATATTATATATCCACCT |
| 270 | CTCTATATTATATATCCAC |
| 271 | TCTCTATATTATATATCCA |
| 272 | ATTCTCTATATTATATATCC |
| 273 | CCAATTCTCTATATTATAT |
| 274 | TCCAATTCTCTATATTATA |
| 275 | TCTCCAATTCTCTATATTAT |
| 276 | ATCTCCAATTCTCTATATTA |
| 277 | AATCTCCAATTCTCTATATT |
| 278 | TAAATCTCCAATTCTCTATA |
| 279 | GAATTTATCTCCAAACTCA |
| 280 | TGTCTACACATATTACC |
| 281 | TGATCCCATCTTATAC |
| 282 | TATATTTCTCCATAATAC |
| 283 | TATTCCTCAATAAACCTA |
| 284 | GACTTCCTATTTTACTCA |
| 285 | TTTCTCATATATTCTCCC |
| 286 | TTTTCTCATATATTCTCC |
| 287 | CTATTTTCTCATATATTCT |
| 288 | TTTACTATTTTCTCATATAT |
| 289 | TTACTATTTTCTCATATA |
| 290 | AACAAATATTACATACCCT |
| 291 | TGCCATTAAATAAATACA |
| 292 | TGCCATTCAAAAATACAAT |
| 293 | TAATATACTTTTATCATACA |
| 294 | ATTACTTTATTCATCTCAT |
| 295 | TAATTACTTTATTCATCTCA |
| 296 | TTAATTACTTTATTCATCTC |
| 297 | TTTAATTACTTTATTCATCT |
| 298 | ATTTAATTACTTTATTCATC |
| 299 | TTCTATCTTTTCTTTCTTTA |
| 300 | CATGCATTTTTTCCTACA |
| 301 | GAAATTCTAATTCTTTCT |
| 302 | AACATCTGTTGAAATTCT |
| 303 | ATTTAATCCATCATTATTCT |

| SEQID | Contiguous Nucleotide Sequence |
|---|---|
| 304 | TAACTCCATATCATCAATA |
| 305 | ATTAACTCCATATCATCAA |
| 306 | AATTAACTCCATATCATCA |
| 307 | TTTACCTAAAATCATACCA |
| 308 | TTATATATCAATCCCCA |
| 309 | TTTTATATATCAATCCCC |
| 310 | TTTTTATATATCAATCCC |
| 311 | CTAAAAAGACTTGTTCT |
| 312 | ACTAAAAAGACTTGTTC |
| 313 | CCTTATCTATTATCACC |
| 314 | GCCTTATCTATTATCAC |
| 315 | TTGCCTTATCTATTATC |
| 316 | TCCTTACGCTGTCATCA |
| 317 | TAATCCAAATTTCTTCATA |
| 318 | CTTTCAAGCCTAATCA |
| 319 | TGTTTTCATATAAACCAT |
| 320 | GATTATTACATACCTTCCA |
| 321 | TATCTTTACCATCATTTAA |
| 322 | GTTATCTTTACCATCATT |
| 323 | AGACTTACCAAATTTCC |
| 324 | GAACATGTTGACTCAC |
| 325 | AGTTTTAATACCATTTCA |
| 326 | CAGTTTTAATACCATTTC |
| 327 | ATAATTTATCCTTAATTCT |
| 328 | TCAATGTTTCCAATCTT |
| 329 | CATCTGGTTACATACCACC |
| 330 | ATCACAAAATAATTTCCAC |
| 331 | CATCACAAAATAATTTCCA |
| 332 | TCATCACAAAATAATTTCC |
| 333 | TAGATCACATCATCACAA |
| 334 | CCTAAATACCTTTCTTTTCA |
| 335 | ATACCTAAATACCTTTCTT |
| 336 | CCCTAAATAATACCTAAACA |
| 337 | TCCACCCTAAATAATACC |
| 338 | AGTTAACACTAATTCTACA |
| 339 | GTCTCTAATATTTCTATA |
| 340 | TAGCATTCATCTATCATT |
| 341 | CCTAGCATTCATCTATC |
| 342 | GTTTCACATAATTTATTCC |
| 343 | TTAGAATAAATTCACG |
| 344 | TAATTTCTCAAAAAATTAAA |
| 345 | CCTTCATTATTTCTCAATT |
| 346 | CACAACCATCACTATTTC |
| 347 | TTATTACAATCTATTTTACA |
| 348 | CACTCAATTCCATACTTAT |
| 349 | ACTCAATTCCATACTTA |
| 350 | TCTCTTTTAAATTCAATCT |
| 351 | TATCTCTTTTAAATTCAATC |
| 352 | GCTATCTCTTTTAAATTCA |
| 353 | GTAATTTATCAATTTCCA |
| 354 | AATCTTTTCTTAATCTTTTA |
| 355 | GTACAATACCATTACAACA |
| 356 | CAGTTTTACTTTTCAATA |
| 357 | ATCAATTCTACTTAATACA |
| 358 | TATTCTTATTTTCATATATA |
| 359 | ATATTCTTATTTTCATATA |
| 360 | AATGATCAATCACCCTT |
| 361 | TTGATCTACTTAATTTA |
| 362 | AGTCCCATAACTAACA |
| 363 | TATCACTTATTCATTCATA |
| 364 | TTATCCATCTTTTAATTTA |
| 365 | ATATCTTTCCATATTTTTCA |
| 366 | GGTAACAACTTTTAAATA |
| 367 | CTAGTATACAACATCATA |
| 368 | ACCTAGTATACAACATC |
| 369 | ACCACATTAAATTCTCAAT |
| 370 | TTACAACTTTATCTTTTTA |
| 371 | ACAACCTATACCCTAT |
| 372 | AGGACAACCTATACCC |
| 373 | TGATCTTTCTATCTACAC |
| 374 | TTGATCTTTCTATCTACA |
| 375 | AGCCTTATTTAATAATC |
| 376 | TGTCTTTATTTTCCAATC |
| 377 | TGTTTCCATAATATTTCT |
| 378 | CCATATACCTTCTCCAT |
| 379 | TTTCCATATACCTTCTC |

| SEQID | Contiguous Nucleotide Sequence |
|---|---|
| 380 | TCTTTTCCATATACCTTC |
| 381 | CACTATACAAAACTCTACCA |
| 382 | ACCCTCACTATACAAAC |
| 383 | CACCCTCACTATACAAA |
| 384 | AGCACAATATAAAACCAC |
| 385 | TTAACATTATCTTTCCAA |
| 386 | CTAGCACTTTAATTTCCA |
| 387 | GAATCTCTTCTTAACTCT |
| 388 | AAATAAATGACTATAACT |
| 389 | ACACCTTTCTAAACAATA |
| 390 | AGTCTTTAAACCACTTTC |
| 391 | ACCAAATAATTTCAACACC |
| 392 | TCCCTCAACCAAATAATTT |
| 393 | TCCACCAGATTTTTCC |
| 394 | AAGCTTTCAAACCAAC |
| 395 | TTATCCTAAAACTACCAT |
| 396 | AAGCACCTCATATCTTC |
| 397 | TTACCACTCATTTATTTCT |
| 398 | AGTTACCACTCATTTAT |
| 399 | TACTCTAAAATTATCCTTA |
| 400 | CAGATTCTTCTTATTCTA |
| 401 | GTTCTAATATTCCTCACA |
| 402 | CTCTTATCTTCCAATTTTA |
| 403 | TCTATAATTTCTTCTTATTT |
| 404 | CTTCTATAATTTCTTCTTA |
| 405 | TCCTTCTATAATTTCTTCTT |
| 406 | ATTCCTTCTATAATTTCTT |
| 407 | CATTCCTTCTATAATTTCT |
| 408 | ACATTCCTTCTATAATTTC |
| 409 | GCCATATCTCTTAATTTAA |
| 410 | AGCCATATCTCTTAATT |
| 411 | ACAGCCATATCTCTTAA |
| 412 | TAAGTTTCAAATAACCC |
| 413 | TCCATTATTTTCCACTTA |
| 414 | ACATCCATTATTTTCCAC |
| 415 | TCACATCCATTATTTTCCA |
| 416 | TTCACATCCATTATTTTC |
| 417 | TCATTCACATCCATTATTT |

| SEQID | Contiguous Nucleotide Sequence |
|---|---|
| 418 | TTATATATTTATCTATTTCA |
| 419 | AGCAATACAATCAATACA |
| 420 | CCACAATTACCATAACC |
| 421 | CACCAAAGATCTACCAA |
| 422 | TATTTTCTTACCCTCATT |
| 423 | AGTATTTTCTTACCCTCA |
| 424 | TAGTATTTTCTTACCCT |
| 425 | TTAGTATTTTCTTACCCC |
| 426 | TTATAATTCCACTTACTTT |
| 427 | GTTATAATTCCACTTACT |
| 428 | TAGTTATAATTCCACTTA |
| 429 | TTTAGTTATAATTCCAC |
| 430 | GTTTTCTCAAATATAATT |
| 431 | GAATTCTAATACCACCTT |
| 432 | ATATACTAAACTATTCTCC |
| 433 | TTCATTTATCCTTCAAAATA |
| 434 | TTCATTATTTCATTTATCCT |
| 435 | TTTAATCCTTTCTTTATTTC |
| 436 | CAGTTTTCTTTAATCCT |
| 437 | ATGATCCTATTATTACCA |
| 438 | TTGACTAACATTCATAA |
| 439 | TTCCATCGCACATTTT |
| 440 | ACATAACCTTTTATTTTTA |
| 441 | CATTCTAAATCTTAGTC |
| 442 | ATAATCGTCCATCCCTT |
| 443 | TCACATAAACTCATCCAA |
| 444 | TTCACATAAACTCATCC |
| 445 | ACTTATTTCACATAAACTC |
| 446 | CTTCAAATAACTACAAAG |
| 447 | TGTATTCATTACATACT |
| 448 | ACTCTTAACAATTTATTCA |
| 449 | TCACTCTTAACAATTTATTC |
| 450 | TAACATAATCACTCTTAACA |
| 451 | CCAGAACCTATTATTTA |
| 452 | ATTATTCAATCCTCTATA |
| 453 | TAACCTTCATCACATACT |
| 454 | ATCTAACCTTCATCACATAC |
| 455 | TCTAACCTTCATCACATA |

| SEQID | Contiguous Nucleotide Sequence |
|---|---|
| 456 | CTCTATCTAACCTTCATC |
| 457 | TGACTCTATCTAACCTTC |
| 458 | CCTCTTTTATCAACACAATT |
| 459 | TCTCCAAATCTTAAATTTC |
| 460 | TTTACTATTTCTCCAAATC |
| 461 | TCTTTTACTATTTCTCCAAA |
| 462 | CATCTTTTACTATTTCTCCA |
| 463 | TCATCTTTTACTATTTCTC |
| 464 | CCTCATCTTTTACTATTT |
| 465 | AACCTCATCTTTTACTA |
| 466 | TTTTTATATCTACTCTCA |
| 467 | TTAATAAACATCAATCTCC |
| 468 | ATATTTCCTATTCTCCATT |
| 469 | CATACTGCTCTTTCTA |
| 470 | ATGCAAATAACTTCATCA |
| 471 | TTTAACTTTCTTACCACAA |
| 472 | TTAACTTTCTTACCACA |
| 473 | CATATTCATCTCACCTAC |
| 474 | TCATATTCATCTCACCTA |
| 475 | TTCATATTCATCTCACCT |
| 476 | AATTTTCATATTCATCTCAC |
| 477 | CTACCTTTTTAATTCTAAAT |
| 478 | ACTACCTTTTTAATTCTA |
| 479 | TGACTACCTTTTTAATTC |
| 480 | TATATTTTTTTACCCCT |
| 481 | TCAAATATACATCCTTG |
| 482 | GTCAAATATACATCCT |
| 483 | GGTCAAATATACATCC |
| 484 | AGGTCAAATATACATC |
| 485 | ACCACATTTATCCAATATA |
| 486 | ATAAAAACCACATTTATCCA |
| 487 | ATCACAACCACAAAATCA |
| 488 | ATAAATATTCTTACCTACA |
| 489 | AAGTATAATTTCCTTCTA |
| 490 | AATTTATAGATTAATAAAT |
| 491 | TTTCCACATATTTCCTAC |
| 492 | TGTCTATTTCCACATATT |
| 493 | TCTTTCAACCTTTTATTTA |
| 494 | ATATAAATCACCTGAAAT |
| 495 | ATTAATTCCATCTTCCTT |
| 496 | TCATTAATTCCATCTTCC |
| 497 | TGTCATTAATTCCATCTT |
| 498 | AACATGTCATTAATTCC |
| 499 | CCTTCAACTGAACTTC |
| 500 | AGCCATATCTTTTTATT |
| 501 | TAAGCACCTCAAAATATA |
| 502 | TTATTCATACTAAACACATA |
| 503 | AAAGATCTCATATTCCT |
| 504 | TCTCATTCTTTAACCATAA |
| 505 | TCCCTACTTAAATTATCAA |
| 506 | GCAATGTAAAAACATTAA |
| 507 | CCCATATTTTTTATTTTACA |
| 508 | CCCTTATCTACAAAAATTTA |
| 509 | CTGCTTTATTTACATAT |
| 510 | ACTGCTTTATTTACATA |
| 511 | TCTCAAGTATAACTACA |
| 512 | ACTGCTGAGCAGGATCA |
| 512 | ACTGCTGAGCAGGATCA |
| 512 | ACTGCTGAGCAGGATCA |
| 513 | GCTGAGCAGGATCATGA |
| 513 | GCTGAGCAGGATCATGA |
| 513 | GCTGAGCAGGATCATGA |
| 513 | GCTGAGCAGGATCATGA |
| 514 | AAAATCCAGCCAGTTCCA |
| 514 | AAAATCCAGCCAGTTCCA |
| 514 | AAAATCCAGCCAGTTCCA |
| 514 | AAAATCCAGCCAGTTCCA |
| 515 | ACTGCAATGTACATGTT |
| 515 | ACTGCAATGTACATGTT |
| 515 | ACTGCAATGTACATGTT |
| 515 | ACTGCAATGTACATGTT |
| 515 | ACTGCAATGTACATGTT |
| 516 | TCTATTTGCTTAGCTG |
| 516 | TCTATTTGCTTAGCTG |
| 516 | TCTATTTGCTTAGCTG |

| SEQID | Contiguous Nucleotide Sequence |
|---|---|
| 516 | TCTATTTGCTTAGCTG |
| 516 | TCTATTTGCTTAGCTG |
| 516 | TCTATTTGCTTAGCTG |
| 516 | TCTATTTGCTTAGCTG |
| 517 | CTATTTGCTTAGCTGTT |
| 517 | CTATTTGCTTAGCTGTT |
| 517 | CTATTTGCTTAGCTGTT |
| 517 | CTATTTGCTTAGCTGTT |
| 517 | CTATTTGCTTAGCTGTT |
| 517 | CTATTTGCTTAGCTGTT |
| 517 | CTATTTGCTTAGCTGTT |
| 518 | CTGAGCAGGATCATGA |
| 518 | CTGAGCAGGATCATGA |
| 518 | CTGAGCAGGATCATGA |
| 518 | CTGAGCAGGATCATGA |
| 518 | CTGAGCAGGATCATGA |
| 518 | CTGAGCAGGATCATGA |
| 519 | AAAATCCAGCCAGTTCC |
| 519 | AAAATCCAGCCAGTTCC |
| 519 | AAAATCCAGCCAGTTCC |
| 519 | AAAATCCAGCCAGTTCC |
| 519 | AAAATCCAGCCAGTTCC |
| 519 | AAAATCCAGCCAGTTCC |
| 520 | TCTATTTGCTTAGCTGT |
| 520 | TCTATTTGCTTAGCTGT |
| 520 | TCTATTTGCTTAGCTGT |
| 520 | TCTATTTGCTTAGCTGT |
| 520 | TCTATTTGCTTAGCTGT |
| 521 | TCTATTTGCTTAGCTGTT |
| 521 | TCTATTTGCTTAGCTGTT |
| 521 | TCTATTTGCTTAGCTGTT |
| 521 | TCTATTTGCTTAGCTGTT |
| 521 | TCTATTTGCTTAGCTGTT |
| 522 | TGCTGAGCAGGATCAT |
| 522 | TGCTGAGCAGGATCAT |
| 522 | TGCTGAGCAGGATCAT |
| 522 | TGCTGAGCAGGATCAT |
| 523 | ACTGCAATGTACATGT |
| 523 | ACTGCAATGTACATGT |
| 523 | ACTGCAATGTACATGT |
| 523 | ACTGCAATGTACATGT |
| 523 | ACTGCAATGTACATGT |
| 524 | ATTAGGTTCTCTAAT |
| 525 | ACTGCAATGTACATG |
| 526 | GCAATGTACATGTTCAC |
| 527 | CAATGTACATGTTCAC |
| 528 | GTAGATGAACATGACCAG |
| 529 | GTAGATGAACATGACCAGGA |
| 530 | GTAGATGAACATGACCA |
| 531 | GTAGATGAACATGACCAGG |
| 532 | TAGATGAACATGACC |
| 533 | TAGATGAACATGACCA |
| 534 | TAGATGAACATGACCAGG |
| 535 | TAGATGAACATGACCAGGA |
| 536 | TAGATGAACATGACCAGGAA |
| 537 | AGATGAACATGACCAGGA |
| 538 | AGATGAACATGACCAGG |
| 539 | AGATGAACATGACCAGGAA |
| 540 | GATGAACATGACCAGG |
| 541 | GATGAACATGACCAGGAA |
| 542 | GATGAACATGACCAGGA |
| 543 | ATGAACATGACCAGGA |
| 544 | TGAACATGACCAGGAA |
| 545 | GTGAAGTAGTAGTG |
| 546 | ACTTATCTTCTTTTTCTGTT |
| 547 | ACTTATCTTCTTTTTCTGT |
| 548 | CTTATCTTCTTTTTCTGT |
| 549 | CTTATCTTCTTTTTCTGTTG |
| 550 | CTTATCTTCTTTTTCTGTT |
| 551 | TTATCTTCTTTTTCTGTT |
| 552 | TTATCTTCTTTTTCTGT |
| 553 | TTATCTTCTTTTTCTGTTG |
| 554 | TATCTTCTTTTTCTGTTG |
| 555 | ATCTTCTTTTTCTGTTG |
| 556 | TCCCATGATGCTGAA |

| SEQID | Contiguous Nucleotide Sequence |
|---|---|
| 557 | ACTGCTGAGCAGGATCAT |
| 558 | CTGCTGAGCAGGATCAT |
| 559 | TGCTGAGCAGGATCATG |
| 560 | TGAGCAGGATCATGA |
| 561 | TCTCTATCCACTCTCCA |
| 562 | CTCTATCCACTCTCCA |
| 563 | CTCTATCCACTCTCCAC |
| 564 | CTCTATCCACTCTCCACA |
| 565 | GGAAGGAGTGGAAGAAGTCG |
| 566 | GAAGGAGTGGAAGAAGTCGT |
| 567 | GAAGGAGTGGAAGAAGTCG |
| 568 | AAGGAGTGGAAGAAGTCG |
| 569 | AAGGAGTGGAAGAAGTCGT |
| 570 | AGGAGTGGAAGAAGTCG |
| 571 | AGGAGTGGAAGAAGTCGT |
| 572 | GGAGTGGAAGAAGTCG |
| 573 | GGAGTGGAAGAAGTCGT |
| 574 | GAGTGGAAGAAGTCGTTC |
| 575 | GAGTGGAAGAAGTCGTT |
| 576 | GAGTGGAAGAAGTCGTTCAT |
| 577 | GAGTGGAAGAAGTCG |
| 578 | GAGTGGAAGAAGTCGTTCA |
| 579 | GAGTGGAAGAAGTCGT |
| 580 | AGTGGAAGAAGTCGTTCA |
| 581 | AGTGGAAGAAGTCGTTCAT |
| 582 | AGTGGAAGAAGTCGTTCATG |
| 583 | AGTGGAAGAAGTCGT |
| 584 | AGTGGAAGAAGTCGTT |
| 585 | AGTGGAAGAAGTCGTTC |
| 586 | GTGGAAGAAGTCGTTC |
| 587 | GTGGAAGAAGTCGT |
| 588 | GTGGAAGAAGTCGTTCAT |
| 589 | GTGGAAGAAGTCGTTCATG |
| 590 | GTGGAAGAAGTCGTTCA |
| 591 | GTGGAAGAAGTCGTTCATGT |
| 592 | GTGGAAGAAGTCGTT |
| 593 | TGGAAGAAGTCGTTCATGTG |
| 594 | TGGAAGAAGTCGTTCA |
| 595 | TGGAAGAAGTCGTTCATG |
| 596 | TGGAAGAAGTCGTTC |
| 597 | TGGAAGAAGTCGTTCAT |
| 598 | TGGAAGAAGTCGTTCATGT |
| 599 | GGAAGAAGTCGTTCA |
| 600 | GGAAGAAGTCGTTCAT |
| 601 | GGAAGAAGTCGTTCATGT |
| 602 | GGAAGAAGTCGTTCATGTGC |
| 603 | GGAAGAAGTCGTTCATG |
| 604 | GGAAGAAGTCGTTCATGTG |
| 605 | GAAGAAGTCGTTCATGTG |
| 606 | GAAGAAGTCGTTCATGTGC |
| 607 | GAAGAAGTCGTTCATGTGCC |
| 608 | GAAGAAGTCGTTCAT |
| 609 | GAAGAAGTCGTTCATG |
| 610 | GAAGAAGTCGTTCATGT |
| 611 | AAGAAGTCGTTCATGT |
| 612 | AAGAAGTCGTTCATGTGC |
| 613 | AAGAAGTCGTTCATGTGCCA |
| 614 | AAGAAGTCGTTCATG |
| 615 | AAGAAGTCGTTCAT |
| 616 | AAGAAGTCGTTCATGTGCC |
| 617 | AAGAAGTCGTTCATGTG |
| 618 | AGAAGTCGTTCATGTGCC |
| 619 | AGAAGTCGTTCATGTG |
| 620 | AGAAGTCGTTCATGT |
| 621 | AGAAGTCGTTCATGTGC |
| 622 | AGAAGTCGTTCATG |
| 623 | AGAAGTCGTTCATGTGCCA |
| 624 | GAAGTCGTTCATGTGCC |
| 625 | GAAGTCGTTCATGTGCCA |
| 626 | GAAGTCGTTCATGTGC |
| 627 | AAGTCGTTCATGTGCC |
| 628 | AAGTCGTTCATGTGCCA |
| 629 | AGTCGTTCATGTGCC |
| 630 | AGTCGTTCATGTGCCA |
| 631 | GTCGTTCATGTGCC |
| 632 | TCGTTCATGTGCCA |

| SEQID | Contiguous Nucleotide Sequence |
|---|---|
| 633 | GGCCAGGATTTTGCCA |
| 634 | GGCCAGGATTTTGCC |
| 635 | TCAAAGCTCGTGTAG |
| 636 | CAAAGCTCGTGTAG |
| 637 | AAAGTTCGAAGAGCTG |
| 638 | TATTTGCTTAGCTGTT |
| 639 | GTAGATGAACATGACC |
| 640 | TAGATGAACATGACCAG |
| 641 | ATGAACATGACCAGGAA |
| 642 | TTCACTAAATTTCACTAATC |
| 643 | AATGTACTTATACCCA |
| 644 | CTTACGCAAAAACAAT |
| 645 | ACTTACGCAAAAACAAT |
| 646 | TCACACCAATTACTTCTT |
| 647 | CTTCACACCAATTACTTCTT |
| 648 | TTACTTTATTCATCTCATA |
| 649 | TACTTTATTCATCTCATA |
| 650 | TTGAACCTTCATTATTTC |

The invention provides antisense oligonucleotides which comprise a contiguous nucleotide sequence selected from the group consisting of SEQ ID NO 50-641.

The invention provides antisense oligonucleotides which comprise a contiguous nucleotide sequence selected from the group consisting of SEQ ID NO 642-650.

The invention provides antisense oligonucleotides which comprise a contiguous nucleotide sequence of at least 12 contiguous nucleotides which are identical to a sequence selected from the group consisting of SEQ ID NO 50-641; or SEQ ID NO 642-650.

The invention provides antisense oligonucleotides which comprise a contiguous nucleotide sequence of at least 14 contiguous nucleotides which are identical to a sequence selected from the group consisting of SEQ ID NO 50-641; or SEQ ID NO 642-650.

In some embodiments, with reference to SEQ ID NO 50-641, or SEQ ID Nos 642-650, T may represent either a T or a U nucleobase, and a C may represent a C or a 5-methylC nucleobase.

In some embodiments, with reference to SEQ ID NO 50-641, or SEQ ID Nos 642-650, T is a T nucleobase, A is an A nucleobase, G is a G nucleobase and a C may represent a C or a 5-methylC nucleobase.

In some embodiments the oligonucleotide sequence or contiguous nucleotide sequence of the invention is 100% complementary to a corresponding target nucleic acid region (target sequence) present in SEQ ID NO: 1. In some embodiments the oligonucleotide sequence or contiguous nucleotide sequence is 100% complementary to a corresponding target nucleic acid region present in SEQ ID NO: 1 and SEQ ID NO: 2. In some embodiments the oligonucleotide sequence contiguous nucleotide sequence is 100% complementary to a corresponding target nucleic acid region present SEQ ID NO: 1, 2 and 3.

In some embodiments, the oligonucleotide comprises a contiguous nucleotide sequence of 10 to 30 nucleotides in length with at least 90% complementary, such as 100% complementarity, to a corresponding target sequence selected from any region in Target Sequence List 1.

In some embodiments, the oligonucleotide comprises a contiguous nucleotide sequence of 10 to 30 nucleotides in length with at least 90% complementary, such as 100% complementarity, to a corresponding target sequence selected from any region in Target Sequence List 2.

In some embodiments, the oligonucleotide comprises a contiguous nucleotide sequence of 10 to 30 nucleotides in length with at least 90% complementary, such as 100% complementarity, to a corresponding target sequence selected from any region in Target Sequence List 3.

In some embodiments, the oligonucleotide comprises a contiguous nucleotide sequence of 10 to 30 nucleotides in length with at least 90% complementary, such as 100% complementarity, to a corresponding target sequence selected from any region in Target Sequence List 4.

In some embodiments, the oligonucleotide comprises a contiguous nucleotide sequence of 10 to 30 nucleotides in length with at least 90% complementary, such as 100% complementarity, to a corresponding target sequence selected from SEQ ID NO 17-49.

In one embodiment, the oligonucleotide comprises or consists of a contiguous nucleotide sequence of 12 to 22 nucleotides in length with at least 90% complementary, such as 100% complementarity, to the target sequence of SEQ ID NO 1, selected from the group consisting of 99525-99542; 70094-70110; 133396-133411; 20666-20682; 103244-103261; 20666-20683; 103244-103262; 147238-147253; 171787-171803; 171787-171803; 147238-147253; 171788-171803; 103244-103260; 103244-103262; 130009-130025; 103244-103261; 98600-98616; 103244-103262; 171788-171803; 103244-103261; 70094-70110; 70094-70110; 70094-70110; 70094-70110; 70094-70110; 70094-70110; 70094-70110; 20666-20683; 97712-97728; 75261-75277; 75260-75276; 97713-97730; 75261-75277; 97712-97729; 20666-20683; 97712-97729; 20666-20683; 4426-4443; 75260-75276; 97715-97731; 20666-20683; 97712-97728; 4427-4443; 20666-20683; 97712-97729; 89475-89493; 99308-99324; 13076-13094; 87509-87527; 103272-103290; 82676-82692; 99526-99543; 82675-82691; 87510-87528; 97704-97720; 82675-82691; 89477-89495; and 13076-13094. Such oligonucleotides may be a gapmer, such as an LNA gapmer.

In some embodiments, the oligonucleotide of the invention does not comprise a sequence selected from the group consisting of 301, 311, 312, 323, 342, 343, and 394.

In some embodiments, the oligonucleotide of the invention does not comprise a sequence of 10 or more contiguous nucleotides which are identical to a sequence selected from the group consisting of 301, 311, 312, 323, 342, 343, and 394.

In some embodiments, the oligonucleotide of the invention does not comprise a sequence of 12 or more contiguous nucleotides which are identical to a sequence selected from the group consisting of 301, 311, 312, 323, 342, 343, and 394.

Mismatches

Advantageously, the contiguous nucleotide sequence of the oligonucleotide of the invention is full complementary to the target nucleic acid sequence, such as SEQ ID NO 1, such as a targets sequence selected from those disclosed in Target Sequence lists 1, 2, 3 & 4, or SEQ ID NO 17-49.

In some embodiments however, the oligonucleotide of the invention comprises a mismatch between the oligonucleotide and the target nucleic acid. Despite the mismatch, hybridization to the target nucleic acid may still be sufficient to show a desired modulation of SCN9A expression. Reduced binding affinity resulting from a mismatch may advantageously be compensated by increased number of nucleotides in the oligonucleotide and/or an increased number of modified nucleosides capable of increasing the binding affinity to the target, such as 2' sugar modified nucleosides, including LNA, present within the oligonucleotide sequence.

An aspect described in the present application relates to an antisense oligonucleotide of 10 to 30 nucleotides in length which comprises a contiguous nucleotide sequence of 10 to 30 nucleotides in length with at least 90% complementarity, such as 100% complementarity, to SEQ ID NO: 1. It is generally understood that the contiguous nucleotide sequence is the same length or in some embodiments may be shorter than the antisense oligonucleotide (the sequence of the oligonucleotide may comprise or consist of the contiguous nucleotide sequence).

Oligonucleotide Length

In some embodiments, the oligonucleotide of the invention comprises or consists of 10 to 30 nucleotides in length, such as from 11 to 28, such as from 10 to 22, such as from 12 to 22, such as from 14 to 20, such as from 15 to 20 such as from 16 to 18 such as from 17 to 20 or 18 to 20 contiguous nucleotides in length. In a preferred embodiment, the oligonucleotide comprises or consists of 17 to 20 nucleotides in length.

In some embodiments, the oligonucleotide or contiguous nucleotide sequence thereof comprises or consists of 24 or less nucleotides, such as 22 or less nucleotides, such as 20 or less nucleotides, such as 17, 18, 19 or 20 nucleotides. It is to be understood that any range given herein includes the range endpoints. Accordingly, if an oligonucleotide is said to include from 10 to 30 nucleotides, both 10 and 30 nucleotides are included.

In some embodiments, the contiguous nucleotide sequence comprises or consists of 10, 11, 12, 13, 14, 15, 16, 17, 18, 19, 20, 21, 22, 23, 24, 25, 26, 27, 28, 29 or 30 contiguous nucleotides in length.

Modified Oligonucleotides

The oligonucleotide of the invention is a modified oligonucleotide—i.e. it comprises modified nucleosides or modified nucleotides, other than unmodified RNA or unmodified DNA.

It is understood that the contiguous nucleobase sequences (motif sequence) can be modified to for example increase nuclease resistance and/or binding affinity to the target nucleic acid.

The pattern in which the modified nucleosides (such as high affinity modified nucleosides) are incorporated into the oligonucleotide sequence is generally termed oligonucleotide design.

The oligonucleotides of the invention are designed with modified nucleosides and DNA nucleosides. Advantageously, high affinity modified nucleosides are used.

In an embodiment, the oligonucleotide comprises at least 1 modified nucleoside, such as at least 2, at least 3, at least 4, at least 5, at least 6, at least 7, at least 8, at least 9, at least 10, at least 11, at least 12, at least 13, at least 14, at least 15 or at least 16 modified nucleosides. In an embodiment the oligonucleotide comprises from 1 to 10 modified nucleosides, such as from 2 to 9 modified nucleosides, such as from 3 to 8 modified nucleosides, such as from 4 to 7 modified nucleosides, such as 6 or 7 modified nucleosides. Suitable modifications are described in the "Definitions" section under "modified nucleoside", "high affinity modified nucleosides", "sugar modifications", "2' sugar modifications" and Locked nucleic acids (LNA)".

In an embodiment, the oligonucleotide comprises one or more sugar modified nucleosides, such as 2' sugar modified nucleosides. Preferably the oligonucleotide of the invention comprise one or more 2' sugar modified nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides. It is advantageous if one or more of the modified nucleoside(s) is a locked nucleic acid (LNA).

In a further embodiment the oligonucleotide or contiguous nucleotide sequence comprises at least one modified internucleoside linkage, such as at least one phosphorothioate internucleoside linkages. Suitable internucleoside modifications are described in the "Definitions" section under "Modified internucleoside linkage". It is advantageous if at least 75%, such as all, the internucleoside linkages within the contiguous nucleotide sequence are phosphorothioate internucleoside linkages. In some embodiments all the internucleotide linkages in the contiguous sequence of the oligonucleotide are phosphorothioate linkages.

In some embodiments, the oligonucleotide of the invention comprises at least one LNA nucleoside, such as 1, 2, 3, 4, 5, 6, 7, or 8 LNA nucleosides, such as from 2 to 6 LNA nucleosides, such as from 3 to 7 LNA nucleosides, 4 to 8 LNA nucleosides or 3, 4, 5, 6, 7 or 8 LNA nucleosides. In some embodiments, at least 75% of the modified nucleosides in the oligonucleotide are LNA nucleosides, such as 80%, such as 85%, such as 90% of the modified nucleosides are LNA nucleosides. In a still further embodiment all the modified nucleosides in the oligonucleotide are LNA nucleosides. In a further embodiment, the oligonucleotide may comprise both beta-D-oxy-LNA, and one or more of the following LNA nucleosides: thio-LNA, amino-LNA, oxy-LNA, ScET and/or ENA in either the beta-D or alpha-L configurations or combinations thereof. In a further embodiment, all LNA cytosine units are 5-methyl-cytosine. It is advantageous for the nuclease stability of the oligonucleotide or contiguous nucleotide sequence to have at least 1 LNA nucleoside at the 5' end and at least 2 LNA nucleosides at the 3' end of the nucleotide sequence.

In an embodiment of the invention the oligonucleotide of the invention is capable of recruiting RNase H, such as human RNaseH1.

In the current invention an advantageous structural design is a gapmer design as described in the "Definitions" section under for example "Gapmer", "LNA Gapmer", "MOE gapmer" and "Mixed Wing Gapmer" "Alternating Flank Gapmer". The gapmer design includes gapmers with uniform flanks, mixed wing flanks, alternating flanks, and gapbreaker designs. In the present invention it is advantageous if the oligonucleotide of the invention is a gapmer with an F-G-F' design where region F and F' independently comprise 1-8 nucleosides, of which 1-5 are 2' sugar modified and defines the 5' and 3' end of the F and F' region, and G is a region between 6 and 16 nucleosides which are capable of recruiting RNaseH. In one embodiment the G region consists of 6-16 contiguous DNA nucleosides. In a further embodiment region F and F' each comprise at least one LNA nucleoside.

In all instances the F-G-F' design may further include region D' and/or D" as described in the "Definitions" section under "Region D' or D" in an oligonucleotide". In some embodiments the oligonucleotide of the invention has 1, 2 or 3 phosphodiester linked nucleoside units, such as DNA units, at the 5' or 3' end of the gapmer region.

Oligonucleotides

In some embodiments of the invention, the oligonucleotide is selected from the group of oligonucleotide compounds with CMP-ID-NO: 50_1; 51_1; 52_1; 53_1; 54_1; 55_1; 56_1; 57_1; 58_1; 59_1; 60_1; 61_1; 62_1; 63_1; 64_1; 65_1; 66_1; 67_1; 68_1; 69_1; 70_1; 71_1; 72_1; 73_1; 74_1; 75_1; 76_1; 77_1; 78_1; 79_1; 80_1; 81_1; 82_1; 83_1; 84_1; 85_1; 86_1; 87_1; 88_1; 89_1; 90_1; 91_1; 92_1; 93_1; 94_1; 95_1; 96_1; 97_1; 98_1; 99_1; 100_1; 101_1; 102_1; 103_1; 104_1; 105_1; 106_1; 107_1; 108_1; 109_1 110_1; 111_1; 112_1; 113_1; 114_1; 115_1; 116_1; 117_1; 118_1; 119_1; 120_1; 121_1; 122_1; 123_1; 124_1; 125_1; 126_1; 127_1; 128_1; 129_1; 130_1; 131_1; 132_1; 133_1; 134_1; 135_1; 136_1; 137_1; 138_1; 139_1; 140_1; 141_1; 142_1; 143_1; 144_1; 145_1; 146_1; 147_1; 148_1; 149_1; 150_1; 151_1; 152_1; 153_1; 154_1; 155_1; 156_1; 157_1; 158_1; 159_1; 160_1; 161_1; 162_1; 163_1; 164_1; 165_1; 166_1; 167_1; 168_1; 169_1; 170_1; 171_1; 172_1; 173_1; 174_1; 175_1; 176_1; 177_1; 178_1; 179_1; 180_1; 181_1; 182_1; 183_1; 184_1; 185_1; 186_1; 187_1; 188_1; 189_1; 190_1; 191_1; 192_1; 193_1; 194_1; 195_1; 196_1; 197_1; 198_1; 199_1; 200_1; 201_1; 202_1; 203_1; 204_1; 205_1; 206_1; 207_1; 208_1; 209_1; 210_1; 211_1; 212_1; 213_1; 214_1; 215_1; 216_1; 217_1; 218_1; 219_1; 220_1; 221_1; 222_1; 223_1; 224_1; 225_1; 226_1; 227_1; 228_1; 229_1; 230_1; 231_1; 232_1; 233_1; 234_1; 235_1; 236_1; 237_1; 238_1; 239_1; 240_1; 241_1; 242_1; 243_1; 244_1; 245_1; 246_1; 247_1; 248_1; 249_1; 250_1; 251_1; 252_1; 253_1; 254_1; 255_1; 256_1; 257_1; 258_1; 259_1; 260_1; 261_1; 262_1; 263_1; 264_1; 265_1; 266_1; 267_1; 268_1; 269_1; 270_1; 271_1; 272_1; 273_1; 274_1; 275_1; 276_1; 277_1; 278_1; 279_1; 280_1; 281_1; 282_1; 283_1; 284_1; 285_1; 286_1; 287_1; 288_1; 289_1; 290_1; 291_1; 292_1; 293_1; 294_1; 295_1; 296_1; 297_1; 298_1; 299_1; 300_1; 301_1; 302_1; 303_1; 304_1; 305_1; 306_1; 307_1; 308_1; 309_1; 310_1; 311_1; 312_1; 313_1; 314_1; 315_1; 316_1; 317_1; 318_1; 319_1; 320_1; 321_1; 322_1; 323_1; 324_1; 325_1; 326_1; 327_1; 328_1; 329_1; 330_1; 331_1; 332_1; 333_1; 334_1; 335_1; 336_1; 337_1; 338_1; 339_1; 340_1; 341_1; 342_1; 343_1; 344_1; 345_1; 346_1; 347_1; 348_1; 349_1; 350_1; 351_1; 352_1; 353_1; 354_1; 355_1; 356_1; 357_1; 358_1; 359_1; 360_1; 361_1; 362_1; 363_1; 364_1; 365_1; 366_1; 367_1; 368_1; 369_1; 370_1; 371_1; 372_1; 373_1; 374_1; 375_1; 376_1; 377_1; 378_1; 379_1; 380_1; 381_1; 382_1; 383_1; 384_1; 385_1; 386_1; 387_1; 388_1; 389_1; 390_1; 391_1; 392_1; 393_1; 394_1; 395_1; 396_1; 397_1; 398_1; 399_1; 400_1; 401_1; 402_1; 403_1; 404_1; 405_1; 406_1; 407_1; 408_1; 409_1; 410_1; 411_1; 412_1; 413_1; 414_1; 415_1; 416_1; 417_1; 418_1; 419_1; 420_1; 421_1; 422_1; 423_1; 424_1; 425_1; 426_1; 427_1; 428_1; 429_1; 430_1; 431_1; 432_1; 433_1; 434_1; 435_1; 436_1; 437_1; 438_1; 439_1; 440_1; 441_1; 442_1; 443_1; 444_1; 445_1; 446_1; 447_1; 448_1; 449_1; 450_1; 451_1; 452_1; 453_1; 454_1; 455_1; 456_1; 457_1; 458_1; 459_1; 460_1; 461_1; 462_1; 463_1; 464_1; 465_1; 466_1; 467_1; 468_1; 469_1; 470_1; 471_1; 472_1; 473_1; 474_1; 475_1; 476_1; 477_1; 478_1; 479_1; 480_1; 481_1; 482_1; 483_1; 484_1; 485_1; 486_1; 487_1; 488_1; 489_1; 490_1; 491_1; 492_1; 493_1; 494_1; 495_1; 496_1; 4971; 498_1; 499_1; 500_1; 501_1; 502_1; 503_1; 504_1; 505_1; 506_1; 507_1; 508_1; 509_1; 510_1; 511_1; 512_1; 512_2; 512_3; 513_1; 513_2; 513_3; 513_4; 514_1; 514_2; 514_3; 514_4; 515_1; 515_2; 515_3; 515_4; 515_5; 515_6; 516_1; 516_2; 516_3; 516_4; 516_5; 516_6; 516_7; 517_1; 517_2; 517_3; 517_4; 517_5; 517_6; 517_7; 517_8; 518_1; 518_2; 518_3; 518_4; 518_5; 518_6; 519_1; 519_2; 519_3; 519_4; 519_5; 519_6; 520_1; 520_2; 520_3; 520_4; 520_5; 521_1; 521_2; 521_3; 521_4; 521_5; 522_1; 522_2; 522_3; 522_4; 523_1; 523_2; 523_3; 523_4; 523_5; 524_1; 525_1; 526_1; 527_1; 528_1; 529_1; 530_1; 531_1; 532_1; 533_1; 534_1; 535_1; 536_1; 537_1; 538_1; 539_1; 540_1; 541_1; 542_1; 543_1; 544_1; 545_1; 546_1; 547_1; 548_1; 549_1; 550_1; 551_1; 552_1; 553_1; 554_1; 555_1; 556_1; 557_1; 558_1; 559_1; 560_1; 561_1; 562_1; 563_1; 564_1; 565_1; 566_1; 567_1; 568_1; 569_1; 570_1; 571_1; 572_1; 573_1; 574_1; 575_1; 576_1; 577_1; 578_1; 579_1; 580_1; 581_1; 582_1; 583_1; 584_1; 585_1; 586_1; 587_1; 588_1; 589_1; 590_1; 591_1; 592_1; 593_1; 594_1; 595_1; 596_1; 597_1; 598_1; 599_1; 600_1; 601_1; 602_1; 603_1; 604_1; 605_1; 606_1; 607_1; 608_1; 609_1; 610_1; 611_1; 612_1; 613_1; 614_1; 615_1; 616_1; 617_1; 618_1; 619_1; 620_1; 621_1; 622_1; 623_1; 624_1; 625_1; 626_1; 6271; 628_1; 629_1; 630_1; 631_1; 632_1; 633_1; 634_1; 635_1; 636_1; 637_1; 638_1; 639_1; 640_1; and 641_1.

In some embodiments of the invention, the oligonucleotide is selected from the group of oligonucleotide compounds with CMP-ID-NO: 642_1, 643_1, 644_1, 645_1, 646_1, 647_1, 6481, 649_1 and 650_1.

In some embodiments, the invention provides a compound selected from the group consisting of CMP-ID-NO: 50_1-641_1.

In some embodiments, the invention provides a compound selected from the group consisting of CMP-ID-NO: 642_1, 643_1, 644_1, 645_1, 646_1, 647_1, 648_1, 649_1 and 650_1.

These compounds are listed in the compound table at the end of the example section and were tested for their ability to inhibit SCN9A in vitro via gymnotic delivery.

The following compounds gave at least 40% inhibition of SCN9A expression:

51_1, 59_1, 127_1, 161_1, 67_1, 106_1, 72_1, 124_1, 163_1, 99_1, 125_1, 110_1, 65_1, 94_1, 64_1, 57_1, 13_6_1, 15_8_1, 159_1, 356_1, 197_1, 132_1, 83_1, 76_1, 130_1, 135_1, 77_1, 186_1, 105_1, 445_1, 325_1, 265_1, 200_1, 288_1, 346_1, 86_1, 281_1, 339_1, 256_1, 289_1, 414_1, 286_1, 241_1, 82_1, 475_1, 91_1, 50_1, 971, 322_1, 148_1, 443_1, 251_1, 451_1, 179_1, 466_1, 357_1, 109_1, 472_1, 471_1, 376_1, 413_1, 270_1, 379_1, 416_1, 311_1, 411_1, 368_1, 333_1, 347_1, 152_1, 89_1, 380_1, 390_1, 429_1, 63_1, 90_1, 415_1, 199_1, 503_1, 476_1, 92_1, 268_1, 371_1, 302_1, 485_1, 205_1, 274_1, 122_1, 419_1, 470_1, 498_1, 156_1, 478_1, 393_1, 312_1, 287_1, 96_1, 226_1, 71_1, 137_1, 365_1, 58_1, 370_1, 280_1, 385_1, 442_1, 134_1, 463_1, 140_1, 440_1, 230_1, 310_1, 479_1, 363_1, 340_1, 495_1, 467_1, 444_1, 418_1, 338_1, 335_1, 496_1, 196_1, 317_1, 341_1, 406_1, 330_1, 173_1, 377_1, 474_1, 482_1, 282_1, 266_1, 73_1, 257_1, 342_1, 190_1, 492_1, 87_1, 188_1, 456_1, 372_1, 417_1, 404_1, 239_1, 206_1, 433_1, 486_1, 175_1, 461_1, 56_1, 408_1, 334_1, 504_1, 453_1, 222_1, 410_1, 104_1, 460_1, 439_1, 255_1, 489_1, 203_1, 398_1, 171_1, 407_1, 172_1, 412_1, 321_1, 305_1, 328_1, 120_1, 434_1, 449_1, 350_1, 487_1, 146_1, 420_1, 426_1, 352_1, 150_1, 316_1, 353_1, 469_1, 306_1, 3841, 155_1, 450_1, 279_1, 267_1, 337_1, 184_1, 459_1, 360_1, 75_1, 468_1, 180_1, 245_1, 387_1, 345_1, 98_1,

435_1, 295_1, 369_1, 218_1, 182_1, 448_1, 300_1, 481_1, 427_1, 207_1, 367_1, 240_1, 231_1, 364_1, 355_1, 431_1, 497_1, 397_1, 465_1, 271_1, 502_1, 151_1, 178_1, 499_1, 421_1, 131_1, 309_1, 491_1, 261_1, 121_1, 128_1, 84_1, 304_1, 264_1, 493_1, 185_1, 237_1, 139_1, 441_1, 169_1, 160_1, 102_1, 296_1, 164_1, 362_1, 500_1, and 100_1.

The following compounds gave at least 50% inhibition of SCN9A expression:

51_1, 59_1, 127_1, 161_1, 67_1, 106_1, 72_1, 124_1, 163_1, 99_1, 125_1, 110_1, 65_1, 94_1, 64_1, 57_1, 136_1, 158_1, 159_1, 356_1, 197_1, 132_1, 83_1, 76_1, 130_1, 135_1, 77_1, 186_1, 105_1, 445_1, 325_1, 265_1, 200_1, 288_1, 346_1, 86_1, 281_1, 339_1, 256_1, 289_1, 414_1, 286_1, 241_1, 82_1, 475_1, 91_1, 50_1, 97_1, 322_1, 148_1, 443_1, 251_1, 451_1, 179_1, 466_1, 357_1, 109_1, 472_1, 471_1, 376_1, 413_1, 270_1, 379_1, 416_1, 311_1, 411_1, 368_1, 333_1, 347_1, 152_1, 89_1, 380_1, 390_1, 429_1, 63_1, 90_1, 415_1, 199_1, 503_1, 476_1, 92_1, 268_1, 371_1, 302_1, 485_1, 205_1, 274_1, 122_1, 419_1, 470_1, 498_1, 156_1, 478_1, 393_1, 312_1, 287_1, 96_1, 226_1, 71_1, 137_1, 365_1, 58_1, 370_1, 280_1, 385_1, 442_1, 134_1, 463_1, 140_1, 440_1, 230_1, 310_1, 479_1, 363_1, 340_1, 495_1, 467_1, 444_1, 418_1, 338_1, 335_1, 496_1, 196_1, 317_1, 341_1, 406_1, 330_1, 173_1, 377_1, 474_1, 482_1, 282_1, 266_1, 73_1, 257_1, 342_1, 190_1, 492_1, 87_1, 188_1, 456_1, 372_1, 417_1, 404_1, 239_1, 206_1, 433_1, 486_1, 175_1, 461_1, 56_1, 408_1, 334_1, 504_1, 453_1, 222_1, 410_1, 104_1, 460_1, 439_1, 255_1, 489_1, 203_1, 398_1, 171_1, 407_1, 172_1, 412_1, 321_1, 305_1, 328_1, 120_1, 434_1, 449_1, 350_1, 487_1, 146_1, 420_1, 426_1, 352_1, 150_1, 316_1, 353_1, 469_1, 306_1, 384_1, 155_1, 450_1, 279_1, 267_1, 337_1, 184_1, 459_1, 360_1, 75_1, 468_1, 180_1, 245_1, 387_1, 345_1, 98_1, 435_1, 295_1, 369_1, 218_1, 182_1, 448_1, 300_1, 481_1, 427_1, 207_1

The following compounds gave at least 60% inhibition of SCN9A expression:

51_1, 59_1, 127_1, 161_1, 67_1, 106_1, 72_1, 124_1, 163_1, 99_1, 125_1, 110_1, 65_1, 94_1, 64_1, 57_1, 136_1, 158_1, 159_1, 356_1, 197_1, 132_1, 83_1, 76_1, 130_1, 135_1, 77_1, 186_1, 105_1, 445_1, 325_1, 265_1, 200_1, 288_1, 346_1, 86_1, 281_1, 339_1, 256_1, 289_1, 414_1, 286_1, 241_1, 82_1, 475_1, 91_1, 50_1, 97_1, 322_1, 148_1, 443_1, 251_1, 451_1, 179_1, 466_1, 357_1, 109_1, 472_1, 471_1, 376_1, 413_1, 270_1, 379_1, 416_1, 311_1, 411_1, 368_1, 333_1, 347_1, 152_1, 89_1, 380_1, 390_1, 429_1, 63_1, 90_1, 415_1, 199_1, 503_1, 476_1, 92_1, 268_1, 371_1, 302_1, 485_1, 205_1, 274_1, 122_1, 419_1, 470_1, 498_1, 156_1, 478_1, 393_1, 312_1, 287_1, 96_1, 226_1, 71_1, 137_1, 365_1, 58_1, 370_1, 280_1, 385_1, 442_1, 134_1, 463_1, 140_1, 440_1, 230_1, 310_1, 479_1, 363_1, 340_1, 495_1, 467_1, 444_1, 418_1, 338_1, 335_1, 496_1, 196_1, 317_1, 341_1, 406_1, 330_1, 173_1, 377_1, 474_1, 482_1, 282_1, 266_1, 73_1, 257_1, 342_1, 190_1, 492_1, 87_1, 188_1, 456_1, 372_1, 417_1, 404_1, 239_1, 206_1, 433_1, 486_1, 175_1, 461_1, 56_1, 408_1, 334_1, 504_1, and 453_1.

The following compounds gave at least 70% inhibition of SCN9A expression:

51_1, 59_1, 127_1, 161_1, 67_1, 106_1, 72_1, 124_1, 163_1, 99_1, 125_1, 110_1, 65_1, 94_1, 64_1, 57_1, 136_1, 158_1, 159_1,3 56_1, 197_1, 132_1, 83_1, 76_1, 130_1, 135_1, 77_1, 186_1, 105_1, 445_1, 325_1, 265_1, 200_1, 288_1, 346_1, 86_1, 281_1, 339_1, 256_1, 289_1, 414_1, 286_1, 241_1, 82_1, 475_1, 91_1, 50_1, 971, 322_1, 148_1, 443_1, 251_1, 451_1, 179_1, 466_1, 357_1, 109_1, 472_1, 471_1, 376_1, 413_1, 270_1, 379_1, 416_1, 311_1, 411_1, 368_1, 333_1, 347_1, 152_1, 89_1, 380_1, 390_1, 429_1, 63_1, 90_1, 415_1, 199_1, 503_1, 476_1, 92_1, 268_1, 371_1, 302_1, 485_1, 205_1, 274_1.

The following compounds gave at least 80% inhibition of SCN9A expression:

51_1, 59_1, 127_1, 161_1, 67_1, 106_1, 72_1, 124_1, 163_1, 99_1, 125_1, 110_1, 65_1, 94_1, 64_1, 57_1, 136_1, 158_1, 159_1, 356_1, 197_1, 132_1, 83_1, 76_1, 130_1, 135_1, 77_1, 186_1, 105_1, 445_1, and 325_1.

The following compounds gave at least 90% inhibition of SCN9A expression:

51_1, 59_1, 127_1, 161_1, 67_1, 106_1, 72_1, 124_1, 163_1, 99_1, 125_1, and 110_1.

In the compounds identified by a compound ID, Capital letters are beta-D-oxy LNA nucleosides, lowercase letters are DNA nucleosides, all LNA C are 5-methyl cytosine, all internucleoside linkages are phosphorothioate internucleoside linkages.

In some embodiments, the oligonucleotide of the invention comprises a contiguous nucleotide sequence comprising at least 10 or at least 12 contiguous nucleotides of a sequence selected from the group consisting of SEQ ID NO 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; 110; 111; 112; 113; 114; 115; 116; 117; 118; 119; 120; 121; 122; 123; 124; 125; 126; 127; 128; 129; 130; 131; 132; 133; 134; 135; 136; 137; 138; 139; 140; 141; 142; 143; 144; 145; 146; 147; 148; 149; 150; 151; 152; 153; 154; 155; 156; 157; 158; 159; 160; 161; 162; 163; 164; 165; 166; 167; 168; 169; 170; 171; 172; 173; 174; 175; 176; 177; 178; 179; 180; 181; 182; 183; 184; 185; 186; 187; 188; 189; 190; 191; 192; 193; 194; 195; 196; 197; 198; 199; 200; 201; 202; 203; 204; 205; 206; 207; 208; 209; 210; 211; 212; 213; 214; 215; 216; 217; 218; 219; 220; 221; 222; 223; 224; 225; 226; 227; 228; 229; 230; 231; 232; 233; 234; 235; 236; 237; 238; 239; 240; 241; 242; 243; 244; 245; 246; 247; 248; 249; 250; 251; 252; 253; 254; 255; 256; 257; 258; 259; 260; 261; 262; 263; 264; 265; 266; 267; 268; 269; 270; 271; 272; 273; 274; 275; 276; 277; 278; 279; 280; 281; 282; 283; 284; 285; 286; 287; 288; 289; 290; 291; 292; 293; 294; 295; 296; 297; 298; 299; 300; 301; 302; 303; 304; 305; 306; 307; 308; 309; 310; 311; 312; 313; 314; 315; 316; 317; 318; 319; 320; 321; 322; 323; 324; 325; 326; 327; 328; 329; 330; 331; 332; 333; 334; 335; 336; 337; 338; 339; 340; 341; 342; 343; 344; 345; 346; 347; 348; 349; 350; 351; 352; 353; 354; 355; 356; 357; 358; 359; 360; 361; 362; 363; 364; 365; 366; 367; 368; 369; 370; 371; 372; 373; 374; 375; 376; 377; 378; 379; 380; 381; 382; 383; 384; 385; 386; 387; 388; 389; 390; 391; 392; 393; 394; 395; 396; 397; 398; 399; 400; 401; 402; 403; 404; 405; 406; 407; 408; 409; 410; 411; 412; 413; 414; 415; 416; 417; 418; 419; 420; 421; 422; 423; 424; 425; 426; 427; 428; 429; 430; 431; 432; 433; 434; 435; 436; 437; 438; 439; 440; 441; 442; 443; 444; 445; 446; 447; 448; 449; 450; 451; 452; 453; 454; 455; 456; 457; 458; 459; 460; 461; 462; 463; 464; 465; 466; 467; 468; 469; 470; 471; 472; 473; 474; 475; 476; 477; 478; 479; 480; 481; 482; 483; 484; 485; 486; 487; 488; 489; 490; 491; 492; 493; 494; 495; 496; 497; 498; 499; 500; 501; 502; 503; 504; 505;

506; 507; 508; 509; 510; 511; 512; 513; 514; 515; 516; 517; 518; 519; 520; 521; 522; 523; 524; 525; 526; 527; 528; 529; 530; 531; 532; 533; 534; 535; 536; 537; 538; 539; 540; 541; 542; 543; 544; 545; 546; 547; 548; 549; 550; 551; 552; 553; 554; 555; 556; 557; 558; 559; 560; 561; 562; 563; 564; 565; 566; 567; 568; 569; 570; 571; 572; 573; 574; 575; 576; 577; 578; 579; 580; 581; 582; 583; 584; 585; 586; 587; 588; 589; 590; 591; 592; 593; 594; 595; 596; 597; 598; 599; 600; 601; 602; 603; 604; 605; 606; 607; 608; 609; 610; 611; 612; 613; 614; 615; 616; 617; 618; 619; 620; 621; 622; 623; 624; 625; 626; 627; 628; 629; 630; 631; 632; 633; 634; 635; 636; 637; 638; 639; 640; and 641.

In some embodiments, the oligonucleotide of the invention comprises a contiguous nucleotide sequence comprising at least 10 or at least 12 contiguous nucleotides of a sequence selected from the group consisting of SEQ ID NO 642, 643, 644, 645, 646, 647, 648, 649 and 650.

In some embodiments, the oligonucleotide of the invention comprises a contiguous nucleotide sequence comprising at least 10 or at least 12 contiguous nucleotides of a sequence selected from the group consisting of SEQ ID NO 51, 59, 127, 161, 67, 106, 72, 124, 163, 99, 125, 110, 65, 94, 64, 57, 136, 158,159, 356, 197, 132, 83, 76, 130, 135, 77, 186, 105, 445, 325, 265, 200, 288, 346, 86, 281, 339, 256, 289, 414, 286, 241, 82, 475, 91, 50, 97, 322, 148, 443, 251, 451, 179, 466, 357, 109, 472, 471, 376, 413, 270, 379, 416, 311, 411, 368, 333, 347, 152, 89, 380, 390, 429, 63, 90, 415, 199, 503, 476, 92, 268, 371, 302, 485, 205, 274, 122, 419, 470, 498, 156, 478, 393, 312, 287, 96, 226, 71, 137, 365, 58, 370, 280, 385, 442, 134, 463, 140, 440, 230, 310, 479, 363, 340, 495, 467, 444, 418, 338, 335, 496, 196, 317, 341, 406, 330, 173, 377, 474, 482, 282, 266, 73, 257, 342, 190, 492, 87, 188, 456, 372, 417, 404, 239, 206, 433, 486, 175, 461, 56, 408, 334, 504, 453, 222, 410, 104, 460, 439, 255, 489, 203, 398, 171, 407, 172, 412, 321, 305, 328,120, 434, 449, 350, 487,146, 420, 426, 352, 150, 316, 353, 469, 306, 384, 155, 450, 279, 267, 337, 184, 459, 360, 75, 468, 180, 245, 387, 345, 98, 435, 295, 369, 218, 182, 448, 300, 481, 427, 207, 367, 240, 231, 364, 355, 431, 497, 397, 465, 271, 502, 151, 178, 499, 421, 131, 309, 491, 261, 121, 128, 84, 304, 264, 493, 185, 237, 139, 441, 169,160, 102, 296, 164, 362, 500, and 100.

In some embodiments, the oligonucleotide of the invention comprises a contiguous nucleotide sequence comprising at least 10 or at least 12 contiguous nucleotides of a sequence selected from the group consisting of SEQ ID NO 51, 59, 127, 161, 67, 106, 72, 124, 163, 99, 125, 110, 65, 94, 64, 57, 136, 158,159, 356, 197, 132, 83, 76, 130, 135, 77, 186, 105, 445, 325, 265, 200, 288, 346, 86, 281, 339, 256, 289, 414, 286, 241, 82, 475, 91, 50, 97, 322, 148, 443, 251, 451, 179, 466, 357, 109, 472, 471, 376, 413, 270, 379, 416, 311, 411, 368, 333, 347, 152, 89, 380, 390, 429, 63, 90, 415, 199, 503, 476, 92, 268, 371, 302, 485, 205, 274, 122, 419, 470, 498, 156, 478, 393, 312, 287, 96, 226, 71, 137, 365, 58, 370, 280, 385, 442, 134, 463, 140, 440, 230, 310, 479, 363, 340, 495, 467, 444, 418, 338, 335, 496, 196, 317, 341, 406, 330, 173, 377, 474, 482, 282, 266, 73, 257, 342, 190, 492, 87, 188, 456, 372, 417, 404, 239, 206, 433, 486, 175, 461, 56, 408, 334, 504, 453, 222, 410, 104, 460, 439, 255, 489, 203, 398, 171, 407, 172, 412, 321, 305, 328,120, 434, 449, 350, 487,146, 420, 426, 352, 150, 316, 353, 469, 306, 384, 155, 450, 279, 267, 337, 184, 459, 360, 75, 468, 180, 245, 387, 345, 98, 435, 295, 369, 218, 182, 448, 300, 481, 427, and 207.

In some embodiments, the oligonucleotide of the invention comprises a contiguous nucleotide sequence comprising at least 10 or at least 12 contiguous nucleotides of a sequence selected from the group consisting of 51, 59, 127, 161, 67, 106, 72, 124, 163, 99, 125, 110, 65, 94, 64, 57, 136, 158, 159, 356, 197, 132, 83, 76, 130, 135, 77, 186, 105, 445, 325, 265, 200, 288, 346, 86, 281, 339, 256, 289, 414, 286, 241, 82, 475, 91, 50, 97, 322, 148, 443, 251, 451, 179, 466, 357, 109, 472, 471, 376, 413, 270, 379, 416, 311, 411, 368, 333, 347,152, 89, 380, 390, 429, 63, 90, 415, 199, 503, 476, 92, 268, 371, 302, 485, 205, 274, 122, 419, 470, 498, 156, 478, 393, 312, 287, 96, 226, 71, 137, 365, 58, 370, 280, 385, 442, 134, 463, 140, 440, 230,310, 479, 363, 340, 495, 467, 444, 418, 338, 335, 496,196, 317, 341, 406, 330,173, 377, 474, 482, 282, 266, 73, 257, 342, 190, 492, 87, 188, 456, 372, 417, 404, 239, 206, 433, 486, 175,461, 56, 408, 334, 504, and 453.

In some embodiments, the oligonucleotide of the invention comprises a contiguous nucleotide sequence comprising at least 10 or at least 12 contiguous nucleotides of a sequence selected from the group consisting of SEQ ID NO 51, 59, 127, 161, 67, 106, 72, 124, 163, 99, 125, 110, 65, 94, 64, 57, 136, 158,159, 356, 197, 132, 83, 76, 130, 135, 77, 186, 105, 445, 325, 265, 200, 288, 346, 86, 281, 339, 256, 289, 414, 286, 241, 82, 475, 91, 50, 97, 322, 148, 443, 251, 451, 179, 466, 357, 109, 472, 471, 376, 413, 270, 379, 416, 311, 411, 368, 333, 347, 152, 89, 380, 390, 429, 63, 90, 415, 199, 503, 476, 92, 268, 371, 302, 485, 205, and 274.

In some embodiments, the oligonucleotide of the invention comprises a contiguous nucleotide sequence comprising at least 10 or at least 12 contiguous nucleotides of a sequence selected from the group consisting of SEQ ID NO 51, 59, 127, 161, 67, 106, 72, 124, 163, 99, 125, 110, 65, 94, 64, 57, 136, 158,159, 356, 197, 132, 83, 76, 130, 135, 77, 186, 105, 445, and 325.

In some embodiments, the oligonucleotide of the invention comprises a contiguous nucleotide sequence comprising at least 10 or at least 12 contiguous nucleotides of a sequence selected from the group consisting of SEQ ID NOs 512-641.

In some embodiments, the oligonucleotide of the invention comprises a contiguous nucleotide sequence comprising at least 13 or at least 14 contiguous nucleotides of a sequence selected from the group consisting of SEQ ID NOs 512-641.

In some embodiments, the oligonucleotide of the invention comprises a contiguous nucleotide sequence selected from the group consisting of SEQ ID NOs 512-641.

In some embodiments, the oligonucleotide of the invention comprises a contiguous nucleotide sequence comprising at least 14 contiguous nucleotides of the selected sequence.

In some embodiments, the oligonucleotide of the invention comprises a contiguous nucleotide sequence comprising at least 15 contiguous nucleotides of the selected sequence.

In some embodiments, the oligonucleotide of the invention comprises a contiguous nucleotide sequence which comprises or consists of the selected sequence.

Method of Manufacture

In a further aspect, the invention provides methods for manufacturing the oligonucleotides of the invention comprising reacting nucleotide units and thereby forming covalently linked contiguous nucleotide units comprised in the oligonucleotide. Preferably, the method uses phophoramidite chemistry (see for example Caruthers et al, 1987, Methods in Enzymology vol. 154, pages 287-313). In a further embodiment the method further comprises reacting the contiguous nucleotide sequence with a conjugating moiety (ligand) to covalently attach the conjugate moiety to the oligonucleotide. In a further aspect a method is provided for manufacturing the composition of the invention, comprising mixing the oligonucleotide or conjugated oligonucleotide of the invention with a pharmaceutically acceptable diluent, solvent, carrier, salt and/or adjuvant.

Pharmaceutical Salt

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin, Organic Process Research & Development 2000, 4, 427-435 or in Ansel, In: Pharmaceutical Dosage Forms and Drug Delivery Systems, 6th ed. (1995), pp. 196 and 1456-1457. For example, the pharmaceutically acceptable salt of the compounds provided herein may be a sodium salt.

In a further aspect the invention provides a pharmaceutically acceptable salt of the antisense oligonucleotide or a conjugate thereof. In a preferred embodiment, the pharmaceutically acceptable salt is a sodium or a potassium salt.

Pharmaceutical Composition

In a further aspect, the invention provides pharmaceutical compositions comprising any of the aforementioned oligonucleotides and/or oligonucleotide conjugates or salts thereof and a pharmaceutically acceptable diluent, carrier, salt and/or adjuvant. A pharmaceutically acceptable diluent includes phosphate-buffered saline (PBS) and pharmaceutically acceptable salts include, but are not limited to, sodium and potassium salts. In some embodiments the pharmaceutically acceptable diluent is sterile phosphate buffered saline or sterile sodium carbonate buffer.

In some embodiments the oligonucleotide of the invention is in the form of a solution in the pharmaceutically acceptable diluent, for example dissolved in PBS or sodium carbonate buffer.

The oligonucleotide may be pre-formulated in the solution or in some embodiments may be in the form of a dry powder (e.g. a lyophilized powder) which may be dissolved in the in the pharmaceutically acceptable diluent prior to administration. Suitably, for example the oligonucleotide may be dissolved in a concentration of 0.1-100 mg/ml, such as 1-10 mg/the pharmaceutically acceptable diluent.

In some embodiments the oligonucleotide of the invention is formulated in a unit dose of between 0.5-100 mg, such as 1 mg-50 mg, or 2-25 mg.

Oligonucleotides or oligonucleotide conjugates of the invention may be mixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Pharmaceutical compositions, such as solutions, may be sterilized by conventional sterilization techniques, or may be sterile filtered. The resulting solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

In some embodiments, the oligonucleotide or oligonucleotide conjugate of the invention is a prodrug. In particular with respect to oligonucleotide conjugates the conjugate moiety is cleaved off the oligonucleotide once the prodrug is delivered to the site of action, e.g. the target cell.

Applications

The oligonucleotides of the invention may be utilized as research reagents for, for example, diagnostics, therapeutics and prophylaxis.

In research, such oligonucleotides may be used to specifically modulate the synthesis of $Na_v1.7$ or in some aspects $Na_v1.8$ protein in cells (e.g. in vitro cell cultures) and experimental animals thereby facilitating functional analysis of the target or an appraisal of its usefulness as a target for therapeutic intervention. Typically the target modulation is achieved by degrading or inhibiting the mRNA producing the protein, thereby prevent protein formation or by degrading or inhibiting a modulator of the gene or mRNA producing the protein.

If employing the oligonucleotide of the invention in research or diagnostics the target nucleic acid may be a cDNA or a synthetic nucleic acid derived from DNA or RNA.

The present invention provides an in vivo or in vitro method for modulating SCN9A expression in a target cell which is expressing SCN9A, said method comprising administering an oligonucleotide of the invention in an effective amount to said cell.

In some embodiments, the target cell, is a mammalian cell in particular a human cell. The target cell may be an in vitro cell culture or an in vivo cell forming part of a tissue in a mammal. In preferred embodiments the target cell is present in the peripheral nervous system, such as the dorsal root ganglion.

In diagnostics the oligonucleotides may be used to detect and quantitate SCN9A expression in cell and tissues by northern blotting, in-situ hybridization or similar techniques.

Therapeutic Applications

The oligonucleotides of the invention, or the conjugates, salts or pharmaceutical compositions of the invention, may be administered to an animal or a human for the prevention or treatment of pain, such as chronic pain, neuropathic pain, inflammatory pain, spontaneous pain, or nociceptive pain. The oligonucleotides of the invention, or the conjugates, salts or pharmaceutical compositions of the invention may be for use as a local analgesic.

The pain which may be treated by the oligonucleotides of the invention, or the conjugates, salts or pharmaceutical compositions of the invention may be pain wherein the pain signal in the peripheral nervous system. Indications associated with pain with a significant peripheral component include for example, diabetic neuropathies, cancer, cranial neuralgia, postherpetic neuralgia and post-surgical neuralgia.

Pain which may be prevented, treated or ameliorated using the oligonucleotide, conjugate, composition or salt of the invention may for example be selected from the group consisting of pain associated with inherited erythromelalgia (EIM), paroxysmal extreme pain disorder (PEPD), trigeminal neuralgia, neurophathic pain, chronic pain, but also general treatment of nociceptive (e.g. decompression of a nerve), neuropathic pain (e.g. diabetic neuropathy), visceral pain, or mixed pain.

The invention provides for the oligonucleotide, conjugate, composition or salt of the invention for the use for the prevention or for the treatment of pain, such as chronic pain, neuropathic pain, inflammatory pain, spontaneous pain, or nociceptive pain.

The invention further relates to use of an oligonucleotide, oligonucleotide conjugate or a pharmaceutical composition of the invention for the manufacture of a medicament for the treatment or prevention of pain, such as chronic pain, neuropathic pain, inflammatory pain, spontaneous pain, or nociceptive pain.

The invention provides for the oligonucleotide, conjugate, composition or salt of the invention for the use as a local analgesic.

The invention provides for the use of the oligonucleotide, conjugate, composition or salt of the invention for manufacture of a local analgesic.

The invention provides for the oligonucleotide, conjugate, composition or salt of the invention for the use for the prevention or for the treatment of pain associated with inherited erythromelalgia (EIM), paroxysmal extreme pain disorder (PEPD), trigeminal neuralgia, neurophathic pain, chronic pain, but also general treatment of nociceptive (e.g. decompression of a nerve), neuropathic pain (e.g. diabetic neuropathy), visceral pain, or mixed pain.

The invention further relates to use of an oligonucleotide, oligonucleotide conjugate or a pharmaceutical composition of the invention for the manufacture of a medicament for the treatment or prevention of pain associated with inherited erythromelalgia (EIM), paroxysmal extreme pain disorder (PEPD), trigeminal neuralgia, neurophathic pain, chronic pain, but also general treatment of nociceptive (e.g. decompression of a nerve), neuropathic pain (e.g. diabetic neuropathy), visceral pain, or mixed pain.

Method of Treatments

The invention provides methods for treating or preventing pain in a subject, such as a human, who is suffering from or is likely to suffer pain, comprising administering a therapeutically or prophylactically effective amount of an oligonucleotide, an oligonucleotide conjugate or a pharmaceutical composition of the invention to a subject who is suffering from or is susceptible to suffering from pain, such as chronic pain, neuropathic pain, inflammatory pain, spontaneous pain, or nociceptive pain.

By way of example, the method of treatment may be in subjects whose are suffering from an indication selected from the group consisting of diabetic neuropathies, cancer, cranial neuralgia, postherpetic neuralgia and post-surgical neuralgia.

The method of the invention may be for treating and relieving pain, such as pain associated with inherited erythromelalgia (EIM), paroxysmal extreme pain disorder (PEPD), trigeminal neuralgia, neurophathic pain, chronic pain, but also general treatment of nociceptive (e.g. decompression of a nerve), neuropathic pain (e.g. diabetic neuropathy), visceral pain, or mixed pain.

The methods of the invention are preferably employed for treatment or prophylaxis against pain which is mediated by $Na_v1.7$, or in some aspects, $Na_v1.7$ and $Na_v1.8$.

Administration

The oligonucleotides or pharmaceutical compositions of the present invention may be administered via parenteral administration.

In some embodiments, the administration route is subcutaneous or intrevenous.

In some embodiments the administration route is selected from the group consisting of intravenous, subcutaneous, intra-muscular, intracerebral, epidural, intracerebroventricular intraocular, intrathecal administration, or transforaminal administration).

In some advantageous embodiments, the administration is via intrathecal administration, or epidural administration or transforaminal administration.

Advantageously, the oligonucleotide or pharmaceutical compositions of the present invention are administered intrathecally.

The invention also provides for the use of the oligonucleotide of the invention, or conjugate thereof, such as pharmaceutical salts or compositions of the invention, for the manufacture of a medicament for the prevention or treatment of pain wherein the medicament is in a dosage form for intrathecal administration.

The invention also provides for the use of the oligonucleotide or oligonucleotide conjugate of the invention as described for the manufacture of a medicament for the manufacture of a medicament for the prevention or treatment of pain wherein the medicament is in a dosage form for intrathecal administration.

The invention also provides for the oligonucleotide of the invention, or conjugate thereof, such as pharmaceutical salts or compositions of the invention, for use as a medicament for the prevention or treatment of pain wherein the medicament is in a dosage form for intrathecal administration.

The invention also provides for the oligonucleotide or oligonucleotide conjugate of the invention, for use as a medicament for the prevention or treatment of pain wherein the medicament is in a dosage form for intrathecal administration.

Combination Therapies

In some embodiments the oligonucleotide, oligonucleotide conjugate or pharmaceutical composition of the invention is for use in a combination treatment with another therapeutic agent. The therapeutic agent can for example be the standard of care for the diseases or disorders described above. In some embodiments the compound of the invention is used in combination with small molecule analgesics which may be administered concurrently or independently of the administration of the compound or compositions of the invention. An advantage of a combination therapy of the compounds of the invention with small molecule analgesics is that small molecule analgesics have a rapid onset of pain relieving activity, typically with a short duration of action (hours-days), whereas the compounds of the invention has a delayed onset of activity (typically a few days or even a week+), but with a long duration of action (weeks-months, e.g. 2+, 3+ or 4 months+).

Embodiments—The Following is a List of Exemplary Embodiments of the Invention

1. An antisense oligonucleotide of 10 to 30 nucleotides in length, which comprises a contiguous nucleotide sequence of 10 to 30 nucleotides in length with at least 90% complementarity, such as 100% complementarity, to SEQ ID NO: 1.
2. The antisense oligonucleotide of embodiment 2, wherein the contiguous nucleotide sequence is at least 90% complementary, such as 100% complementary to a region of SEQ ID NO 1 selected from the group consisting of the sequences shown in Target Sequence List 1.
3. The antisense oligonucleotide of embodiment 1 or 2 wherein the contiguous nucleotide sequence is at least 90% complementary, such as 100% complementary to a region of SEQ ID NO 1 selected from the group consisting of the sequences shown in Target Sequence List 2.
4. The antisense oligonucleotide of embodiment 1-3 wherein the contiguous nucleotide sequence is at least 90% complementary, such as 100% complementary to a region of SEQ ID NO 1 selected from the group consisting of Target Sequence List 3.
5. The antisense oligonucleotide of embodiment 1-4 wherein the contiguous nucleotide sequence is at least 90% complementary, such as 100% complementary to a region of SEQ ID NO 1 selected from the group consisting of Target List 4.
6. The antisense oligonucleotide of embodiment 1-5, wherein the contiguous nucleotide sequence comprises a sequence which is 100% complementary to at least at least 10 contiguous nucleotides present in a sequence selected from the group consisting of SEQ ID NO 17-49.
7. The antisense oligonucleotide of embodiment 1-5 wherein the contiguous nucleotide sequence comprises a sequence which is 100% complementary to at least at least 12 contiguous nucleotides present in a sequence selected from the group consisting of SEQ ID NO 17-49.
8. The antisense oligonucleotide of embodiment 1-6 wherein the contiguous nucleotide sequence comprises a sequence which is 100% complementary to at least at least 14 contiguous nucleotides present in a sequence selected from the group consisting of SEQ ID NO 17-49.
9. The antisense oligonucleotide of embodiment 1-7 wherein the contiguous nucleotide sequence is 100% complementary to a sequence selected from the group consisting of SEQ ID NO 17-49.
10. The antisense oligonucleotide of any one of embodiments 1-9, wherein the contiguous nucleotide sequence comprises at least 10 contiguous nucleotides present in a sequence selected from the group consisting of SEQ ID NO 50-641, or 642-650.
11. The antisense oligonucleotide of any one of embodiments 1-9, wherein the contiguous nucleotide sequence comprises at least 12 contiguous nucleotides present in a sequence selected from the group consisting of SEQ ID NO 50-641, or 642-650.
12. The antisense oligonucleotide of any one of embodiments 1-9, wherein the contiguous nucleotide sequence comprises at least 14 contiguous nucleotides present in a sequence selected from the group consisting of SEQ ID NO 50-641, or 642-650.
13. The antisense oligonucleotide of any one of embodiments 1-9, wherein the contiguous nucleotide sequence is a sequence selected from the group consisting of SEQ ID NO 50-641, or 642-650.
14. The antisense oligonucleotide of any one of embodiments 1-13, one or more nucleoside in the contiguous nucleotide sequence is a 2' sugar modified nucleoside.
15. The antisense oligonucleotide of embodiment 14, wherein the one or more 2' sugar modified nucleoside is independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.
16. The antisense oligonucleotide of any one of embodiments 1-15, wherein the antisense oligonucleotide or contiguous nucleotide sequence thereof comprises one or more LNA nucleoside.
17. The antisense oligonucleotide of any one of embodiments 1-16, wherein at least one internucleoside linkage in the contiguous nucleotide sequence is a phosphorothioate internucleoside linkages.
18. The antisense oligonucleotide of any one of embodiments 1-17, wherein all the internucleoside linkages within the contiguous nucleotide sequence are phosphorothioate internucleoside linkages.
19. The antisense oligonucleotide of any one of embodiments embodiment 1-18, wherein the oligonucleotide is capable of recruiting RNase H, such as human RNaseH1.
20. The antisense oligonucleotide of any one of embodiments 1-19, wherein the antisense oligonucleotide, or contiguous nucleotide sequence thereof, consists or comprises a gapmer, such as a gapmer of formula 5'-F-G-F'-3', wherein region G is a region comprising a contiguous sequence of nucleotides capable of recruiting RNaseH, and regions F and F' each comprise at least one 2' sugar modified nucleoside.
21. The antisense oligonucleotide according to embodiment 20, wherein region G comprises of 6-16 DNA nucleosides and at least one of region F and F' comprises at least one LNA nucleoside, or both region F and F' comprise at least one LNA nucleoside.
22. The antisense oligonucleotide according to any one of embodiments 1-21, wherein the antisense oligonucleotide is a compound selected from the group consisting of CMP ID NO 50_1; 51_1; 52_1; 53_1; 54_1; 55_1; 56_1; 57_1; 58_1; 59_1; 60_1; 61_1; 62_1; 63_1; 64_1; 65_1; 66_1; 67_1; 68_1; 69_1; 70_1; 71_1; 72_1; 73_1; 74_1; 75_1; 76_1; 77_1; 78_1; 79_1; 80_1; 81_1; 82_1; 83_1; 84_1; 85_1; 86_1; 87_1; 88_1; 89_1; 90_1; 91_1; 92_1; 93_1; 94_1; 95_1; 96_1; 97_1; 98_1; 99_1; 100_1; 101_1; 102_1; 103_1; 104_1; 105_1; 106_1; 107_1; 108_1; 109_1; 110_1; 111_1; 112_1; 113_1; 114_1; 115_1; 116_1; 117_1; 118_1; 119_1; 120_1; 121_1; 122_1; 123_1; 124_1; 125_1; 126_1; 127_1; 128_1; 129_1; 130_1; 131_1; 132_1; 133_1; 134_1; 135_1; 136_1; 137_1; 138_1; 139_1; 140_1; 141_1; 142_1; 143_1; 144_1; 145_1; 146_1; 147_1; 148_1; 149_1; 150_1; 151_1; 152_1; 153_1; 154_1; 155_1; 156_1; 157_1; 158_1; 159_1; 160_1; 161_1; 162_1; 163_1; 164_1; 165_1; 166_1; 167_1; 168_1; 169_1; 170_1; 171_1; 172_1; 173_1; 174_1; 175_1; 176_1; 177_1; 178_1; 179_1; 180_1; 181_1; 182_1; 183_1; 1841; 185_1; 186_1; 1871; 1881; 189_1; 190_1; 191_1; 192_1; 193_1; 194_1; 195_1; 196_1; 197_1; 198_1; 199_1; 200_1; 201_1; 202_1; 203_1; 204_1; 205_1; 206_1; 207_1; 208_1; 209_1; 210_1; 211_1; 212_1; 213_1; 214_1; 215_1; 216_1; 217_1; 218_1; 219_1; 220_1; 221_1; 222_1; 223_1; 224_1; 225_1; 226_1; 227_1; 228_1; 229_1;

230_1; 231_1; 232_1; 233_1; 234_1; 235_1; 236_1; 237_; 238_1; 239_1; 240_1; 241_1; 242_1; 243_1; 244_1; 245_1; 246_1; 247_1; 248_1; 249_1; 250_1; 25_1; 252_1; 253_1; 254_1; 255_1; 256_1; 257_1; 258_1; 259_1; 260_1; 261_1; 262_1; 263_1; 264_1; 265_1; 266_1; 267_1; 268_1; 269_1; 270_1; 271_1; 272_1; 273_1; 274_1; 275_1; 276_1; 277_1; 278_1; 279_1; 280_1; 281_1; 282_1; 283_1; 284_1; 285_1; 286_1; 287_1; 288_1; 289_1; 290_1; 291_1; 292_1; 293_1; 294_1; 295_1; 296_1; 297_1; 298_1; 299_1; 300_1; 301_1; 302_1; 303_1; 304_1; 305_1; 306_1; 307_1; 308_1; 309_1; 310_1; 311_1; 312_1; 313_1; 314_1; 315_1; 316_1; 317_1; 318_1; 319_1; 320_1; 321_1; 322_1; 323_1; 324_1; 325_1; 326_1; 327_1; 328_1; 329_1; 330_1; 331_1; 332_1; 333_1; 334_1; 335_1; 336_1; 337_1; 338_1; 339_1; 340_1; 341_1; 342_1; 343_1; 344_1; 345_1; 346_1; 347_1; 348_1; 349_1; 350_1; 351_1; 352_1; 353_1; 354_1; 355_1; 356_1; 357_1; 358_1; 359_1; 360_1; 361_1; 362_1; 363_1; 364_1; 365_1; 366_1; 367_1; 368_1; 369_1; 370_1; 371_1; 372_1; 373_1; 3741; 3751; 376_1; 377_1; 378_1; 379_1; 380_1; 381_1; 382_1; 383_1; 384_1; 385_1; 386_1; 387_1; 388_1; 389_1; 390_1; 391_1; 392_1; 393_1; 394_1; 395_1; 396_1; 3971; 398_1; 399_1; 400_1; 401_1; 402_1; 403_1; 404_1; 405_1; 406_1; 407_1; 408_1; 409_1; 410_1; 411_1; 412_1; 413_1; 414_1; 415_1; 416_1; 417_1; 418_1; 419_1; 420_1; 421_1; 422_1; 423_1; 424_1; 425_1; 426_1; 427_1; 428_1; 429_1; 430_1; 431_1; 432_1; 433_1; 434_1; 435_1; 436_1; 437_1; 438_1; 439_1; 440_1; 441_1; 442_1; 443_1; 444_1; 445_1; 446_1; 447_1; 448_1; 449_1; 450_1; 451_1; 452_1; 453_1; 454_1; 455_1; 456_1; 457_1; 458_1; 459_1; 460_1; 461_1; 462_1; 463_1; 464_1; 465_1; 466_1; 467_1; 468_1; 469_1; 470_1; 471_1; 472_1; 473_1; 474_1; 475_1; 476_1; 477_1; 478_1; 479_1; 480_1; 481_1; 482_1; 483_1; 484_1; 485_1; 486_1; 487_1; 488_1; 489_1; 490_1; 491_1; 492_1; 493_1; 494_1; 495_1; 496_1; 4971; 498_1; 499_1; 500_1; 501_1; 502_1; 503_1; 504_1; 505_1; 506_1; 507_1; 508_1; 509_1; 510_1; 511_1; 512_1; 512_2; 512_3; 513_1; 513_2; 513_3; 513_4; 514_1; 514_2; 514_3; 514_4; 515_1; 515_2; 515_3; 515_4; 515_5; 515_6; 516_1; 516_2; 516_3; 516_4; 516_5; 516_6; 516_7; 517_1; 517_2; 517_3; 517_4; 517_5; 517_6; 517_7; 517_8; 518_1; 518_2; 518_3; 518_4; 518_5; 518_6; 519_1; 519_2; 519_3; 519_4; 519_5; 519_6; 520_1; 520_2; 520_3; 520_4; 520_5; 521_1; 521_2; 521_3; 521_4; 521_5; 522_1; 522_2; 522_3; 522_4; 523_1; 523_2; 523_3; 523_4; 523_5; 524_1; 525_1; 526_1; 5271; 528_1; 529_1; 530_1; 531_1; 532_1; 533_1; 534_1; 535_1; 536_1; 537_1; 538_1; 539_1; 540_1; 541_1; 542_1; 543_1; 544_1; 545_1; 546_1; 547_1; 548_1; 549_1; 550_1; 551_1; 552_1; 553_1; 554_1; 555_1; 556_1; 557_1; 558_1; 559_1; 560_1; 561_1; 562_1; 563_1; 564_1; 565_1; 566_1; 567_1; 568_1; 569_1; 570_1; 571_1; 572_1; 573_1; 574_1; 575_1; 576_1; 577_1; 578_1; 579_1; 580_1; 581_1; 582_1; 583_1; 584_1; 585_1; 586_1; 587_1; 588_1; 589_1; 590_1; 591_1; 592_1; 593_1; 594_1; 595_1; 596_1; 597_1; 598_1; 599_1; 600_1; 601_1; 602_1; 603_1; 604_1; 605_1; 606_1; 607_1; 608_1; 609_1; 610_1; 611_1; 612_1; 613_1; 614_1; 615_1; 616_1; 617_1; 618_1; 619_1; 620_1; 621_1; 622_1; 623_1; 624_1; 625_1; 626_1; 627_1; 628_1; 629_1; 630_1; 631_1; 632_1; 633_1; 634_1; 635_1; 636_1; 637_1; 638_1; 639_1; 640_1; and 641_1; or 642_1; 643_1; 644_1; 645_1; 646_1; 647_1; 648_1; 649_1; 650_1

23. The antisense oligonucleotide according to any one of embodiments 1-21, wherein the antisense oligonucleotide comprises a contiguous nucleotide sequence comprising at least 10 or at least 12 contiguous nucleotides of a sequence selected from the group consisting of 51, 59, 127, 161, 67, 106, 72, 124, 163, 99, 125, 110, 65, 94, 64, 57, 136, 158, 159, 356, 197,132, 83, 76, 130, 135, 77, 186, 105, 445, 325, 265, 200, 288, 346, 86, 281, 339, 256, 289, 414, 286, 241, 82, 475, 91, 50, 97, 322, 148, 443, 251, 451, 179, 466, 357, 109, 472, 471, 376, 413, 270, 379, 416, 311, 411, 368, 333, 347, 152, 89, 380, 390, 429, 63, 90, 415, 199, 503, 476, 92, 268, 371, 302, 485, 205, 274, 122, 419, 470, 498, 156, 478, 393, 312, 287, 96, 226, 71, 137, 365, 58, 370, 280, 385, 442, 134, 463, 140, 440, 230, 310, 479, 363, 340, 495, 467, 444, 418, 338, 335, 496, 196, 317, 341, 406, 330, 173, 377, 474, 482, 282, 266, 73, 257, 342, 190, 492, 87, 188, 456, 372, 417, 404, 239, 206, 433, 486, 175, 461, 56, 408, 334, 504, 453, 222, 410, 104, 460, 439, 255, 489, 203, 398, 171, 407, 172, 412, 321, 305, 328, 120, 434, 449, 350, 487, 146, 420, 426, 352, 150, 316, 353, 469, 306, 384, 155, 450, 279, 267, 337, 184, 459, 360, 75, 468, 180, 245, 387, 345, 98, 435, 295, 369, 218, 182, 448, 300, 481, 427, 207, 367, 240, 231, 364, 355, 431, 497, 397, 465, 271, 502, 151, 178, 499, 421, 131, 309, 491, 261, 121, 128, 84, 304, 264, 493, 185, 237, 139, 441, 169, 160, 102, 296, 164, 362, 500, and 100.

24. The antisense oligonucleotide according to any one of embodiments 1-21, wherein the antisense oligonucleotide comprises a contiguous nucleotide sequence comprising at least 10 or at least 12 contiguous nucleotides of a sequence selected from the group consisting of 51, 59, 127, 161, 67, 106, 72, 124, 163, 99, 125, 110, 65, 94, 64, 57, 136, 158, 159, 356, 197, 132, 83, 76, 130, 135, 77, 186, 105, 445, 325, 265, 200, 288, 346, 86, 281, 339, 256, 289, 414, 286, 241, 82, 475, 91, 50, 97, 322, 148, 443, 251, 451, 179, 466, 357, 109, 472, 471, 376, 413, 270, 379, 416, 311, 411, 368, 333, 347, 152, 89, 380, 390, 429, 63, 90, 415, 199, 503, 476, 92, 268, 371, 302, 485, 205, 274, 122, 419, 470, 498, 156, 478, 393, 312, 287, 96, 226, 71, 137, 365, 58, 370, 280, 385, 442, 134, 463, 140, 440, 230, 310, 479, 363, 340, 495, 467, 444, 418, 338, 335, 496, 196, 317, 341, 406, 330, 173, 377, 474, 482, 282, 266, 73, 257, 342, 190, 492, 87, 188, 456, 372, 417, 404, 239, 206, 433, 486, 175, 461, 56, 408, 334, 504, 453, 222, 410, 104, 460, 439, 255, 489, 203, 398, 171, 407, 172, 412, 321, 305, 328, 120, 434, 449, 350, 487, 146, 420, 426, 352, 150, 316, 353, 469, 306, 384, 155, 450, 279, 267, 337, 184, 459, 360, 75, 468, 180, 245, 387, 345, 98, 435, 295, 369, 218, 182, 448, 300, 481, 427, and 207.

25. The antisense oligonucleotide according to any one of embodiments 1-21, wherein the antisense oligonucleotide comprises a contiguous nucleotide sequence comprising at least 10 or at least 12 contiguous nucleotides of a sequence selected from the group consisting of 51, 59, 127, 161, 67, 106, 72, 124, 163, 99, 125, 110, 65, 94, 64, 57, 136, 158, 159, 356, 197, 132, 83, 76, 130, 135, 77, 186, 105, 445, 325, 265, 200, 288, 346, 86, 281, 339, 256, 289, 414, 286, 241, 82, 475, 91, 50, 97, 322, 148, 443, 251, 451, 179, 466, 357, 109, 472, 471, 376, 413, 270, 379, 416, 311, 411, 368, 333, 347, 152, 89, 380, 390, 429, 63, 90, 415, 199, 503, 476, 92, 268, 371, 302, 485, 205, 274, 122, 419, 470, 498, 156, 478, 393, 312, 287, 96, 226, 71, 137, 365, 58, 370, 280, 385, 442, 134, 463, 140, 440, 230, 310, 479, 363, 340, 495, 467, 444, 418, 338, 335, 496, 196, 317, 341, 406, 330, 173, 377, 474, 482, 282, 266, 73, 257, 342, 190, 492, 87, 188, 456, 372, 417, 404, 239, 206, 433, 486, 175, 461, 56, 408, 334, 504, and 453.

26. The antisense oligonucleotide according to any one of embodiments 1-21, wherein the antisense oligonucleotide comprises a contiguous nucleotide sequence comprising at least 10 or at least 12 contiguous nucleotides of a sequence selected from the group consisting of 51, 59, 127, 161, 67, 106, 72, 124, 163, 99, 125, 110, 65, 94, 64, 57, 136, 158, 159, 356, 197, 132, 83, 76, 130, 135, 77, 186, 105, 445, 325, 265, 200, 288, 346, 86, 281, 339, 256, 289, 414, 286, 241, 82, 475, 91, 50, 97, 322, 148, 443, 251, 451, 179, 466, 357, 109, 472, 471, 376, 413, 270, 379, 416, 311, 411, 368, 333, 347, 152, 89, 380, 390, 429, 63, 90, 415, 199, 503, 476, 92, 268, 371, 302, 485, 205, and 274.

27. The antisense oligonucleotide according to any one of embodiments 1-21, wherein the antisense oligonucleotide comprises a contiguous nucleotide sequence comprising at least 10 or at least 12 contiguous nucleotides of a sequence selected from the group consisting of 51, 59, 127, 161, 67, 106, 72, 124, 163, 99, 125, 110, 65, 94, 64, 57, 136, 158, 159, 356, 197, 132, 83, 76, 130, 135, 77, 186, 105, 445, and 325, such as a compound selected from the group consisting of 51, 59, 127, 161, 67, 106, 72, 124, 163, 99, 125, and 110.

28. The antisense oligonucleotide according to any one of embodiments 1-21, wherein the antisense oligonucleotide comprises a contiguous nucleotide sequence comprising at least 10 or at least 12 contiguous nucleotides of a sequence selected from the group consisting of is a compound selected from the group consisting of SEQ ID NOs 512-641.

29. The antisense oligonucleotide according to any one of embodiments 23-28 wherein the contiguous nucleotide sequence of the antisense oligonucleotide comprises at least 14 contiguous nucleotides of the selected sequence, or consists of the selected sequence.

30. A conjugate comprising the antisense oligonucleotide according to any one of embodiments 1-29, and at least one conjugate moiety covalently attached to said oligonucleotide.

31. A pharmaceutically acceptable salt of the antisense oligonucleotide according to any one of embodiments 1-29, or the conjugate according to embodiment 30.

32. A pharmaceutical composition comprising the antisense oligonucleotide of embodiment 1-29 or the conjugate of embodiment 30 and a pharmaceutically acceptable diluent, solvent, carrier, salt and/or adjuvant.

33. An in vivo or in vitro method for modulating SCN9A expression in a target cell which is expressing SCN9A, said method comprising administering an antisense oligonucleotide of any one of embodiments 1-29 or the conjugate of embodiment 30 or the pharmaceutical salt or composition of embodiment 31 or 32 in an effective amount to said cell.

34. A method for treating or preventing pain in a subject such as a human, who is suffering from or is likely to suffer pain, comprising administering a therapeutically or prophylactically effective amount of an antisense oligonucleotide of any one of embodiments 1-29 or the conjugate of embodiment 30 or the pharmaceutical salt or composition of embodiment 31 or 32, such as to prevent or alleviate the pain.

35. The method of embodiment 34, wherein the pain is either
   i) chronic pain, neuropathic pain, inflammatory pain, spontaneous pain, or nociceptive pain; or
   ii) pain caused by or associated with a disorder selected from the group consisting of diabetic neuropathies, cancer, cranial neuralgia, postherpetic neuralgia and post-surgical neuralgia; or
   iii) pain caused by or associated with inherited erythromelalgia (EIM) or paroxysmal extreme pain disorder (PEPD) or trigeminal neuralgia; or
   iv) neurophathic pain, chronic pain, but also general treatment of nociceptive pain (e.g. decompression of a nerve), or neuropathic pain (e.g. diabetic neuropathy), visceral pain, or mixed pain.

36. The oligonucleotide of any one of embodiments 1-29 or the conjugate according to embodiment 30 or the pharmaceutical salt or composition of embodiment 31 or 32 for use in medicine.

37. The oligonucleotide of any one of embodiments 1-29 or the conjugate according to embodiment 30 or the pharmaceutical salt or composition of embodiment 31 or 32 for use in the treatment or prevention or alleviation of pain, such as the pain as defined according to parts I), ii), iii) or iv) of embodiment 35.

38. The use of an oligonucleotide of any one of embodiments 1-29 or the conjugate according to embodiment 30 or the pharmaceutical salt or composition of embodiment 31 or 32, for the preparation of a medicament for the treatment, prevention or alleviation of pain, such as the pain as defined according to parts 1), ii), iii) or iv) of embodiment 35.

EXAMPLES

Oligonucleotide Synthesis

Compounds are listed in the Compound Table, which also illustrates the nucleobase sequence, complementary target sequence region on SEQ ID NO 1 (start and end), the gapmer design, the Tm (dG), and the level of remaining mRNA in the cells after treatment with the compounds (see Example 1 below) Oligonucleotide synthesis is generally known in the art. Below is a protocol which may be applied. The oligonucleotides of the present invention may have been produced by slightly varying methods in terms of apparatus, support and concentrations used.

Oligonucleotides are synthesized on uridine universal supports using the phosphoramidite approach on an Oligomaker 48 at 1 µmol scale. At the end of the synthesis, the oligonucleotides are cleaved from the solid support using aqueous ammonia for 5-16 hours at 60° C. The oligonucleotides are purified by reverse phase HPLC (RP-HPLC) or by solid phase extractions and characterized by UPLC, and the molecular mass is further confirmed by ESI-MS.

Elongation of the Oligonucleotide:

The coupling of β-cyanoethyl-phosphoramidites (DNA-A(Bz), DNA-G(ibu), DNA-C(Bz), DNA-T, LNA-5-methyl-C(Bz), LNA-A(Bz), LNA-G(dmf), or LNA-T) is performed by using a solution of 0.1 M of the 5'-O-DMT-protected amidite in acetonitrile and DCI (4,5-dicyanoimidazole) in acetonitrile (0.25 M) as activator. For the final cycle a phosphoramidite with desired modifications can be used, e.g. a C6 linker for attaching a conjugate group or a conjugate group as such. Thiolation for introduction of phosphorthioate linkages is carried out by using xanthane hydride (0.01 M in acetonitrile/pyridine 9:1). Phosphordiester linkages can be introduced using 0.02 M iodine in THF/Pyridine/water 7:2:1. The rest of the reagents are the ones typically used for oligonucleotide synthesis.

For post solid phase synthesis conjugation a commercially available C6 aminolinker phorphoramidite can be used in the last cycle of the solid phase synthesis and after deprotection and cleavage from the solid support the aminolinked deprotected oligonucleotide is isolated. The conjugates are introduced via activation of the functional group using standard synthesis methods.

Purification by RP-HPLC:

The crude compounds are purified by preparative RP-HPLC on a Phenomenex Jupiter C18 10μ 150×10 mm column. 0.1 M ammonium acetate pH 8 and acetonitrile is used as buffers at a flow rate of 5 mL/min. The collected fractions are lyophilized to give the purified compound typically as a white solid.

Abbreviations

DCI: 4,5-Dicyanoimidazole
DCM: Dichloromethane
DMF: Dimethylformamide
DMT: 4,4'-Dimethoxytrityl
THF: Tetrahydrofurane
Bz: Benzoyl
Ibu: Isobutyryl
RP-HPLC: Reverse phase high performance liquid chromatography $T_m$ Assay:

Oligonucleotide and RNA target (phosphate linked, PO) duplexes are diluted to 3 mM in 500 ml RNase-free water and mixed with 500 ml 2×$T_m$-buffer (200 mM NaCl, 0.2 mM EDTA, 20 mM Naphosphate, pH 7.0). The solution is heated to 95° C. for 3 min and then allowed to anneal in room temperature for 30 min. The duplex melting temperatures ($T_m$) is measured on a Lambda 40 UV/VIS Spectrophotometer equipped with a Peltier temperature programmer PTP6 using PE Templab software (Perkin Elmer). The temperature is ramped up from 20° C. to 95° C. and then down to 25° C., recording absorption at 260 nm. First derivative and the local maximums of both the melting and annealing are used to assess the duplex $T_m$.

Example 1: In Vitro Reduction of Nav1.7 in SK-N-AS Human Cell Line Using Oligonucleotides LNA modified oligonucleotides targeting human Nav1.7 were tested for their ability to reduce Nav1.7 mRNA expression in human SK-N-AS neuroblastoma cells acquired from ATCC (CRL-2137). SK-N-AS cells (ECACC-94092302) were cultured according to the vendor guidelines in Dulbecco's Modified Eagle's Medium, supplemented with 0.1 mM Non-Essential Amino Acids (NEAA) and fetal bovine serum to a final concentration of 10%. Cells were cultured at 37° C., 5% C02 and 95% humidity in an active evaporation incubator (Thermo C10). Cells were seeded at a density of 9300 cells per well (96-well plate) in 95 ul of SK-N-AS cell culture medium and left to attach for 24 hours in the incubator. Hereafter, oligos diluted to a final concentration of 5 μM in PBS (5.0 μl) were added to the cell cultures from pre-made 96-well dilution plates. The cell culture plates were incubated for 96 hours in the incubator.

After incubation, cells were harvested by removal of media followed by cell lysis and RNA purification using QIAGEN RNeasy 96 Kit (cat 74181), following manufacturers protocol. RNA was diluted 10 fold in water prior to the one-step qPCR reaction. For one-step qPCR reaction qPCR-mix (qScript™ XLT One-Step RT-qPCR ToughMix® Low ROX from QuantaBio, cat.no 95134-500) and QPCR was run as duplex QPCR using assays from Integrated DNA technologies for $Na_v1.7$ (Hs.PT.58.20989243) and GUSB (Hs.PT.58v.27737538).

The reactions were then mixed in a qPCR plate (MICROAMP®optical 384 well, 4309849). After sealing, the plate was given a quick spin, 1000 g for 1 minute at RT, and transferred to a Viia™ 7 system (Applied Biosystems, Thermo), and the following PCR conditions used: 50° C. for 15 minutes; 95° C. for 3 minutes; 40 cycles of: 95° C. for 5 see followed by a temperature decrease of 1.6° C./sec followed by 60° C. for 45 sec. The data was analyzed using the QuantStudio™ Real_time PCR Software and quantity calculated by the delta delta Ct method (Quantity=2^(-Ct) *1000000000). Quantity is normalized to the calculated quantity for the housekeeping gene assay (GUSB) run in the same well. Relative Target Quantity=QUANTITY_target/QUANTITY_housekeeping (RNA knockdown) was calculated for each well by division with the mean of all PBS-treated wells on the same plate. Normalised Target Quantity=(Relative Target Quantity/[mean] Relative Target Quantity]_pbs_wells)*100.

Compounds based on SEQ ID NOs 512-641 are being evaluated in the above assay.

The target knock-down data is presented in the following Compound Table:

In the Compound table, motif sequences represent the contiguous sequence of nucleobases present in the oligonucleotide.

Design refers to the gapmer design, F-G-F', wherein G is a region of DNA nucleosides, and F and F' are regions of LNA nucleosides.

Oligonucleotide compound represent specific designs of a motif sequence. Capital letters represent beta-D-oxy LNA nucleosides, lowercase letters represent DNA nucleosides, all LNA C are 5-methyl cytosine, all internucleoside linkages are phosphorothioate internucleoside linkages.

Example 2: In Vitro Reduction of Nav1.8 Alone or in Combination with Reduction of Nav1.7 in Modified SK-N-AS Human Cell Line (CRISPR Activation of Nav1.8) Using Oligonucleotides Activation of Nav1.8 expression in SK-N-AS cells:

SK-N-AS cells were transduced with lentiviral particles coding for hCMV-Blast-dCas9-VPR (#VCAS11918, Dharmacon) at 0.5 MOI, and selected with Blasticidin at 2 ug/ml for 10 days.

SK-N-AS stably expressing dCas9-VPR protein were subsequently engineered to express Nav1.8 specific sgRNA. Briefly, an expression cassette driven by U6 promoter has been synthesized as a gBlock and then subcloned in PiggyBac vector (#PB511B-1, System Biosciences). The identity of the vector has been Sanger-sequencing validated. Stable integration of the U6 driven cassette expressing $Na_v1.8$ specific sgRNA was obtained with the use of the transposase expression plasmid (#PB210PA-1, System Biosciences) following the manufacturer's instructions. Selection of sgRNA stably expressing cells was obtained in presence of Puromycin at 2 ug/ml for 10 days.

The sgRNA sequence used in $Na_v1.8$ activation is GGCAAGCTGTCACCTCTCTG (SEQ ID NO 652).

The full sequence of the U6 promoter-sgRNA is the following:

(SEQ ID NO 653)
GAGGGCCTATTTCCCATGATTCCTTCATATTTGCATATACGATACAAGGC

TGTTAGAGAGATAATTAGAATTAATTTGACTGTAAACACAAAGATATTAG

TACAAAATACGTGACGTAGAAAGTAATAATTTCTTGGGTAGTTTGCAGTT

TTAAAATTATGTTTTAAAATGGACTATCATATGCTTACCGTAACTTGAAA

GTATTTCGATTTCTTGGCTTTATATATCTTGTGGAAAGGACGAAACACCG

GGCAAGCTGTCACCTCTCTGGTTTTAGAGCTAGAAATAGCAAGTTAAAAT

AAGGCTAGTCCGTTATCAACTTGAAAAAGTGGCACCGAGTCGGTGCTTTT

TTT.

LNA modified oligonucleotides targeting human $Na_v1.8$ singlehanded or also $Na_v1.7$ as a dual-specific compound were tested for their ability to reduce the expression of their respective mRNA targets in human SK-N-AS neuroblastoma cells acquired from ATCC (CRL-2137). The SK-N-AS cells (ECACC-94092302) have underwent an activation of transcription of $Na_v1.8$ using CRISPR activation (CRISPRa) as described above. The modified SK-N-AS cells were cultured according to the vendor guidelines for the parent cell line in Dulbecco's Modified Eagle's Medium, supplemented with 0.1 mM Non-Essential Amino Acids (NEAA), fetal bovine serum to a final concentration of 10% along with Blasticidin (2.5 μg/ml) and Puromycin (1 μg/ml). Cells were cultured at 37° C., 5% $CO_2$ and 95% humidity in an active evaporation incubator (Thermo C10). Cells were seeded at a density of 10,000 cells per well (96-well plate) in 190 ul of SK-N-AS cell culture medium and left to attach for 4 hours in the incubator. Hereafter, oligos were diluted in pre-made 96-well dilution plates to the desired concentration and 10 μl hereof was added to the cell culture plate for a final concentration of 10 μM. The cell culture plates were incubated for 72 hours in the incubator.

After incubation, cells were harvested by removal of media followed by cell lysis and RNA purification using QIAGEN RNeasy 96 Kit (cat 74181), following manufacturers protocol. RNA was diluted 10 fold in water prior to the one-step qPCR reaction. For one-step qPCR reaction qPCR-mix (qScript™ XLT One-Step RT-qPCR ToughMix® Low ROX from QuantaBio, cat.no 95134-500) and QPCR was run as duplex QPCR using assays from Integrated DNA technologies for Nav1.7 (Hs.PT.58.20989243), Nav1.8 (Hs.PT.58.23220090) and GUSB (Hs.PT.58v.27737538).

Results

This table below lists dual-specific compounds targeting both Nav1.7 (SCN9a) and Nav1.8 (SCN10a)

The effect is here provided as residual target RNA (normalised to GUSB) relative to PBS control.

The test was performed in regular SK-N-AS cells and in SK-N-AS following CRISPRa of Nav1.8.

| Compound | SK-N-AS SCN9a/GUSB | SK-N-AS 1.8 SCN9a/GUSB | SK-N-AS 1.8 SCN10a/GUSB |
|---|---|---|---|
| 515_3 | 0.340 | 0.423 | 1.136 |
| 526_1 | 0.238 | 0.252 | 0.851 |
| 528_1 | 0.210 | 0.236 | 0.468 |
| 631_1 | 0.086 | 0.142 | 0.496 |
| 632_1 | 0.032 | 0.054 | 0.391 |
| 636_1 | 0.021 | 0.070 | 0.286 |
| 519_6 | 0.361 | 0.490 | 0.432 |

Compound Table

| SEQ ID NO | Motif sequence | position on SEQ ID NO: 1 Start | end | Design | CMP ID NO | Oligonucleotide Compound | dG | SNC9A mRNA % (vs Saline control 100%) |
|---|---|---|---|---|---|---|---|---|
| 50 | ATGTTTACTATAATCACA | 1037 | 1054 | 4-10-4 | 50_1 | ATGTttactataatCACA | -21 | 22.9 |
| 51 | GGCATATCATATATCC | 1779 | 1794 | 2-12-2 | 51_1 | GGcatatcatatatCC | -18 | 4.6 |
| 52 | CCAATTTTTCTTAAAATAT | 3456 | 3475 | 3-14-3 | 52_1 | CCAattttttcttaaaaTAT | -19 | 105.5 |
| 53 | TCTCATAAATCCTCATAT | 4379 | 4396 | 2-12-4 | 53_1 | TCtcataaatcctcATAT | -20 | 71.2 |
| 54 | TATTCTACCCACATTCT | 4405 | 4421 | 2-13-2 | 54_1 | TAttctacccacattCT | -20 | 64.6 |
| 55 | AGTATTCTACCCACATT | 4407 | 4423 | 2-13-2 | 55_1 | AGtattctacccacaTT | -19 | 66.8 |
| 56 | AAGTATTCTACCCACAT | 4408 | 4424 | 2-12-3 | 56_1 | AAgtattctacccaCAT | -20 | 39.5 |
| 57 | TATCTCATATTCCACAAA | 4424 | 4441 | 4-12-2 | 57_1 | TATCtcatattccacaAA | -19 | 13.4 |
| 58 | TTATCTCATATTCCACA | 4426 | 4442 | 3-12-2 | 58_1 | TTAtctcatattccaCA | -19 | 31.6 |
| 59 | GTTATCTCATATTCCAC | 4427 | 4443 | 2-12-3 | 59_1 | GTtatctcatattcCAC | -19 | 5.3 |
| 60 | TTCAATGAAGAAATTTCA | 4472 | 4489 | 4-7-7 | 60_1 | TTCAatgaagaAATTTCA | -20 | 95.3 |
| 61 | GCTCAATTTTCCAATTATT | 5276 | 5294 | 2-15-2 | 61_1 | GCtcaattttccaattaTT | -20 | 88.6 |
| 62 | TCTAATCTTATTTATCTTTC | 5302 | 5321 | 3-15-2 | 62_1 | TCTaatcttatttatctttTC | -19 | 76.4 |

Compound Table

| SEQ ID NO | Motif sequence | position on SEQ ID NO: 1 Start | end | Design | CMP ID NO | Oligonucleotide Compound | dG | SNC9A mRNA % (vs Saline control 100%) |
|---|---|---|---|---|---|---|---|---|
| 63 | TCCCATAATATTTACCTA | 6333 | 6350 | 3-13-2 | 63_1 | TCCcataatatttaccTA | -22 | 28.6 |
| 64 | ATCACTTCAACTTTATAATA | 6386 | 6405 | 4-12-4 | 64_1 | ATCActtcaactttatAATA | -21 | 13.0 |
| 65 | TTCATCACTTCAACTTTA | 6391 | 6408 | 4-11-3 | 65_1 | TTCAtcacttcaactTTA | -20 | 11.4 |
| 66 | TCCTACCTGAATTACC | 6468 | 6483 | 2-12-2 | 66_1 | TCctacctgaattaCC | -20 | 77.2 |
| 67 | GCTTTTAACACTTTATA | 6652 | 6668 | 4-11-2 | 67_1 | GCTTttaacactttaTA | -19 | 8.2 |
| 68 | CTCCTAATATATAATATACT | 6839 | 6858 | 4-13-3 | 68_1 | CTCCtaatatataatatACT | -21 | 86.9 |
| 69 | TCTCCTAATATATAATATA | 6841 | 6859 | 4-11-4 | 69_1 | TCTCctaatatataaTATA | -21 | 86.3 |
| 70 | ATATATCTCCTAATATATA | 6846 | 6864 | 4-11-4 | 70_1 | ATATatctcctaataTATA | -21 | 99.7 |
| 71 | ACATATATCTCCTAATA | 6850 | 6868 | 4-11-4 | 71_1 | ACAtatatctcctAATA | -21 | 31.3 |
| 72 | CTCATATCTACTTATCAT | 6920 | 6937 | 4-11-3 | 72_1 | CTCAtatctacttatCAT | -22 | 9.0 |
| 73 | TACTCATATCTACTTATCA | 6921 | 6939 | 3-12-4 | 73_1 | TACtcatatctacttATCA | -22 | 36.6 |
| 74 | TCTACTCATATCTACTTA | 6924 | 6941 | 2-13-3 | 74_1 | TCtactcatatctacTTA | -19 | 85.3 |
| 75 | ACATCTACTCATATCTACT | 6926 | 6944 | 3-13-3 | 75_1 | ACAtctactcatatctACT | -21 | 48.3 |
| 76 | AATTACACCATTCCTCT | 8389 | 8405 | 3-10-4 | 76_1 | AATtacaccattcCTCT | -22 | 17.3 |
| 77 | CCCTTTTAATTACACCAT | 8395 | 8412 | 1-13-4 | 77_1 | Cccttttaattacacc CCAT | -23 | 18.7 |
| 78 | ACACTATTATACATTCCCA | 9395 | 9413 | 3-14-2 | 78_1 | ACActattatacattccCA | -22 | 83.5 |
| 79 | AGCTACACTATTATACAT | 9400 | 9417 | 3-13-2 | 79_1 | AGCtacactattatacAT | -19 | 98.7 |
| 80 | ACTTCCATATTATTTTCCAT | 9421 | 9440 | 2-15-3 | 80_1 | ACttccatattattttcCAT | -23 | 65.2 |
| 81 | TCTCCTTAAATACATCAAAT | 10395 | 10414 | 4-12-4 | 81_1 | TCTCcttaaatacatcAAAT | -21 | 68.9 |
| 82 | ATATTACTGTACTCCC | 10916 | 10931 | 1-12-3 | 82_1 | AtattactgtactCCC | -19 | 22.7 |
| 83 | ATATTTATACAACAACTCA | 12492 | 12510 | 4-11-4 | 83_1 | ATATttatacaacaaCTCA | -21 | 16.5 |
| 84 | TAGTCACCATTTTTCAT | 13016 | 13032 | 3-12-2 | 84_1 | TAGtcaccattttt cAT | -19 | 57.3 |
| 85 | AGAAAATAATTCCTATCCT | 13384 | 13402 | 2-14-3 | 85_1 | AGaaaataattcctatCCT | -20 | 108.7 |
| 86 | ATACATGTATCCACTTC | 15449 | 15465 | 1-12-4 | 86_1 | AtacatgtatccaCTTC | -18 | 21.6 |
| 87 | TTCCAATATTATTATACA | 15461 | 15478 | 4-10-4 | 87_1 | TTCCaatattattaTACA | -21 | 37.7 |
| 88 | ACCCTTATTTAAATAATTA | 15493 | 15511 | 4-11-4 | 88_1 | ACCCttatttaaataATTA | -22 | 92.5 |
| 89 | TCACGTTAAATCCCATCT | 15581 | 15598 | 2-14-2 | 89_1 | TCacgttaaatcccatCT | -21 | 27.6 |
| 90 | ACGTTAAATCCCATC | 15582 | 15596 | 4-9-2 | 90_1 | ACGTtaaatcccaTC | -18 | 28.7 |
| 91 | TTCACGTTAAATCCCA | 15584 | 15599 | 1-11-4 | 91_1 | TtcacgttaaatCCCA | -21 | 22.8 |
| 92 | GGATATCGTATTTTCT | 16909 | 16924 | 3-10-3 | 92_1 | GGAatatcgtatttTCT | -19 | 29.1 |
| 93 | TCTGGATATCGTATT | 16913 | 16927 | 5-8-2 | 93_1 | TCTGGatatcgtaTT | -19 | 98.8 |
| 94 | GATATATTATCCATCTCA | 17171 | 17188 | 4-11-3 | 94_1 | GATAtattatccatcTCA | -22 | 12.0 |
| 95 | TGATATATTATCCATCT | 17173 | 17189 | 4-9-4 | 95_1 | TGATatattatccATCT | -21 | 104.6 |
| 96 | AGCATCTACATTTTAATT | 17339 | 17356 | 4-10-4 | 96_1 | AGCAtctacattttAATT | -21 | 31.1 |

-continued

Compound Table

| SEQ ID NO | Motif sequence | position on SEQ ID NO: 1 Start | end | Design | CMP ID NO | Oligonucleotide Compound | dG | SNC9A mRNA % (vs Saline control 100%) |
|---|---|---|---|---|---|---|---|---|
| 97 | TCTTAATTCTTATCATTTTA | 17606 | 17625 | 4-12-4 | 97_1 | TCTTaattcttatcatTTTA | -21 | 22.9 |
| 98 | AACTTCTTAATTCTTATCA | 17611 | 17629 | 4-11-4 | 98_1 | AACTtcttaattcttATCA | -21 | 48.8 |
| 99 | TACAATAATTATCTTCTCA | 19084 | 19102 | 4-11-4 | 99_1 | TACAataattatcttCTCA | -22 | 9.8 |
| 100 | TGCAAATAATACCCTAT | 19281 | 19297 | 3-10-4 | 100_1 | TGCaaataataccCTAT | -22 | 60.6 |
| 101 | CTCTATTCTAAATAAACCTT | 19713 | 19732 | 4-14-2 | 101_1 | CTCTattctaaataaaccTT | -20 | 69.3 |
| 102 | ACTCTATTCTAAATAAACC | 19715 | 19733 | 4-11-4 | 102_1 | ACTCtattctaaataAACC | -21 | 59.8 |
| 103 | ATGACTCTATTCTAAATA | 19719 | 19736 | 4-10-4 | 103_1 | ATGActctattctaAATA | -20 | 70.5 |
| 104 | TAAGCATATATTTTCCCA | 20666 | 20683 | 1-14-3 | 104_1 | TaagcatatattttcCCA | -20 | 41.0 |
| 105 | TCATTTCCATTAAATCCAA | 21212 | 21230 | 4-12-3 | 105_1 | TCATttccattaaatcCAA | -22 | 19.0 |
| 106 | TTTCATTTCCATTAAATCC | 21214 | 21232 | 4-12-3 | 106_1 | TTTCatttccattaaaTCC | -22 | 8.8 |
| 107 | TTTTATCCTACTTCTAC | 22208 | 22224 | 1-12-4 | 107_1 | TtttatcctacttCTAC | -18 | 94.6 |
| 108 | TCCCTCAAATATAAATTC | 22299 | 22316 | 4-11-3 | 108_1 | TCCCtcaaatataaaTTC | -21 | 86.8 |
| 109 | ACTGTTTCTCTAAACC | 23036 | 23052 | 2-11-4 | 109_1 | ACtgttttctctaAACC | -20 | 24.9 |
| 110 | AGATTCACTACATCCA | 24286 | 24301 | 3-10-3 | 110_1 | AGAttcactacatCCA | -22 | 10.8 |
| 111 | GCACTCTGATTACATTTCCT | 24422 | 24441 | 1-17-2 | 111_1 | GcactctgattacatttcCT | -23 | 62.0 |
| 112 | TATTTAATCACTTTATCTAA | 24503 | 24522 | 2-14-4 | 112_1 | TAtttaatcactttatCTAA | -18 | 102.4 |
| 113 | ATATTTAATCACTTTATCT | 24505 | 24523 | 2-13-4 | 113_1 | ATatttaatcactttATCT | -18 | 125.6 |
| 114 | ATCAACCACACAATTACTTT | 24715 | 24734 | 1-15-4 | 114_1 | AtcaaccacacaattaCTTT | -20 | 72.4 |
| 115 | TATCAACCACACAATTACTT | 24716 | 24735 | 2-15-3 | 115_1 | TAtcaaccacacaattaCTT | -21 | 88.8 |
| 116 | TTATCAACCACACAATTAC | 24718 | 24736 | 3-13-3 | 116_1 | TTAtcaaccacacaatTAC | -19 | 81.8 |
| 117 | TCAATAAAATTCCTTATACT | 25826 | 25845 | 2-14-4 | 117_1 | TCaataaaattccttaTACT | -19 | 99.6 |
| 118 | TCATTTTATTTATTTCAATT | 26537 | 26556 | 4-12-4 | 118_1 | TCATtttatttatttcAATT | -19 | 86.7 |
| 119 | TATACACTCTTTCTCTATTC | 26697 | 26716 | 2-14-4 | 119_1 | TAtacactctttctctATTC | -22 | 94.0 |
| 120 | TGACCATCTTATTCATC | 26782 | 26798 | 4-10-3 | 120_1 | TGAccatcttattcATC | -21 | 43.6 |
| 121 | CCTGATACTCATTCCCA | 27287 | 27303 | 1-14-2 | 121_1 | CctgatactcattccCA | -21 | 57.2 |
| 122 | TTTCTCTTATCTTTTATC | 27498 | 27516 | 4-12-3 | 122_1 | TTTCtcttatcttttATC | -20 | 30.1 |
| 123 | AAATCAACCCTAAACCC | 27530 | 27546 | 3-10-4 | 123_1 | AAAtcaaccctaaACCC | -22 | 105.9 |
| 124 | AAAGTACCATTTACTCCC | 27603 | 27620 | 4-12-2 | 124_1 | AAAGtaccatttactcCC | -23 | 9.1 |
| 125 | TTCATATACTCTTATTTTA | 27669 | 27687 | 4-11-4 | 125_1 | TTCatatactcttatTTTA | -20 | 10.5 |
| 126 | CTAATTTTCATATACTCTT | 27675 | 27694 | 1-15-4 | 126_1 | CtaattttcatatacTCTT | -19 | 100.5 |
| 127 | TCTAATTTTCATATACTC | 27677 | 27695 | 4-11-4 | 127_1 | TCTAattttcatatACTC | -21 | 7.0 |
| 128 | CTCTAATTTTCATATACT | 27678 | 27696 | 3-12-4 | 128_1 | CTCtaattttcataTACT | -21 | 57.2 |
| 129 | ACATTTTCCTACAAACTA | 27781 | 27799 | 3-12-4 | 129_1 | ACAttttcctacaaACTA | -22 | 115.4 |
| 130 | CTACTATTCCATCATTTTT | 28331 | 28349 | 4-13-2 | 130_1 | CTACtattccatcatttTT | -22 | 17.3 |
| 131 | CAATTACACCTACAACTTC | 28710 | 28728 | 2-13-4 | 131_1 | CAattacacctacaaCTTC | -21 | 55.7 |

Compound Table

| SEQ ID NO | Motif sequence | position on SEQ ID NO: 1 Start | end | Design | CMP ID NO | Oligonucleotide Compound | dG | SNC9A mRNA % (vs Saline control 100%) |
|---|---|---|---|---|---|---|---|---|
| 132 | TCCAATTACACCTACAAC | 28713 | 28730 | 3-11-4 | 132_1 | TCCaattacacctaCAAC | -23 | 16.5 |
| 133 | GCCTTAATCAATTTCTCAA | 29790 | 29808 | 3-14-2 | 133_1 | GCCttaatcaatttctcAA | -22 | 78.6 |
| 134 | CACTTTCCAATATTACT | 30079 | 30095 | 3-11-3 | 134_1 | CACtttccaatattACT | -19 | 32.1 |
| 135 | TTACACTTTCCAATATTAC | 30080 | 30098 | 4-11-4 | 135_1 | TTACactttccaataTTAC | -22 | 18.0 |
| 136 | CATTACACTTTCCAATATTA | 30081 | 30100 | 4-13-3 | 136_1 | CATTacactttccaataTTA | -23 | 14.3 |
| 137 | ACATTACACTTTCCAATA | 30084 | 30101 | 4-10-4 | 137_1 | ACATtacactttccAATA | -21 | 31.4 |
| 138 | ATATACCCCAATTACTCCA | 30949 | 30967 | 1-16-2 | 138_1 | AtataccccaattactcCA | -22 | 77.5 |
| 139 | ATACTAGCAATTCATCA | 31411 | 31427 | 4-9-4 | 139_1 | ATACtagcaattcATCA | -21 | 58.4 |
| 140 | ATACCATTAACTATCACC | 31626 | 31643 | 2-12-4 | 140_1 | ATaccattaactatCACC | -22 | 32.4 |
| 141 | AGATACCATTAACTATCA | 31628 | 31645 | 4-11-3 | 141_1 | AGATaccattaactaTCA | -22 | 81.6 |
| 142 | CCCATCTTCATTATATTA | 32138 | 32155 | 2-12-4 | 142_1 | CCcatcttcattatATTA | -22 | 94.9 |
| 143 | TTCTGATCTCTCTTATA | 34051 | 34067 | 1-12-4 | 143_1 | TtctgatctctctTATA | -18 | 76.2 |
| 144 | ATTTCATTCAGGAAATAC | 34107 | 34124 | 1-10-7 | 144_1 | AtttcattcagGAAATAC | -19 | 95.0 |
| 145 | TCATTTCATCAATAACATTA | 34132 | 34151 | 3-15-2 | 145_1 | TCAtttcatcaataacatTA | -18 | 83.0 |
| 146 | TTGCTTTTTTACTAACA | 34181 | 34197 | 4-11-2 | 146_1 | TTGCttttttactaaCA | -20 | 45.3 |
| 147 | GTTTCATTTCTTTATTAT | 34206 | 34223 | 2-12-4 | 147_1 | GTttcatttctttaTTAT | -19 | 78.5 |
| 148 | GCTATTATATTACTTTT | 34269 | 34285 | 4-9-4 | 148_1 | GCTAttatattacTTTT | -20 | 23.6 |
| 149 | GTCCTCTAATCATATCACA | 35539 | 35557 | 1-15-3 | 149_1 | GtcctctaatcatatcACA | -21 | 71.5 |
| 150 | TAGTCCTCTAATCATATC | 35542 | 35559 | 2-12-4 | 150_1 | TAgtcctctaatcaTATC | -21 | 46.3 |
| 151 | TTAGTCCTCTAATCATA | 35544 | 35560 | 4-10-3 | 151_1 | TTAGtcctctaatcATA | -21 | 55.1 |
| 152 | ACTTAGTCCTCTAATCA | 35546 | 35562 | 4-11-2 | 152_1 | ACTTagtcctctaatCA | -21 | 27.0 |
| 153 | TAAATAAACAATCCCCA | 36850 | 36867 | 2-12-4 | 153_1 | TAaataaacaatcCCCA | -21 | 73.2 |
| 154 | TAATTAAATAAACAATCCC | 36852 | 36871 | 2-14-4 | 154_1 | TAattaaataaacaaTCCC | -18 | 94.5 |
| 155 | ATACATACCTCTATTATT | 38088 | 38105 | 4-10-4 | 155_1 | ATACatacctctatTATT | -21 | 47.1 |
| 156 | TCAATACATACCTCTATTA | 38090 | 38108 | 4-11-4 | 156_1 | TCAAtacatacctctATTA | -22 | 30.7 |
| 157 | CTCAATACATACCTCTATT | 38091 | 38109 | 1-14-4 | 157_1 | CtcaatacatacctcTATT | -20 | 100.7 |
| 158 | GAACTCAATACATACCTC | 38095 | 38112 | 4-11-3 | 158_1 | GAACtcaatacatacCTC | -21 | 14.4 |
| 159 | AGAACTCAATACATACC | 38097 | 38113 | 2-11-4 | 159_1 | AGaactcaatacaTACC | -19 | 15.4 |
| 160 | TGAATTTTATTCCCTTC | 42260 | 42277 | 2-13-3 | 160_1 | TGaattttattcccTTC | -19 | 59.5 |
| 161 | ACACAATACCATATTTCA | 42376 | 42393 | 4-10-4 | 161_1 | ACACaataccatatTTCA | -22 | 7.5 |
| 162 | TGCTATAATATTTATCT | 42912 | 42929 | 4-10-4 | 162_1 | TGCTataatattttATCT | -22 | 65.7 |
| 163 | ACAACTTTCAATACTCTA | 43082 | 43100 | 4-11-4 | 163_1 | ACAacttcaatacTCTA | -21 | 9.6 |
| 164 | TCTTCTACACTATTATTC | 43218 | 43235 | 2-12-4 | 164_1 | TCttctacactattATTC | -19 | 60.1 |
| 165 | ATATCTTCTACACTATTATT | 43219 | 43238 | 3-13-4 | 165_1 | ATAtcttctacactatTATT | -21 | 97.4 |

Compound Table

| SEQ ID NO | Motif sequence | position on SEQ ID NO: 1 Start | end | Design | CMP ID NO | Oligonucleotide Compound | dG | SNC9A mRNA % (vs Saline control 100%) |
|---|---|---|---|---|---|---|---|---|
| 166 | TATATCTTCTACACTATTA | 43221 | 43239 | 4-11-4 | 166_1 | TATAtcttctacactATTA | -21 | 93.3 |
| 167 | TTATATCTTCTACACTA | 43224 | 43240 | 3-10-4 | 167_1 | TTAtatcttctacACTA | -19 | 81.7 |
| 168 | AGCTCATTTTCCTATAC | 43713 | 43729 | 3-12-2 | 168_1 | AGCtcattttcctatAC | -21 | 67.8 |
| 169 | TACTTTTTTTCTATCCAA | 44082 | 44100 | 4-12-3 | 169_1 | TACTttttttctatcCAA | -22 | 59.2 |
| 170 | TCTACTTTTTTTCTATC | 44085 | 44102 | 2-12-4 | 170_1 | TCtactttttttcTATC | -20 | 72.4 |
| 171 | TTTATTAATTTACTCCTT | 44846 | 44863 | 4-10-4 | 171_1 | TTTAttaatttactCCTT | -21 | 41.8 |
| 172 | ATTTTATTAATTTACTCC | 44848 | 44865 | 4-10-4 | 172_1 | ATTTtattaatttaCTCC | -20 | 42.1 |
| 173 | ACCAATACCATAAATTCCA | 44868 | 44886 | 2-14-3 | 173_1 | ACcaataccataaattCCA | -22 | 35.9 |
| 174 | ATTAATATTTTTCTCCAT | 45728 | 45746 | 3-12-4 | 174_1 | ATTaatatttttctCCAT | -22 | 70.9 |
| 175 | TTTATTAATATTTTTCTCC | 45730 | 45749 | 3-13-4 | 175_1 | TTTattaatatttttCTCC | -22 | 39.4 |
| 176 | TCCTTTTATTAATATTTTT | 45734 | 45753 | 4-14-2 | 176_1 | TCCTtttattaatattttTT | -20 | 92.9 |
| 177 | CCTCCTTTTATTAATATT | 45738 | 45755 | 4-11-3 | 177_1 | CCTCcttttattaatATT | -22 | 94.9 |
| 178 | GCCTCCTTTTATTAATAT | 45739 | 45756 | 2-13-3 | 178_1 | GCctccttttattaaTAT | -22 | 55.4 |
| 179 | TAACATATCTACCATCTC | 46470 | 46487 | 3-11-4 | 179_1 | TAAcatatctaccaTCTC | -21 | 24.1 |
| 180 | AATCCCTTACCATTATT | 47155 | 47171 | 4-10-3 | 180_1 | AATCccttaccattATT | -21 | 48.5 |
| 181 | ACAGCTTCATTTAACTA | 48015 | 48031 | 4-10-3 | 181_1 | ACAGcttcatttaaCTA | -21 | 61.0 |
| 182 | TTAACCAAATCTATACACT | 48381 | 48399 | 4-11-4 | 182_1 | TTAAccaaatctataCACT | -21 | 49.8 |
| 183 | TTAGACTAACCATCCTA | 49270 | 49286 | 3-11-3 | 183_1 | TTAgactaaccatcCTA | -21 | 64.0 |
| 184 | TATTAGACTAACCATCC | 49272 | 49288 | 4-10-3 | 184_1 | TATTagactaaccaTCC | -22 | 47.9 |
| 185 | ACCTCATAATACTTTTC | 49305 | 49321 | 3-10-4 | 185_1 | ACCtcataatactTTTC | -20 | 58.1 |
| 186 | TACCTGATAACATCTTT | 49578 | 49594 | 4-9-4 | 186_1 | TACCtgataacatCTTT | -22 | 18.9 |
| 187 | TTACTAATCTAAATACCT | 49590 | 49607 | 4-10-4 | 187_1 | TTACtaatctaaatACCT | -20 | 90.4 |
| 188 | TCTCATTTTACTAATCTA | 49597 | 49614 | 4-11-3 | 188_1 | TCTCattttactaatCTA | -21 | 38.0 |
| 189 | TTCTCATTTTACTAATCT | 49598 | 49615 | 3-12-3 | 189_1 | TTCtcattttactaaTCT | -19 | 87.2 |
| 190 | AACCAAGTCTATATCCA | 49655 | 49671 | 3-10-4 | 190_1 | AACcaagtctataTCCA | -22 | 37.6 |
| 191 | TCACCTTCATAACTTATC | 50050 | 50067 | 4-11-3 | 191_1 | TCACcttcataacttATC | -21 | 69.9 |
| 192 | ATTTTAAATTACTCTCCTAT | 50079 | 50098 | 4-13-3 | 192_1 | ATTTtaaattactctccTAT | -21 | 93.0 |
| 193 | ATATTTTAAATTACTCTCCT | 50081 | 50100 | 3-14-3 | 193_1 | ATAttttaaattactctCCT | -22 | 101.6 |
| 194 | AGTACAATTTAACTCCCT | 50396 | 50413 | 1-14-3 | 194_1 | AgtacaatttaactcCCT | -21 | 93.8 |
| 195 | ATTATCTATAATATACCTA | 50755 | 50773 | 4-11-4 | 195_1 | ATTAtctataatataCCTA | -22 | 102.1 |
| 196 | TCCATAAATCTATTCCAA | 50889 | 50906 | 4-11-3 | 196_1 | TCCAtaaatctattcCAA | -22 | 34.6 |
| 197 | TTCCATAAATCTATTCCA | 50890 | 50907 | 3-12-3 | 197_1 | TTCcataaatctattCCA | -22 | 16.2 |
| 198 | TTTCCATAAATCTATTCC | 50891 | 50908 | 4-10-4 | 198_1 | TTTCcataaatctaTTCC | -22 | 70.6 |
| 199 | AGCAAATAAATTCCAACAC | 52815 | 52833 | 4-12-3 | 199_1 | AGCAaataaattccaaCAC | -22 | 28.9 |
| 200 | TCATGCTTCCATAATTA | 53336 | 53352 | 2-11-4 | 200_1 | TCatgcttccataATTA | -19 | 21.2 |

Compound Table

| SEQ ID NO | Motif sequence | position on SEQ ID NO: 1 Start | end | Design | CMP ID NO | Oligonucleotide Compound | dG | SNC9A mRNA % (vs Saline control 100%) |
|---|---|---|---|---|---|---|---|---|
| 201 | CCTTTCCCATTACAATTT | 53599 | 53616 | 1-13-4 | 201_1 | CctttcccattacaATTT | -21 | 63.4 |
| 202 | ACATGATACTTAATACC | 55294 | 55310 | 4-9-4 | 202_1 | ACATgatacttaaTACC | -21 | 97.9 |
| 203 | CAACAATATCAATCTTCC | 55360 | 55377 | 4-10-4 | 203_1 | CAAcaatatcaatcTTCC | -21 | 41.4 |
| 204 | TTATTAATATTTCTTCTTCA | 55509 | 55528 | 3-14-3 | 204_1 | TTAttaatatttcttctTCA | -19 | 82.5 |
| 205 | TCAGTTAATCATCTCAC | 56328 | 56344 | 4-10-3 | 205_1 | TCAGttaatcatctCAC | -21 | 29.8 |
| 206 | TTGCCATTAAAATTTCC | 56848 | 56864 | 2-11-4 | 206_1 | TTgccattaaaatTTCC | -19 | 39.2 |
| 207 | GATGAACAGACCAAACT | 57524 | 57540 | 2-9-6 | 207_1 | GAtgaacagacCAAACT | -20 | 50.9 |
| 208 | ATCCATACATCCTAAAAT | 57753 | 57770 | 4-10-4 | 208_1 | ATCCatacatcctaAAAT | -21 | 83.7 |
| 209 | CTCATCCATACATCCTA | 57757 | 57773 | 1-13-3 | 209_1 | CtcatccatacatCCTA | -21 | 91.9 |
| 210 | GTCCAAATATCATATCAT | 58334 | 58351 | 4-11-3 | 210_1 | GTCCaaatatcatatCAT | -22 | 92.5 |
| 211 | TGTCCAAATATCATATC | 58336 | 58352 | 4-9-4 | 211_1 | TGTCcaaatatcaTATC | -21 | 114.5 |
| 212 | ACCATTAATCTCATATT | 58538 | 58554 | 4-9-4 | 212_1 | ACCAttaatctcaTATT | -21 | 61.8 |
| 213 | TCACCATTAATCTCATAT | 58539 | 58556 | 4-11-3 | 213_1 | TCACcattaatctcaTAT | -22 | 78.6 |
| 214 | CACCATTAATCTCATA | 58540 | 58555 | 2-10-4 | 214_1 | CAccattaatctCATA | -19 | 65.7 |
| 215 | ATCAATCAATATTTATTCTT | 58702 | 58721 | 3-14-3 | 215_1 | ATCaatcaatatttattCTT | -18 | 111.2 |
| 216 | ATACTTTACTTTTCAAATTT | 58822 | 58841 | 4-14-2 | 216_1 | ATACtttacttttcaaatTT | -18 | 86.5 |
| 217 | TATACTTTACTTTTCAAATT | 58823 | 58842 | 4-14-2 | 217_1 | TATActttacttttcaaaTT | -18 | 106.2 |
| 218 | CTTTATACTTTACTTTTCAA | 58826 | 58845 | 2-14-4 | 218_1 | CTttatactttacttttTCAA | -20 | 49.3 |
| 219 | TCTTTATACTTTACTTTTCA | 58827 | 58846 | 2-16-2 | 219_1 | TCtttatactttacttttCA | -19 | 105.0 |
| 220 | CCAATATTCCTATTCTC | 60635 | 60651 | 2-12-3 | 220_1 | CCaatattcctattCTC | -21 | 75.8 |
| 221 | TGTAACCACTCTTATCAAT | 62608 | 62626 | 2-13-4 | 221_1 | TGtaaccactcttatCAAT | -21 | 92.3 |
| 222 | AATGTAACCACTCTTATC | 62611 | 62628 | 2-12-4 | 222_1 | AAtgtaaccactctTATC | -19 | 40.3 |
| 223 | TTCCAATTTCCTATTAAT | 63501 | 63518 | 4-10-4 | 223_1 | TTCCaatttcctatTAAT | -22 | 100.2 |
| 224 | CATTCCAATTTCCTATTA | 63503 | 63520 | 3-12-3 | 224_1 | CATtccaatttcctaTTA | -21 | 121.2 |
| 225 | AAATTTTCCTAAATTCCCC | 63916 | 63934 | 1-15-3 | 225_1 | AaattttcctaaattcCCC | -22 | 90.1 |
| 226 | TTCACTAATCTCAATTTA | 64566 | 64583 | 4-10-4 | 226_1 | TTCActaatctcaaTTTA | -19 | 31.2 |
| 227 | ACTAAATTTCACTAATCTCA | 64571 | 64590 | 1-15-4 | 227_1 | ActaaatttcactaatCTCA | -19 | 62.4 |
| 228 | TTATTCACTAAATTTCACT | 64578 | 64596 | 4-11-4 | 228_1 | TTATtcactaaatttCACT | -21 | 89.1 |
| 229 | TGCTAAACAATTATACTA | 66548 | 66565 | 4-12-2 | 229_1 | TGCTaaacaattatacTA | -19 | 96.5 |
| 230 | AATTATTCATCCATTCTTTC | 67741 | 67760 | 1-15-4 | 230_1 | AattattcatccattcTTTC | -20 | 32.5 |
| 231 | ATCAATTTTCACATCAATA | 68866 | 68885 | 4-12-4 | 231_1 | ATCAattttcacatcAATA | -21 | 51.1 |
| 232 | TTATACCCACTTACTC | 69491 | 69506 | 3-11-2 | 232_1 | TTAtacccacttacTC | -18 | 102.6 |
| 233 | GTACTTATACCCACTTAC | 69493 | 69510 | 1-14-3 | 233_1 | GtacttatacccactTAC | -20 | 101.0 |
| 234 | ATGTACTTATACCCACTT | 69495 | 69512 | 1-14-3 | 234_1 | AtgtacttatacccaCTT | -20 | 95.9 |

-continued

Compound Table

| SEQ ID NO | Motif sequence | position on SEQ ID NO: 1 Start | end | Design | CMP ID NO | Oligonucleotide Compound | dG | SNC9A mRNA % (vs Saline control 100%) |
|---|---|---|---|---|---|---|---|---|
| 235 | TGTACTTATACCCACT | 69496 | 69511 | 2-12-2 | 235_1 | TGtacttatacccaCT | -19 | 98.5 |
| 236 | AAATGTACTTATACCCAC | 69497 | 69514 | 1-13-4 | 236_1 | AaatgtacttatacCCAC | -20 | 93.0 |
| 237 | CATCTAATTTTTCTAATCT | 69660 | 69678 | 4-11-4 | 237_1 | CATCtaattttctaATCT | -22 | 58.2 |
| 238 | TTATAAACATACACCCA | 69755 | 69772 | 3-11-4 | 238_1 | TTAtaaacatacaCCCA | -22 | 74.9 |
| 239 | ATTATAAACATACACCC | 69756 | 69773 | 4-10-4 | 239_1 | ATTAtaaacatacACCC | -21 | 39.1 |
| 240 | CTTCTATCAAAAATTCACC | 69800 | 69818 | 4-12-3 | 240_1 | CTTCtatcaaaaattcACC | -21 | 51.1 |
| 241 | CAAAGTATATATTCCA | 70094 | 70110 | 3-8-6 | 241_1 | CAAagtatatATTCCA | -20 | 22.6 |
| 242 | TACGCAAAAACAATGAC | 70197 | 70213 | 4-7-6 | 242_1 | TACGcaaaaacAATGAC | -20 | 65.7 |
| 243 | TTACGCAAAAACAATG | 70199 | 70214 | 5-5-6 | 243_1 | TTACGcaaaaACAATG | -19 | 111.1 |
| 244 | TACTTACGCAAAAACA | 70202 | 70217 | 5-8-3 | 244_1 | TACTTacgcaaaaACA | -18 | 99.6 |
| 245 | CAGCTCTTTTACAAATAT | 70637 | 70654 | 4-12-2 | 245_1 | CAGCtcttttacaaatAT | -21 | 48.5 |
| 246 | TCTATGATACTTACCT | 71617 | 71632 | 2-10-4 | 246_1 | TCtatgatacttACCT | -19 | 96.9 |
| 247 | ACACCAATTACTTCTTACC | 71764 | 71782 | 1-16-2 | 247_1 | AcaccaattacttcttaCC | -20 | 101.9 |
| 248 | CACACCAATTACTTCTTAC | 71765 | 71783 | 1-15-3 | 248_1 | CacaccaattacttctTAC | -19 | 98.1 |
| 249 | TTCACACCAATTACTTCTTA | 71766 | 71785 | 1-17-2 | 249_1 | TtcacaccaattacttctTA | -19 | 115.8 |
| 250 | GCTTCACACCAATTACTTC | 71769 | 71787 | 1-16-2 | 250_1 | GcttcacaccaattactTC | -20 | 63.0 |
| 251 | CCTAATGCTTCACACC | 71778 | 71793 | 1-12-3 | 251_1 | CctaatgcttcacACC | -20 | 24.0 |
| 252 | ACAACTCCCAAATAGTT | 71808 | 71824 | 4-10-3 | 252_1 | ACAActcccaaataGTT | -21 | 96.1 |
| 253 | AAATTTAATTAAAATTGC | 72045 | 72062 | 6-5-7 | 253_1 | AAATTTaattaAAATTGC | -18 | 112.6 |
| 254 | ATGCATTATATCAAATCA | 72601 | 72618 | 4-10-4 | 254_1 | ATGCattatatcaaATCA | -22 | 92.9 |
| 255 | AAAACACAAGCTTTCCTA | 72626 | 72643 | 6-9-3 | 255_1 | AAAACacaagctttcCTA | -22 | 41.2 |
| 256 | TCATCCAATATTCATCA | 73726 | 73742 | 3-11-3 | 256_1 | TCAtccaatattcaTCA | -20 | 21.9 |
| 257 | ATATTACTTTTTATTATCTA | 73925 | 73944 | 4-12-4 | 257_1 | ATATtacttttattaTCTA | -21 | 37.0 |
| 258 | GCTAAATTCCTCATCAAAT | 74127 | 74145 | 2-15-2 | 258_1 | GCtaaattcctcatcaaAT | -20 | 79.8 |
| 259 | TGCTAAATTCCTCATCAAA | 74128 | 74146 | 3-13-3 | 259_1 | TGCtaaattcctcatcAAA | -21 | 70.9 |
| 260 | ATATGCTAAATTCCTCATCA | 74130 | 74149 | 1-17-2 | 260_1 | AtatgctaaattcctcatCA | -19 | 95.2 |
| 261 | ATGCTAAATTCCTCATC | 74131 | 74147 | 3-10-4 | 261_1 | ATGctaaattcctCATC | -22 | 56.8 |
| 262 | TATGCTAAATTCCTCAT | 74132 | 74148 | 2-12-3 | 262_1 | TAtgctaaattcctCAT | -18 | 72.9 |
| 263 | GAAAATATGCTAAATTCCT | 74135 | 74153 | 3-10-6 | 263_1 | GAAaatatgctaaATTCCT | -22 | 85.3 |
| 264 | TGCAATCTAACTTCATA | 74761 | 74777 | 3-12-2 | 264_1 | TGCaatctaacttcaTA | -18 | 58.0 |
| 265 | CTTGATTTAAACACCTCT | 75260 | 75277 | 2-13-3 | 265_1 | CTtgatttaaacaccTCT | -20 | 20.9 |
| 266 | ACTTGATTTAAACACCT | 75262 | 75278 | 2-12-3 | 266_1 | ACttgatttaaacaCCT | -18 | 36.6 |
| 267 | GCTTCTTACTATCTTTTA | 75590 | 75607 | 3-13-2 | 267_1 | GCTtcttactatctttTA | -21 | 47.6 |
| 268 | GTCTTCTTTAATCCATCA | 76043 | 76060 | 1-13-4 | 268_1 | GtcttcttaatccATCA | -21 | 29.5 |
| 269 | CTATATTATATATCCACCT | 76205 | 76223 | 2-15-2 | 269_1 | CTatattatatatccacCT | -20 | 97.7 |

-continued

Compound Table

| SEQ ID NO | Motif sequence | position on SEQ ID NO: 1 Start | end | Design | CMP ID NO | Oligonucleotide Compound | dG | SNC9A mRNA % (vs Saline control 100%) |
|---|---|---|---|---|---|---|---|---|
| 270 | CTCTATATTATATATCCAC | 76207 | 76225 | 3-13-3 | 270_1 | CTCtatattatatatcCAC | -20 | 25.7 |
| 271 | TCTCTATATTATATATCCA | 76208 | 76226 | 2-14-3 | 271_1 | TCtctatattatatatCCA | -20 | 53.9 |
| 272 | ATTCTCTATATTATATATCC | 76209 | 76228 | 2-15-3 | 272_1 | ATtctctatattatataTCC | -20 | 92.3 |
| 273 | CCAATTCTCTATATTATAT | 76213 | 76231 | 2-14-3 | 273_1 | CCaattctctatattaTAT | -19 | 88.5 |
| 274 | TCCAATTCTCTATATTATA | 76214 | 76232 | 3-13-3 | 274_1 | TCCaattctctatattATA | -21 | 30.0 |
| 275 | TCTCCAATTCTCTATATTAT | 76215 | 76234 | 2-15-3 | 275_1 | TCtccaattctctatatTAT | -21 | 62.8 |
| 276 | ATCTCCAATTCTCTATATTA | 76216 | 76235 | 1-15-4 | 276_1 | AtctccaattctctatATTA | -20 | 98.1 |
| 277 | AATCTCCAATTCTCTATATT | 76217 | 76236 | 2-14-4 | 277_1 | AAtctccaattctctaTATT | -21 | 93.8 |
| 278 | TAAATCTCCAATTCTCTATA | 76219 | 76238 | 2-16-2 | 278_1 | TAaatctccaattctctaTA | -19 | 100.0 |
| 279 | GAATTTATCTCCAAACTCA | 76262 | 76280 | 3-12-4 | 279_1 | GAAtttatctccaaaCTCA | -22 | 47.5 |
| 280 | TGTCTACACATATTACC | 76709 | 76725 | 2-11-4 | 280_1 | TGtctacacatatTACC | -21 | 31.7 |
| 281 | TGATCCCATCTTATAC | 77011 | 77026 | 3-11-2 | 281_1 | TGAcccatcttatAC | -18 | 21.9 |
| 282 | TATATTTCTCCATAATAC | 77663 | 77680 | 3-12-3 | 282_1 | TATatttctccataaTAC | -18 | 36.3 |
| 283 | TATTCCTCAATAAACCTA | 78216 | 78233 | 2-12-4 | 283_1 | TAttcctcaataaaCCTA | -21 | 61.6 |
| 284 | GACTTCCTATTTTACTCA | 79981 | 79998 | 2-14-2 | 284_1 | GActtcctattttactCA | -20 | 82.6 |
| 285 | TTTCTCATATATTCTCCC | 81181 | 81198 | 1-15-2 | 285_1 | TttctcatatattctcCC | -20 | 81.7 |
| 286 | TTTTCTCATATATTCTCC | 81182 | 81199 | 3-12-3 | 286_1 | TTTtctcatatattcTCC | -21 | 22.6 |
| 287 | CTATTTTCTCATATATTCT | 81184 | 81202 | 4-12-3 | 287_1 | CTATtttctcatatatTCT | -22 | 31.1 |
| 288 | TTTACTATTTTCTCATATAT | 81187 | 81206 | 4-12-4 | 288_1 | TTTActattttctcatATAT | -21 | 21.4 |
| 289 | TTACTATTTTCTCATATA | 81188 | 81205 | 4-10-4 | 289_1 | TTACtattttctcaTATA | -21 | 22.1 |
| 290 | AACAAATATTACATACCCT | 81401 | 81419 | 3-12-4 | 290_1 | AACaaatattacataCCCT | -22 | 93.8 |
| 291 | TGCCATTAAATAAATACA | 82068 | 82085 | 4-10-4 | 291_1 | TGCCattaaataaaTACA | -22 | 87.4 |
| 292 | TGCCATTCAAAAATACAAT | 82794 | 82812 | 3-12-4 | 292_1 | TGCcattcaaaaataCAAT | -21 | 76.6 |
| 293 | TAATATACTTTATCATACA | 83724 | 83743 | 2-14-4 | 293_1 | TAatatactttatcaTACA | -18 | 80.4 |
| 294 | ATTACTTTATTCATCTCAT | 86909 | 86927 | 2-14-3 | 294_1 | ATtactttattcatctCAT | -19 | 87.1 |
| 295 | TAATTACTTTATTCATCTCA | 86910 | 86929 | 3-14-3 | 295_1 | TAAttactttattcatcTCA | -20 | 49.2 |
| 296 | TTAATTACTTTATTCATCTC | 86911 | 86930 | 2-15-3 | 296_1 | TTaattactttattcatCTC | -18 | 60.0 |
| 297 | TTTAATTACTTTATTCATCT | 86912 | 86931 | 4-14-2 | 297_1 | TTTAattactttattcatCT | -19 | 87.2 |
| 298 | ATTTAATTACTTTATTCATC | 86913 | 86932 | 2-14-4 | 298_1 | ATttaattactttattCATC | -18 | 101.8 |
| 299 | TTCTATCTTTTCTTTCTTTA | 86984 | 87003 | 1-15-4 | 299_1 | TtctatcttttctttcTTTA | -20 | 107.9 |
| 300 | CATGCATTTTTCCTACA | 87092 | 87109 | 3-13-2 | 300_1 | CATgcatttttcctaCA | -22 | 50.4 |
| 301 | GAAATTCTAATTCTTTCT | 87504 | 87521 | 4-10-4 | 301_1 | GAAAttctaattctTTCT | -18 | 90.2 |
| 302 | AACATCTGTTGAAATTCT | 87514 | 87531 | 2-10-6 | 302_1 | AAcatctgttgaAATTCT | -19 | 29.8 |
| 303 | ATTTAATCCATCATTATTCT | 88639 | 88658 | 2-14-4 | 303_1 | ATttaatccatcattaTTCT | -21 | 74.3 |

Compound Table

| SEQ ID NO | Motif sequence | position on SEQ ID NO: 1 Start | end | Design | CMP ID NO | Oligonucleotide Compound | dG | SNC9A mRNA % (vs Saline control 100%) |
|---|---|---|---|---|---|---|---|---|
| 304 | TAACTCCATATCATCAATA | 89002 | 89020 | 4-11-4 | 304_1 | TAACtccatatcatcAATA | -21 | 57.7 |
| 305 | ATTAACTCCATATCATCAA | 89004 | 89022 | 4-11-4 | 305_1 | ATTAactccatatcaTCAA | -22 | 42.2 |
| 306 | AATTAACTCCATATCATCA | 89005 | 89023 | 4-11-4 | 306_1 | AATTaactccatatcATCA | -22 | 46.8 |
| 307 | TTTACCTAAAATCATACCA | 89772 | 89790 | 2-13-4 | 307_1 | TTtacctaaaatcatACCA | -20 | 61.4 |
| 308 | TTATATATCAATCCCCA | 90811 | 90827 | 3-11-3 | 308_1 | TTAtatatcaatccCCA | -22 | 78.2 |
| 309 | TTTTATATATCAATCCCC | 90812 | 90829 | 3-13-2 | 309_1 | TTTtatatatcaatccCC | -20 | 56.1 |
| 310 | TTTTTATATATCAATCCC | 90813 | 90830 | 4-10-4 | 310_1 | TTTTtatatatcaaTCCC | -22 | 32.6 |
| 311 | CTAAAAGACTTGTTCT | 91226 | 91242 | 4-8-5 | 311_1 | CTAAaaagacttGTTCT | -20 | 26.3 |
| 312 | ACTAAAAGACTTGTTC | 91227 | 91243 | 5-8-4 | 312_1 | ACTAAaaagacttGTTC | -18 | 31.0 |
| 313 | CCTTATCTATTATCACC | 91516 | 91532 | 3-12-2 | 313_1 | CCTtatctattatcaCC | -22 | 88.1 |
| 314 | GCCTTATCTATTATCAC | 91517 | 91533 | 3-12-2 | 314_1 | GCCttatctattatcAC | -21 | 97.4 |
| 315 | TTGCCTTATCTATTATC | 91519 | 91535 | 1-12-4 | 315_1 | TtgccttatctatTATC | -18 | 82.9 |
| 316 | TCCTTACGCTGTCATCA | 91540 | 91556 | 2-13-2 | 316_1 | TCcttacgctgtcatCA | -22 | 46.4 |
| 317 | TAATCCAAATTTCTTCATA | 91902 | 91920 | 3-12-4 | 317_1 | TAAtccaaatttcttCATA | -20 | 34.9 |
| 318 | CTTTCAAGCCTAATCA | 92437 | 92452 | 1-11-4 | 318_1 | CtttcaagcctaATCA | -19 | 77.5 |
| 319 | TGTTTTCATATAAACCAT | 93022 | 93039 | 2-12-4 | 319_1 | TGttttcatataaaCCAT | -20 | 67.3 |
| 320 | GATTATTACATACCTTCCA | 94318 | 94336 | 1-15-3 | 320_1 | GattattacataccttCCA | -22 | 86.0 |
| 321 | TATCTTTACCATCATTTAA | 94440 | 94458 | 4-11-4 | 321_1 | TATCtttaccatcatTTAA | -22 | 42.1 |
| 322 | GTTATCTTTACCATCATT | 94443 | 94460 | 3-11-4 | 322_1 | GTTatctttaccatCATT | -23 | 23.0 |
| 323 | AGACTTACCAAATTTCC | 95637 | 95653 | 4-11-2 | 323_1 | AGACttaccaaatttCC | -21 | 90.7 |
| 324 | GAACATGTTGACTCAC | 97243 | 97258 | 4-8-4 | 324_1 | GAACatgttgacTCAC | -20 | 61.8 |
| 325 | AGTTTTAATACCATTTCA | 97712 | 97729 | 3-13-2 | 325_1 | AGTtttaataccatttCA | -19 | 20.1 |
| 326 | CAGTTTTAATACCATTTC | 97713 | 97730 | 4-12-2 | 326_1 | CAGTtttaataccattTC | -20 | 72.1 |
| 327 | ATAATTTATCCTTAATTCT | 98353 | 98371 | 3-13-3 | 327_1 | ATAatttatccttaatTCT | -19 | 65.3 |
| 328 | TCAATGTTTCCAATCTT | 98600 | 98616 | 2-12-3 | 328_1 | TCaatgtttccaatCTT | -18 | 42.4 |
| 329 | CATCTGGTTACATACCACC | 99016 | 99034 | 1-16-2 | 329_1 | CatctggttacataccaCC | -23 | 74.8 |
| 330 | ATCACAAAATAATTTCCAC | 99056 | 99074 | 2-13-4 | 330_1 | ATcacaaaataatttCCAC | -19 | 35.3 |
| 331 | CATCACAAAATAATTTCCA | 99057 | 99075 | 2-14-3 | 331_1 | CAtcacaaaataatttCCA | -19 | 74.3 |
| 332 | TCATCACAAAATAATTTCC | 99058 | 99076 | 3-14-2 | 332_1 | TCAtcacaaaataatttCC | -18 | 73.0 |
| 333 | TAGATCACATCATCACAA | 99068 | 99085 | 2-13-3 | 333_1 | TAgatcacatcatcaCAA | -19 | 26.6 |
| 334 | CCTAAATACCTTTCTTTTCA | 100896 | 100915 | 1-15-4 | 334_1 | CctaaatacctttcttTTCA | -22 | 39.6 |
| 335 | ATACCTAAATACCTTTCTT | 100900 | 100918 | 4-13-2 | 335_1 | ATACctaaatacctttcTT | -21 | 34.3 |
| 336 | CCCTAAATAATACCTAAACA | 100938 | 100957 | 3-15-2 | 336_1 | CCCtaaataatacctaaaCA | -22 | 98.9 |
| 337 | TCCACCCTAAATAATACC | 100944 | 100961 | 2-14-2 | 337_1 | TCcaccctaaataataCC | -21 | 47.6 |
| 338 | AGTTAACACTAATTCTACA | 101277 | 101295 | 3-12-4 | 338 | AGTtaacactaattcTACA | -21 | 34.2 |

-continued

Compound Table

| SEQ ID NO | Motif sequence | position on SEQ ID NO: 1 Start | end | Design | CMP ID NO | Oligonucleotide Compound | dG | SNC9A mRNA % (vs Saline control 100%) |
|---|---|---|---|---|---|---|---|---|
| 339 | GTCTCTAATATTTCTATA | 101747 | 101764 | 3-11-4 | 339_1 | GTCtctaatatttcTATA | -21 | 21.9 |
| 340 | TAGCATTCATCTATCATT | 102745 | 102762 | 2-12-4 | 340_1 | TAgcattcatctatCATT | -21 | 32.7 |
| 341 | CCTAGCATTCATCTATC | 102748 | 102764 | 2-12-3 | 341_1 | CCtagcattcatctATC | -21 | 35.1 |
| 342 | GTTTCACATAATTTATTCC | 103244 | 103262 | 1-15-3 | 342_1 | GtttcacataatttatTCC | -19 | 37.3 |
| 343 | TTAGAATAAATTCACG | 103271 | 103286 | 5-5-6 | 343_1 | TTAGAataaaTTCACG | -20 | 110.8 |
| 344 | TAATTTCTCAAAAATTAAA | 104848 | 104867 | 7-5-8 | 344_1 | TAATTTCtcaaaAAATTAAA | -20 | 103.0 |
| 345 | CCTTCATTATTTCTCAATT | 107241 | 107259 | 2-13-4 | 345_1 | CCttcattatttctcAATT | -21 | 48.7 |
| 346 | CACAACCATCACTATTTC | 107587 | 107604 | 4-11-3 | 346_1 | CACAaccatcactatTTC | -22 | 21.6 |
| 347 | TTATTACAATCTATTTTACA | 107816 | 107835 | 4-12-4 | 347_1 | TTATtacaatctattTTACA | -21 | 26.9 |
| 348 | CACTCAATTCCATACTTAT | 107902 | 107920 | 3-13-3 | 348_1 | CACtcaattccatactTAT | -22 | 70.5 |
| 349 | ACTCAATTCCATACTTA | 107903 | 107919 | 2-11-4 | 349_1 | ACtcaattccataCTTA | -20 | 66.8 |
| 350 | TCTCTTTTAAATTCAATCT | 107954 | 107972 | 4-11-4 | 350_1 | TCTCttttaaattcaATCT | -22 | 44.7 |
| 351 | TATCTCTTTTAAATTCAATC | 107955 | 107974 | 4-12-4 | 351_1 | TATCtcttttaaattcAATC | -20 | 70.9 |
| 352 | GCTATCTCTTTTAAATTCA | 107958 | 107976 | 2-13-4 | 352_1 | GCtatctcttttaaaTTCA | -22 | 46.3 |
| 353 | GTAATTTATCAATTTCCA | 108181 | 108198 | 3-11-4 | 353_1 | GTAatttatcaattTCCA | -22 | 46.7 |
| 354 | AATCTTTTCTTAATCTTTTA | 113283 | 113302 | 4-12-4 | 354_1 | AATCttttcttaatctTTTA | -21 | 66.3 |
| 355 | GTACAATACCATTACAACA | 113456 | 113474 | 4-12-3 | 355_1 | GTACaataccattacaACA | -22 | 51.2 |
| 356 | CAGTTTTACTTTTCAATA | 113624 | 113641 | 4-10-4 | 356_1 | CAGTtttacttttcAATA | -21 | 15.9 |
| 357 | ATCAATTCTACTTAATACA | 114122 | 114140 | 4-11-4 | 357_1 | ATCAattctacttaaTACA | -21 | 24.7 |
| 358 | TATTCTTATTTTCATATATA | 115013 | 115032 | 3-13-4 | 358_1 | TATtcttattttcataTATA | -20 | 98.0 |
| 359 | ATATTCTTATTTTCATATA | 115015 | 115033 | 4-11-4 | 359_1 | ATATtcttattttcaTATA | -21 | 108.9 |
| 360 | AATGATCAATCACCCTT | 115389 | 115405 | 2-11-4 | 360_1 | AAtgatcaatcacCCTT | -20 | 48.1 |
| 361 | TTGATCTACTTAATTTA | 117183 | 117199 | 5-6-6 | 361_1 | TTGATctacttAATTTA | -21 | 108.2 |
| 362 | AGTCCCATAACTAACA | 117429 | 117444 | 4-8-4 | 362_1 | AGTCccataactAACA | -22 | 60.2 |
| 363 | TATCACTTATTCATTCATA | 117533 | 117551 | 3-12-4 | 363_1 | TATcacttattcattCATA | -22 | 32.7 |
| 364 | TTATCCATCTTTTAATTTA | 120075 | 120093 | 3-12-4 | 364_1 | TTAtccatcttttaaTTTA | -20 | 51.2 |
| 365 | ATATCTTTCCATATTTTCA | 120837 | 120856 | 2-14-4 | 365_1 | ATatctttccatatttTTCA | -22 | 31.4 |
| 366 | GGTAACAACTTTTAAATA | 122088 | 122105 | 4-7-7 | 366_1 | GGTAacaacttTTAAATA | -22 | 92.3 |
| 367 | CTAGTATACAACATCATA | 122809 | 122826 | 4-10-4 | 367_1 | CTAGtatacaacatCATA | -22 | 51.0 |
| 368 | ACCTAGTATACAACATC | 122812 | 122828 | 3-10-4 | 368_1 | ACCtagtatacaaCATC | -21 | 26.6 |
| 369 | ACCACATTAAATTCTCAAT | 122841 | 122859 | 4-11-4 | 369_1 | ACCAcattaaattctCAAT | -23 | 49.2 |
| 370 | TTACAACTTTATCTTTTTTA | 123014 | 123033 | 4-12-4 | 370_1 | TTACaactttatctttTTTA | -21 | 31.7 |
| 371 | ACAACCTATACCCTAT | 123731 | 123746 | 4-9-3 | 371_1 | ACAAcctataccTAT | -21 | 29.7 |
| 372 | AGGACAACCTATACCC | 123734 | 123749 | 1-11-4 | 372_1 | AggacaacctatACCC | -22 | 38.3 |

-continued

Compound Table

| SEQ ID NO | Motif sequence | position on SEQ ID NO: 1 Start | end | Design | CMP ID NO | Oligonucleotide Compound | dG | SNC9A mRNA % (vs Saline control 100%) |
|---|---|---|---|---|---|---|---|---|
| 373 | TGATCTTTCTATCTACAC | 123918 | 123935 | 2-13-3 | 373_1 | TGatctttctatctaCAC | -19 | 113.5 |
| 374 | TTGATCTTTCTATCTACA | 123919 | 123936 | 2-13-3 | 374_1 | TTgatctttctatctACA | -18 | 115.1 |
| 375 | AGCCTTATTTAATAATC | 124037 | 124053 | 4-9-4 | 375_1 | AGCCttatttaatAATC | -21 | 102.4 |
| 376 | TGTCTTTATTTTCCAATC | 125837 | 125854 | 4-12-2 | 376_1 | TGTCtttattttccaaTC | -21 | 25.3 |
| 377 | TGTTTCCATAATATTTCT | 126386 | 126403 | 4-12-2 | 377_1 | TGTTtccataatatttCT | -20 | 36.0 |
| 378 | CCATATACCTTCTCCAT | 126732 | 126748 | 1-13-3 | 378_1 | CcatataccttctcCAT | -21 | 73.8 |
| 379 | TTTCCATATACCTTCTC | 126735 | 126751 | 4-11-2 | 379_1 | TTTCcatataccttcTC | -21 | 25.9 |
| 380 | TCTTTTCCATATACCTTC | 126737 | 126754 | 2-12-4 | 380_1 | TCttttccatatacCTTC | -23 | 27.7 |
| 381 | CACTATACAAAACTCTACCA | 127548 | 127567 | 3-15-2 | 381_1 | CACtatacaaaactctacCA | -21 | 103.7 |
| 382 | ACCCTCACTATACAAAAC | 127555 | 127572 | 4-12-2 | 382_1 | ACCCtcactatacaaaAC | -22 | 93.9 |
| 383 | CACCCTCACTATACAAA | 127557 | 127573 | 4-10-3 | 383_1 | CACCctcactatacAAA | -22 | 80.3 |
| 384 | AGCACAATATAAAACCAC | 128165 | 128182 | 3-11-4 | 384_1 | AGCacaatataaaaCCAC | -22 | 46.9 |
| 385 | TTAACATTATCTTTCCAA | 128646 | 128663 | 4-10-4 | 385_1 | TTAAcattatctttCCAA | -21 | 32.0 |
| 386 | CTAGCACTTTAATTTCCA | 130008 | 130025 | 1-14-3 | 386_1 | CtagcactttaatttCCA | -21 | 72.4 |
| 387 | GAATCTCTTCTTAACTCT | 131220 | 131237 | 3-13-2 | 387_1 | GAAtctcttcttaactCT | -19 | 48.6 |
| 388 | AAATAAATGACTATAACT | 132580 | 132597 | 6-5-7 | 388_1 | AAATAAatgacTATAACT | -20 | 102.4 |
| 389 | ACACCTTTCTAAACAATA | 132904 | 132921 | 4-10-4 | 389_1 | ACACctttctaaacAATA | -20 | 85.0 |
| 390 | AGTCTTTAAACCACTTTC | 133059 | 133076 | 4-12-2 | 390_1 | AGTCtttaaaccactTTC | -21 | 28.3 |
| 391 | ACCAAATAATTTCAACACC | 133229 | 133247 | 4-13-2 | 391_1 | ACCAaataatttcaacaCC | -22 | 88.5 |
| 392 | TCCCTCAACCAAATAATTT | 133236 | 133254 | 3-13-3 | 392_1 | TCCctcaaccaaataaTTT | -22 | 87.9 |
| 393 | TCCACCAGATTTTTCC | 133396 | 133411 | 2-12-2 | 393_1 | TCcaccagattttTCC | -21 | 30.9 |
| 394 | AAGCTTTCAAACCAAC | 133448 | 133463 | 4-10-2 | 394_1 | AAGCtttcaaaccaAC | -18 | 78.6 |
| 395 | TTATCCTAAAACTACCAT | 134579 | 134596 | 3-11-4 | 395_1 | TTAtcctaaaactaCCAT | -22 | 117.4 |
| 396 | AAGCACCTCATATCTTC | 134917 | 134933 | 2-11-4 | 396_1 | AAgcacctcatatCTTC | -21 | 85.2 |
| 397 | TTACCACTCATTTATTTCT | 135999 | 136017 | 4-13-2 | 397_1 | TTACcactcatttatttCT | -22 | 53.6 |
| 398 | AGTTACCACTCATTTAT | 136003 | 136019 | 3-10-4 | 398_1 | AGTtaccactcatTTAT | -21 | 41.4 |
| 399 | TACTCTAAAATTATCCTTA | 136533 | 136551 | 3-12-4 | 399_1 | TACtctaaaattatcCTTA | -20 | 83.1 |
| 400 | CAGATTCTTCTTATTCTA | 136566 | 136583 | 4-12-2 | 400_1 | CAGattcttcttattcTA | -21 | 80.9 |
| 401 | GTTCTAATATTCCTCACA | 138079 | 138096 | 2-13-3 | 401_1 | GTtctaatattcctcACA | -20 | 69.8 |
| 402 | CTCTTATCTTCCAATTTTA | 138305 | 138323 | 1-15-3 | 402_1 | CtcttatcttccaattTTA | -19 | 106.3 |
| 403 | TCTATAATTTCTTCTTATTT | 139861 | 139880 | 4-12-4 | 403_1 | TCTAtaatttcttcttATTT | -21 | 78.2 |
| 404 | CTTCTATAATTTCTTCTTA | 139864 | 139882 | 4-12-3 | 404_1 | CTTCtataatttcttcTTA | -21 | 38.6 |
| 405 | TCCTTCTATAATTTCTTCTT | 139865 | 139884 | 2-16-2 | 405_1 | TCccttctataatttcttcTT | -20 | 81.4 |
| 406 | ATTCCTTCTATAATTTCTT | 139868 | 139886 | 4-12-3 | 406_1 | ATTCcttctataatttcTT | -22 | 35.2 |
| 407 | CATTCCTTCTATAATTTCT | 139869 | 139887 | 2-13-4 | 407_1 | CAttccttctataatTTCT | -21 | 41.9 |

-continued

Compound Table

| SEQ ID NO | Motif sequence | position on SEQ ID NO: 1 Start | end | Design | CMP ID NO | Oligonucleotide Compound | dG | SNC9A mRNA % (vs Saline control 100%) |
|---|---|---|---|---|---|---|---|---|
| 408 | ACATTCCTTCTATAATTTC | 139870 | 139888 | 4-12-3 | 408_1 | ACATccttctataatTTC | -21 | 39.6 |
| 409 | GCCATATCTCTTAATTTAA | 140051 | 140069 | 4-13-2 | 409_1 | GCCAtatctcttaatttAA | -22 | 68.7 |
| 410 | AGCCATATCTCTTAATT | 140054 | 140070 | 3-10-4 | 410_1 | AGCcatatctcttAATT | -21 | 40.8 |
| 411 | ACAGCCATATCTCTTAA | 140056 | 140072 | 4-10-3 | 411_1 | ACAGccatatctctTAA | -22 | 26.5 |
| 412 | TAAGTTTCAAATAACCC | 140590 | 140606 | 4-9-4 | 412_1 | TAAGtttcaaataACCC | -21 | 42.1 |
| 413 | TCCATTATTTTCCACTTA | 141294 | 141311 | 3-13-2 | 413_1 | TCCattattttccactTA | -22 | 25.5 |
| 414 | ACATCCATTATTTTCCAC | 141297 | 141314 | 3-12-3 | 414_1 | ACAtccattattttcCAC | -22 | 22.3 |
| 415 | TCACATCCATTATTTTCCA | 141298 | 141316 | 2-15-2 | 415_1 | TCacatccattattttcCA | -22 | 28.7 |
| 416 | TTCACATCCATTATTTTC | 141300 | 141317 | 4-10-4 | 416_1 | TTCAcatccattatTTTC | -22 | 26.2 |
| 417 | TCATTCACATCCATTATTT | 141302 | 141320 | 4-13-2 | 417_1 | TCATtcacatccattatTT | -21 | 38.5 |
| 418 | TTATATATTTATCTATTTCA | 141537 | 141556 | 4-12-4 | 418_1 | TTATatatttatctatTTCA | -20 | 33.1 |
| 419 | AGCAATACAATCAATACA | 141785 | 141802 | 4-10-4 | 419_1 | AGCAatacaatcaaTACA | -22 | 30.2 |
| 420 | CCACAATTACCATAACC | 141860 | 141876 | 4-11-2 | 420_1 | CCACaattaccataaCC | -23 | 45.9 |
| 421 | CACCAAAGATCTACCAA | 141996 | 142012 | 3-10-4 | 421_1 | CACcaaagatctaCCAA | -22 | 55.5 |
| 422 | TATTTTCTTACCCTCATT | 142656 | 142673 | 1-13-4 | 422_1 | TattttcttaccctCATT | -21 | 95.0 |
| 423 | AGTATTTTCTTACCCTCA | 142658 | 142675 | 1-15-2 | 423_1 | AgtattttcttaccctCA | -20 | 108.7 |
| 424 | TAGTATTTTCTTACCCT | 142660 | 142676 | 1-13-3 | 424_1 | TagtattttcttacCCT | -20 | 110.1 |
| 425 | TTAGTATTTTCTTACCC | 142661 | 142677 | 1-13-3 | 425_1 | TtagtattttcttaCCC | -20 | 109.3 |
| 426 | TTATAATTCCACTTACTTT | 143602 | 143620 | 3-12-4 | 426_1 | TTAtaattccacttaCTTT | -20 | 46.1 |
| 427 | GTTATAATTCCACTTACT | 143604 | 143621 | 4-11-3 | 427_1 | GTTAtaattccacttACT | -21 | 50.9 |
| 428 | TAGTTATAATTCCACTTA | 143606 | 143623 | 3-11-4 | 428_1 | TAGttataattccaCTTA | -21 | 112.9 |
| 429 | TTTAGTTATAATTCCAC | 143609 | 143625 | 4-9-4 | 429_1 | TTTAgttataattCCAC | -21 | 28.4 |
| 430 | GTTTTCTCAAATATAATT | 143624 | 143641 | 4-7-7 | 430_1 | GTTTtctcaaaTATAATT | -21 | 109.1 |
| 431 | GAATTCTAATACCACCTT | 144747 | 144764 | 3-11-4 | 431_1 | GAAttctaataccaCCTT | -23 | 51.4 |
| 432 | ATATACTAAACTATTCTCC | 144920 | 144938 | 3-12-4 | 432_1 | ATAtactaaactattCTCC | -22 | 78.0 |
| 433 | TTCATTTATCCTTCAAATA | 145012 | 145031 | 4-12-4 | 433_1 | TTCAttatccttcaaAATA | -22 | 39.2 |
| 434 | TTCATTATTTCATTTATCCT | 145020 | 145039 | 4-14-2 | 434_1 | TTCAttatttcatttatcCT | -22 | 44.3 |
| 435 | TTTAATCCTTTCTTTATTTC | 146253 | 146272 | 3-13-4 | 435_1 | TTTaatcctttctttaTTTC | -21 | 48.9 |
| 436 | CAGTTTTCTTTAATCCT | 146264 | 146281 | 2-13-3 | 436_1 | CAgttttctttaatCCT | -22 | 66.5 |
| 437 | ATGATCCTATTATTACCA | 146574 | 146591 | 4-12-2 | 437_1 | ATGAtcctattattacCA | -22 | 62.2 |
| 438 | TTGACTAACATTCATAA | 147223 | 147239 | 4-7-6 | 438_1 | TTGActaacatTCATAA | -21 | 88.7 |
| 439 | TTCCATCGCACATTTT | 147238 | 147253 | 4-9-3 | 439_1 | TTCCatcgcacatTTT | -22 | 41.2 |
| 440 | ACATAACCTTTATTTTTA | 148020 | 148039 | 4-12-4 | 440_1 | ACATaacctttatttTTTA | -22 | 32.5 |
| 441 | CATTCTAAATCTTAGTC | 148085 | 148101 | 2-9-6 | 441_1 | CAttctaaatcTTAGTC | -20 | 58.7 |

-continued

Compound Table

| SEQ ID NO | Motif sequence | position on SEQ ID NO: 1 Start | end | Design | CMP ID NO | Oligonucleotide Compound | dG | SNC9A mRNA % (vs Saline control 100%) |
|---|---|---|---|---|---|---|---|---|
| 442 | ATAATCGTCCATCCCTT | 148288 | 148304 | 1-12-4 | 442_1 | AtaatcgtccatcCCTT | -23 | 32.0 |
| 443 | TCACATAAACTCATCCAA | 148809 | 148826 | 3-11-4 | 443_1 | TCAcataaactcatCCAA | -22 | 23.8 |
| 444 | TTCACATAAACTCATCC | 148811 | 148827 | 4-9-4 | 444_1 | TTCAcataaactcATCC | -22 | 33.0 |
| 445 | ACTTATTTCACATAAACTC | 148815 | 148833 | 4-11-4 | 445_1 | ACTTatttcacataaACTC | -21 | 20.1 |
| 446 | CTTCAAATAACTACAAAG | 149050 | 149067 | 6-5-7 | 446_1 | CTTCAAataacTACAAAG | -23 | 102.5 |
| 447 | TGTATTCATTACATACT | 149111 | 149127 | 3-10-4 | 447_1 | TGTattcattacaTACT | -20 | 94.2 |
| 448 | ACTCTTAACAATTTATTCA | 149131 | 149149 | 4-11-4 | 448_1 | ACTCttaacaatttaTTCA | -21 | 50.1 |
| 449 | TCACTCTTAACAATTTATTC | 149132 | 149151 | 4-12-4 | 449_1 | TCACtcttaacaatttATTC | -22 | 44.6 |
| 450 | TAACATAATCACTCTTAACA | 149140 | 149159 | 4-12-4 | 450_1 | TAACataatcactcttAACA | -20 | 47.4 |
| 451 | CCAGAACCTATTATTTA | 149630 | 149646 | 3-10-4 | 451_1 | CCAgaacctattaTTTA | -21 | 24.0 |
| 452 | ATTATTCAATCCTCTATA | 149720 | 149737 | 2-12-4 | 452_1 | ATtattcaatcctcTATA | -20 | 64.7 |
| 453 | TAACCTTCATCACATACT | 150502 | 150519 | 4-12-2 | 453_1 | TAACcttcatcacataCT | -21 | 40.0 |
| 454 | ATCTAACCTTCATCACATAC | 150503 | 150522 | 3-15-2 | 454_1 | ATCtaaccttcatcacatAC | -21 | 70.8 |
| 455 | TCTAACCTTCATCACATA | 150504 | 150521 | 2-12-4 | 455_1 | TCtaaccttcatcaCATA | -22 | 74.1 |
| 456 | CTCTATCTAACCTTCATC | 150509 | 150526 | 1-13-4 | 456_1 | CtctatctaaccttCATC | -21 | 38.2 |
| 457 | TGACTCTATCTAACCTTC | 150512 | 150529 | 2-14-2 | 457_1 | TGactctatctaaccttTC | -19 | 63.2 |
| 458 | CCTCTTTTATCAACACAATT | 150801 | 150820 | 2-14-4 | 458_1 | CCtcttttatcaacacAATT | -22 | 76.7 |
| 459 | TCTCCAAATCTTAAATTTC | 150860 | 150878 | 4-13-2 | 459_1 | TCTCcaaatcttaaattTC | -19 | 48.0 |
| 460 | TTTACTATTTCTCCAAATC | 150869 | 150887 | 3-13-3 | 460_1 | TTTactatttctccaaATC | -19 | 41.2 |
| 461 | TCTTTTACTATTTCTCCAAA | 150871 | 150890 | 2-14-4 | 461_1 | TCttttactatttctcCAAA | -21 | 39.5 |
| 462 | CATCTTTTACTATTTCTCCA | 150873 | 150892 | 2-16-2 | 462_1 | CAtcttttactatttctcCA | -22 | 72.6 |
| 463 | TCATCTTTTACTATTTCTC | 150875 | 150893 | 3-13-3 | 463_1 | TCAtcttttactatttCTC | -21 | 32.2 |
| 464 | CCTCATCTTTTACTATTT | 150878 | 150895 | 2-12-4 | 464_1 | CCtcatcttttactATTT | -21 | 62.8 |
| 465 | AACCTCATCTTTTACTA | 150881 | 150897 | 4-11-2 | 465_1 | AACCtcatcttttacTA | -20 | 53.8 |
| 466 | TTTTTATATCTACTCTCA | 150908 | 150925 | 3-11-4 | 466_1 | TTTttatatctactCTCA | -20 | 24.6 |
| 467 | TTAATAAACATCAATCTCC | 150999 | 151017 | 4-11-4 | 467_1 | TTAAtaaacatcaatCTCC | -21 | 32.8 |
| 468 | ATATTTCCTATTCTCCATT | 151333 | 151351 | 1-14-4 | 468_1 | AtatttcctattctcCATT | -22 | 48.4 |
| 469 | CATACTGCTCTTTCTA | 151839 | 151854 | 1-12-3 | 469_1 | CatactgctctttCTA | -18 | 46.8 |
| 470 | ATGCAAATAACTTCATCA | 155977 | 155994 | 4-11-3 | 470_1 | ATGCaaataacttcaTCA | -21 | 30.4 |
| 471 | TTTAACTTTCTTACCACAA | 156180 | 156198 | 4-11-4 | 471_1 | TTTAactttcttaccACAA | -21 | 25.3 |
| 472 | TTAACTTTCTTACCACA | 156181 | 156197 | 4-9-4 | 472_1 | TTAActttcttacCACA | -21 | 25.1 |
| 473 | CATATTCATCTCACCTAC | 168185 | 168202 | 2-12-4 | 473_1 | CAtattcatctcacCTAC | -22 | 68.5 |
| 474 | TCATATTCATCTCACCTA | 168186 | 168203 | 3-13-2 | 474_1 | TCAtattcatctcaccTA | -21 | 36.1 |
| 475 | TTCATATTCATCTCACCT | 168187 | 168204 | 4-12-2 | 475_1 | TTCAtattcatctcacCT | -22 | 22.8 |
| 476 | AATTTCATATTCATCTCAC | 168189 | 168208 | 4-12-4 | 476_1 | AATTtcatattcatcTCAC | -22 | 29.0 |

-continued

Compound Table

| SEQ ID NO | Motif sequence | position on SEQ ID NO: 1 Start | end | Design | CMP ID NO | Oligonucleotide Compound | dG | SNC9A mRNA % (vs Saline control 100%) |
|---|---|---|---|---|---|---|---|---|
| 477 | CTACCTTTTTAATTCTAAAT | 169169 | 169188 | 4-12-4 | 477_1 | CTACctttttaattctAAAT | -21 | 64.2 |
| 478 | ACTACCTTTTTAATTCTA | 169172 | 169189 | 4-11-3 | 478_1 | ACTAcctttttaattCTA | -22 | 30.7 |
| 479 | TGACTACCTTTTTAATTC | 169174 | 169191 | 4-11-3 | 479_1 | TGACtaccttttaaTTC | -21 | 32.6 |
| 480 | TATATTTTTTACCCCT | 171639 | 171655 | 2-12-3 | 480_1 | TAtattttttaccCCT | -21 | 109.9 |
| 481 | TCAAATATACATCCTTG | 171786 | 171802 | 2-9-6 | 481_1 | TCaaatatacaTCCTTG | -21 | 50.4 |
| 482 | GTCAAATATACATCCT | 171788 | 171803 | 4-8-4 | 482_1 | GTCAaatatacaTCCT | -22 | 36.2 |
| 483 | GGTCAAATATACATCC | 171789 | 171804 | 4-8-4 | 483_1 | GGTCaaatatacATCC | -22 | 63.6 |
| 484 | AGGTCAAATATACATC | 171790 | 171805 | 4-8-4 | 484_1 | AGGTcaaatataCATC | -20 | 61.0 |
| 485 | ACCACATTTATCCAATATA | 171913 | 171931 | 4-13-2 | 485_1 | ACCAcatttatccaataTA | -22 | 29.8 |
| 486 | ATAAAAACCACATTTATCCA | 171918 | 171937 | 2-14-4 | 486_1 | ATaaaaaccacatttaTCCA | -22 | 39.2 |
| 487 | ATCACAACCACAAAATCA | 172016 | 172033 | 4-11-3 | 487_1 | ATCAcaaccacaaaaTCA | -21 | 45.0 |
| 488 | ATAAATATTCTTACCTACA | 172043 | 172061 | 4-11-4 | 488_1 | ATAAatattcttaccTACA | -21 | 81.9 |
| 489 | AAGTATAATTTCCTTCTA | 172270 | 172287 | 4-11-3 | 489_1 | AAGTataatttccttCTA | -21 | 41.3 |
| 490 | AATTTATAGATTAATAAAT | 173412 | 173430 | 7-5-7 | 490_1 | AATTTATagattAATAAAT | -19 | 105.9 |
| 491 | TTTCCACATATTTCCTAC | 173713 | 173730 | 2-12-4 | 491_1 | TTtccacatatttcCTAC | -22 | 56.2 |
| 492 | TGTCTATTTCCACATATT | 173719 | 173736 | 4-12-2 | 492_1 | TGTCtatttccacataTT | -21 | 37.6 |
| 493 | TCTTTCAACCTTTTATTTA | 173858 | 173876 | 2-13-4 | 493_1 | TCttttcaaccttttaTTTA | -20 | 58.1 |
| 494 | ATATAAATCACCTGAAAT | 175481 | 175498 | 4-7-7 | 494_1 | ATATaaatcacCTGAAAT | -23 | 82.6 |
| 495 | ATTAATTCCATCTTCCTT | 176374 | 176391 | 1-13-4 | 495_1 | AttaattccatcttCCTT | -21 | 32.8 |
| 496 | TCATTAATTCCATCTTCC | 176376 | 176393 | 3-13-2 | 496_1 | TCAttaattccatcttCC | -22 | 34.4 |
| 497 | TGTCATTAATTCCATCTT | 176378 | 176395 | 2-13-3 | 497_1 | TGtcattaattccatCTT | -20 | 52.1 |
| 498 | AACATGTCATTAATTCC | 176383 | 176399 | 4-9-4 | 498_1 | AACAtgtcattaaTTCC | -20 | 30.6 |
| 499 | CCTTCAACTGAACTTC | 176531 | 176546 | 2-11-3 | 499_1 | CCttcaactgaacTTC | -19 | 55.5 |
| 500 | AGCCATATCTTTTTTATT | 177145 | 177162 | 3-12-3 | 500_1 | AGCcatatcttttttATT | -21 | 60.2 |
| 501 | TAAGCACCTCAAAATATA | 177860 | 177877 | 2-12-4 | 501_1 | TAagcacctcaaaaTATA | -19 | 73.2 |
| 502 | TTATTCATACTAAACACATA | 178456 | 178475 | 4-12-4 | 502_1 | TTATtcatactaaacaCATA | -21 | 55.0 |
| 503 | AAAGATCTCATATTCCT | 178779 | 178795 | 3-10-4 | 503_1 | AAAgatctcatatTCCT | -20 | 29.0 |
| 504 | TCTCATTCTTTAACCATAA | 179038 | 179056 | 4-12-3 | 504_1 | TCTCattctttaaccaTAA | -22 | 39.9 |
| 505 | TCCCTACTTAAATTATCAA | 179303 | 179321 | 3-12-4 | 505_1 | TCCctacttaaattaTCAA | -22 | 64.8 |
| 506 | GCAATGTAAAAACATTAA | 179500 | 179517 | 5-6-7 | 506_1 | GCAATgtaaaaACATTAA | -22 | 101.2 |
| 507 | CCCATATTTTTATTTTACA | 179528 | 179547 | 2-15-3 | 507_1 | CCcatattttttattttACA | -22 | 72.1 |
| 508 | CCCTTATCTACAAAAATTTA | 180108 | 180127 | 3-14-3 | 508_1 | CCCttatctacaaaaatTTA | -22 | 79.0 |
| 509 | CTGCTTTATTTACATAT | 180433 | 180449 | 3-11-3 | 509_1 | CTGctttatttacaTAT | -19 | 68.6 |
| 510 | ACTGCTTTATTTACATA | 180434 | 180450 | 4-11-2 | 510_1 | ACTGctttatttacaTA | -19 | 66.9 |

-continued

Compound Table

| SEQ ID NO | Motif sequence | position on SEQ ID NO: 1 Start | end | Design | CMP ID NO | Oligonucleotide Compound | dG | SNC9A mRNA % (vs Saline control 100%) |
|---|---|---|---|---|---|---|---|---|
| 511 | TCTCAAGTATAACTACA | 180753 | 180769 | 4-9-4 | 511_1 | TCTCaagtataacTACA | -21 | 63.4 |
| 512 | ACTGCTGAGCAGGATCA | 133475 | 133491 | 1-14-2 | 512_1 | ActgctgagcaggatCA | -20 | 84.7 |
| 512 | ACTGCTGAGCAGGATCA | 133475 | 133491 | 1-13-3 | 512_2 | ActgctgagcaggaTCA | -21 | 90.8 |
| 512 | ACTGCTGAGCAGGATCA | 133475 | 133491 | 2-13-2 | 512_3 | ACtgctgagcaggatCA | -22 | 98.0 |
| 513 | GCTGAGCAGGATCATGA | 133472 | 133488 | 1-14-2 | 513_1 | GctgagcaggatcatGA | -20 | 89.5 |
| 513 | GCTGAGCAGGATCATGA | 133472 | 133488 | 1-12-4 | 513_2 | GctgagcaggatcATGA | -22 | 90.2 |
| 513 | GCTGAGCAGGATCATGA | 133472 | 133488 | 1-13-3 | 513_3 | GctgagcaggatcaTGA | -21 | 91.2 |
| 513 | GCTGAGCAGGATCATGA | 133472 | 133488 | 2-13-2 | 513_4 | GCtgagcaggatcatGA | -22 | 96.8 |
| 514 | AAAATCCAGCCAGTTCCA | 70176 | 70193 | 1-15-2 | 514_1 | AaaatccagccagttcCA | -21 | 70.2 |
| 514 | AAAATCCAGCCAGTTCCA | 70176 | 70193 | 2-14-2 | 514_2 | AAaatccagccagttcCA | -22 | 77.3 |
| 514 | AAAATCCAGCCAGTTCCA | 70176 | 70193 | 3-13-2 | 514_3 | AAAatccagccagttcCA | -22 | 82.0 |
| 514 | AAAATCCAGCCAGTTCCA | 70176 | 70193 | 4-12-2 | 514_4 | AAAAtccagccagttcCA | -23 | 82.7 |
| 515 | ACTGCAATGTACATGTT | 176620 | 176636 | 1-12-4 | 515_1 | ActgcaatgtacaTGTT | -19 | 32.7 |
| 515 | ACTGCAATGTACATGTT | 176620 | 176636 | 3-12-2 | 515_2 | ACTgcaatgtacatgTT | -19 | 34.0 |
| 515 | ACTGCAATGTACATGTT | 176620 | 176636 | 4-11-2 | 515_3 | ACTGcaatgtacatgTT | -20 | 37.2 |
| 515 | ACTGCAATGTACATGTT | 176620 | 176636 | 2-11-4 | 515_4 | ACtgcaatgtacaTGTT | -20 | 43.2 |
| 515 | ACTGCAATGTACATGTT | 176620 | 176636 | 3-11-3 | 515_5 | ACTgcaatgtacatGTT | -20 | 45.3 |
| 515 | ACTGCAATGTACATGTT | 176620 | 176636 | 3-10-4 | 515_6 | ACTgcaatgtacaTGTT | -22 | 46.4 |
| 516 | TCTATTTGCTTAGCTG | 41022 | 41037 | 1-11-4 | 516_1 | TctatttgcttaGCTG | -20 | 10.3 |
| 516 | TCTATTTGCTTAGCTG | 41022 | 41037 | 1-12-3 | 516_2 | TctatttgcttagCTG | -18 | 10.4 |
| 516 | TCTATTTGCTTAGCTG | 41022 | 41037 | 2-12-2 | 516_3 | TCtatttgcttagcTG | -17 | 14.3 |
| 516 | TCTATTTGCTTAGCTG | 41022 | 41037 | 2-11-3 | 516_4 | TCtatttgcttagCTG | -19 | 36.2 |
| 516 | TCTATTTGCTTAGCTG | 41022 | 41037 | 3-11-2 | 516_5 | TCTatttgcttagcTG | -19 | 41.6 |
| 516 | TCTATTTGCTTAGCTG | 41022 | 41037 | 4-10-2 | 516_6 | TCTAtttgcttagcTG | -20 | 54.1 |
| 516 | TCTATTTGCTTAGCTG | 41022 | 41037 | 3-10-3 | 516_7 | TCTatttgcttagCTG | -21 | 64.6 |
| 517 | CTATTTGCTTAGCTGTT | 41020 | 41036 | 1-12-4 | 517_1 | CtatttgcttagcTGTT | -21 | 6.6 |
| 517 | CTATTTGCTTAGCTGTT | 41020 | 41036 | 1-13-3 | 517_2 | CtatttgcttagctGTT | -19 | 14.4 |
| 517 | CTATTTGCTTAGCTGTT | 41020 | 41036 | 2-13-2 | 517_3 | CTatttgcttagctgTT | -19 | 18.3 |
| 517 | CTATTTGCTTAGCTGTT | 41020 | 41036 | 2-12-3 | 517_4 | CTatttgcttagctGTT | -20 | 18.3 |
| 517 | CTATTTGCTTAGCTGTT | 41020 | 41036 | 3-12-2 | 517_5 | CTAtttgcttagctgTT | -20 | 18.7 |
| 517 | CTATTTGCTTAGCTGTT | 41020 | 41036 | 4-11-2 | 517_6 | CTATttgcttagctgTT | -21 | 32.4 |
| 517 | CTATTTGCTTAGCTGTT | 41020 | 41036 | 3-11-3 | 517_7 | CTAtttgcttagctGTT | -21 | 46.3 |
| 517 | CTATTTGCTTAGCTGTT | 41020 | 41036 | 2-11-4 | 517_8 | CTatttgcttagcTGTT | -22 | 56.2 |
| 518 | CTGAGCAGGATCATGA | 133472 | 133487 | 1-12-3 | 518_1 | CtgagcaggatcaTGA | -19 | 78.6 |
| 518 | CTGAGCAGGATCATGA | 133472 | 133487 | 2-12-2 | 518_2 | CTgagcaggatcatGA | -19 | 88.3 |

Compound Table

| SEQ ID NO | Motif sequence | position on SEQ ID NO: 1 Start | end | Design | CMP ID NO | Oligonucleotide Compound | dG | SNC9A mRNA % (vs Saline control 100%) |
|---|---|---|---|---|---|---|---|---|
| 518 | CTGAGCAGGATCATGA | 133472 | 133487 | 2-11-3 | 518_3 | CTgagcaggatcaTGA | -21 | 92.1 |
| 518 | CTGAGCAGGATCATGA | 133472 | 133487 | 3-11-2 | 518_4 | CTGagcaggatcatGA | -20 | 92.5 |
| 518 | CTGAGCAGGATCATGA | 133472 | 133487 | 2-10-4 | 518_5 | CTgagcaggatcATGA | -22 | 99.7 |
| 518 | CTGAGCAGGATCATGA | 133472 | 133487 | 1-11-4 | 518_6 | CtgagcaggatcATGA | -20 | 99.9 |
| 519 | AAAATCCAGCCAGTTCC | 70177 | 70193 | 1-13-3 | 519_1 | AaaatccagccagtTCC | -21 | 44.5 |
| 519 | AAAATCCAGCCAGTTCC | 70177 | 70193 | 2-13-2 | 519_2 | AAaatccagccagttCC | -21 | 49.4 |
| 519 | AAAATCCAGCCAGTTCC | 70177 | 70193 | 2-12-3 | 519_3 | AAaatccagccagtTCC | -22 | 62.1 |
| 519 | AAAATCCAGCCAGTTCC | 70177 | 70193 | 3-12-2 | 519_4 | AAAatccagccagttCC | -21 | 63.4 |
| 519 | AAAATCCAGCCAGTTCC | 70177 | 70193 | 4-11-2 | 519_5 | AAAAtccagccagttCC | -22 | 71.1 |
| 519 | AAAATCCAGCCAGTTCC | 70177 | 70193 | 3-11-3 | 519_6 | AAAatccagccagtTCC | -22 | 71.9 |
| 520 | TCTATTTGCTTAGCTGT | 41021 | 41037 | 1-13-3 | 520_1 | TctatttgcttagcTGT | -20 | 9.2 |
| 520 | TCTATTTGCTTAGCTGT | 41021 | 41037 | 2-13-2 | 520_2 | TCtatttgcttagctGT | -19 | 12.3 |
| 520 | TCTATTTGCTTAGCTGT | 41021 | 41037 | 2-12-3 | 520_3 | TCtatttgcttagcTGT | -21 | 19.0 |
| 520 | TCTATTTGCTTAGCTGT | 41021 | 41037 | 3-12-2 | 520_4 | TCTatttgcttagctGT | -21 | 47.1 |
| 520 | TCTATTTGCTTAGCTGT | 41021 | 41037 | 4-11-2 | 520_5 | TCTAtttgcttagctGT | -22 | 54.6 |
| 521 | TCTATTTGCTTAGCTGTT | 41020 | 41037 | 1-14-3 | 521_1 | TctatttgcttagctGTT | -20 | 7.1 |
| 521 | TCTATTTGCTTAGCTGTT | 41020 | 41037 | 2-14-2 | 521_2 | TCtatttgcttagctgTT | -20 | 14.3 |
| 521 | TCTATTTGCTTAGCTGTT | 41020 | 41037 | 2-13-3 | 521_3 | TCtatttgcttagcTGTT | -21 | 24.3 |
| 521 | TCTATTTGCTTAGCTGTT | 41020 | 41037 | 3-12-3 | 521_4 | TCTatttgcttagctGTT | -23 | 54.2 |
| 521 | TCTATTTGCTTAGCTGTT | 41020 | 41037 | 1-13-4 | 521_5 | TctatttgcttagcTGTT | -21 | 60.3 |
| 522 | TGCTGAGCAGGATCAT | 133474 | 133489 | 2-12-2 | 522_1 | TGctgagcaggatcAT | -19 | 71.9 |
| 522 | TGCTGAGCAGGATCAT | 133474 | 133489 | 2-11-3 | 522_2 | TGctgagcaggatCAT | -21 | 76.7 |
| 522 | TGCTGAGCAGGATCAT | 133474 | 133489 | 2-10-4 | 522_3 | TGctgagcaggaTCAT | -22 | 88.1 |
| 522 | TGCTGAGCAGGATCAT | 133474 | 133489 | 3-11-2 | 522_4 | TGCtgagcaggatcAT | -22 | 90.2 |
| 523 | ACTGCAATGTACATGT | 176621 | 176636 | 2-11-3 | 523_1 | ACtgcaatgtacaTGT | -18 | 32.0 |
| 523 | ACTGCAATGTACATGT | 176621 | 176636 | 4-10-2 | 523_2 | ACTGcaatgtacatGT | -19 | 33.0 |
| 523 | ACTGCAATGTACATGT | 176621 | 176636 | 2-10-4 | 523_3 | ACtgcaatgtacATGT | -19 | 41.6 |
| 523 | ACTGCAATGTACATGT | 176621 | 176636 | 3-10-3 | 523_4 | ACTgcaatgtacaTGT | -20 | 42.9 |
| 523 | ACTGCAATGTACATGT | 176621 | 176636 | 4-8-4 | 523_5 | ACTGcaatgtacATGT | -22 | 60.7 |
| 524 | ATTAGGTTCTCTAAT | 180266 | 180280 | 4-7-4 | 524_1 | ATTAggttctcTAAT | -18 | 110.1 |
| 525 | ACTGCAATGTACATG | 176622 | 176636 | 4-7-4 | 525_1 | ACTGcaatgtaCATG | -20 | 79.6 |
| 526 | GCAATGTACATGTTCAC | 176617 | 176633 | 3-11-3 | 526_1 | GCAatgtacatgttCAC | -21 | 15.4 |
| 527 | CAATGTACATGTTCAC | 176617 | 176632 | 4-8-4 | 527_1 | CAATgtacatgtTCAC | -20 | 18.2 |
| 528 | GTAGATGAACATGACCAG | 176320 | 176337 | 3-12-3 | 528_1 | GTAgatgaacatgacCAG | -22 | 10.3 |

-continued

Compound Table

| SEQ ID NO | Motif sequence | position on SEQ ID NO: 1 Start | end | Design | CMP ID NO | Oligonucleotide Compound | dG | SNC9A mRNA % (vs Saline control 100%) |
|---|---|---|---|---|---|---|---|---|
| 529 | GTAGATGAACATGACCAGGA | 176318 | 176337 | 1-16-3 | 529_1 | GtagatgaacatgaccaGGA | −23 | 32.0 |
| 530 | GTAGATGAACATGACCA | 176321 | 176337 | 3-11-3 | 530_1 | GTAgatgaacatgaCCA | −22 | 10.5 |
| 531 | GTAGATGAACATGACCAGG | 176319 | 176337 | 1-14-4 | 531_1 | GtagatgaacatgacCAGG | −23 | 35.0 |
| 532 | TAGATGAACATGACC | 176322 | 176336 | 4-7-4 | 532_1 | TAGAtgaacatGACC | −20 | 6.4 |
| 533 | TAGATGAACATGACCA | 176321 | 176336 | 4-9-3 | 533_1 | TAGAtgaacatgaCCA | −21 | 5.1 |
| 534 | TAGATGAACATGACCAGG | 176319 | 176336 | 3-12-3 | 534_1 | TAGatgaacatgaccAGG | −22 | 6.7 |
| 535 | TAGATGAACATGACCAGGA | 176318 | 176336 | 3-14-2 | 535_1 | TAGatgaacatgaccagGA | −22 | 20.3 |
| 536 | TAGATGAACATGACCAGGAA | 176317 | 176336 | 4-14-2 | 536_1 | TAGAtgaacatgaccaggAA | −23 | 23.1 |
| 537 | AGATGAACATGACCAGGA | 176318 | 176335 | 1-13-4 | 537_1 | AgatgaacatgaccAGGA | −22 | 9.4 |
| 538 | AGATGAACATGACCAGG | 176319 | 176335 | 2-11-4 | 538_1 | AGatgaacatgacCAGG | −22 | 15.0 |
| 539 | AGATGAACATGACCAGGAA | 176317 | 176335 | 2-13-4 | 539_1 | AGatgaacatgaccaGGAA | −23 | 12.0 |
| 540 | GATGAACATGACCAGG | 176319 | 176334 | 4-9-3 | 540_1 | GATGaacatgaccAGG | −22 | 4.1 |
| 541 | GATGAACATGACCAGGAA | 176317 | 176334 | 4-11-3 | 541_1 | GATGaacatgaccagGAA | −23 | 8.8 |
| 542 | GATGAACATGACCAGGA | 176318 | 176334 | 2-11-4 | 542_1 | GAtgaacatgaccAGGA | −22 | 7.5 |
| 543 | ATGAACATGACCAGGA | 176318 | 176333 | 3-9-4 | 543_1 | ATGaacatgaccAGGA | −22 | 9.4 |
| 544 | TGAACATGACCAGGAA | 176317 | 176332 | 4-8-4 | 544_1 | TGAAcatgaccaGGAA | −22 | 9.4 |
| 545 | GTGAAGTAGTAGTG | 171984 | 171997 | 4-7-3 | 545_1 | GTGAagtagtaGTG | −18 | 31.4 |
| 546 | ACTTATCTTCTTTTTCTGTT | 149422 | 149441 | 1-15-4 | 546_1 | ActtatcttcttttcTGTT | −22 | 104.7 |
| 547 | ACTTATCTTCTTTTTCTGT | 149423 | 149441 | 1-14-4 | 547_1 | ActtatcttcttttCTGT | −22 | 96.4 |
| 548 | CTTATCTTCTTTTTCTGT | 149423 | 149440 | 1-13-4 | 548_1 | CttatcttcttttCTGT | −21 | 90.3 |
| 549 | CTTATCTTCTTTTTCTGTTG | 149421 | 149440 | 2-15-3 | 549_1 | CTtatcttcttttctgTTG | −22 | 96.2 |
| 550 | CTTATCTTCTTTTTCTGTT | 149422 | 149440 | 1-14-4 | 550_1 | CttatcttcttttcTGTT | −22 | 102.8 |
| 551 | TTATCTTCTTTTTCTGTT | 149422 | 149439 | 4-12-2 | 551_1 | TTATcttcttttctgTT | −20 | 72.0 |
| 552 | TTATCTTCTTTTTCTGT | 149423 | 149439 | 1-12-4 | 552_1 | TtatcttcttttCTGT | −19 | 101.0 |
| 553 | TTATCTTCTTTTTCTGTTG | 149421 | 149439 | 4-13-2 | 553_1 | TTATcttcttttctgtTG | −21 | 70.7 |
| 554 | TATCTTCTTTTTCTGTTG | 149421 | 149438 | 3-12-3 | 554_1 | TATcttcttttctgTTG | −21 | 71.8 |
| 555 | ATCTTCTTTTTCTGTTG | 149421 | 149437 | 3-11-3 | 555_1 | ATCttcttttctgTTG | −20 | 60.0 |
| 556 | TCCCATGATGCTGAA | 147108 | 147122 | 4-9-2 | 556_1 | TCCCatgatgctgAA | −22 | 61.0 |
| 557 | ACTGCTGAGCAGGATCAT | 133474 | 133491 | 1-14-3 | 557_1 | ActgctgagcaggatCAT | −22 | 98.9 |
| 558 | CTGCTGAGCAGGATCAT | 133474 | 133490 | 1-13-3 | 558_1 | CtgctgagcaggatCAT | −22 | 85.9 |
| 559 | TGCTGAGCAGGATCATG | 133473 | 133489 | 2-13-2 | 559_1 | TGctgagcaggatcaTG | −21 | 88.2 |
| 560 | TGAGCAGGATCATGA | 133472 | 133486 | 3-8-4 | 560_1 | TGAgcaggatcATGA | −21 | 118.1 |
| 561 | TCTCTATCCACTCTCCA | 98920 | 98936 | 1-14-2 | 561_1 | TctctatccactctcCA | −21 | 75.8 |
| 562 | CTCTATCCACTCTCCA | 98920 | 98935 | 1-12-3 | 562_1 | CtctatccactctCCA | −23 | 52.3 |
| 563 | CTCTATCCACTCTCCAC | 98919 | 98935 | 1-13-3 | 563_1 | CtctatccactctcCAC | −23 | 63.8 |

-continued

Compound Table

| SEQ ID NO | Motif sequence | position on SEQ ID NO: 1 Start | end | Design | CMP ID NO | Oligonucleotide Compound | dG | SNC9A mRNA % (vs Saline control 100%) |
|---|---|---|---|---|---|---|---|---|
| 564 | CTCTATCCACTCTCCACA | 98918 | 98935 | 1-13-4 | 564_1 | CtctatccactctcCACA | -26 | 35.7 |
| 565 | GGAAGGAGTGGAAGAAGTCG | 98878 | 98897 | 2-16-2 | 565_1 | GGaaggagtggaagaagtCG | -22 | 70.8 |
| 566 | GAAGGAGTGGAAGAAGTCGT | 98877 | 98896 | 1-16-3 | 566_1 | GaaggagtggaagaagtCGT | -22 | 71.6 |
| 567 | GAAGGAGTGGAAGAAGTCG | 98878 | 98896 | 3-13-3 | 567_1 | GAaggagtggaagaagTCG | -22 | 70.7 |
| 568 | AAGGAGTGGAAGAAGTCG | 98878 | 98895 | 3-11-4 | 568_1 | AAGgagtggaagaaGTCG | -23 | 21.2 |
| 569 | AAGGAGTGGAAGAAGTCGT | 98877 | 98895 | 2-13-4 | 569_1 | AAggagtggaagaagTCGT | -23 | 29.5 |
| 570 | AGGAGTGGAAGAAGTCG | 98878 | 98894 | 2-11-4 | 570_1 | AGgagtggaagaaGTCG | -22 | 23.2 |
| 571 | AGGAGTGGAAGAAGTCGT | 98877 | 98894 | 1-13-4 | 571_1 | AggagtggaagaagTCGT | -22 | 37.9 |
| 572 | GGAGTGGAAGAAGTCG | 98878 | 98893 | 4-10-2 | 572_1 | GGAGtggaagaagtCG | -21 | 40.9 |
| 573 | GGAGTGGAAGAAGTCGT | 98877 | 98893 | 3-12-2 | 573_1 | GGAgtggaagaagtcGT | -22 | 44.1 |
| 574 | GAGTGGAAGAAGTCGTTC | 98875 | 98892 | 2-12-4 | 574_1 | GAgtggaagaagtcGTTC | -22 | 28.0 |
| 575 | GAGTGGAAGAAGTCGTT | 98876 | 98892 | 4-11-2 | 575_1 | GAGTggaagaagtcgTT | -22 | 40.6 |
| 576 | GAGTGGAAGAAGTCGTTCAT | 98873 | 98892 | 1-15-4 | 576_1 | GagtggaagaagtcgtTCAT | -23 | 65.1 |
| 577 | GAGTGGAAGAAGTCG | 98878 | 98892 | 4-7-4 | 577_1 | GAGTggaagaaGTCG | -22 | 99.7 |
| 578 | GAGTGGAAGAAGTCGTTCA | 98874 | 98892 | 1-14-4 | 578_1 | GagtggaagaagtcgTTCA | -22 | 52.8 |
| 579 | GAGTGGAAGAAGTCGT | 98877 | 98892 | 3-9-4 | 579_1 | GAGtggaagaagTCGT | -22 | 71.2 |
| 580 | AGTGGAAGAAGTCGTTCA | 98874 | 98891 | 2-12-4 | 580_1 | AGtggaagaagtcgTTCA | -22 | 38.3 |
| 581 | AGTGGAAGAAGTCGTTCAT | 98873 | 98891 | 1-14-4 | 581_1 | AgtggaagaagtcgtTCAT | -22 | 59.0 |
| 582 | AGTGGAAGAAGTCGTTCATG | 98872 | 98891 | 2-16-2 | 582_1 | AGtggaagaagtcgttcaTG | -22 | 87.1 |
| 583 | AGTGGAAGAAGTCGT | 98877 | 98891 | 3-8-4 | 583_1 | AGTggaagaagTCGT | -21 | 68.1 |
| 584 | AGTGGAAGAAGTCGTT | 98876 | 98891 | 3-9-4 | 584_1 | AGTggaagaagtCGTT | -21 | 32.2 |
| 585 | AGTGGAAGAAGTCGTTC | 98875 | 98891 | 3-10-4 | 585_1 | AGTggaagaagtcGTTC | -22 | 17.6 |
| 586 | GTGGAAGAAGTCGTTC | 98875 | 98890 | 3-9-4 | 586_1 | GTGgaagaagtcGTTC | -21 | 16.6 |
| 587 | GTGGAAGAAGTCGT | 98877 | 98890 | 3-7-4 | 587_1 | GTGgaagaagTCGT | -20 | 73.5 |
| 588 | GTGGAAGAAGTCGTTCAT | 98873 | 98890 | 4-12-2 | 588_1 | GTGGaagaagtcgttcAT | -23 | 48.0 |
| 589 | GTGGAAGAAGTCGTTCATG | 98872 | 98890 | 1-14-4 | 589_1 | GtggaagaagtcgttCATG | -22 | 71.8 |
| 590 | GTGGAAGAAGTCGTTCA | 98874 | 98890 | 2-11-4 | 590_1 | GTggaagaagtcgTTCA | -22 | 27.8 |
| 591 | GTGGAAGAAGTCGTTCATGT | 98871 | 98890 | 1-16-3 | 591_1 | GtggaagaagtcgttcaTGT | -23 | 82.0 |
| 592 | GTGGAAGAAGTCGTT | 98876 | 98890 | 3-8-4 | 592_1 | GTGgaagaagtCGTT | -21 | 34.1 |
| 593 | TGGAAGAAGTCGTTCATGTG | 98870 | 98889 | 2-16-2 | 593_1 | TGgaagaagtcgttcatgTG | -22 | 65.8 |
| 594 | TGGAAGAAGTCGTTCA | 98874 | 98889 | 4-10-2 | 594_1 | TGGAagaagtcgttCA | -21 | 21.3 |
| 595 | TGGAAGAAGTCGTTCATG | 98872 | 98889 | 2-12-4 | 595_1 | TGgaagaagtcgttCATG | -22 | 49.3 |
| 596 | TGGAAGAAGTCGTTC | 98875 | 98889 | 4-7-4 | 596_1 | TGGAagaagtcGTTC | -21 | 86.5 |
| 597 | TGGAAGAAGTCGTTCAT | 98873 | 98889 | 3-10-4 | 597_1 | TGGaagaagtcgtTCAT | -22 | 82.1 |

-continued

Compound Table

| SEQ ID NO | Motif sequence | position on SEQ ID NO: 1 Start | end | Design | CMP ID NO | Oligonucleotide Compound | dG | SNC9A mRNA % (vs Saline control 100%) |
|---|---|---|---|---|---|---|---|---|
| 598 | TGGAAGAAGTCGTTCATGT | 98871 | 98889 | 3-14-2 | 598_1 | TGGaagaagtcgttcatGT | -22 | 42.0 |
| 599 | GGAAGAAGTCGTTCA | 98874 | 98888 | 3-8-4 | 599_1 | GGAagaagtcgTTCA | -20 | 106.6 |
| 600 | GGAAGAAGTCGTTCAT | 98873 | 98888 | 4-9-3 | 600_1 | GGAAgaagtcgttCAT | -21 | 30.3 |
| 601 | GGAAGAAGTCGTTCATGT | 98871 | 98888 | 2-13-3 | 601_1 | GGaagaagtcgttcaTGT | -22 | 34.6 |
| 602 | GGAAGAAGTCGTTCATGTGC | 98869 | 98888 | 1-17-2 | 602_1 | GgaagaagtcgttcatgtGC | -23 | 70.1 |
| 603 | GGAAGAAGTCGTTCATG | 98872 | 98888 | 4-10-3 | 603_1 | GGAAgaagtcgttcATG | -22 | 17.9 |
| 604 | GGAAGAAGTCGTTCATGTG | 98870 | 98888 | 2-14-3 | 604_1 | GGaagaagtcgttcatGTG | -22 | 20.3 |
| 605 | GAAGAAGTCGTTCATGTG | 98870 | 98887 | 2-12-4 | 605_1 | GAagaagtcgttcaTGTG | -22 | 20.4 |
| 606 | GAAGAAGTCGTTCATGTGC | 98869 | 98887 | 1-15-3 | 606_1 | GaagaagtcgttcatgTGC | -22 | 52.0 |
| 607 | GAAGAAGTCGTTCATGTGCC | 98868 | 98887 | 1-16-3 | 607_1 | GaagaagtcgttcatgtGCC | -25 | 49.3 |
| 608 | GAAGAAGTCGTTCAT | 98873 | 98887 | 4-7-4 | 608_1 | GAAGaagtcgtTCAT | -19 | 114.8 |
| 609 | GAAGAAGTCGTTCATG | 98872 | 98887 | 4-8-4 | 609_1 | GAAGaagtcgttCATG | -21 | 86.8 |
| 610 | GAAGAAGTCGTTCATGT | 98871 | 98887 | 4-10-3 | 610_1 | GAAGaagtcgttcaTGT | -22 | 18.5 |
| 611 | AAGAAGTCGTTCATGT | 98871 | 98886 | 4-8-4 | 611_1 | AAGAagtcgttcATGT | -21 | 59.0 |
| 612 | AAGAAGTCGTTCATGTGC | 98869 | 98886 | 1-13-4 | 612_1 | AagaagtcgttcatGTGC | -22 | 33.6 |
| 613 | AAGAAGTCGTTCATGTGCCA | 98867 | 98886 | 1-17-2 | 613_1 | AagaagtcgttcatgtgcCA | -23 | 64.9 |
| 614 | AAGAAGTCGTTCATG | 98872 | 98886 | 4-7-4 | 614_1 | AAGAagtcgttCATG | -19 | 100.1 |
| 615 | AAGAAGTCGTTCAT | 98873 | 98886 | 4-6-4 | 615_1 | AAGAagtcgTCAT | -18 | 95.9 |
| 616 | AAGAAGTCGTTCATGTGCC | 98868 | 98886 | 2-15-2 | 616_1 | AAgaagtcgttcatgtgCC | -23 | 38.7 |
| 617 | AAGAAGTCGTTCATGTG | 98870 | 98886 | 3-10-4 | 617_1 | AAGaagtcgttcaTGTG | -21 | 15.7 |
| 618 | AGAAGTCGTTCATGTGCC | 98868 | 98885 | 1-15-2 | 618_1 | AgaagtcgttcatgtGCC | -22 | 36.5 |
| 619 | AGAAGTCGTTCATGTG | 98870 | 98885 | 2-10-4 | 619_1 | AGaagtcgttcaTGTG | -20 | 13.4 |
| 620 | AGAAGTCGTTCATGT | 98871 | 98885 | 4-7-4 | 620_1 | AGAagtcgttcATGT | -21 | 59.2 |
| 621 | AGAAGTCGTTCATGTGC | 98869 | 98885 | 3-12-2 | 621_1 | AGAagtcgttcatgtGC | -22 | 8.8 |
| 622 | AGAAGTCGTTCATG | 98872 | 98885 | 4-6-4 | 622_1 | AGAagtcgttCATG | -20 | 93.7 |
| 623 | AGAAGTCGTTCATGTGCCA | 98867 | 98885 | 1-16-2 | 623_1 | AgaagtcgttcatgtgCA | -23 | 43.3 |
| 624 | GAAGTCGTTCATGTGCC | 98868 | 98884 | 1-13-3 | 624_1 | GaagtcgttcatgtGCC | -23 | 18.0 |
| 625 | GAAGTCGTTCATGTGCCA | 98867 | 98884 | 1-15-2 | 625_1 | GaagtcgttcatgtgCA | -22 | 36.7 |
| 626 | GAAGTCGTTCATGTGC | 98869 | 98884 | 4-10-2 | 626_1 | GAAGtcgttcatgtGC | -22 | 9.6 |
| 627 | AAGTCGTTCATGTGCC | 98868 | 98883 | 2-11-3 | 627_1 | AAgtcgttcatgtGCC | -22 | 7.8 |
| 628 | AAGTCGTTCATGTGCCA | 98867 | 98883 | 3-12-2 | 628_1 | AAGtcgttcatgtgCA | -22 | 7.1 |
| 629 | AGTCGTTCATGTGCC | 98868 | 98882 | 1-11-3 | 629_1 | AgtcgttcatgtGCC | -21 | 9.2 |
| 630 | AGTCGTTCATGTGCCA | 98867 | 98882 | 2-12-2 | 630_1 | AGtcgttcatgtgCA | -22 | 12.1 |
| 631 | GTCGTTCATGTGCC | 98868 | 98881 | 1-10-3 | 631_1 | GtcgttcatgtGCC | -20 | 11.5 |

-continued

Compound Table

| SEQ ID NO | Motif sequence | position on SEQ ID NO: 1 Start | end | Design | CMP ID NO | Oligonucleotide Compound | dG | SNC9A mRNA % (vs Saline control 100%) |
|---|---|---|---|---|---|---|---|---|
| 632 | TCGTTCATGTGCCA | 98867 | 98880 | 4-8-2 | 632_1 | TCGTtcatgtgcCA | -21 | 3.8 |
| 633 | GGCCAGGATTTTGCCA | 98679 | 98694 | 1-13-2 | 633_1 | GgccaggattttgcCA | -22 | 88.1 |
| 634 | GGCCAGGATTTTGCC | 98680 | 98694 | 1-12-2 | 634_1 | GgccaggattttgCC | -22 | 108.7 |
| 635 | TCAAAGCTCGTGTAG | 82684 | 82698 | 4-7-4 | 635_1 | TCAAagctcgtGTAG | -21 | 27.4 |
| 636 | CAAAGCTCGTGTAG | 82684 | 82697 | 3-7-4 | 636_1 | CAAagctcgtGTAG | -18 | 12.9 |
| 637 | AAAGTTCGAAGAGCTG | 71708 | 71723 | 4-8-4 | 637_1 | AAAGttcgaagaGCTG | -21 | 102.9 |
| 638 | TATTTGCTTAGCTGTT | 41020 | 41035 | 4-8-4 | 638_1 | TATTtgcttagcTGTT | -22 | 18.1 |
| 639 | GTAGATGAACATGACC | 176322 | 176337 | 3-9-4 | 639 | GTAgatgaacatGACC | -21 | 19.8 |
| 640 | TAGATGAACATGACCAG | 176320 | 176336 | 4-10-3 | 640_1 | TAGAtgaacatgacCAG | -22 | 8.1 |
| 641 | ATGAACATGACCAGGAA | 176317 | 176333 | 3-10-4 | 641_1 | ATGaacatgaccaGGAA | -21 | 9.1 |
| 642 | TTCACTAAATTTCACTAATC | 64574 | 64593 | 4-12-4 | 642_1 | TTCActaaatttcactAATC | -20 | 20.2 |
| 643 | AATGTACTTATACCCA | 69498 | 69513 | 1-11-4 | 643_1 | AatgtacttataCCCA | -20 | 71.9 |
| 644 | CTTACGCAAAAACAAT | 70200 | 70215 | 5-5-6 | 644_1 | CTTACgcaaaAACAAT | -20 | 84.8 |
| 645 | ACTTACGCAAAAACAAT | 70200 | 70216 | 4-8-5 | 645_1 | ACTTacgcaaaaACAAT | -19 | 94.9 |
| 646 | TCACACCAATTACTTCTT | 71767 | 71784 | 2-13-3 | 646_1 | TCacaccaattacttCTT | -20 | 43.1 |
| 647 | CTTCACACCAATTACTTCTT | 71767 | 71786 | 1-16-3 | 647_1 | CttcacaccaattacttCTT | -22 | 81.2 |
| 648 | TTACTTTATTCATCTCATA | 86908 | 86926 | 3-13-3 | 648_1 | TTActtattcatctcATA | -20 | 47.0 |
| 649 | TACTTTATTCATCTCATA | 86908 | 86925 | 3-13-2 | 649_1 | TACttattcatctcaTA | -18 | 80.3 |
| 650 | TTGAACCTTCATTATTTC | 107247 | 107264 | 4-11-3 | 650_1 | TTGAaccttcattatTTC | -20 | 20 |

SEQUENCE LISTING

The patent contains a lengthy sequence listing. A copy of the sequence listing is available in electronic form from the USPTO web site (https://seqdata.uspto.gov/?pageRequest=docDetail&DocID=US12116576B2). An electronic copy of the sequence listing will also be available from the USPTO upon request and payment of the fee set forth in 37 CFR 1.19(b)(3).

The invention claimed is:

1. An oligonucleotide of 10 to 30 nucleotides in length comprising a contiguous nucleotide sequence of 10 to 30 nucleotides in length and having at least 90% complementarity to SEQ ID NO: 1, wherein the oligonucleotide is capable of inhibiting the expression of Nav1.7 and Nav1.8 in a cell, and wherein the contiguous nucleotide sequence is complementary to human Nav1.7 and human Nav1.8 target nucleic acids, wherein the oligonucleotide comprises at least 10 or at least 12 contiguous nucleosides present in a sequence selected from the group consisting of SEQ ID NOs: 512, 513, 514, 515, 516, 517, 518, 519, 520, 521, 522, 523, 524, 525, 557, 558, 559, 560, 577, 579, 583, 638, and 587, and wherein the oligonucleotide is, or forms part of, an RNAi agent.

2. The oligonucleotide of claim 1, wherein one or more nucleosides in the contiguous nucleotide sequence is a 2′ sugar-modified nucleoside.

3. The oligonucleotide of claim 2, wherein the 2′ sugar-modified nucleoside is independently selected from the group consisting of a 2′-O-alkyl-RNA, 2′-O-methyl-RNA, 2′-alkoxy-RNA, 2′-O-methoxyethyl-RNA, 2′-amino-DNA, 2′-fluoro-DNA, arabino nucleic acid (ANA), 2′-fluoro-ANA, and LNA nucleoside.

4. The oligonucleotide of claim 1, wherein the oligonucleotide or contiguous nucleotide sequence thereof comprises one or more LNA nucleosides.

5. The oligonucleotide of claim 1, wherein at least one internucleoside linkage in the contiguous nucleotide sequence is a phosphorothioate internucleoside linkage.

6. The oligonucleotide of claim 5, wherein all of the internucleoside linkages within the contiguous nucleotide sequence are phosphorothioate internucleoside linkages.

7. A conjugate comprising the oligonucleotide of claim 1 and at least one conjugate moiety covalently attached to the oligonucleotide.

8. A pharmaceutically acceptable salt of the oligonucleotide of claim 1.

9. A pharmaceutical composition comprising the oligonucleotide of claim 1, and a pharmaceutically acceptable diluent, solvent, carrier, salt, and/or adjuvant.

10. An in vivo or in vitro method for inhibiting SCN9A expression in a target cell expressing SCN9A, the method comprising administering the oligonucleotide of claim 1 in an effective amount to the cell.

11. The method of claim 10, wherein the cell further expresses SCN10A, and the administering further inhibits SCN10A expression in the cell.

12. A method for treating or preventing pain in a subject suffering from or at risk of developing pain, the method comprising administering a therapeutically or prophylactically effective amount of the oligonucleotide of claim 1 to the subject, thereby preventing or alleviating the pain in the subject.

13. The method of claim 12, wherein the pain is:
    (i) chronic pain, neuropathic pain, inflammatory pain, spontaneous pain, or nociceptive pain;
    (ii) pain caused by or associated with a disorder selected from the group consisting of diabetic neuropathies, cancer, cranial neuralgia, postherpetic neuralgia, and post-surgical neuralgia;
    (iii) pain caused by or associated with inherited erythromelalgia (EIM), paroxysmal extreme pain disorder (PEPD), or trigeminal neuralgia; or
    (iv) visceral pain or mixed pain.

14. A pharmaceutically acceptable salt of the conjugate of claim 7.

15. A pharmaceutical composition comprising the conjugate of claim 7 and a pharmaceutically acceptable diluent, solvent, carrier, salt, and/or adjuvant.

16. A pharmaceutical composition comprising the pharmaceutically acceptable salt of claim 8 and a pharmaceutically acceptable diluent, solvent, carrier, salt, and/or adjuvant.

* * * * *

UNITED STATES PATENT AND TRADEMARK OFFICE
CERTIFICATE OF CORRECTION

| | | |
|---|---|---|
| PATENT NO. | : 12,116,576 B2 | Page 1 of 1 |
| APPLICATION NO. | : 17/130451 | |
| DATED | : October 15, 2024 | |
| INVENTOR(S) | : Pedersen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 188 days.

Signed and Sealed this
Twelfth Day of August, 2025

Coke Morgan Stewart
*Acting Director of the United States Patent and Trademark Office*